(12) United States Patent
Hamel et al.

(10) Patent No.: US 7,635,482 B2
(45) Date of Patent: Dec. 22, 2009

(54) STREPTOCOCCUS ANTIGENS

(75) Inventors: Josee Hamel, Quebec (CA); Bernard R. Brodeur, Quebec (CA); Isabelle Pineau, Quebec (CA); Denis Martin, Quebec (CA); Clement Rioux, Quebec (CA); Nathalie Charland, Quebec (CA)

(73) Assignee: ID Biomedical Corporation, Laval (CA)

( * ) Notice: Subject to any disclaimer, the term of this patent is extended or adjusted under 35 U.S.C. 154(b) by 0 days.

(21) Appl. No.: 11/513,421

(22) Filed: Aug. 29, 2006

(65) Prior Publication Data

US 2007/0116712 A1 May 24, 2007

Related U.S. Application Data

(63) Continuation of application No. 09/471,255, filed on Dec. 23, 1999, now Pat. No. 7,128,918.

(60) Provisional application No. 60/113,800, filed on Dec. 23, 1998.

(51) Int. Cl.
*A61K 39/02* (2006.01)
*C07H 21/04* (2006.01)

(52) U.S. Cl. ............... 424/190.1; 424/244.1; 530/350; 536/23.7; 435/252.3

(58) Field of Classification Search .................... None
See application file for complete search history.

(56) References Cited

U.S. PATENT DOCUMENTS

| | | | |
|---|---|---|---|
| 4,242,501 A | 12/1980 | Cano et al. .................... 536/1 |
| 6,503,511 B1 | 1/2003 | Wizemann et al. ........ 424/190.1 |
| 6,573,082 B1* | 6/2003 | Choi et al. ................. 435/252.3 |
| 6,582,706 B1* | 6/2003 | Johnson et al. ........... 424/244.1 |
| 6,699,703 B1* | 3/2004 | Doucette-Stamm et al. ........................ 435/252.3 |
| 6,800,744 B1 | 10/2004 | Doucette-Stamm et al. |
| 6,833,356 B1* | 12/2004 | Koenig et al. .................. 514/12 |
| 7,056,510 B1* | 6/2006 | Choi et al. ................. 424/165.1 |
| 7,074,415 B2 | 7/2006 | Hamel et al. |
| 7,122,194 B2* | 10/2006 | Johnson et al. ........... 424/234.1 |
| 2003/0138447 A1 | 7/2003 | Wizemann et al. ........ 424/190.1 |
| 2003/0232976 A1 | 12/2003 | Hamel et al. |
| 2004/0005331 A1 | 1/2004 | Johnson et al. ........... 424/190.1 |

(Continued)

FOREIGN PATENT DOCUMENTS

EP 0837130 4/1998

(Continued)

OTHER PUBLICATIONS

Adamou, John E. et al, Infection and Immunity, vol. 69(2), pp. 949-958, Feb. 2001, Identificaiton and Characterization of a Novel Family of Pneumococcal proteins that are protective against Sepsis.*

(Continued)

*Primary Examiner*—Robert B Mondesi
*Assistant Examiner*—Ginny Portner
(74) *Attorney, Agent, or Firm*—Seed IP Law Group PLLC

(57) ABSTRACT

*Streptococcus* proteins and polynucleotides encoding them are disclosed. Said proteins are antigenic and therefore useful vaccine components for the prophylaxis or therapy of *streptococcus* infection in animals. Also disclosed are recombinant methods of producing the protein antigens as well as diagnostic assays for detecting *streptococcus* bacterial infection.

16 Claims, 33 Drawing Sheets

U.S. PATENT DOCUMENTS

| | | | |
|---|---|---|---|
| 2004/0052781 A1 | 3/2004 | Johnson et al. | 424/130.1 |
| 2004/0081662 A1 | 4/2004 | Hermand et al. | 424/190.1 |
| 2006/0051361 A1* | 3/2006 | Laferriere et al. | 424/190.1 |
| 2006/0263846 A1* | 11/2006 | Meinke et al. | 435/69.1 |

FOREIGN PATENT DOCUMENTS

| | | |
|---|---|---|
| WO | WO94/21685 | 9/1994 |
| WO | WO96/40928 | 12/1996 |
| WO | WO98/18930 | 5/1998 |
| WO | WO98/18931 | 5/1998 |
| WO | WO99/15675 | 4/1999 |
| WO | WO99/42588 | 8/1999 |
| WO | WO00/06737 | 2/2000 |
| WO | WO00/06738 | 2/2000 |
| WO | WO00/17370 | 3/2000 |
| WO | WO00/37105 | 6/2000 |
| WO | WO00/39299 | 7/2000 |
| WO | WO00/76540 A2 | 12/2000 |
| WO | WO01/14421 A1 | 3/2001 |
| WO | WO01/98334 | 12/2001 |
| WO | WO02/077021 | 10/2002 |
| WO | WO2004/092209 | 10/2004 |

OTHER PUBLICATIONS

Hamel, Josee et al, Infection and Immunity, May 2004, vol. 72(5), pp. 2659-2670.*

Adamou, John E. et al, Infection and Immunity, vol. 69(3), pp. 949-958, Feb. 2001.*

Adamou et al., "Identification and Characterization of a Novel Family of Pneumococcal Proteins that are Protective against Sepsis," *Infection and Immunity*, pp. 949-958, Feb. 2001.

Boslego et al., Chapter 17: 'Gonorrhea Vaccines', *Vaccines and Immunotherapy* Pergamon Press, pp. 211-223, 1991.

Bolton et al., "Use of the Surface Proteins GapC and Mig of *Streptococcus dysgalactiae* as Potential Protective Antigens against Bovine Mastitis," *Canadian Journal of Microbiology* 50(6):423-32, Jun. 2004 (abstract only).

Briles et al., "Immunization of Humans and Recombinant Pneumococcal Surface Protein A (rPspA) Elecits Antibodies that Passively Protect Mice from Fatal Infection with *Streptococcus pneumoniae* Bearing Heterologous PspA," *Journal of Infectious Disease 182*, pp. 1694-1701, Dec. 2000.

Briles et al., "Intranasal Immunization of Mice with a Mixture of the Penumococcal Proteins PsaA and PspA is Highly Protective against Nastopharyngeal Carriage of *Streptococcus pneumoniae*," *Infection and Immunity* 68(2):796-800, Feb. 2000.

Creighton, *Proteins: Structures and Molecular Principles*, 1984, pp. 314-315.

Creighton, *Protein Structure: A Practical Approach*, 1989, pp. 184-186.

Ellis et al., "New Technologies for Making Vaccines," *Vaccines*, W. B. Sanders Co., 1988, Chapter 29, pp. 568-575.

Hernandez et al., "Antigenicity of Chimeric Synthetic Peptides based on HTLV-1 Antigens and the Impact of Epitope Orientation," *Biochemical and Biophysical Research Communications* 276(3):1085-1088, Oct. 2000.

Kurstak, "Recent Progress in Vaccines Development and New Trends in Immunisation," *Vaccine* 19:2198-2200, 2001.

Nosoh et al., "Protein Stability and Stabilization through Protein Engineering," 197-217, 1991.

Oishi et al., "The Effect of Amino Acid Spacers on the Antigenicity of Dimeric Peptide-Inducing Cross-Reacting Antibodies t a Cell Surface Protein Antigen of *Streptococcus* mutans," *Oral Microbiology Immunology* 16:40-44, 2001.

Okamoto et al., "Vaccination with Formali-Inactivated Influenza Vaccine Protects Mice against Legal Influenza *Streptococcus Pyogenes* Superinfection," *Vaccine* 22:2887-2893, 2004.

Oli et al., "Redirecting the Humoral Immune Response against *Streptococcus* Mutans Antigen P1 with Monoclonal Antibodies," *Infection and Immunity*, 6951-6960, Dec. 2004.

Orihuela et al., "Organ-Specific Models of *Streptococcus pneumoniae* Disease," *Scandinavian Journal of Infectious Diseases* 35(9):647-652, 2003.

Partidos et al., "The Influence of Orientation and Number of Copies of T and B Cell Epitopes on the Specificity and Affinity of Antbodies Induced by Chimeric Peptides," *European Journal of Immunology* 22:2675-2680, 1992.

Sa-Leao et al., "Abstracts of the General Meeting of the American Society for Microbiology," May 20-24, 2001.

Spellerberg et al., "LMB, a Protein with Similarities to the Lral Adhesin Family, Mediates Attachment of *Streptococcus agalactiae* to Human Laminin," *Infection and Immunity*, 871-878, Feb. 1999.

Swildens et al., "Intestinal Translocation of *Streptococcus* Suits Type $2EF^+$ in Pigs," *Veterinary Microbiology* 103:29-33, 2004.

Whittam et al., "Inferences from Whole-Genome Sequences of Bacterial Pathogens," *Current Opinion in Genetics and Development* 12(6):719-725, Dec. 2002.

Wizemann et al., "Use of a Whole Genome Approach to Identify Vaccine Molecules Affording Protection against *Streptococcus pneumoniae* Infection," *Infection and Immunity*, 1593-1596, Mar. 2001.

Zhang et al., "Recominant RhpA Protein, a Unique Histidine Motif-Containing Protein from *Streptococcus pneumoniae*, Protects Mice against Intranasal Pneumococcal Challenge," *Infection and Immunity*, 3827-3836, Jun. 2001.

Zysk et al., "Detection of 23 Immunogenic Pneumococcal Proteins using Convalescent-Phase Serum," *Infection and Immunity* 68(6)3740-3743, Jun. 2000.

PCT Notification of Transmittal of The International Search Report or The Declaration dated Jul. 24, 2000.

Hopp, "Retrospective: 12 Years of Antigenic Determinant Predictions, and More," *Peptide Research* 6(4):183-190, 1993.

Hofmann et al., "On the theoretical prediction of protein antigenic determinants from amino acid sequences," *Biomed. Biochim. Acta* 46(11):855-866, 1987.

Jameson et al., "The antigenic index: a novel algorithm for predicting antigenic determinants," *Computer Application Bioscience* 4(1):181-186, 1988.

Kolaskar et al., "A semi-empirical method for prediction of antigenic determinants on protein antigens," *FEBS* 276(1,2):172-174, 1990.

Lipman et al., "Monoclonal Versus Polyclonal Antibodies: Distinguishing Characteristics, Applications, and Information Resources," *ILAR Journal* 46(3):258-268, 2005.

Martin et al., "Bioinformatics tools for identifying class I-restricted epitopes," *Methods* 29:289-298, 2003.

Menendez-Arias et al., "A BASIC microcomputer program for prediction of B and T cell epitopes in proteins," *Comput. Appl. Biosci.* 6(2):101-105, 1990.

Roitt et al., *Immunology*, $4^{th}$ Edition, 1998, pp. 7.7-7.8, Mosby, London.

Thornton et al., "Location of 'continuous' antigenic determinants in the protruding regions of proteins," *EMBO Journal* 5(2):409-413, 1986.

Tong et al., "Methods and protocols for prediction of immunogenic epitopes," *Briefings in Bioinformatics* 8(2):96-108, 2006.

Wan et al., "Epitope Map for a Growth Hormone Receptor Agonist Monoclonal Antibody, MAb 263," *Molecular Endocrinology* 17(11):2240-2250, 2003.

Swiss Prot Accession No. Q9ANY1_Strpn.

* cited by examiner

```
ATGAAATTTA GTAAAAAATA TATAGCAGCT GGATCAGCTG TTATCGTATC CTTGAGTCTA    60
TGTGCCTATG CACTAAACCA GCATCGTTCG CAGGAAAATA AGGACAATAA TCGTGTCTCT   120
TATGTGGATG GCAGCCAGTC AAGTCAGAAA AGTGAAAACT TGACACCAGA CCAGGTTAGC   180
CAGAAAGAAG GAATTCAGGC TGAGCAAATT GTAATCAAAA TTACAGATCA GGGCTATGTA   240
ACGTCACACG GTGACCACTA TCATTACTAT AATGGGAAAG TTCCTTATGA TGCCCTCTTT   300
AGTGAAGAAC TCTTGATGAA GGATCCAAAC TATCAACTTA AGACGCTGA TATTGTCAAT    360
GAAGTCAAGG GTGGTTATAT CATCAAGGTC GATGGAAAAT ATTATGTCTA CCTGAAAGAT   420
GCAGCTCATG CTGATAATGT TCGAACTAAA GATGAAATCA ATCGTCAAAA ACAAGAACAT   480
GTCAAAGATA ATGAGAAGGT TAACTCTAAT GTTGCTGTAG CAAGGTCTCA GGGACGATAT   540
ACGACAAATG ATGGTTATGT CTTTAATCCA GCTGATATTA TCGAAGATAC GGGTAATGCT   600
TATATCGTTC CTCATGGAGG TCACTATCAC TACATTCCCA AAAGCGATTT ATCTGCTAGT   660
GAATTAGCAG CAGCTAAAGC ACATCTGGCT GGAAAAAATA TGCAACCGAG TCAGTTAAGC   720
TATTCTTCAA CAGCTAGTGA CAATAACACG CAATCTGTAG CAAAAGGATC AACTAGCAAG   780
CCAGCAAATA AATCTGAAAA TCTCCAGAGT CTTTTGAAGG AACTCTATGA TTCACCTAGC   840
GCCCAACGTT ACAGTGAATC AGATGGCCTG GTCTTTGACC CTGCTAAGAT TATCAGTCGT   900
ACACCAAATG GAGTTGCGAT TCCGCATGGC GACCATTACC ACTTTATTCC TTACAGCAAG   960
CTTTCTGCTT TAGAAGAAAA GATTGCCAGA ATGGTGCCTA TCAGTGGAAC TGGTTCTACA  1020
GTTTCTACAA ATGCAAAACC TAATGAAGTA GTGTCTAGTC TAGGCAGTCT TTCAAGCAAT  1080
CCTTCTTCTT TAACGACAAG TAAGGAGCTC TCTTCAGCAT CTGATGGTTA TATTTTTAAT  1140
CCAAAAGATA TCGTTGAAGA AACGGCTACA GCTTATATTG TAAGACATGG TGATCATTTC  1200
CATTACATTC CAAAATCAAA TCAAATTGGG CAACCGACTC TTCCAAACAA TAGTCTAGCA  1260
ACACCTTCTC CATCTCTTCC AATCAATCCA GGAACTTCAC ATGAGAAACA TGAAGAAGAT  1320
GGATACGGAT TTGATGCTAA TCGTATTATC GCTGAAGATG AATCAGGTTT TGTCATGAGT  1380
CACGGAGACC ACAATCATTA TTTCTTCAAG AAGGACTTGA CAGAAGAGCA AATTAAGGCT  1440
GCGCAAAAAC ATTTAGAGGA AGTTAAAACT AGTCATAATG GATTAGATTC TTTGTCATCT  1500
CATGAACAGG ATTATCCAGG TAATGCCAAA GAAATGAAAG ATTTAGATAA AAAAATCGAA  1560
GAAAAAATTG CTGGCATTAT GAAACAATAT GGTGTCAAAC GTGAAAGTAT TGTCGTGAAT  1620
AAAGAAAAAA ATGCGATTAT TTATCCGCAT GGAGATCACC ATCATGCAGA TCCGATTGAT  1680
GAACATAAAC CGGTTGGAAT TGGTCATTCT CACAGTAACT ATGAACTGTT TAAACCCGAA  1740
GAAGGAGTTG CTAAAAAAGA AGGGAATAAA GTTTATACTG GAGAAGAATT AACGAATGTT  1800
GTTAATTTGT TAAAAAATAG TACGTTTAAT AATCAAAACT TTACTCTAGC CAATGGTCAA  1860
AAACGCGTTT CTTTTAGTTT TCCGCCTGAA TTGGAGAAAA AATTAGGTAT CAATATGCTA  1920
GTAAAATTAA TAACACCAGA TGGAAAAGTA TTGGAGAAAG TATCTGGTAA AGTATTTGGA  1980
GAAGGAGTAG GGAATATTGC AAACTTTGAA TTAGATCAAC CTTATTTACC AGGACAAACA  2040
TTTAAGTATA CTATCGCTTC AAAAGATTAT CCAGAAGTAA GTTATGATGG TACATTTACA  2100
GTTCCAACCT CTTTAGCTTA CAAAATGGCC AGTCAAACGA TTTTCTATCC TTTCCATGCA  2160
GGGGATACTT ATTTAAGAGT GAACCCTCAA TTTGCAGTGC CTAAAGGAAC TGATGCTTTA  2220
GTCAGAGTGT TTGATGAATT TCATGGAAAT GCTTATTTAG AAAATAACTA TAAAGTTGGT  2280
GAAATCAAAT TACCGATTCC GAAATTAAAC CAAGGAACAA CCAGAACGGC CGGAAATAAA  2340
ATTCCTGTAA CCTTCATGGC AAATGCTTAT TTGGACAATC AATCGACTTA TATTGTGGAA  2400
GTACCTATCT TGGAAAAAGA AAATCAAACT GATAAACCAA GTATTCTACC ACAATTTAAA  2460
AGGAATAAAG CACAAGAAAA CTCAAAACTT GATGAAAAGG TAGAAGAACC AAAGACTAGT  2520
GAGAAGGTAG AAAAAGAAAA ACTTTCTGAA ACTGGGAATA GTACTAGTAA TTCAACGTTA  2580
GAAGAAGTTC CTACAGTGGA TCCTGTACAA GAAAAAGTAG CAAAATTTGC TGAAAGTTAT  2640
GGGATGAAGC TAGAAAATGT CTTGTTTAAT ATGGACGGAA CAATTGAATT ATATTTACCA  2700
TCAGGAGAAG TCATTAAAAA GAATATGGCA GATTTTACAG GAGAAGCACC TCAAGGAAAT  2760
GGTGAAAAAT AACCATCTGA AAATGGAAAA GTATCTACTG GAACAGTTGA GAACCAACCA  2820
ACAGAAAATA AACCAGCAGA TTCTTTACCA GAGGCACCAA ACGAAAAACC TGTAAAACCA  2880
GAAAACTCAA CGGATAATGG AATGTTGAAT CCAGAAGGGA ATGTGGGGAG TGACCCTATG  2940
TTAGATCCAG CATTAGAGGA AGCTCCAGCA GTAGATCCTG TACAAGAAAA ATTAGAAAAA  3000
TTTACAGCTA GTTACGGATT AGGCTTAGAT AGTGTTATAT TCAATATGGA TGGAACGATT  3060
GAATTAAGAT TGCCAAGTGG AGAAGTGATA AAAAAGAATT TATCTGATTT CATAGCGTAA  3120
(SEQ ID NO: 1)
```

*FIG. 1*

```
MKFSKKYIAA  GSAVIVSLSL  CAYALNQHRS  QENKDNNRVS  YVDGSQSSQK        50
SENLTPDQVS  QKEGIQAEQI  VIKITDQGYV  TSHGDHYHYY  NGKVPYDALF       100
SEELLMKDPN  YQLKDADIVN  EVKGGYIIKV  DGKYYVYLKD  AAHADNVRTK       150
DEINRQKQEH  VKDNEKVNSN  VAVARSQGRY  TTNDGYVFNP  ADIIEDTGNA       200
YIVPHGGHYH  YIPKSDLSAS  ELAAAKAHLA  GKNMQPSQLS  YSSTASDNNT       250
QSVAKGSTSK  PANKSENLQS  LLKELYDSPS  AQRYSESDGL  VFDPAKIISR       300
TPNGVAIPHG  DHYHFIPYSK  LSALEEKIAR  MVPISGTGST  VSTNAKPNEV       350
VSSLGSLSSN  PSSLTTSKEL  SSASDGYIFN  PKDIVEETAT  AYIVRHGDHF       400
HYIPKSNQIG  QPTLPNNSLA  TPSPSLPINP  GTSHEKHEED  GYGFDANRII       450
AEDESGFVMS  HGDHNHYFFK  KDLTEEQIKA  AQKHLEEVKT  SHNGLDSLSS       500
HEQDYPGNAK  EMKDLDKKIE  EKIAGIMKQY  GVKRESIVVN  KEKNAIIYPH       550
GDHHHADPID  EHKPVGIGHS  HSNYELFKPE  EGVAKKEGNK  VYTGEELTNV       600
VNLLKNSTFN  NQNFTLANGQ  KRVSFSFPPE  LEKKLGINML  VKLITPDGKV       650
LEKVSGKVFG  EGVGNIANFE  LDQPYLPGQT  FKYTIASKDY  PEVSYDGTFT       700
VPTSLAYKMA  SQTIFYPFHA  GDTYLRVNPQ  FAVPKGTDAL  VRVFDEFHGN       750
AYLENNYKVG  EIKLPIPKLN  QGTTRTAGNK  IPVTFMANAY  LDNQSTYIVE       800
VPILEKENQT  DKPSILPQFK  RNKAQENSKL  DEKVEEPKTS  EKVEKEKLSE       850
TGNSTSNSTL  EEVPTVDPVQ  EKVAKFAESY  GMKLENVLFN  MDGTIELYLP       900
SGEVIKKNMA  DFTGEAPQGN  GENKPSENGK  VSTGTVENQP  TENKPADSLP       950
EAPNEKPVKP  ENSTDNGMLN  PEGNVGSDPM  LDPALEEAPA  VDPVQEKLEK      1000
FTASYGLGLD  SVIFNMDGTI  ELRLPSGEVI  KKNLSDFIA   (SEQ ID NO: 2)  1039
```

*FIG. 2*

| | | | | | | |
|---|---|---|---|---|---|---|
|ATGAAAATCA|ATAAAAAATA|TCTAGCTGGG|TCAGTAGCTA|CACTTGTTTT|AAGTGTCTGT|60|
|GCTTATGAAC|TAGGTTTGCA|TCAAGCTCAA|ACTGTAAAAG|AAAATAATCG|TGTTTCCTAT|120|
|ATAGATGGAA|AACAAGCGAC|GCAAAAAACG|GAGAATTTGA|CTCCTGATGA|GGTTAGCAAG|180|
|CGTGAAGGAA|TCAACGCCGA|ACAAATCGTC|ATCAAGATTA|CGGATCAAGG|TTATGTGACC|240|
|TCTCATGGAG|ACCATTATCA|TTACTATAAT|GGCAAGGTCC|CTTATGATGC|CATCATCAGT|300|
|GAAGAGCTCC|TCATGAAAGA|TCCGAATTAT|CAGTTGAAGG|ATTCAGACAT|TGTCAATGAA|360|
|ATCAAGGGTG|GTTATGTCAT|TAAGGTAAAC|GGTAAATACT|ATGTTTACCT|TAAGGATGCA|420|
|GCTCATGCGG|ATAATGTCCG|TACAAAAGAA|GAAATCAATC|GGCAAAAACA|GAACATAGT|480|
|CAGCATCGTG|AAGGAGGGAC|TTCAGCAAAC|GATGGTGCGG|TAGCCTTTGC|ACGTTCACAG|540|
|GGACGCTACA|CCACAGATGA|TGGTTATATC|TTCAATGCAT|CTGATATCAT|CGAAGATACG|600|
|GGCGATGCCT|ATATCGTTCC|TCATGGAGAT|CATTACCATT|ACATTCCTAA|GAATGAGTTA|660|
|TCAGCTAGCG|AGTTGGCTGC|TGCAGAAGCC|TTCCTATCTG|GTCGGGAAAA|TCTGTCAAAT|720|
|TTAAGAACCT|ATCGCCGACA|AAATAGCGAT|AACACTCCAA|GAACAAACTG|GGTACCTTCT|780|
|GTAAGCAATC|CAGGAACTAC|AAATACTAAC|ACAAGCAACA|ACAGCAACAC|TAACAGTCAA|840|
|GCAAGTCAAA|GTAATGACAT|TGATAGTCTC|TTGAAACAGC|TCTACAAACT|GCCTTTGAGT|900|
|CAACGCCATG|TAGAATCTGA|TGGCCTTATT|TTCGACCCAG|CGCAAATCAC|AAGTCGAACC|960|
|GCCAGAGGTG|TAGCTGTCCC|TCATGGTAAC|CATTACCACT|TTATCCCTTA|TGAACAAATG|1020|
|TCTGAATTGG|AAAAACGAAT|TGCTCGTATT|ATTCCCCTTC|GTTATCGTTC|AAACCATTGG|1080|
|GTACCAGATT|CAAGACCAGA|AGAACCAAGT|CCACAACCGA|CTCCAGAACC|TAGTCCAAGT|1140|
|CCGCAACCTG|CACCAAATCC|TCAACCAGCT|CCAAGCAATC|CAATTGATGA|GAAATTGGTC|1200|
|AAAGAAGCTG|TTCGAAAAGT|AGGCGATGGT|TATGTCTTTG|AGGAGAATGG|AGTTTCTCGT|1260|
|TATATCCCAG|CCAAGAATCT|TTCAGCAGAA|ACAGCAGCAG|GCATTGATAG|CAAACTGGCC|1320|
|AAGCAGGAAA|GTTTATCTCA|TAAGCTAGGA|GCTAAGAAAA|CTGACCTCCC|ATCTAGTGAT|1380|
|CGAGAATTTT|ACAATAAGGC|TTATGACTTA|CTAGCAAGAA|TTCACCAAGA|TTTACTTGAT|1440|
|AATAAAGGTC|GACAAGTTGA|TTTTGAGGCT|TTGGATAACC|TGTTGGAACG|ACTCAAGGAT|1500|
|GTCTCAAGTG|ATAAAGTCAA|GTTAGTGGAT|GATATTCTTG|CCTTCTTAGC|TCCGATTCGT|1560|
|CATCCAGAAC|GTTTAGGAAA|ACCAAATGCG|CAAATTACCT|ACACTGATGA|TGAGATTCAA|1620|
|GTAGCCAAGT|TGGCAGGCAA|GTACACAACA|GAAGACGGTT|ATATCTTTGA|TCCTCGTGAT|1680|
|ATAACCAGTG|ATGAGGGGA|TGCCTATGTA|ACTCCACATA|TGACCCATAG|CCACTGGATT|1740|
|AAAAAAGATA|GTTTGTCTGA|AGCTGAGAGA|GCGGCAGCCC|AGGCTTATGC|TAAAGAGAAA|1800|
|GGTTTGACCC|CTCCTTCGAC|AGACCATCAG|GATTCAGGAA|ATACTGAGGC|AAAAGGAGCA|1860|
|GAAGCTATCT|ACAACCGCGT|GAAAGCAGCT|AAGAAGGTGC|CACTTGATCG|TATGCCTTAC|1920|
|AATCTTCAAT|ATACTGTAGA|AGTCAAAAAC|GGTAGTTTAA|TCATACCTCA|TTATGACCAT|1980|
|TACCATAACA|TCAAATTTGA|GTGGTTTGAC|GAAGGCCTTT|ATGAGGCACC|TAAGGGGTAT|2040|
|ACTCTTGAGG|ATCTTTTGGC|GACTGTCAAG|TACTATGTCG|AACATCCAAA|CGAACGTCCG|2100|
|CATTCAGATA|ATGGTTTTGG|TAACGCTAGC|GACCATGTTC|AAAGAAACAA|AAATGGTCAA|2160|
|GCTGATACCA|ATCAAACGGA|AAAACCAAGC|GAGGAGAAAC|CTCAGACAGA|AAAACCTGAG|2220|
|GAAGAAACCC|CTCGAGAAGA|GAAACCACAA|AGCGAGAAAC|CAGAGTCTCC|AAAACCAACA|2280|
|GAGGAACCAG|AAGAAGAATC|ACCAGAGGAA|TCAGAAGAAC|CTCAGGTCGA|GACTGAAAAG|2340|
|GTTGAAGAAA|AACTGAGAGA|GGCTGAAGAT|TTACTTGGAA|AAATCCAGGA|TCCAATTATC|2400|
|AAGTCCAATG|CCAAAGAGAC|TCTCACAGGA|TTAAAAAATA|ATTTACTATT|TGGCACCCAG|2460|
|GACAACAATA|CTATTATGGC|AGAAGCTGAA|AAACTATTGG|CTTTATTAAA|GGAGAGTAAG|2520|
|TAA|(SEQ ID NO: 3)| | | | |2523|

*FIG. 3*

| | | | | | |
|---|---|---|---|---|---|
|MKINKKYLAG|SVATLVLSVC|AYELGLHQAQ|TVKENNRVSY|IDGKQATQKT|50|
|ENLTPDEVSK|REGINAEQIV|IKITDQGYVT|SHGDHYHYYN|GKVPYDAIIS|100|
|EELLMKDPNY|QLKDSDIVNE|IKGGYVIKVN|GKYYVYLKDA|AHADNVRTKE|150|
|EINRQKQEHS|QHREGGTSAN|DGAVAFARSQ|GRYTTDDGYI|FNASDIIEDT|200|
|GDAYIVPHGD|HYHYIPKNEL|SASELAAAEA|FLSGRENLSN|LRTYRRQNSD|250|
|NTPRTNWVPS|VSNPGTTNTN|TSNNSNTNSQ|ASQSNDIDSL|LKQLYKLPLS|300|
|QRHVESDGLI|FDPAQITSRT|ARGVAVPHGN|HYHFIPYEQM|SELEKRIARI|350|
|IPLRYRSNHW|VPDSRPEEPS|PQPTPEPSPS|PQPAPNPQPA|PSNPIDEKLV|400|
|KEAVRKVGDG|YVFEENGVSR|YIPAKNLSAE|TAAGIDSKLA|KQESLSHKLG|450|
|AKKTDLPSSD|REFYNKAYDL|LARIHQDLLD|NKGRQVDFEA|LDNLLERLKD|500|
|VSSDKVKLVD|DILAFLAPIR|HPERLGKPNA|QITYTDDEIQ|VAKLAGKYTT|550|
|EDGYIFDPRD|ITSDEGDAYV|TPHMTHSHWI|KKDSLSEAER|AAAQAYAKEK|600|
|GLTPPSTDHQ|DSGNTEAKGA|EAIYNRVKAA|KKVPLDRMPY|NLQYTVEVKN|650|
|GSLIIPHYDH|YHNIKFEWFD|EGLYEAPKGY|TLEDLLATVK|YVVEHPNERP|700|
|HSDNGFGNAS|DHVQRNKNGQ|ADTNQTEKPS|EEKPQTEKPE|EETPREEKPQ|750|
|SEKPESPKPT|EEPEEESPEE|SEEPQVETEK|VEEKLREAED|LLGKIQDPII|800|
|KSNAKETLTG|LKNNLLFGTQ|DNNTIMAEAE|KLLALLKESK|(SEQ ID NO: 4)|840|

FIG. 4

| | | | | | |
|---|---|---|---|---|---|
|ATGGAGAATA|TAGACATGTT|TAAATCAAAT|CATGAGCGAA|GAATGCGTTA|TTCCATTCGT|60|
|AAATTTAGTG|TAGGAGTAGC|TAGCGTAGCT|GTTGCCAGTC|TTTTTATGGG|AAGTGTTGTA|120|
|CATGCGACAG|AGAAAGAGGG|AAGTACCCAA|GCAGCCACTT|CTTTTAATAG|GGGAAATGGA|180|
|AGTCAGGCAG|AACAACGTGG|AGAACTCGAT|TTAGAACGAG|ATAAGGCAAT|GAAAGCGGTC|240|
|AGTGAATATG|TAGGAAAAAT|GGTGAGAGAT|GCCTATGTAA|AATCAGATAG|AAAACGACAT|300|
|AAAAATACTG|TAGCTCTAGT|TAACCAGTTG|GGAAACATTA|GAACAGGTA|TTTGAATGAA|360|
|ATAGTTCATT|CAACCTCAAA|AAGCCAACTA|CAGGAACTGA|TGATGAAGAG|TCAATCAGAA|420|
|GTAGATGAAG|CTGTGTCTAA|ATTTGAAAAG|GACTCATTTT|CTTCGTCAAG|TTCAGGATCC|480|
|TCCACTAAAC|CAGAAACTCC|GCAGCCGGAA|AATCCAGAGC|ATCAAAAACC|AACAACTCCA|540|
|TCTCCGGATA|CCAAACCAAG|CCCTCAACCA|GAAGGCAAGA|AACCAAGCGT|ACCAGACATT|600|
|AATCAGGAAA|AGAAAAAGC|TAAGCTTGCT|GTAGTAACCT|ACATGAGCAA|GATTTTAGAT|660|
|GATATACAAA|AACATCATCT|GCAGAAAGAA|AAACATCGTC|AGATTGTTGC|TCTTATTAAG|720|
|GAGCTTGATG|AGCTTAAAAA|GCAAGCTCTT|TCTGAAATTG|ATAATGTAAA|TACCAAAGTA|780|
|GAAATTGAAA|ATACAGTCCA|AAGATATTT|GCAGACATGG|ATGCAGTTGT|GACTAAATTC|840|
|AAAAAAGGCT|TAACTCAGGA|CACACCAAAA|GAACCAGGTA|ACAAAAAACC|ATCTGCTCCA|900|
|AAACCAGGTA|TGCAACCAAG|TCCTCAACCA|GAGGTTAAAC|CGCAGCTGGA|AAAACCAAAA|960|
|CCAGAGGTTA|AACCGCAACC|AGAAAAACCA|AAACCAGAGG|TTAAACCGCA|GCCGGAAAAA|1020|
|CCAAAACCAG|AGGTTAAACC|GCAGCCGGAA|AAACCAAAAC|CAGAGGTTAA|ACCGCAGCCG|1080|
|GAAAAACCAA|AACCAGAGGT|TAAACCGCAG|CCGGAAAAAC|CAAAACCAGA|GGTTAAACCG|1140|
|CAGCCGGAAA|AACCAAAACC|AGAGGTTAAA|CCGCAGCCGG|AAAAACCAAA|ACCAGAGGTT|1200|
|AAACCGCAGC|CGGAAAAACC|AAAACCAGAG|GTTAAACCGC|AGCCGGAAAA|ACCAAAACCA|1260|
|GAGGTTAAAC|CGCAGCCGGA|AAAACCAAAA|CCAGAGGTTA|AACCGCAACC|AGAAAAACCA|1320|
|AAACCAGAGG|TTAAACCGCA|ACCAGAAAAA|CCAAAACCAG|ATAATAGCAA|GCCACAAGCA|1380|
|GATGATAAGA|AGCCATCAAC|TACAAATAAT|TTAAGCAAGG|ACAAGCAACC|TTCTAACCAA|1440|
|GCTTCAACAA|ACGAAAAAGC|AACAAATAAA|CCGAAGAAGT|CATTGCCATC|AACTGGATCT|1500|
|ATTTCAAATC|TAGCACTTGA|AATTGCAGGT|CTTCTTACCT|TGGCGGGGGC|AACCATTCTT|1560|
|GCTAAGAAAA|GAATGAAATA|G|(SEQ ID NO: 5)| |1581|

FIG. 5

```
MENIDMFKSN HERRMRYSIR KFSVGVASVA VASLFMGSVV HATEKEGSTQ      50
AATSFNRGNG SQAEQRGELD LERDKAMKAV SEYVGKMVRD AYVKSDRKRH     100
KNTVALVNQL GNIKNRYLNE IVHSTSKSQL QELMMKSQSE VDEAVSKFEK     150
DSFSSSSSGS STKPETPQPE NPEHQKPTTP SPDTKPSPQP EGKKPSVPDI     200
NQEKEKAKLA VVTYMSKILD DIQKHHLQKE KHRQIVALIK ELDELKKQAL     250
SEIDNVNTKV EIENTVHKIF ADMDAVVTKF KKGLTQDTPK EPGNKKPSAP     300
KPGMQPSPQP EVKPQLEKPK PEVKPQPEKP KPEVKPQPEK PKPEVKPQPE     350
KPKPEVKPQP EKPKPEVKPQ PEKPKPEVKP QPEKPKPEVK PQPEKPKPEV     400
KPQPEKPKPE VKPQPEKPKP EVKPQPEKPK PEVKPQPEKP KPEVKPQPEK     450
PKPDNSKPQA DDKKPSTTNN LSKDKQPSNQ ASTNEKATNK PKKSLPSTGS     500
ISNLALEIAG LLTLAGATIL AKKRMK       (SEQ ID NO: 6)          526
```

FIG. 6

```
ATGAAATTTA GTAAAAAATA TATAGCAGCT GGATCAGCTG TTATCGTATC CTTGAGTCTA      60
TGTGCCTATG CACTAAACCA GCATCGTTCG CAGGAAAATA AGGACAATAA TCGTGTCTCT     120
TATGTGGATG GCAGCCAGTC AAGTCAGAAA AGTGAAAACT TGACACCAGA CCAGGTTAGC     180
CAGAAAGAAG GAATTCAGGC TGAGCAAATT GTAATCAAAA TTACAGATCA GGGCTATGTA     240
ACGTCACACG GTGACCACTA TCATTACTAT AATGGGAAAG TTCCTTATGA TGCCCTCTTT     300
AGTGAAGAAC TCTTGATGAA GGATCCAAAC TATCAACTTA AAGACGCTGA TATTGTCAAT     360
GAAGTCAAGG GTGGTTATAT CATCAAGGTC GATGGAAAAT ATTATGTCTA CCTGAAAGAT     420
GCAGCTCATG CTGATAATGT TCGAACTAAA GATGAAATCA ATCGTCAAAA ACAAGAACAT     480
GTCAAAGATA ATGAGAAGGT TAACTCTAAT GTTGCTGTAG CAAGGTCTCA GGGACGATAT     540
ACGACAAATG ATGGTTATGT CTTTAATCCA GCTGATATTA TCGAAGATAC GGGTAATGCT     600
TATATCGTTC CTCATGGAGG TCACTATCAC TACATTCCCA AAAGCGATTT ATCTGCTAGT     660
GAATTAGCAG CAGCTAAAGC ACATCTGGCT GGAAAAAATA TGCAACCGAG TCAGTTAAGC     720
TATTCTTCAA CAGCTAGTGA CAATAACACG CAATCTGTAG CAAAAGGATC AACTAGCAAG     780
CCAGCAAATA AATCTGAAAA TCTCCAGAGT CTTTTGAAGG AACTCTATGA TTCACCTAGC     840
GCCCAACGTT ACAGTGAATC AGATGGCCTG GTCTTTGACC CTGCTAAGAT TATCAGTCGT     900
ACACCAAATG GAGTTGCGAT TCCGCATGGC GACCATTACC ACTTTATTCC TTACAGCAAG     960
CTTTCTGCTT TAGAAGAAAA GATTGCCAGA ATGGTGCCTA TCAGTGGAAC TGGTTCTACA    1020
GTTTCTACAA ATGCAAAACC TAATGAAGTA GTGTCTAGTC TAGGCAGTCT TTCAAGCAAT    1080
CCTTCTTCTT TAACGACAAG TAAGGAGCTC TCTTCAGCAT CTGATGGTTA TATTTTTAAT    1140
CCAAAAGATA TCGTTGAAGA AACGGCTACA GCTTATATTG TAAGACATGG TGATCATTTC    1200
CATTACATTC CAAAATCAAA TCAAATTGGG CAACCGACTC TTCCAAACAA TAGTCTAGCA    1260
ACACCTTCTC CATCTCTTCC AATCAATCCA GGAACTTCAC ATGAGAAACA TGAAGAAGAT    1320
GGATACGGAT TTGATGCTAA TCGTATTATC GCTGAAGATG AATCAGGTTT TGTCATGAGT    1380
CACGGAGACC ACAATCATTA TTTCTTCAAG AAGGACTTGA CAGAAGAGCA AATTAAGGTG    1440
CGCAAAAACA TTTAG    (SEQ ID NO: 7)                                   1455
```

FIG. 7

| | | | | | |
|---|---|---|---|---|---|
| MKFSKKYIAA | GSAVIVSLSL | CAYALNQHRS | QENKDNNRVS | YVDGSQSSQK | 50 |
| SENLTPDQVS | QKEGIQAEQI | VIKITDQGYV | TSHGDHYHYY | NGKVPYDALF | 100 |
| SEELLMKDPN | YQLKDADIVN | EVKGGYIIKV | DGKYYVYLKD | AAHADNVRTK | 150 |
| DEINRQKQEH | VKDNEKVNSN | VAVARSQGRY | TTNDGYVFNP | ADIIEDTGNA | 200 |
| YIVPHGGHYH | YIPKSDLSAS | ELAAAKAHLA | GKNMQPSQLS | YSSTASDNNT | 250 |
| QSVAKGSTSK | PANKSENLQS | LLKELYDSPS | AQRYSESDGL | VFDPAKIISR | 300 |
| TPNGVAIPHG | DHYHFIPYSK | LSALEEKIAR | MVPISGTGST | VSTNAKPNEV | 350 |
| VSSLGSLSSN | PSSLTTSKEL | SSASDGYIFN | PKDIVEETAT | AYIVRHGDHF | 400 |
| HYIPKSNQIG | QPTLPNNSLA | TPSPSLPINP | GTSHEKHEED | GYGFDANRII | 450 |
| AEDESGFVMS | HGDHNHYFFK | KDLTEEQIKV | RKNI | (SEQ ID NO: 8) | 484 |

*FIG. 8*

| | | | | | |
|---|---|---|---|---|---|
| ATGAAAGATT | TAGATAAAAA | AATCGAAGAA | AAAATTGCTG | GCATTATGAA | ACAATATGGT | 60 |
| GTCAAACGTG | AAAGTATTGT | CGTGAATAAA | GAAAAAAATG | CGATTATTTA | TCCGCATGGA | 120 |
| GATCACCATC | ATGCAGATCC | GATTGATGAA | CATAAACCGG | TTGGAATTGG | TCATTCTCAC | 180 |
| AGTAACTATG | AACTGTTTAA | ACCCGAAGAA | GGAGTTGCTA | AAAAAGAAGG | GAATAAAGTT | 240 |
| TATACTGGAG | AAGAATTAAC | GAATGTTGTT | AATTTGTTAA | AAAATAGTAC | GTTTAATAAT | 300 |
| CAAAACTTTA | CTCTAGCCAA | TGGTCAAAAA | CGCGTTTCTT | TTAGTTTTCC | GCCTGAATTG | 360 |
| GAGAAAAAAT | TAGGTATCAA | TATGCTAGTA | AAATTAATAA | CACCAGATGG | AAAAGTATTG | 420 |
| GAGAAAGTAT | CTGGTAAAGT | ATTTGGAGAA | GGAGTAGGGA | ATATTGCAAA | CTTTGAATTA | 480 |
| GATCAACCTT | ATTTACCAGG | ACAAACATTT | AAGTATACTA | TCGCTTCAAA | AGATTATCCA | 540 |
| GAAGTAAGTT | ATGATGGTAC | ATTTACAGTT | CCAACCTCTT | TAGCTTACAA | AATGGCCAGT | 600 |
| CAAACGATTT | TCTATCCTTT | CCATGCAGGG | GATACTTATT | TAAGAGTGAA | CCCTCAATTT | 660 |
| GCAGTGCCTA | AAGGAACTGA | TGCTTTAGTC | AGAGTGTTTG | ATGAATTTCA | TGGAAATGCT | 720 |
| TATTTAGAAA | ATAACTATAA | AGTTGGTGAA | ATCAAATTAC | CGATTCCGAA | ATTAAACCAA | 780 |
| GGAACAACCA | GAACGGCCGG | AAATAAAATT | CCTGTAACCT | TCATGGCAAA | TGCTTATTTG | 840 |
| GACAATCAAT | CGACTTATAT | TGTGGAAGTA | CCTATCTTGG | AAAAAGAAAA | TCAAACTGAT | 900 |
| AAACCAAGTA | TTCTACCACA | ATTTAAAAGG | AATAAAGCAC | AAGAAAACTC | AAAACTTGAT | 960 |
| GAAAAGGTAG | AAGAACCAAA | GACTAGTGAG | AAGGTAGAAA | AAGAAAAACT | TTCTGAAACT | 1020 |
| GGGAATAGTA | CTAGTAATTC | AACGTTAGAA | GAAGTTCCTA | CAGTGGATCC | TGTACAAGAA | 1080 |
| AAAGTAGCAA | AATTTGCTGA | AAGTTATGGG | ATGAAGCTAG | AAAATGTCTT | GTTTAATATG | 1140 |
| GACGGAACAA | TTGAATTATA | TTTACCATCA | GGAGAAGTCA | TTAAAAAGAA | TATGGCAGAT | 1200 |
| TTTACAGGAG | AAGCACCTCA | AGGAAATGGT | GAAATAAAC | CATCTGAAAA | TGGAAAAGTA | 1260 |
| TCTACTGGAA | CAGTTGAGAA | CCAACCAACA | GAAAATAAAC | CAGCAGATTC | TTTACCAGAG | 1320 |
| GCACCAAACG | AAAAACCTGT | AAAACCAGAA | AACTCAACGG | ATAATGGAAT | GTTGAATCCA | 1380 |
| GAAGGGAATG | TGGGGAGTGA | CCCTATGTTA | GATCCAGCAT | TAGAGGAAGC | TCCAGCAGTA | 1440 |
| GATCCTGTAC | AAGAAAAATT | AGAAAAATTT | ACAGCTAGTT | ACGGATTAGG | CTTAGATAGT | 1500 |
| GTTATATTCA | ATATGGATGG | AACGATTGAA | TTAAGATTGC | CAAGTGGAGA | AGTGATAAAA | 1560 |
| AAGAATTTAT | CTGATTTCAT | AGCGTAA | (SEQ ID NO: 9) | | | 1587 |

*FIG. 9*

```
MKDLDKKIEE KIAGIMKQYG VKRESIVVNK EKNAIIYPHG DHHHADPIDE      50
HKPVGIGHSH SNYELFKPEE GVAKKEGNKV YTGEELTNVV NLLKNSTFNN     100
QNFTLANGQK RVSFSFPPEL EKKLGINMLV KLITPDGKVL EKVSGKVFGE     150
GVGNIANFEL DQPYLPGQTF KYTIASKDYP EVSYDGTFTV PTSLAYKMAS     200
QTIFYPFHAG DTYLRVNPQF AVPKGTDALV RVFDEFHGNA YLENNYKVGE     250
IKLPIPKLNQ GTTRTAGNKI PVTFMANAYL DNQSTYIVEV PILEKENQTD     300
KPSILPQFKR NKAQENSKLD EKVEEPKTSE KVEKEKLSET GNSTSNSTLE     350
EVPTVDPVQE KVAKFAESYG MKLENVLFNM DGTIELYLPS GEVIKKNMAD     400
FTGEAPQGNG ENKPSENGKV STGTVENQPT ENKPADSLPE APNEKPVKPE     450
NSTDNGMLNP EGNVGSDPML DPALEEAPAV DPVQEKLEKF TASYGLGLDS     500
VIFNMDGTIE LRLPSGEVIK KNLSDFIA  (SEQ ID NO: 10)            528
```

*FIG. 10*

```
BVH3 WU2      1   CAYALNQHRSQENKDNNRVSYVDGSQSSQKSENLTPDQVSQKEGIQAEQIVIKITDQGYV   60
BVH3 RX1      1   CAYALNQHRSQENKDNNRVSYVDGSQSSQKSENLTPDQVSQKEGIQAEQIVIKITDQGYV   60
BVH3 JNR7/87  1   CAYALNQHRSQENKDNNRVSYVDGSQSSQKSENLTPDQVSQKEGIQAEQIVIKITDQGYV   60
BVH3 SP64     1   CAYALNQHRSQENKDNNRVSYVDGSQSSQKSENLTPDQVSQKEGIQAEQIVIKITDQGYV   60
BVH3 P4241    1   CAYALNQHRSQENKDNNRVSYVDGSQSSQKSENLTPDQVSQKEGIQAEQIVIKITDQGYV   60
BVH3 A66      1   CAYALNQHRSQENKDNNRVSYVDGSQSSQKSENLTPDQVSQKEGIQAEQIVIKITDQGYV   60
                  ************************************************************

BVH3 WU2      61  TSHGDHYHYYNGKVPYDALFSEELLMKDPNYQLKDADIVNEVKGGYIIKVDGKYYVYLKD   120
BVH3 RX1      61  TSHGDHYHYYNGKVPYDALFSEELLMKDPNYQLKDADIVNEVKGGYIIKVDGKYYVYLKD   120
BVH3 JNR7/87  61  TSHGDHYHYYNGKVPYDALFSEELLMKDPNYQLKDADIVNEVKGGYIIKVDGKYYVYLKD   120
BVH3 SP64     61  TSHGDHYHYYNGKVPYDALFSEELLMKDPNYQLKDADIVNEVKGGYIIKVDGKYYVYLKD   120
BVH3 P4241    61  TSHGDHYHYYNGKVPYDALFSEELLMKDPNYQLKDADIVNEVKGGYIIKVDGKYYVYLKD   120
BVH3 A66      61  TSHGDHYHYYNGKVPYDALFSEELLMKDPNYQLKDADIVNEVKGGYIIKVDGKYYVYLKD   120
                  ************************************************************

BVH3 WU2      121 AAHADNVRTKDEINRQKQEHVKDNEKVNSNVAVARSQGRYTTNDGYVFNPADIIEDTGNA   180
BVH3 RX1      121 AAHADNVRTKDEINRQKQEHVKDNEKVNSNVAVARSQGRYTTNDGYVFNPADIIEDTGNA   180
BVH3 JNR7/87  121 AAHADNVRTKDEINRQKQEHVKDNEKVNSNVAVARSQGRYTTNDGYVFNPADIIEDTGNA   180
BVH3 SP64     121 AAHADNVRTKDEINRQKQEHVKDNEKVNSNVAVARSQGRYTTNDGYVFNPADIIEDTGNA   180
BVH3 P4241    121 AAHADNVRTKDEINRQKQEHVKDNEKVNSNVAVARSQGRYTTNDGYVFNPADIIEDTGNA   180
BVH3 A66      121 AAHADNVRTKDEINRQKQEHVKDNEKVNSNVAVARSQGRYTTNDGYVFNPADIIEDTGNA   180
                  ************************************************************

BVH3 WU2      181 YIVPHRGHYHYIPKSDLSASELAAAKAHLAGKNMQPSQLSYSSTASDNNTQSVAKGSTSK   240
BVH3 RX1      181 YIVPHGGHYHYIPKSDLSASELAAAKAHLAGKNMQPSQLSYSSTASDNNTQSVAKGSTSK   240
BVH3 JNR7/87  181 YIVPHGGHYHYIPKSDLSASELAAAKAHLAGKNMQPSQLSYSSTASDNNTQSVAKGSTSK   240
BVH3 SP64     181 YIVPHGGHYHYIPKSDLSASELAAAKAHLAGKNMQPSQLSYSSTASDNNTQSVAKGSTSK   240
BVH3 P4241    181 YIVPHRGHYHYIPKSDLSASELAAAKAHLAGKNMQPSQLSYSSTASDNNTQSVAKGSTSK   240
BVH3 A66      181 YIVPHRGHYHYIPKSDLSASELAAAKAHLAGKNMQPSQLSYSSTASDNNTQSVAKGSTSK   240
                  ***** ******************************************************

BVH3 WU2      241 PANKSENLQSLLKELYDSPSAQRYSESDGLVFDPAKIISRTPNGVAIPHGDHYHFIPYSK   300
BVH3 RX1      241 PANKSENLQSLLKELYDSPSAQRYSESDGLVFDPAKIISRTPNGVAIPHGDHYHFIPYSK   300
BVH3 JNR7/87  241 PANKSENLQSLLKELYDSPSAQRYSESDGLVFDPAKIISRTPNGVAIPHGDHYHFIPYSK   300
BVH3 SP64     241 PANKSENLQSLLKELYDSPSAQRYSESDGLVFDPAKIISRTPNGVAIPHGDHYHFIPYSK   300
BVH3 P4241    241 PANKSENLQSLLKELYDSPSAQRYSESDGLVFDPAKIISRTPNGVAIPHGDHYHFIPYSK   300
BVH3 A66      241 PANKSENLQSLLKELYDSPSAQRYSESDGLVFDPAKIISRTPNGVAIPHGDHYHFIPYSK   300
                  ************************************************************

BVH3 WU2      301 LSALEEKIARMVPISGTGSTVSTNAKPNEVVSSLGSLSSNPSSLTTSKELSSASDGYIFN   360
BVH3 RX1      301 LSALEEKIARRVPISGTGSTVSTNAKPNEVVSSLGSLSSNPSSLTTSKELSSASDGYIFN   360
BVH3 JNR7/87  301 LSALEEKIARMVPISGTGSTVSTNAKPNEVVSSLGSLSSNPSSLTTSKELSSASDGYIFN   360
BVH3 SP64     301 LSALEEKIARMVPISGTGSTVSTNAKPNEVVSSLGSLSSNPSSLTTSKELSSASDGYIFN   360
BVH3 P4241    301 LSALEEKIARMVPISGTGSTVSTNAKPNEVVSSLGSLSSNPSSLTTSKELSSASDGYIFN   360
BVH3 A66      301 LSALEEKIARMVPISGTGSTVSTNAKPNEVVSSLGSLSSNPSSLTTSKELSSASDGYIFN   360
                  ********** *************************************************

BVH3 WU2      361 PKDIVEETATAYIVRHGDHFHYIPKSNQIGQPTLPNNSLATPSPSLPINPGTSHEKHEED   420
BVH3 RX1      361 PKDIVEETATAYIVRHGDHFHYIPKSNQIGQPTLPNNSLATPSPSLPINPGISHEKHEED   420
BVH3 JNR7/87  361 PKDIVEETATAYIVRHGDHFHYIPKSNQIGQPTLPNNSLATPSPSLPINPGTSHEKHEED   420
BVH3 SP64     361 PKDIVEETATAYIVRHGDHFHYIPKSNQIGQPTLPNNSLATPSPSLPINPGTSHEKHEED   420
BVH3 P4241    361 PKDIVEETATAYIVRHGDHFHYIPKSNQIGQPTLPNNSLATPSPSLPINPGTSHEKHEED   420
BVH3 A66      361 PKDIVEETATAYIVRHGDHFHYIPKSNQIGQPTLPNNSLATPSPSLPINPGTSHEKHEED   420
                  ************************************************* **********

BVH3 WU2      421 GYGFDANRIIAEDESGFVMSHGDHNHYFFKKDLTEEQIKAAQKHLEEVKTSHNGLDSLSS   480
BVH3 RX1      421 GYGFDANRIIAEDESGFIMSHGNHNHYFFKKDLTEEQIKAAQKHLEEVKTSHNGLDSLSS   480
BVH3 JNR7/87  421 GYGFDANRIIAEDESGFVMSHGDHNHYFFKKDLTEEQIKAAQKHLEEVKTSHNGLDSLSS   480
BVH3 SP64     421 GYGFDANRIIAEDESGFVMSHGDHNHYFFKKDLTEEQIKAAQKHLEEVKTSHNGLDSLSS   480
BVH3 P4241    421 GYGFDANRIIAEDESGFVMSHGDHNHYFFKKDLTEEQIKAAQKHLEEVKTSHNGLDSLSS   480
BVH3 A66      421 GYGFDANRIIAEDESGFVMSHGDHNHYFFKKDLTEEQIKAAQKHLEEVKTSHNGLDSLSS   480
                  ***************** **** *************************************
```

*FIG. 11A*

```
BVH3 WU2      481 HEQDYPSNAKEMKDLDKKIEEKIAGIMKQYGVKRESIVVNKEKNAIIYPHGDHHHADPID 540
BVH3 RX1      481 HEQDYPGNAKEMKDLDKKIEEKIAGIMKQYGVKRESIVVNKEKNAIIYPHGDHHHADPID 540
BVH3 JNR7/87  481 HEQDYPSNAKEMKDLDKKIEEKIAGIMKQYGVKRESIVVNKEKNAIIYPHGDHHHADPID 540
BVH3 SP64     481 HEQDYPGNAKEMKDLDKKIEEKIAGIMKQYGVKRESIVVNKEKNAIIYPHGDHHHADPID 540
BVH3 P4241    481 HEQDYPSNAKEMKDLDKKIEEKIAGIMKQYGVKRESIVVNKEKNAIIYPHGDHHHADPID 540
BVH3 A66      481 HEQDYPSNAKEMKDLDKKIEEKIAGIMKQYGVKRESIVVNKEKNAIIYPHGDHHHADPID 540
                  ****** *****************************************************

BVH3 WU2      541 EHKPVGIGHSHSNYELFKPEEGVAKKEGNKVYTGEELTNVVNLLKNSTFNNQNFTLANGQ 600
BVH3 RX1      541 EHKPVGIGHSHSNYELFKPEEGVAKKEGNKVYTGEELTNVVNLLKNSTFNNQNFTLANGQ 600
BVH3 JNR7/87  541 EHKPVGIGHSHSNYELFKPEEGVAKKEGNKVYTGEELTNVVNLLKNSTFNNQNFTLANGQ 600
BVH3 SP64     541 EHKPVGIGHSHSNYELFKPEEGVAKKEGNKVYTGEELTNVVNLLKNSTFNNQNFTLANGQ 600
BVH3 P4241    541 EHKPVGIGHSHSNYELFKPEEGVAKKEGNKVYTGEELTNVVNLLKNSTFNNQNFTLANGQ 600
BVH3 A66      541 EHKPVGIGHSHSNYELFKPEEGVAKKEGNKVYTGEELTNVVNLLKNSTFNNQNFTLANGQ 600
                  ************************************************************

BVH3 WU2      601 KRVSFSFPPELEKKLGINMLVKLITPDGKVLEKVSGKVFGEGVGNIANFELDQPYLPGQT 660
BVH3 RX1      601 KRVSFSFPPELEKKLGINMLVKLITPDGKVLEKVSGKVFGEGVGNIANFELDQPYLPGQT 660
BVH3 JNR7/87  601 KRVSFSFPPELEKKLGINMLVKLITPDGKVLEKVSGKVFGEGVGNIANFELDQPYLPGQT 660
BVH3 SP64     601 KRVSFSFPPELEKKLGINMLVKLITPDGKVLEKVSGKVFGEGVGNIANFELDQPYLPGQT 660
BVH3 P4241    601 KRVSFSFPPELEKKLGINMLVKLITPDGKVLEKVSGKVFGEGVGNIANFELDQPYLPGQT 660
BVH3 A66      601 KRVSFSFPPELEKKLGINMLVKLITPDGKVLEKVSGKVFGEGVGNIANFELDQPYLPGQT 660
                  ************************************************************

BVH3 WU2      661 FKYTIASKDYPEVSYDGTFTVPTSLAYKMASQTIFYPFHAGDTYLRVNPQFAVPKGTDAL 720
BVH3 RX1      661 FKYTIASKDYPEVSYDGTFTVPTSLAYKMASQTIFYPFHAGDTYLRVNPQFAVPKGTDAL 720
BVH3 JNR7/87  661 FKYTIASKDYPEVSYDGTFTVPTSLAYKMASQTIFYPFHAGDTYLRVNPQFAVPKGTDAL 720
BVH3 SP64     661 FKYTIASKDYPEVSYDGTFTVPTSLAYKMASQTIFYPFHAGDTYLRVNPQFAVPKGTDAL 720
BVH3 P4241    661 FKYTIASKDYPEVSYDGTFTVPTSLAYKMASQTIFYPFHAGDTYLRVNPQFAVPKGTDAL 720
BVH3 A66      661 FKYTIASKDYPEVSYDGTFTVPTSLAYKMASQTIFYPFHAGDTYLRVNPQFAVPKGTDAL 720
                  ************************************************************

BVH3 WU2      721 VRVFDEFHGNAYLENNYKVGEIKLPIPKLNQGTTRTAGNKIPVTFMANAYLDNQSTYIVE 780
BVH3 RX1      721 VRVFDEFHGNAYLENNYKVGEIKLPIPKLNQGTTRTAGNKIPVTFMANAYLDNQSTYIVE 780
BVH3 JNR7/87  721 VRVFDEFHGNAYLENNYKVGEIKLPIPKLNQGTTRTAGNKIPVTFMANAYLDNQSTYIVE 780
BVH3 SP64     721 VRVFDEFHGNAYLENNYKVGEIKLPIPKLNQGTTRTAGNKIPVTFMANAYLDNQSTYIVE 780
BVH3 P4241    721 VRVFDEFHGNAYLENNYKVGEIKLPIPKLNQGTTRTAGNKIPVTFMANAYLDNQSTYIVE 780
BVH3 A66      721 VRVFDEFHGNAYLENNYKVGEIKLPIPKLNQGTTRTAGNKIPVTFMANAYLDNQSTYIVE 780
                  ************************************************************

BVH3 WU2      781 VPILEKENQTDKPSILPQFKRNKAQENSKFDEKVEEPKTSEKVEKEKLSETGNSTSNSTL 840
BVH3 RX1      781 VPILEKENQTDKPSILPQFKRNKAQENSKLDEKVEEPKTSEKVEKEKLSETGNSTSNSTL 840
BVH3 JNR7/87  781 VPILEKENQTDKPSILPQFKRNKAQENLKLDEKVEEPKTSEKVEKEKLSETGNSTSNSTL 840
BVH3 SP64     781 VPILEKENQTDKPSILPQFKRNKAQENSKLDEKVEEPKTSEKVEKEKLSETGNSTSNSTL 840
BVH3 P4241    781 VPILEKENQTDKPSILPQFKRNKAQENSKFDEKVEEPKTSEKVEKEKLSETGNSTSNSTL 840
BVH3 A66      781 VPILEKENQTDKPSILPQFKRNKAQENSKFDEKVEEPKTSEKVEKEKLSETGNSTSNSTL 840
                  *************************** * **********************************

BVH3 WU2      841 EEVPTVDPVQEKVAKFAESYGMKLENVLFNMDGTIELYLPSGEVIKKNMADFTGEAPQGN 900
BVH3 RX1      841 EEVPTVDPVQEKVAKFAESYGMKLENVLFNMDGTIELYLPSGEVIKKNMADFTGEAPQGN 900
BVH3 JNR7/87  841 EEVPTVDPVQEKVAKFAESYGMKLENVLFNMDGTIELYLPSGEVIKKNMADFTGEAPQGN 900
BVH3 SP64     841 EEVPTVDPVQEKVAKFAESYGMKLENVLFNMDGTIELYLPSGEVIKKNMADFTGEAPQGN 900
BVH3 P4241    841 EEVPTVDPVQEKVAKFAESYGMKLENVLFNMDGTIELYLPSGEVIKKNMADFTGEAPQGN 900
BVH3 A66      841 EEVPTVDPVQEKVAKFAESYGMKLENVLFNMDGTIELYLPSGEVIKKNMADFTGEAPQGN 900
                  ************************************************************

BVH3 WU2      901 GENKPSENGKVSTGTVENQPTENKPADSLPEAPNEKPVKPENSTDNGMLNPEGNVGSDPM 960
BVH3 RX1      901 GENKPSENGKVSTGTVENQPTENKPADSLPEAPNEKPVKPENSTDNGMLNPEGNVGSDPM 960
BVH3 JNR7/87  901 GENKPSENGKVSTGTVENQPTENKPADSLPEAPNEKPVKPENSTDNGMLNPEGNVGSDPM 960
BVH3 SP64     901 GENKPSENGKVSTGTVENQPTENKPADSLPEAPNEKPVKPENSTDNGMLNPEGNVGSDPM 960
BVH3 P4241    901 GENKPSENGKVSTGTVENQPTENKPADSLPEAPNEKPVKPENSTDNGMLNPEGNVGSDPM 960
BVH3 A66      901 GENKPSENGKVSTGTVENQPTENKPADSLPEAPNEKPVKPENSTDNGMLNPEGNVGSDPM 960
                  ************************************************************

BVH3 WU2      961 LDPALEEAPAVDPVQEKLEKFTASYGLGLDSVIFNMDGTIELRLPSGEVIKKNLSDLIA 1019
BVH3 RX1      961 LDPALEEAPAVDPVQEKLEKFTASYGLGLDSVIFNMDGTIELRLPSGEVIKKNLSDLIA 1019
BVH3 JNR7/87  961 LDPALEEAPAVDPVQEKLEKFTASYGLGLDSVIFNMDGTIELRLPSGEVIKKNLSDLIA 1019
BVH3 SP64     961 LDPALEEAPAVDPVQEKLEKFTASYGLGLDSVIFNMDGTIELRLPSGEVIKKNLSDFIA 1019
BVH3 P4241    961 LDPALEEAPAVDPVQEKLEKFTASYGLGLDSVIFNMDGTIELRLPSGEVIKKNLSDLIA 1019
BVH3 A66      961 LDPALEEAPAVDPVQEKLEKFTASYGLGLDSVIFNMDGTIELRLPSGEVIKKNLSDLIA 1019
                  ******************************************************** **
```

*FIG. 11B*

```
BVH11-2 SP64      1 CSYELGRHQAGQVKKESNRVSYIDGDQAGQKAENLTPDEVSKREGINAEQIVIKITDQGY  60
BVH11-2 JNR7/87   1 CSYELGRHQAGQVKKESNRVSYIDGDQAGQKAENLTPDEVSKREGINAEQIVIKITDQGY  60
BVH11-2 P4241     1 CSYELGRHQAGQDKKESNRVAYIDGDQAGQKAENLTPDEVSKREGINAEQIVIKITDQGY  60
BVH11-2 A66       1 CSYELGRHQAGQDKKESNRVAYIDGDQAGQKAENLTPDEVSKREGINAEQIVIKITDQGY  60
BVH11-2 WU2       1 CSYELGRHQAGQDKKESNRVAYIDGDQAGQKAENLTPDEVSKREGINAEQIVIKITDQGY  60
BVH11-2 Rx1       1 CSYELGRHQAGQVKKESNRVSYIDGDQAGQKAENLTPDEVSKREGINAEQIVIKITDQGY  60
BVH11   P4241     1 CSYELGRHQAGQDKKESNRVAYIDGDQAGQKAENLTPDEVSKREGINAEQIVIKITDQGY  60
BVH11   WU2       1 CSYELGRHQAGQDKKESNRVAYIDGDQAGQKAENLTPDEVSKREGINAEQIVIKITDQGY  60
BVH11   A66       1 CSYELGRHQAGQDKKESNRVAYIDGDQAGQKAENLTPDEVSKREGINAEQIVIKITDQGY  60
BVH11   Rx1       1 CSYELGRHQAGQVKKESNRVSYIDGDQAGQKAENLTPDEVSKREGINAEQIVIKITDQGY  60
BVH11   JNR7/87   1 CSYELGRHQAGQDKKESNRVAYIDGDQAGQKAENLTPDEVSKREGINAEQIVIKITDQGY  60
BVH11   SP63      1 CSYELGRHQAGQVKKESNRVSYIDGDQAGQKAENLTPDEVSKREGINAEQIVIKITDQGY  60
BVH11   SP64      1 CAYELGLHQA-QTVKENNRVSYIDGKQATQKTENLTPDEVSKREGINAEQIVIKITDQGY  59
                    * ****  *** *  ** ***  **** ** **  *************************

BVH11-2 SP64     61 VTSHGDHYHYYNGKVPYDAIISEELLMKDPNYQLKDSDIVNEIKGGYVIKVDGKYYVYLK 120
BVH11-2 JNR7/87  61 VTSHGDHYHYYNGKVPYDAIISEELLMKDPNYQLKDSDIVNEIKGGYVIKVDGKYYVYLK 120
BVH11-2 P4241    61 VTSHGDHYHYYNGKVPYDAIISEELLMKDPNYQLKDSDIVNEIKGGYVIKVNGKYYVYLK 120
BVH11-2 A66      61 VTSHGDHYHYYNGKVPYDAIISEELLMKDPNYQLKDSDIVNEIKGGYVIKVNGKYYVYLK 120
BVH11-2 WU2      61 VTSHGDHYHYYNGKVPYDAIISEELLMKDPNYQLKDSDIVNEIKGGYVIKVNGKYYVYLK 120
BVH11-2 Rx1      61 VTSHGDHYHYYNGKVPYDAIISEELLMKDPNYQLKDSDIVNEIKGGYVIKVDGKYYVYLK 120
BVH11   P4241    61 VTSHGDHYHYYNGKVPYDAIISEELLMKDPNYQLKDSDIVNEIKGGYVIKVNGKYYVYLK 120
BVH11   WU2      61 VTSHGDHYHYYNGKVPYDAIISEELLMKDPNYQLKDSDIVNEIKGGYVIKVNGKYYGYLK 120
BVH11   A66      61 VTSHGDHYHYYNGKVPYDAIISEELLMKDPNYQLKDSDIVNEIKGGYVIKVNGKYYVYLK 120
BVH11   Rx1      61 VTSHGDHYHYYNGKVPYDAIISEELLMKDPNYQLKDSDIVNEIKGGYVIKVDGKYYVYLK 120
BVH11   JNR7/87  61 VTSHGDHYHYYNGKVPYDAIISEELLMKDPNYQLKDSDIVNEIKGGYVIKVNGKYYVYLK 120
BVH11   SP63     61 VTSHGDHYHYYNGKVPYDAIISEELLMKDPNYQLKDSDIVNEIKGGYVIKVDGKYYVYLK 120
BVH11   SP64     60 VTSHGDHYHYYNGKVPYDAIISEELLMKDPNYQLKDSDIVNEIKGGYVIKVNGKYYVYLK 119
                    *************************************************** **** ***

BVH11-2 SP64    121 DAAHADNIRTKEEIKRQKQEHSHNHNSRA---DNAVAAARAQGRYTTDDGYIFNASDIIE 177
BVH11-2 JNR7/87 121 DAAHADNIRTKEEIKRQKQEHSHNHGGGSN--DQAVVAARAQGRYTTDDGYIFNASDIIE 178
BVH11-2 P4241   121 DAAHADNIRTKEEIKRQKQEHSHNHGGGSN--DQAVVAARAQGRYTTDDGYIFNASDIIE 178
BVH11-2 A66     121 DAAHADNIRTKEEIKRQRQEHSHNHGGGSN--DQAVVAARAQGRYTTDDGYIFNASDIIE 178
BVH11-2 WU2     121 DAAHADNIRTKEEIKRQKQEHSHNHGGGSN--DQAVVAARAQGRYTTDDGYIFNASDIIE 178
BVH11-2 Rx1     121 DAAHADNIRTKEEIKRQKQERSHNHNSRA---DNAVAAARAQGRYTTDDGYIFNASDIIE 177
BVH11   P4241   121 DAAHADNIRTKEEIKRQKQEHSHNHGGGSN--DQAVVAARAQGRYTTDDGYIFNASDIIE 178
BVH11   WU2     121 DAAHADNIRTKEEIKRQKQEHSHNHGGGSN--DQAVVAARAQGRYTTDDGYIFNASDIIE 178
BVH11   A66     121 DAAHADNIRTKEEIKRQKQEHSHNHGGGSN--DQAVVAARAQGRYTTDDGYIFNASDIIE 178
BVH11   Rx1     121 DAAHADNIRTKEEIKRQKQEHSHNHNSRA---DNAVAAARAQGRYTTDDGYIFNASDIIE 177
BVH11   JNR7/87 121 DAAHADNIRTKEEIKRQKQERSHNHNSRA---DNAVAAARAQGRYTTDDGYIFNASDIIE 177
BVH11   SP63    121 DAAHADNIRTKEEIKRQKQERSHNHNSRA---DNAVAAARAQGRYTTDDGYIFNASDIIE 177
BVH11   SP64    120 DAAHADNVRTKEEINRQKQEHSQHREGGTSANDGAVAFARSQGRYTTDDGYIFNASDIIE 179
                    ******* ****** ** ** ** *          *  ** ******************

BVH11-2 SP64    178 DTGDAYIVPHGDHYHYIPKNELSASELAAAEAYWNGKQGSRPSSSSSYNANPVQPRLSEN 237
BVH11-2 JNR7/87 179 DTGDAYIVPHGDHYHYIPKNELSASELAAAEAYWNGKQGSRPSSSSSYNANPAQPRLSEN 238
BVH11-2 P4241   179 DTGDAYIVPHGNHFHYIPKSDLSASELAAAQAYWNGKQGSRPSSSSSHNANPAQPRLSEN 238
BVH11-2 A66     179 DTGDAYIVPHGNHFHYIPKSDLSASELAAAQAYWNGKQGSRPSSSSSHNANPAQPRLSEN 238
BVH11-2 WU2     179 DTGDAYIVPRGNHFHYIPKSDLSASELAAAQAYWNGKQGSRPSSSSSHNANPAQPRLSEN 238
BVH11-2 Rx1     178 DTGDAYIVPHGDHYHYIPKSDLSASELAAAQAYWNGKQGSRPSSSSSHNANPAQPRLSEN 237
BVH11   P4241   179 DTGDAYIVPHGNHFHYIPKSDLSASELAAAQAYWNGKQGSRPSSSSSHNANPAQPRLSEN 238
BVH11   WU2     179 DTGDAYIVPHGNHFHYIPKSDLSASELAAAQAYWNGKQGSRPSSSSSHNANPAQPRLSEN 238
BVH11   A66     179 DTGDAYIVPHGNHFHYIPKSDLSASELAAAQAYWNGKQGSRPSSSSSHNANPAQPRLSEN 238
BVH11   Rx1     178 DTGDAYIVPHGDHYHYIPKSDLSASELAAAQAYWNGKQGSRPSSSSSHNANPAQPRLSEN 237
BVH11   JNR7/87 178 DTGDAYIVPHGDHYHYIPKNELSASELAAAQAYWNGKQGSRPSSSSSYNANPAQPRLSEN 237
BVH11   SP63    178 DTGDAYIVPHGDHYHYIPKSDLSASELAAAQAYWNGKQGSRPSSSSSHNANPAQPRLSEN 237
BVH11   SP64    180 DTGDAYIVPHGDHYHYIPKNELSASELAAAEAFLSGRENLSNLRTYRRQNSDNTPRTNWV 239
                    ********* * * ***** *********  *  *                    *
```

FIG. 12A

```
BVH11-2 SP64      238 HNLTVTPTYHQN-----------QGENISSLLRELYAKPLSERHVESDGLIFDPAQITS 285
BVH11-2 JNR7/87   239 HNLTVTPTYHQN-----------QGENISSLLRELYAKPLSERHVESDGLIFDPAQITS 286
BVH11-2 P4241     239 HNLTVTPTYHQN-----------QGENISSLLRELYAKPLSERHVESDGLIFDPAQITS 286
BVH11-2 A66       239 HNLTVTPTYHQN-----------QGENISSLLRELYAKPLSERHVESDGLIFDPAQITS 286
BVH11-2 WU2       239 HNLTVTPTYHQN-----------QGENISSLLRELYAKPLSERRVESDGLIFDPAQITS 286
BVH11-2 Rx1       238 HNLTVTPTYHQN-----------QGENISSLLRELYAKPLSERHVESDGLIFDPAQITS 285
BVH11 P4241       239 HNLTVTPTYHQN-----------QGENISSLLRELYAKPLSERHVESDGLIFDPAQITS 286
BVH11 WU2         239 HNLTVTPTYHQN-----------QGENISSLLRELYAKPLSERHVESDGLIFDPAQITS 286
BVH11 A66         239 HNLTVTPTYHQN-----------QGENISSLLRELYAKPLSERHVESDGLIFDPAQITS 286
BVH11 Rx1         238 HNLTVTPTYHQN-----------QGENISSLLRELYAKPLSERHVESDGLIFDPAQITS 285
BVH11 JNR7/87     238 HNLTVTPTYHQN-----------QGENISSLLRELYAKPLSERHVESDGLIFDPAQITS 285
BVH11 SP63        238 HNLTVTPTYHQN-----------QGENISSLLRELYAKPLSERHVESDGLIFDPAQITS 285
BVH11 SP64        240 PSVSNPGTTNTNTSNNSNTNSQASQSNDIDSLLKQLYKLPLSQRHVESDGLIFDPAQITS 299
                       *  *              *  * ***  **  ***  *  *************

BVH11-2 SP64      286 RTARGVAVPHGNHYHFIPYEQMSELEKRIARIIPLRYRSNHWVPDSRPEQPSPQSTPEPS 345
BVH11-2 JNR7/87   287 RTARGVAVPHGNHYHFIPYEQMSELEKRIARIIPLRYRSNHWVPDSRPEQPSPQSTPEPS 346
BVH11-2 P4241     287 RTARGVAVPHGNHYHFIPYEQMSELEERIARIIPLRYRSNHWVPDSRPEQPSPQ----PS 342
BVH11-2 A66       287 RTARGVAVPHGNHYHFIPYEQMSELEERIARIIPLRYRSNHWVPDSRPEQPSPQ----PS 342
BVH11-2 WU2       287 RTARGVAVPHGNHYHFIPYEQMSELEERIARIIPLRYRSNHWVPDSRPEQPSPQ----PS 342
BVH11-2 Rx1       286 RTANGVAVPHGDHYHFIPYSQLSPLEEKLARIIPLRYRSNHWVPDSRPEQPSPQSTPEPS 345
BVH11 P4241       287 RTARGVAVPHGNHYHFIPYEQMSELEERIARIIPLRYRSNHWVPDSRPEQPSPQ----PS 342
BVH11 WU2         287 RTARGVAVPHGNHYHFIPYEQMSELEERIARIIPLRYRSNHWVPDSRPEQPSPQ----PS 342
BVH11 A66         287 RTARGVAVPHGNHYHFIPYEQMSELEERIARIIPLRYRSNHWVPDSRPEQPSPQ----PS 342
BVH11 Rx1         286 RTANGVAVPHGDHYHFIPYSQLSPLEEKLARIIPLRYRSNHWVPDSRPEQPSPQSTPEPS 345
BVH11 JNR7/87     286 RTARGVAVPHGNHYHFIPYEQMSELEKRIARIIPLRYRSNHWVPDSRPEEPSPQPTPEPS 345
BVH11 SP63        286 RTARGVAVPHGNHYHFIPYSQMSELEKRIARIIPLRYRSNHWVPDSRPEQPSPQSTPEPS 345
BVH11 SP64        300 RTARGVAVPHGNHYHFIPYEQMSELEKRIARIIPLRYRSNHWVPDSRPEEPSPQPTPEPS 359
                      *** ******* ******* *  *  **  ******************** ****  **

BVH11-2 SP64      346 PSLQPAPNPQPAPSNPIDEKLVKEAVRKVGDGYVFEENGVSRYIPAKDLSAETAAGIDSK 405
BVH11-2 JNR7/87   347 PSPQPAPNPQPAPSNPIDEKLVKEAVRKVGDGYVFEENGVSRYIPAKDLSAETAAGIDSK 406
BVH11-2 P4241     343 PSPQPAPNPQPAPSNPIDEKLVKEAVRKVGDGYVFEENGVSRYIPAKDLSAETAAGIDSK 402
BVH11-2 A66       343 PSPQPAPNPQPAPSNPIDEKLVKEAVRKVGDGYVFEENGVSRYIPAKDLSAETAAGIDSK 402
BVH11-2 WU2       343 PSPQPAPNPQPAPSNPIDEKLVKEAVRKVGDGYVFEENGVSRYIPAKDLSAETAAGIDSK 402
BVH11-2 Rx1       346 PSPQPAPNPQPAPSNPIDEKLVKEAVRKVGDGYVFEENGVPRYIPAKDLSAETAAGIDSK 405
BVH11 P4241       343 PSPQPAPNPQPAPSNPIDEKLVKEAVRKVGDGYVFEENGVSRYIPAKDLSAETAAGIDSK 402
BVH11 WU2         343 PSPQPAPNPQPAPSNPIDEKLVKEAVRKVGDGYVFEENGVSRYIPAKDLSAETAAGIDSK 402
BVH11 A66         343 PSPQPAPNPQPAPSNPIDEKLVKEAVRKVGDGYVFEENGVSRYIPAKDLSAETAAGIDSK 402
BVH11 Rx1         346 PSPQPAPNPQPAPSNPIDEKLVKEAVRKVGDGYVFEENGVPRYIPAKDLSAETAAGIDSK 405
BVH11 JNR7/87     346 PSP------QPAPSNPIDEKLVKEAVRKVGDGYVFEENGVSRYIPAKDLSAETAAGIDSK 399
BVH11 SP63        346 PSPQSAPNPQPAPSNPIDEKLVKEVVRKVGDGYVFEKNGVSRYIPAKNLSAETAAGIDSK 405
BVH11 SP64        360 PSPQPAPNPQPAPSNPIDEKLVKEAVRKVGDGYVFEENGVSRYIPAKNLSAETAAGIDSK 419
                      **     *********** ******* *************** *** ************

BVH11-2 SP64      406 LAKQESLSHKLGAKKTDLPSSDREFYNKAYDLLARIHQDLLDNKGRQVDFEVLDNLLERL 465
BVH11-2 JNR7/87   407 LAKQESLSHKLGAKKTDLPSSDREFYNKAYDLLARIHQDLLDNKGRQVDFEALDNLLERL 466
BVH11-2 P4241     403 LAKQESLSHKLGTKKTDLPSSDREFYNKAYDLLARIHQDLLDNKGRQVDFEALDNLLERL 462
BVH11-2 A66       403 LAKQESLSHKLGTKKTDLPSSDREFYNKAYDLLARIHQDLLDNKGRQVDFEALDNLLERL 462
BVH11-2 WU2       403 LAKQESLSHKLGTKKTDLPSSDREFYNKAYDLLARIHQDLLDNKGRQVDFEALDNLLERL 462
BVH11-2 Rx1       406 LAKQESLSHKLGAKKTDLPSSDREFYNKAYDLLARIHQDLLDNKGRQVDFEALDNLLERL 465
BVH11 P4241       403 LAKQESLSHKLGTKKTDLPSSDREFYNKAYDLLARIHQDLLDNKGRQVDFEALDNLLERL 462
BVH11 WU2         403 LAKQESLSHKLGTKKTDLPSSDREFYNKAYDLLARIHQDLLDNKGRQVDFEALDNLLERL 462
BVH11 A66         403 LAKQESLSHKLGTKKTDLPSSDREFYNKAYDLLARIHQDLLDNKGRQVDFEALDNLLERL 462
BVH11 Rx1         406 LAKQESLSHKLGAKKTDLPSSDREFYNKAYDLLARIHQDLLDNKGRQVDFEALDNLLERL 465
BVH11 JNR7/87     400 LAKQESLSHKLGAKKTDLPSSDREFYNKAYDLLARIHQDLLDNKGRQVDFEALDNLLERL 459
BVH11 SP63        406 LAKQESLSHKLGAKKTDLPSSDREFYNKAYDLLARIHQDLLDNKGRQVDFEALDNLLERL 465
BVH11 SP64        420 LAKQESLSHKLGAKKTDLPSSDREFYNKAYDLLARIHQDLLDNKGRQVDFEALDNLLERL 479
                      ************ ********************************** ********
```

*FIG. 12B*

```
BVH11-2 SP64     466 KDVSSDKVKLVDDILAFLAPIRHPERLGKPNAQITYTDDEIQVAKLAGKYTTEDGYIFDP 525
BVH11-2 JNR7/87  467 KDVPSDKVKLVDDILAFLAPIRHPERLGKPNAQITYTDDEIQVAKLAGKYTTEDGYIFDP 526
BVH11-2 P4241    463 KDVSSDKVKLVEDILAFLAPIRHPERLGKPNSQITYTDDEIQVAKLAGKYTTEDGYIFDP 522
BVH11-2 A66      463 KDVSSDKVKLVEDILAFLAPIRHPERLGKPNSQITYTDDEIQVAKLAGKYTTEDGYIFDP 522
BVH11-2 WU2      463 KDVSSDKVKLVEDILAFLAPIRHPERLGKPNSQITYTDDEIQVAKLAGKYTTEDGYIFDP 522
BVH11-2 Rx1      466 KDVSSDKVKLVDDILAFLAPIRHPERLGKPNAQITYTDDEIQVAKLAGKYTTEDGYIFDP 525
BVH11   P4241    463 KDVSSDKVKLVEDILAFLAPIRHPERLGKPNSQITYTDDEIQVAKLAGKYTTEDGYIFDP 522
BVH11   WU2      463 KDVSSDKVKLVEDILAFLAPIRHPERLGKPNSQITYTDDEIQVAKLAGKYTTEDGYIFDP 522
BVH11   A66      463 KDVSSDKVKLVEDILAFLAPIRHPERLGKPNSQITYTDDEIQVAKLAGKYTTEDGYIFDP 522
BVH11   Rx1      466 KDVSSDKVKLVDDILAFLAPIRHPERLGKPNAQITYTDDEIQVAKLAGKYTTEDGYIFDP 525
BVH11   JNR7/87  460 KDVSSDKVKLVDDILAFLAPIRHPERLGKPNAQITYTDDEIQVAKLAGKYTTEDGYIFDP 519
BVH11   SP63     466 EDVPSDKVKLVDDILAFLAPIRHPERLGKPNAQITYTDDEIQVAKLAGKYTTEDGYIFDP 525
BVH11   SP64     480 KDVSSDKVKLVDDILAFLAPIRHPERLGKPNAQITYTDDEIQVAKLAGKYTTEDGYIFDP 539
                      ** *******.*********************.***************************

BVH11-2 SP64     526 RDITSDEGDAYVTPHMTHSHWIKKDSLSEAERAAAQAYAKEKGLTPPSTDHQDSGNTEAK 585
BVH11-2 JNR7/87  527 RDITSDEGDAYVTPHMTHSHWIKKDSLSEAERAAAQAYAKEKGLTPPSTDHQDSGNTEAK 586
BVH11-2 P4241    523 RDITSDEGDAYVTPHMTHSHWIKKDSLSEAERAAAQAYAKEKGLTPPSTDHRDSGNTEAK 582
BVH11-2 A66      523 RDITSDEGDAYVTPHMTHSHWIKKDSLSEAERAAAQAYAKEKGLTPPSTDHQDSGNTEAK 582
BVH11-2 WU2      523 RDITSDEGDAYVTPHMTHSHWIKKDSLSEAERAAAQAYAKEKGLTPPSTDHQDSGNTEAK 582
BVH11-2 Rx1      526 RDITSDEGDAYVTPHMTHSHWIKKDSLSEAERAAAQAYAKEKGLTPPSTDHQDSGNTEAK 585
BVH11   P4241    523 RDITSDEGDAYVTPHMTHSHWIKKDSLSEAERAAAQAYAKEKGLTPPSTDHQDSGNTEAK 582
BVH11   WU2      523 RDITSDEGDAYVTPHMTHSHWIKKDSLSEAERAAAQAYAKEKGLTPPSTDHQDSGNTEAK 582
BVH11   A66      523 RDITSDEGDAYVTPHMTHSHWIKKDSLSEAERAAAQAYAKEKGLTPPSTDHQDSGNTEAK 582
BVH11   Rx1      526 RDITSDEGDAYVTPHMTHSHWIKKDSLSEAERAAAQAYAKEKGLTPPSTDHQDSGNTEAK 585
BVH11   JNR7/87  520 RDITSDEGDAYVTPHMTHSHWIKKDSLSEAERAAAQAYAKEKGLTPPSTDHQDSGNTEAK 579
BVH11   SP63     526 RDITSDEGDAYVTPHMTHSHWIKKDSLSEAERAAAQAYAKEKGLTPPSTDHQDSGNTEAK 585
BVH11   SP64     540 RDITSDEGDAYVTPHMTHSHWIKKDSLSEAERAAAQAYAKEKGLTPPSTDHQDSGNTEAK 599
                      ************************************************** *******

BVH11-2 SP64     586 GAEAIYNRVKAAKKVPLDRMPYNLQYTVEVKNGSLIIPHYDHYHNIKFEWFDEGLYEAPK 645
BVH11-2 JNR7/87  587 GAEAIYNRVKAAKKVPLDRMPYNLQYTVEVKNGSLIIPHYDHYHNIKFEWFDEGLYEAPK 646
BVH11-2 P4241    583 GAEAIYNRVKAAKKVPLDRMPYNLQYTVEVKNGSLIIPHYDHYHNIKFEWFDEGLYEAPK 642
BVH11-2 A66      583 GAEAIYNRVKAAKKVPLDRMPYNLQYTVEVKNGSLIIPHYDHYHNIKFEWFDEGLYEAPK 642
BVH11-2 WU2      583 GAEAIYNRVKAAKKVPLDRMPYNLQYTVEVKNGSLIIPHYDHYHNIKFEWFDEGLYEAPK 642
BVH11-2 Rx1      586 GAEAIYNRVKAAKKVPLDRMPYNLQYTVEVKNGSLIIPHYDHYHNIKFEWFDEGLYEAPK 645
BVH11   P4241    583 GAEAIYNRVKAAKKVPLDRMPYNLQYTVEVKNGSLIIPHYDHYHNIKFEWFDEGLYEAPK 642
BVH11   WU2      583 GAEAIYNRVKAAKKVPLDRMPYNLQYTVEVKNGSLIIPHYDHYHNIKFEWFDEGLYEAPK 642
BVH11   A66      583 GAEAIYNRVKAAKKVPLDRMPYNLQYTVEVKNGSLIIPHYDHYHNIKFEWFDEGLYEAPK 642
BVH11   Rx1      586 GAEAIYNRVKAAKKVPLDRMPYNLQYTVEVKNGSLIIPHYDHYHNIKFEWFDEGLYEAPK 645
BVH11   JNR7/87  580 GAEAIYNRVKAAKKVPLDRMPYNLQYTVEVKNGSLIIPHYDHYHNIKFEWFDEGLYEAPK 639
BVH11   SP63     586 GAEAIYNRVKAAKKVPLDRMPYNLQYTVEVKNGSLIIPHYDHYHNIKFEWFDEGLYEAPK 645
BVH11   SP64     600 GAEAIYNRVKAAKKVPLDRMPYNLQYTVEVKNGSLIIPHYDHYHNIKFEWFDEGLYEAPK 659
                      ************************************************************

BVH11-2 SP64     646 GYSLEDLLATVKYYVEHPNERPHSDNGFGNASDHVRKNK---------------ADQDSK 690
BVH11-2 JNR7/87  647 GYTLEDLLATVKYYVEHPNERPHSDNGFGNASDHVRKNK---------------VDQDSK 691
BVH11-2 P4241    643 GYTLEDLLATVKYYVEHPNERPHSDNGFGNASDHVRKNK---------------ADQDSK 687
BVH11-2 A66      643 GYTLEDLLATVKYYVEHPNERPHSDNGFGNASDHVRKNK---------------ADQDSK 687
BVH11-2 WU2      643 GYTLEDLLATVKYYVEHPNERPHSDNGFGNASDHVRKNK---------------ADQDSK 687
BVH11-2 Rx1      646 GYSLEDLLATVKYYVEHPNERPHSDNGFGNASDHVQRNKNGQADTNQTEKPNEEKPQTEK 705
BVH11   P4241    643 GYTLEDLLATVKYYVEHPNERPHSDNGFGNASDHVRKNK---------------ADQDSK 687
BVH11   WU2      643 GYTLEDLLATVKYYVEHPNERPHSDNGFGNASDHVRKNK---------------ADQDSK 687
BVH11   A66      643 GYTLEDLLATVKYYVEHPNERPHSDNGFGNASDHVRKNK---------------ADQDSK 687
BVH11   Rx1      646 GYSLEDLLATVKYYVEHPNERPHSDNGFGNASDHVQRNK-----------------NGQ 687
BVH11   JNR7/87  640 GYSLEDLLATVKYYVEHPNERPHSDNGFGNASDHVQRNK-----------------NGQ 681
BVH11   SP63     646 GYTLEDLLATVKYYVEHPNERPHSDNGFGNASDHVQRNK-----------------NGQ 687
BVH11   SP64     660 GYTLEDLLATVKYYVEHPNERPHSDNGFGNASDHVQRNK-----------------NGQ 701
                      ** ********************************* **                 **
```

*FIG. 12C*

```
BVH11-2 SP64     691 PDEDKEHDEVSEPTHPESDEKENHAGLNPSADNLYKPSTDTEETEEEAEDTTDEAEIPQV 750
BVH11-2 JNR7/87  692 PDEDKEHDEVSEPTHPESDEKENHAGLNPSADNLYKPSTDTEETEEEAEDTTDEAEIPQV 751
BVH11-2 P4241    688 PDEDKGHDEVSEPTHPESDEKENHAGLNPSADNLYKPSTDTEETEEEAEDTTDEAEIPQV 747
BVH11-2 A66      688 PDEDKGHDEVSEPTHPESDEKENHAGLNPSADNLYKPSTDTEETEEEAEDTTDEAEIPQV 747
BVH11-2 WU2      688 PDEDKGHDEVSEPTHPESDEKENHAGLNPSADNLYKPSTDTEETEEEAEDTTDEAEIPQV 747
BVH11-2 Rx1      706 PEEDKEHDEVSEPTHPESDEKENHVGLNPSADNLYKPSTDTEETEEEAEDTTDEAEIPQV 765
BVH11   P4241    688 PDEDKGHDEVSEPTHPESDEKENHAGLNPSADNLYKPSTDTEETEEEAEDTTDEAEIPQV 747
BVH11   WU2      688 PDEDKGHDEVSEPTHPESDEKENHAGLNPSADNLYKPSTDTEETEEEAEDTTDEAEIPQV 747
BVH11   A66      688 PDEDKGHDEVSEPTHPESDEKENHAGLNPSADNLYKPSTDTEETEEEAEDTTDEAEIPQV 747
BVH11   Rx1      688 ADTNQTEKPNEEKPQTEKPEEETPREEKPQSEKPESPKPTEEPEEESPEESPEESEEPQV 747
BVH11   JNR7/87  682 ADTNQTEKPNEEKPQTEKPEEETPREEKPQSEKPESPKPTEEPEEESPEESPEESEEPQV 741
BVH11   SP63     688 ADTNQTEKPSEEKPQTEKPEEETPREEKPQSEKPESP----KPTEEPEEESPEESEEPQV 743
BVH11   SP64     702 ADTNQTEKPSEEKPQTEKPEEETPREEKPQSEKPESP----KPTEEPEEESPEESEEPQV 757
                          *     *   *  *      *       *       **  *     * * ***

BVH11-2 SP64     751 ENSVINAKIADAEALLEKVTDPSIRQNAMETLTGLKSSLLLGTKDNNTISAEVDSLLALL 810
BVH11-2 JNR7/87  752 ENSVINAKIADAEALLEKVTDPSIRQNAMETLTGLKSSLLLGTKDNNTISAEVDSLLALL 811
BVH11-2 P4241    748 EHSVINAKIADAEALLEKVTDPSIRQNAMETLTGLKSSLLLGTKDNNTISAEVDSLLALL 807
BVH11-2 A66      748 EHSVINAKIADAEALLEKVTDPSIRQNAMETLTGLKSSLLLGTKDNNTISAEVDSLLALL 807
BVH11-2 WU2      748 EHSVINAKIADAEALLEKVTDPSIRQNAMETLTGLKSSLLLGTKDNNTISAEVDSLLALL 807
BVH11-2 Rx1      766 EYSVINAKIAEAEALLEKVTDSSIRQNAVETLTGLKSSLLLGTKDNNTISAEVDSLLALL 825
BVH11   P4241    748 EHSVINAKIADAEALLEKVTDPSIRQNAMETLTGLKSSLLLGTKDNNTISAEVDSLLALL 807
BVH11   WU2      748 EHSVINAKIADAEALLEKVTDPSIRQNAMETLTGLKSSLLLGTKDNNTISAEVDSLLALL 807
BVH11   A66      748 EHSVINAKIADAEALLEKVTDPSIRQNAMETLTGLKSSLLLGTKDNNTISAEVDSLLALL 807
BVH11   Rx1      748 ETEKVKEKLREAEDLLGKIQNPIIKSNAKETLTGLKNNLLFGTQDNNTIMAEAEKLLALL 807
BVH11   JNR7/87  742 ETEKVKEKLREAEDLLGKIQNPIIKSNAKETLTGLKNNLLFGTQDNNTIMAEAEKLLALL 801
BVH11   SP63     744 ETEKVEEKLREAEDLLGKIQDPIIKSNAKETLTGLKNNLLFGTQDNNTIMAEAEKLLALL 803
BVH11   SP64     758 ETEKVEEKLREAEDLLGKIQDPIIKSNAKETLTGLKNNLLFGTQDNNTIMAEAEKLLALL 817
                      *       *  ** **  *        *  * ******* ** ** ***** **     *****

BVH11-2 SP64     811 KESQPAPIQ 819
BVH11-2 JNR7/87  812 KESQPAPIQ 820
BVH11-2 P4241    808 KKSQPAPIQ 816
BVH11-2 A66      808 KKSQPAPIQ 816
BVH11-2 WU2      808 KKSQPAPIQ 816
BVH11-2 Rx1      826 KESQPAPIQ 834
BVH11   P4241    808 KESK      811
BVH11   WU2      808 KESK      811
BVH11   A66      808 KESK      811
BVH11   Rx1      808 KESK      811
BVH11   JNR7/87  802 KESK      805
BVH11   SP63     804 KESK      807
BVH11   SP64     818 KESK      821
                         * *
```

| | BVH11 SP64 | BVH11-2 SP64 | BVH11 SP63 | BVH11 JNR.7/87 | BVH11-2 JNR.7/87 | BVH11 WU2 | BVH11-2 WU2 | BVH11 A66 | BVH11-2 A66 | BVH11 P4241 | BVH11-2 P4241 | BVH11 Rx-1 |
|---|---|---|---|---|---|---|---|---|---|---|---|---|
| BVH11-2 Rx-1 | I 81% S 85% | I 94% S 95% | I 89% S 91% | I 88% S 90% | I 94% S 95% | I 92% S 94% | I 93% S 95% | I 92% S 94% | I 93% S 95% | I 92% S 94% | I 93% S 95% | I 91% S 92% |
| BVH11 Rx-1 | I 88% S 91% | I 87% S 90% | I 97% S 97% | I 96% S 96% | I 87% S 90% | I 87% S 91% | I 86% S 90% | I 87% S 91% | I 86% S 90% | I 87% S 91% | I 86% S 90% | |
| BVH11-2 P4241 | I 80% S 85% | I 96% S 97% | I 87% S 90% | I 86% S 90% | I 97% S 98% | I 98% S 98% | I 99% S 99% | I 99% S 99% | I 99% S 99% | I 99% S 99% | | |
| BVH11 P4241 | I 80% S 85% | I 95% S 96% | I 88% S 91% | I 87% S 91% | I 96% S 97% | I 99% S 99% | I 98% S 98% | I 100% | I 99% S 99% | | | |
| BVH11-2 A66 | I 80% S 85% | I 96% S 97% | I 87% S 90% | I 86% S 90% | I 97% S 98% | I 98% S 98% | I 99% S 99% | I 99% S 99% | | | | |
| BVH11 A66 | I 80% S 85% | I 95% S 96% | I 88% S 91% | I 87% S 91% | I 96% S 97% | I 92% S 94% | I 98% S 98% | | | | | |
| BVH11-2 WU2 | I 80% S 85% | I 96% S 97% | I 87% S 90% | I 86% S 90% | I 97% S 98% | I 98% S 98% | | | | | | |
| BVH11 WU2 | I 80% S 85% | I 95% S 96% | I 88% S 91% | I 87% S 91% | I 96% S 97% | | | | | | | |
| BVH11-2 JNR.7/87 | I 82% S 87% | I 98% S 98% | I 88% S 91% | I 87% S 90% | | | | | | | | |
| BVH11 JNR.7/87 | I 88% S 91% | I 87% S 90% | I 96% S 96% | | | | | | | | | |
| BVH11 SP63 | I 88% S 90% | I 87% S 90% | | | | | | | | | | |
| BVH11-2 SP64 | I 81% S 86% | | | | | | | | | | | |

```
AATTCCTTGT CGGGTAAGTT CCGACCCGCA CGAAAGGCGT AATGATTTGG GCACTGTCTC    60
AACGAGAGAC TCGGTGAAAT TTTAGTACCT GTGAAGATGC AGGTTACCCG CGACAGGACG   120
GAAAGACCCC ATGGAGCTTT ACTGCAGTTT GATATTGAGT GTCTGTACCA CATGTACAGG   180
ATAGGTAGGA GTCTAAGAGA TCGGGACGCC AGTTCGAAG GAGACGCTGT TGGGATACTA   240
CCCTTGTGTT ATGGCCACTC TAACCCAGAT AGGTGATCCC TATCGGAGAC AGTGTCTGAC   300
GGGCAGTTTG ACTGGGGCGG TCGCCTCCTA AAAGGTAACG GAGGCGCCCA AAGGTTCCCT   360
CAGAATGGTT GGAAATCATT CGCAGAGTGT AAAGGTATAA GGGAGCTTGA CTGCGAGAGC   420
TACAACTCGA GCAGGGACGA AAGTCGGGCT TAGTGATCCG GTGGTTCCGT ATGGAAGGGC   480
CATCGCTCAA CGGATAAAAG CTACCCTGGG GATAACAGGC TTATCTCCCC AAGAGTTCA    540
CATCGACGGG GAGGTTTGGC ACCTCGATGT CGGCTCGTCG CATCCTGGGG CTGTAGTCGG   600
TCCCAAGGGT TGGGCTGTTC GCCCATTAAA GCGGCACGCG AGCTGGGTTC AGAACGTCGT   660
GAGACAGTTC GGTCCCTATC CGTCGCGGGC GTAGGAAATT TGAGAGGATC TGCTCCTAGT   720
ACGAGAGGAC CAGAGTGGAC TTACCGCTGG TGTACCAGTT GTCTTGCCAA AGGCATCGCT   780
GGGTAGCTAT GTAGGGAAGG GATAAACGCT GAAAGCATCT AAGTGTGAAA CCCACCTCAA   840
GATGAGATTT CCCATGATTA TATATCAGTA AGAGCCCTGA GAGATGATCA GGTAGATAGG   900
TTAGAAGTGG AAGTGTGGCG ACACATGTAG CGGACTAATA CTAATAGCTC GAGGACTTAT   960
CCAAAGTAAC TGAGAATATG AAAGCGAACG GTTTTCTTAA ATTGAATAGA TATTCAATTT  1020
TGAGTAGGTA TTACTCAGAG TTAAGTGACG ATAGCCTAGG AGATACACCT GTACCCATGC  1080
CGAACACAGA AGTTAAGCCC TAGAACGCCG GAAGTAGTTG GGGGTTGCCC CCTGTGAGAT  1140
AGGGAAGTCG CTTAGCTCTA GGGAGTTTAG CTCAGCTGGG AGAGCATCTG CCTTACAAGC  1200
AGAGGGTCAG CGGTTCGATC CCGTTAACTC CCAAAGGTCC CGTAGTGTAG CGGTTATCAC  1260
GTCGCCCTGT CACGGCGAAG ATCGCGGGTT CGATTCCCGT CGGGACCGTT TAAGGTAACG  1320
CAAGTTATTT TAGACTCGTT AGCTCAGTTG GTAGAGCAAT TGACTTTTAA TCAATGGGTC  1380
ACTGGTTCGA GCCCAGTACG GGTCATATAT GCGGGTTTGG CGGAATTCTA ATCTCTTTGA  1440
AATCATCTTC TCTCACTTTC CAAAACTCTA TTACCTCTTA TTATACCACA TTTCAATCTT  1500
CAACTTCCCA GTAATATAAG CACCTCTGGC GAAAGAAGTT TCAATGTCCT AAAGTAATAA  1560
GTGAATCCAA TTCAGGAACT CCAAGAACAA AAGAAACATC TGGTGTCACA AGTATTGGAT  1620
GGCACAGAGT CACGTGGTAG TCTGACCCTA GCAGAAATTT TAAATAGTAA ACTATTTACT  1680
GGTTAATTAA ATGGTTAAAT AACCGGTTTA GAAAACTATT TAATAAAGTA AAGAAGTTG   1740
AGAAAAAACT TCATCATTTA TTGAAATGAG GGATTTATGA AATTTAGTAA AAAATATATA  1800
GCAGCTGGAT CAGCTGTTAT CGTATCCTTG AGTCTATGTG CCTATGCACT AAACCAGCAT  1860
CGTTCGCAGG AAAATAAGGA CAATAATCGT GTCTCTTATG TGGATGGCAG CCAGTCAAGT  1920
CAGAAAAGTG AAAACTTGAC ACCAGACCAG GTTAGCCAGA AGAAGGAAT TCAGGCTGAG   1980
CAAATTGTAA TCAAAATTAC AGATCAGGGC TATGTAACGT CACACGGTGA CCACTATCAT  2040
TACTATAATG GGAAAGTTCC TTATGATGCC CTCTTTAGTG AAGAACTCTT GATGAAGGAT  2100
CCAAACTATC AACTTAAAGA CGCTGATATT GTCAATGAAG TCAAGGGTGG TTATATCATC  2160
AAGGTCGATG GAAAATATTA TGTCTACCTG AAAGATGCAG CTCATGCTGA TAATGTTCGA  2220
ACTAAAGATG AAATCAATCG TCAAAAACAA GAACATGTCA AAGATAATGA GAAGGTTAAC  2280
TCTAATGTTG CTGTAGCAAG GTCTCAGGGA CGATATACGA CAAATGATGG TTATGTCTTT  2340
AATCCAGCTG ATATTATCGA AGATACGGGT AATGCTTATA TCGTTCCTCA TGGAGGTCAC  2400
TATCACTACA TTCCCAAAAG CGATTTATCT GCTAGTGAAT TAGCAGCAGC TAAAGCACAT  2460
CTGGCTGGAA AAAATATGCA ACCGAGTCAG TTAAGCTATT CTTCAACAGC TAGTGACAAT  2520
AACACGCAAT CTGTAGCAAA AGGATCAACT AGCAAGCCAG CAAATAAATC TGAAAATCTC  2580
CAGAGTCTTT TGAAGGAACT CTATGATTCA CCTAGCGCCC AACGTTACAG TGAATCAGAT  2640
GGCCTGGTCT TTGACCCTGC TAAGATTATC AGTCGTACAC CAAATGGAGT TGCGATTCCG  2700
CATGGCGACC ATTACCACTT TATTCCTTAC AGCAAGCTTT CTGCTTTAGA AGAAAAGATT  2760
GCCAGAATGG TGCCTATCAG TGGAACTGGT TCTACAGTTT CTACAAATGC AAAACCTAAT  2820
GAAGTAGTGT CTAGTCTAGG CAGTCTTTCA AGCAATCCTT CTTCTTTAAC GACAAGTAAG  2880
GAGCTCTCTT CAGCATCTGA TGGTTATATT TTTAATCCAA AAGATATCGT TGAAGAAACG  2940
GCTACAGCTT ATATTGTAAG ACATGGTGAT CATTTCCATT ACATTCCAAA ATCAAATCAA  3000
ATTGGGCAAC CGACTCTTCC AAACAATAGT CTAGCAACAC CTTCTCCATC TCTTCCAATC  3060
AATCCAGGAA CTTCACATGA GAAACATGAA GAAGATGGAT ACGGATTTGA TGCTAATCGT  3120
ATTATCGCTG AAGATGAATC AGGTTTTGTC ATGAGTCACG GAGACCACAA TCATTATTTC  3180
TTCAAGAAGG ACTTGACAGA AGAGCAAATT AAGGCTGCGC AAAAACATTT AGAGGAAGTT  3240
AAAACTAGTC ATAATGGATT AGATTCTTTG TCATCTCATG AACAGGATTA TCCAGGTAAT  3300
GCCAAAGAAA TGAAAGATTT AGATAAAAAA ATCGAAGAAA AAATTGCTGG CATTATGAAA  3360
CAATATGGTG TCAAACGTGA AAGTATTGTC GTGAATAAAG AAAAAAATGC GATTATTTAT  3420
CCGCATGGAG ATCACCATCA TGCAGATCCG ATTGATGAAC ATAAACCGGT TGGAATTGGT  3480
CATTCTCACA GTAACTATGA ACTGTTTAAA CCCGAAGAAG GAGTTGCTAA AAAAGAAGGG  3540
```

*FIG. 14A*

```
AATAAAGTTT ATACTGGAGA AGAATTAACG AATGTTGTTA ATTTGTTAAA AAATAGTACG     3600
TTTAATAATC AAAACTTTAC TCTAGCCAAT GGTCAAAAAC GCGTTTCTTT TAGTTTTCCG     3660
CCTGAATTGG AGAAAAAATT AGGTATCAAT ATGCTAGTAA AATTAATAAC ACCAGATGGA     3720
AAAGTATTGG AGAAAGTATC TGGTAAAGTA TTTGGAGAAG GAGTAGGGAA TATTGCAAAC     3780
TTTGAATTAG ATCAACCTTA TTTACCAGGA CAAACATTTA AGTATACTAT CGCTTCAAAA     3840
GATTATCCAG AAGTAAGTTA TGATGGTACA TTTACAGTTC CAACCTCTTT AGCTTACAAA     3900
ATGGCCAGTC AAACGATTTT CTATCCTTTC CATGCAGGGG ATACTTATTT AAGAGTGAAC     3960
CCTCAATTTG CAGTGCCTAA AGGAACTGAT GCTTTAGTCA GAGTGTTTGA TGAATTTCAT     4020
GGAAATGCTT ATTTAGAAAA TAACTATAAA GTTGGTGAAA TCAAATTACC GATTCCGAAA     4080
TTAAACCAAG GAACAACCAG AACGGCCGGA AATAAAATTC CTGTAACCTT CATGGCAAAT     4140
GCTTATTTGG ACAATCAATC GACTTATATT GTGGAAGTAC CTATCTTGGA AAAAGAAAAT     4200
CAAACTGATA AACCAAGTAT CTACCACAA TTTAAAAGGA ATAAAGCACA AGAAAACTCA      4260
AAACTTGATG AAAAGGTAGA AGAACCAAAG ACTAGTGAGA AGGTAGAAAA AGAAAAACTT     4320
TCTGAAACTG GAATAGTAC TAGTAATTCA ACGTTAGAAG AAGTTCCTAC AGTGGATCCT      4380
GTACAAGAAA AAGTAGCAAA ATTTGCTGAA AGTTATGGGA TGAAGCTAGA AAATGTCTTG     4440
TTTAATATGG ACGGAACAAT TGAATTATAT TTACCATCAG GAGAAGTCAT TAAAAAGAAT     4500
ATGGCAGATT TTACAGGAGA AGCACCTCAA GGAAATGGTG AAAATAAACC ATCTGAAAAT     4560
GGAAAAGTAT CTACTGGAAC AGTTGAGAAC CAACCAACAG AAAATAAACC AGCAGATTCT     4620
TTACCAGAGG CACCAAACGA AAAACCTGTA AAACCAGAAA ACTCAACGGA TAATGGAATG     4680
TTGAATCCAG AAGGGAATGT GGGGAGTGAC CCTATGTTAG ATCCAGCATT AGAGGAAGCT     4740
CCAGCAGTAG ATCCTGTACA AGAAAAATTA GAAAATTTA CAGCTAGTTA CGGATTAGGC      4800
TTAGATAGTG TTATATTCAA TATGGATGGA ACGATTGAAT TAAGATTGCC AAGTGGAGAA     4860
GTGATAAAAA AGAATTTATC TGATTTCATA GCGTAAGGAA TAGCAGTAGA AAAAGTCTGA     4920
ATCAAAATG AAGTTCTCTC AAAAGTTAGA AATAAAACTC TGACTTTGGG AGAATTTCAT      4980
TTTATTATTA ATATATAAAA TTTCTTGACA TACAACTTAA AAAGAGGTGG AATATTTACT     5040
AGTTAATT   (SEQ ID NO : 11)                                          5048
```

*FIG. 14B*

```
CAGAGATCTT AGTGAATCAA ATATACTTAA GAAAAGAGGA AAGAATGAAA ATCAATAAAA      60
AATATCTAGC TGGGTCAGTA GCTACACTTG TTTTAAGTGT CTGTGCTTAT GAACTAGGTT     120
TGCATCAAGC TCAAACTGTA AAAGAAAATA ATCGTGTTTC CTATATAGAT GGAAAACAAG     180
CGACGCAAAA AACGGAGAAT TTGACTCCTG ATGAGGTTAG CAAGCGTGAA GGAATCAACG     240
CCGAACAAAT CGTCATCAAG ATTACGGATC AAGGTTATGT GACCTCTCAT GGAGACCATT     300
ATCATTACTA TAATGGCAAG GTCCCTTATG ATGCCATCAT CAGTGAAGAG CTCCTCATGA     360
AAGATCCGAA TTATCAGTTG AAGGATTCAG ACATTGTCAA TGAAATCAAG GGTGGTTATG     420
TCATTAAGGT AAACGGTAAA TACTATGTTT ACCTTAAGGA TGCAGCTCAT GCGGATAATG     480
TCCGTACAAA AGAAGAAATC AATCGGCAAA AACAAGAACA TAGTCAGCAT CGTGAAGGAG     540
GGACTTCAGC AAACGATGGT GCGGTAGCCT TTGCACGTTC ACAGGGACGC TACACCACAG     600
ATGATGGTTA TATCTTCAAT GCATCTGATA TCATCGAAGA TACGGGCGAT GCCTATATCG     660
TTCCTCATGG AGATCATTAC CATTACATTC CTAAGAATGA GTTATCAGCT AGCGAGTTGG     720
CTGCTGCAGA AGCCTTCCTA TCTGGTCGGG AAAATCTGTC AAATTTAAGA ACCTATCGCC     780
GACAAAATAG CGATAACACT CCAAGAACAA ACTGGGTACC TTCTGTAAGC AATCCAGGAA     840
CTACAAATAC TAACACAAGC AACAACAGCA ACACTAACAG TCAAGCAAGT CAAAGTAATG     900
ACATTGATAG TCTCTTGAAA CAGCTCTACA AACTGCCTTT GAGTCAACGC ATGTAGAAT      960
CTGATGGCCT TATTTTCGAC CCAGCGCAAA TCACAAGTCG AACCGCCAGA GGTGTAGCTG    1020
TCCCTCATGG TAACCATTAC CACTTTATCC CTTATGAACA AATGTCTGAA TTGGAAAAAC    1080
GAATTGCTCG TATTATTCCC CTTCGTTATC GTTCAAACCA TTGGGTACCA GATTCAAGAC    1140
CAGAAGAACC AAGTCCACAA CCGACTCCAG AACCTAGTCC AAGTCCGCAA CCTGCACCAA    1200
ATCCTCAACC AGCTCCAAGC AATCCAATTG ATGAGAAATT GGTCAAAGAA GCTGTTCGAA    1260
AAGTAGGCGA TGGTTATGTC TTTGAGGAGA ATGGAGTTTC TCGTTATATC CCAGCCAAGA    1320
ATCTTTCAGC AGAAACAGCA GCAGGCATTG ATAGCAAACT GGCCAAGCAG GAAAGTTTAT    1380
CTCATAAGCT AGGAGCTAAG AAAACTGACC TCCCATCTAG TGATCGAGAA TTTTACAATA    1440
AGGCTTATGA CTTACTAGCA AGAATTCACC AAGATTTACT TGATAATAAA GGTCGACAAG    1500
TTGATTTTGA GGCTTTGGAT AACCTGTTGG AACGACTCAA GGATGTCTCA AGTGATAAAG    1560
TCAAGTTAGT GGATGATATT CTTGCCTTCT TAGCTCCGAT TCGTCATCCA GAACGTTTAG    1620
GAAAACCAAA TGCGCAAATT ACCTACACTG ATGATGAGAT TCAAGTAGCC AAGTTGGCAG    1680
GCAAGTACAC AACAGAAGAC GGTTATATCT TTGATCCTCG TGATATAACC AGTGATGAGG    1740
GGGATGCCTA TGTAACTCCA CATATGACCC ATAGCCACTG GATTAAAAAA GATAGTTTGT    1800
CTGAAGCTGA GAGAGCGGCA GCCCAGGCTT ATGCTAAAGA GAAAGGTTTG ACCCCTCCTT    1860
CGACAGACCA TCAGGATTCA GGAAATACTG AGGCAAAAGG AGCAGAAGCT ATCTACAACC    1920
GCGTGAAAGC AGCTAAGAAG GTGCCACTTG ATCGTATGCC TTACAATCTT CAATATACTG    1980
TAGAAGTCAA AAACGGTAGT TTAATCATAC CTCATTATGA CCATTACCAT AACATCAAAT    2040
TTGAGTGGTT TGACGAAGGC CTTTATGAGG CACCTAAGGG GTATACTCTT GAGGATCTTT    2100
TGGCGACTGT CAAGTACTAT GTCGAACATC CAAACGAACG TCCGCATTCA GATAATGGTT    2160
TTGGTAACGC TAGCGACCAT GTTCAAAGAA ACAAAAATGG TCAAGCTGAT ACCAATCAAA    2220
CGGAAAAACC AAGCGAGGAG AAACCTCAGA CAGAAAAACC TGAGGAAGAA ACCCCTCGAG    2280
AAGAGAAACC ACAAAGCGAG AAACCAGAGT CTCCAAAACC AACAGAGGAA CCAGAAGAAG    2340
AATCACCAGA GGAATCAGAA GAACCTCAGG TCGAGACTGA AAAGGTTGAA GAAAACTGA     2400
GAGAGGCTGA AGATTTACTT GGAAAAATCC AGGATCCAAT TATCAAGTCC AATGCCAAAG    2460
AGACTCTCAC AGGATTAAAA AATAATTTAC TATTTGGCAC CCAGGACAAC AATACTATTA    2520
TGGCAGAAGC TGAAAAACTA TTGGCTTTAT TAAAGGAGAG TAAGTAAAGG TAGCAGCATT    2580
TTCTAACTCC TAAAAACAGG ATAGGAGAAC GGGAAAACGA AAAATGAGAG CAGAATGTGA    2640
GTTCTAG    (SED ID NO : 12)                                          2647
```

*FIG. 15*

```
GGGTCTTAAA ACTCTGAATC CTTTAGAGGC AGACCCACAA AATGACAAGA CCTATTTAGA      60
AAATCTGGAA GAAAATATGA GTGTTCTAGC AGAAGAATTA AAGTGAGGAA AGAATGAAAA     120
TCAATAAAAA ATATCTAGCA GGTTCAGTGG CAGTCCTTGC CCTAAGTGTT TGTTCCTATG     180
AACTTGGTCG TCACCAAGCT GGTCAGGTTA AGAAAGAGTC TAATCGAGTT TCTTATATAG     240
ATGGTGATCA GGCTGGTCAA AAGGCAGAAA ATTTGACACC AGATGAAGTC AGTAAGAGAG     300
AGGGGATCAA CGCCGAACAA ATTGTTATCA AGATTACGGA TCAAGGTTAT GTGACCTCTC     360
ATGGAGACCA TTATCATTAC TATAATGGCA AGGTTCCTTA TGATGCCATC ATCAGTGAAG     420
AACTTCTCAT GAAAGATCCG AATTATCAGT TGAAGGATTC AGACATTGTC AATGAAATCA     480
AGGGTGGCTA TGTGATTAAG GTAGACGGAA AATACTATGT TTACCTTAAA GATGCGGCCC     540
ATGCGGACAA TATTCGGACA AAAGAAGAGA TTAAACGTCA GAAGCAGGAA CACAGTCATA     600
ATCATAACTC AAGAGCAGAT AATGCTGTTG CTGCAGCCAG AGCCCAAGGA CGTTATACAA     660
CGGATGATGG GTATATCTTC AATGCATCTG ATATCATTGA GGACACGGGT GATGCTTATA     720
TCGTTCCTCA CGGCGACCAT TACCATTACA TTCCTAAGAA TGAGTTATCA GCTAGCGAGT     780
TAGCTGCTGC AGAAGCCTAT TGGAATGGGA AGCAGGGATC TCGTCCTTCT TCAAGTTCTA     840
GTTATAATGC AAATCCAGTT CAACCAAGAT TGTCAGAGAA CCACAATCTG ACTGTCACTC     900
CAACTTATCA TCAAAATCAA GGGGAAAACA TTTCAAGCCT TTTACGTGAA TTGTATGCTA     960
AACCCTTATC AGAACGCCAT GTAGAATCTG ATGGCCTTAT TTTCGACCCA GCGCAAATCA    1020
CAAGTCGAAC CGCCAGAGGT GTAGCTGTCC CTCATGGTAA CCATTACCAC TTTATCCCTT    1080
ATGAACAAAT GTCTGAATTG GAAAAACGAA TTGCTCGTAT TATTCCCCTT CGTTATCGTT    1140
CAAACCATTG GGTACCAGAT TCAAGACCAG AACAACCAAG TCCACAATCG ACTCCGGAAC    1200
CTAGTCCAAG TCTGCAACCT GCACCAAATC CTCAACCAGC TCCAAGCAAT CCAATTGATG    1260
AGAAATTGGT CAAAGAAGCT GTTCGAAAAG TAGGCGATGG TTATGTCTTT GAGGAGAATG    1320
GAGTTTCTCG TTATATCCCA GCCAAGGATC TTTCAGCAGA AACAGCAGCA GGCATTGATA    1380
GCAAACTGGC CAAGCAGGAA AGTTTATCTC ATAAGCTAGG AGCTAAGAAA ACTGACCTCC    1440
CATCTAGTGA TCGAGAATTT TACAATAAGG CTTATGACTT ACTAGCAAGA ATTCACCAAG    1500
ATTTACTTGA TAATAAAGGT CGACAAGTTG ATTTTGAGGT TTTGGATAAC CTGTTGGAAC    1560
GACTCAAGGA TGTCTCAAGT GATAAAGTCA AGTTAGTGGA TGATATTCTT GCCTTCTTAG    1620
CTCCGATTCG TCATCCAGAA CGTTTAGGAA AACCAAATGC GCAAATTACC TACACTGATG    1680
ATGAGATTCA AGTAGCCAAG TTGGCAGGCA AGTACACAAC AGAAGACGGT TATATCTTTG    1740
ATCCTCGTGA TATAACCAGT GATGAGGGGG ATGCCTATGT AACTCCACAT ATGACCCATA    1800
GCCACTGGAT TAAAAAAGAT AGTTTGTCTG AAGCTGAGAG AGCGGCAGCC AGGCTTATG     1860
CTAAAGAGAA AGGTTTGACC CCTCCTTCGA CAGACCACCA GGATTCAGGA AATACTGAGG    1920
CAAAAGGAGC AGAAGCTATC TACAACCGCG TGAAAGCAGC TAAGAAGGTG CCACTTGATC    1980
GTATGCCTTA CAATCCTTCAA TATACTGTAG AAGTCAAAAA CGGTAGTTTA ATCATACCTC    2040
ATTATGACCA TTACCATAAC ATCAAATTTG AGTGGTTTGA CGAAGGCCTT TATGAGGCAC    2100
CTAAGGGGTA TAGTCTTGAG GATCTTTTGG CGACTGTCAA GTACTATGTC GAACATCCAA    2160
ACGAACGTCC GCATTCAGAT AATGGTTTTG GTAACGCTAG TGACCATGTT CGTAAAAATA    2220
AGGCAGACCA AGATAGTAAA CCTGATGAAG ATAAGGAACA TGATGAAGTA AGTGAGCCAA    2280
CTCACCCTGA ATCTGATGAA AAAGAGAATC ACGCTGGTTT AAATCCTTCA GCAGATAATC    2340
TTTATAAACC AAGCACTGAT ACGGAAGAGA CAGAGGAAGA AGCTGAAGAT ACCACAGATG    2400
AGGCTGAAAT TCCTCAAGTA GAGAATTCTG TTATTAACGC TAAGATAGCA GATGCGGAGG    2460
CCTTGCTAGA AAAGTAACA GATCCTAGTA TTAGACAAAA TGCTATGGAG ACATTGACTG     2520
GTCTAAAAAG TAGTCTTCTT CTCGGAACGA AAGATAATAA CACTATTTCA GCAGAAGTAG    2580
ATAGTCTCTT GGCTTTGTTA AAAGAAAGTC AACCGGCTCC TATACAGTAG TAAAATGAA     2639
(SEQ ID NO : 13)
```

FIG. 16

| | | | | | |
|---|---|---|---|---|---|
| MKINKKYLAG | SVAVLALSVC | SYELGRHQAG | QVKKESNRVS | YIDGDQAGQK | 50 |
| AENLTPDEVS | KREGINAEQI | VIKITDQGYV | TSHGDHYHYY | NGKVPYDAII | 100 |
| SEELLMKDPN | YQLKDSDIVN | EIKGGYVIKV | DGKYYVYLKD | AAHADNIRTK | 150 |
| EEIKRQKQEH | SHNHNSRADN | AVAAARAQGR | YTTDDGYIFN | ASDIIEDTGD | 200 |
| AYIVPHGDHY | HYIPKNELSA | SELAAAEAYW | NGKQGSRPSS | SSSYNANPVQ | 250 |
| PRLSENHNLT | VTPTYHQNQG | ENISSLLREL | YAKPLSERHV | ESDGLIFDPA | 300 |
| QITSRTARGV | AVPHGNHYHF | IPYEQMSELE | KRIARIIPLR | YRSNHWVPDS | 350 |
| RPEQPSPQST | PEPSPSLQPA | PNPQPAPSNP | IDEKLVKEAV | RKVGDGYVFE | 400 |
| ENGVSRYIPA | KDLSAETAAG | IDSKLAKQES | LSHKLGAKKT | DLPSSDREFY | 450 |
| NKAYDLLARI | HQDLLDNKGR | QVDFEVLDNL | LERLKDVSSD | KVKLVDDILA | 500 |
| FLAPIRHPER | LGKPNAQITY | TDDEIQVAKL | AGKYTTEDGY | IFDPRDITSD | 550 |
| EGDAYVTPHM | THSHWIKKDS | LSEAERAAAQ | AYAKEKGLTP | PSTDHQDSGN | 600 |
| TEAKGAEAIY | NRVKAAKKVP | LDRMPYNLQY | TVEVKNGSLI | IPHYDHYHNI | 650 |
| KFEWFDEGLY | EAPKGYSLED | LLATVKYYVE | HPNERPHSDN | GFGNASDHVR | 700 |
| KNKADQDSKP | DEDKEHDEVS | EPTHPESDEK | ENHAGLNPSA | DNLYKPSTDT | 750 |
| EETEEEAEDT | TDEAEIPQVE | NSVINAKIAD | AEALLEKVTD | PSIRQNAMET | 800 |
| LTGLKSSLLL | GTKDNNTISA | EVDSLLALLK | ESQPAPIQ | | 838 |

(SEQ ID NO : 14)

*FIG. 17*

```
TGTGCCTATG CACTAAACCA GCATCGTTCG CAGGAAAATA AGGACAATAA TCGTGTCTCT    60
TATGTGGATG GCAGCCAGTC AAGTCAGAAA AGTGAAAACT TGACACCAGA CCAGGTTAGC   120
CAGAAAGAAG GAATTCAGGC TGAGCAAATT GTAATCAAAA TTACAGATCA GGGCTATGTA   180
ACGTCACACG GTGATCACTA TCATTACTAT AATGGGAAAG TTCCTTATGA TGCCCTCTTT   240
AGTGAAGAAC TCTTGATGAA GGATCCAAAC TATCAACTTA AAGACGCTGA TATTGTCAAT   300
GAAGTCAAGG GTGGTTATAT CATCAAGGTC GATGGAAAAT ATTATGTCTA CCTGAAAGAT   360
GCAGCTCATG CTGATAATGT TCGAACTAAA GATGAAATCA ATCGTCAAAA ACAAGAACAT   420
GTCAAAGATA ATGAGAAGGT TAACTCTAAT GTTGCTGTAG CAAGGTCTCA GGGACGATAT   480
ACGACAAATG ATGGTTATGT CTTTAATCCA GCTGATATTA TCGAAGATAC GGGTAATGCT   540
TATATCGTTC CTCATGGAGG TCACTATCAC TACATTCCCA AAAGCGATTT ATCTGCTAGT   600
GAATTAGCAG CAGCTAAAGC ACATCTGGCT GGAAAAAATA TGCAACCGAG TCAGTTAAGC   660
TATTCTTCAA CACCTTCTCC ATCTCTTCCA ATCAATCCAG GAACTTCACA TGAGAAACAT   720
GAAGAAGATG GATACGGATT TGATGCTAAT CGTATTATCG CTGAAGATGA ATCAGGTTTT   780
GTCATGAGTC ACGGAGACCA CAATCATTAT TTCTTCAAGA AGGACTTGAC AGAAGAGCAA   840
ATTAAGGCTG CGCAAAAACA TTTAGAGGAA GTTAAAACTA GTCATAATGG ATTAGATTCT   900
TTGTCATCTC ATGAACAGGA TTATCCAAGT AATGCCAAAG AAATGAAAGA TTTAGATAAA   960
AAAATCGAAG AAAAAATTGC TGGCATTATG AAACAATATG GTGTCAAACG TGAAAGTATT  1020
GTCGTGAATA AAGAAAAAAA TGCGATTATT TATCCGCATG GAGATCACCA TCATGCAGAT  1080
CCGATTGATG AACATAAACC GGTTGGAATT GGTCATTCTC ACAGTAACTA TGAACTGTTT  1140
AAACCCGAAG AAGGAGTTGC TAAAAAAGAA GGGAATAAAG TTTATACTGG AGAAGAATTA  1200
ACGAATGTTG TTAATTTGTT AAAAAAATAGT ACGTTAATA ATCAAAACTT TACTCTAGCC  1260
AATGGTCAAA AACGCGTTTC TTTTAGTTTT CCGCCTGAAT TGGAGAAAAA ATTAGGTATC  1320
AATATGCTAG TAAAATTAAT AACACCAGAT GGAAAAGTAT TGGAGAAAGT ATCTGGTAAA  1380
GTATTTGGAG AAGGAGTAGG GAATATTGCA AACTTTGAAT TAGATCAACC TTATTTACCA  1440
GGACAAACAT TTAAGTATAC TATCGCTTCA AAAGATTATC CAGAAGTAAG TTATGATGGT  1500
ACATTTACAG TTCCAACCTC TTTAGCTTAC AAAATGGCCA GTCAAACGAT TTTCTATCCT  1560
TTCCATGCAG GGGATACTTA TTTAAGAGTG AACCCTCAAT TTGCAGTGCC TAAAGGAACT  1620
GATGCTTTAG TCAGAGTGTT TGATGAATTT CATGGAAATG CTTATTTAGA AAATAACTAT  1680
AAAGTTGGTG AAATCAAATT ACCGATTCCG AAATTAAACC AAGGAACAAC CAGAACGGCC  1740
GGAAATAAAA TTCCTGTAAC CTTCATGGCA AATGCTTATT TGGACAATCA ATCGACTTAT  1800
ATTGTGGAAG TACCTATCTT GGAAAAAGAA AATCAAACTG ATAAACCAAG TATTCTACCA  1860
CAATTTAAAA GGAATAAAGC ACAAGAAAAC TCAAACTTG ATGAAAGGT AGAAGAACCA  1920
AAGACTAGTG AGAAGGTAGA AAAAGAAAAA CTTTCTGAAA CTGGGAATAG TACTAGTAAT  1980
TCAACGTTAG AAGAAGTTCC TACAGTGGAT CCTGTACAAG AAAAAGTAGC AAAATTTGCT  2040
GAAAGTTATG GGATGAAGCT AGAAAATGTC TTGTTTAATA TGGACGGAAC AATTGAATTA  2100
TATTTACCAT CGGGAGAAGT CATTAAAAAG AATATGGCAG ATTTTACAGG AGAAGCACCT  2160
CAAGGAAATG GTGAAAATAA ACCATCTGAA AATGGAAAAG TATCTACTGG AACAGTTGAG  2220
AACCAACCAA CAGAAAATAA ACCAGCAGAT TCTTTACCAG AGGCACCAAA CGAAAAACCT  2280
GTAAAACCAG AAAACTCAAC GGATAATGGA ATGTTGAATC CAGAAGGGAA TGTGGGAGT   2340
GACCCTATGT TAGATTCAGC ATTAGAGGAA GCTCCAGCAG TAGATCCTGT ACAAGAAAAA  2400
TTAGAAAAAT TTACAGCTAG TTACGGATTA GGCTTAGATA GTGTTATATT CAATATGGAT  2460
GGAACGATTG AATTAAGATT GCCAAGTGGA GAAGTGATAA AAAAGAATTT ATTGATCTCA  2520
TAGCGTAA      (SEQ ID NO : 15)                                     2528
```

FIG. 18

```
CAYALNQHRS QENKDNNRVS YVDGSQSSQK SENLTPDQVS QKEGIQAEQI      50
VIKITDQGYV TSHGDHYHYY NGKVPYDALF SEELLMKDPN YQLKDADIVN     100
EVKGGYIIKV DGKYYVYLKD AAHADNVRTK DEINRQKQEH VKDNEKVNSN     150
VAVARSQGRY TTNDGYVFNP ADIIEDTGNA YIVPHGGHYH YIPKSDLSAS     200
ELAAAKAHLA GKNMQPSQLS YSSTPSPSLP INPGTSHEKH EEDGYGFDAN     250
RIIAEDESGF VMSHGDHNHY FFKKDLTEEQ IKAAQKHLEE VKTSHNGLDS     300
LSSHEQDYPS NAKEMKDLDK KIEEKIAGIM KQYGVKRESI VVNKEKNAII     350
YPHGDHHHAD PIDEHKPVGI GHSHSNYELF KPEEGVAKKE GNKVYTGEEL     400
TNVVNLLKNS TFNNQNFTLA NGQKRVSFSF PPELEKKLGI NMLVKLITPD     450
GKVLEKVSGK VFGEGVGNIA NFELDQPYLP GQTFKYTIAS KDYPEVSYDG     500
TFTVPTSLAY KMASQTIFYP FHAGDTYLRV NPQFAVPKGT DALVRVFDEF     550
HGNAYLENNY KVGEIKLPIP KLNQGTTRTA GNKIPVTFMA NAYLDNQSTY     600
IVEVPILEKE NQTDKPSILP QFKRNKAQEN SKLDEKVEEP KTSEKVEKEK     650
LSETGNSTSN STLEEVPTVD PVQEKVAKFA ESYGMKLENV LFNMDGTIEL     700
YLPSGEVIKK NMADFTGEAP QGNGENKPSE NGKVSTGTVE NQPTENKPAD     750
SLPEAPNEKP VKPENSTDNG MLNPEGNVGS DPMLDSALEE APAVDPVQEK     800
LEKFTASYGL GLDSVIFNMD GTIELRLPSG EVIKKNLLIS                840
(SEQ ID NO : 16)
```

FIG. 19

```
CAYALNQHRS QENKDNNRVS YVDGSQSSQK SENLTPDQVS QKEGIQAEQI      50
VIKITDQGYV TSHGDHYHYY NGKVPYDALF SEELLMKDPN YQLKDADIVN     100
EVKGGYIIKV DGKYYVYLKD AAHADNVRTK DEINRQKQEH VKDNEKVNSN     150
VAVARSQGRY TTNDGYVFNP ADIIEDTGNA YIVPHGGHYH YIPKSDLSAS     200
ELAAAKAHLA GKNMQPSQLS YSSTASDNNT QSVAKGSTSK PANKSENLQS     250
LLKELYDSPS AQRYSESDGL VFDPAKIISR TPNGVAIPHG DHYHFIPYSK     300
LSALEEKIAR MVPISGTGST VSTNAKPNEV VSSLGSLSSN PSSLTTSKEL     350
SSASDGYIFN PKDIVEETAT AYIVRHGDHF HYIPKSNQIG QPTLPNNSLA     400
TPSPSLPINP GTSHEKHEED GYGFDANRII AEDESGFVMS HGDHNHYFFK     450
KDLTEEQIKA AQKHLEEVKT SHNGLDSLSS HEQDYPGNAK EMKDLDKKIE     500
EKIAGIMKQY GVKRESIVVN KEKNAIIYPH GDHHHADPID EHKPVGIGHS     550
HSNYELFKPE EGVAKKEGNK VYTGEELTNV VNLLKNSTFN NQNFTLANGQ     600
KRVSFSFPPE LEKKLGINML VKLITPDGKV LEKVSGKVFG EGVGNIANFE     650
LDQPYLPGQT FKYTIASKDY PEVSYDGTFT VPTSLAYKMA SQTIFYPFHA     700
GDTYLRVNPQ FAVPKGTDAL VRVFDEFHGN AYLENNYKVG EIKLPIPKLN     750
QGTTRTAGNK IPVTFMANAY LDNQSTYIVE VPILEKENQT DKPSILPQFK     800
RNKAQENSKL DEKVEEPKTS EKVEKEKLSE TGNSTSNSTL EEVPTVDPVQ     850
EKVAKFAESY GMKLENVLFN MDGTIELYLP SGEVIKKNMA DFTGEAPQGN     900
GENKPSENGK VSTGTVENQP TENKPADSLP EAPNEKPVKP ENSTDNGMLN     950
PEGNVGSDPM LDPALEEAPA VDPVQEKLEK FTASYGLGLD SVIFNMDGTI    1000
ELRLPSGEVI KKNLSDFIA        (SEQ ID NO : 55)               1019
```

FIG. 20

```
CAYALNQHRS QENKDNNRVS YVDGSQSSQK SENLTPDQVS QKEGIQAEQI    50
VIKITDQGYV TSHGDHYHYY NGKVPYDALF SEELLMKDPN YQLKDADIVN   100
EVKGGYIIKV DGKYYVYLKD AAHADNVRTK DEINRQKQEH VKDNEKVNSN   150
VAVARSQGRY TTNDGYVFNP ADIIEDTGNA YIVPHGGHYH YIPKSDLSAS   200
ELAAAKAHLA GKNMQPSQLS YSSTASDNNT QSVAKGSTSK PANKSENLQS   250
LLKELYDSPS AQRYSESDGL VFDPAKIISR TPNGVAIPHG DHYHFIPYSK   300
LSALEEKIAR MVPISGTGST VSTNAKPNEV VSSLGSLSSN PSSLTTSKEL   350
SSASDGYIFN PKDIVEETAT AYIVRHGDHF HYIPKSNQIG QPTLPNNSLA   400
TPSPSLPINP GTSHEKHEED GYGFDANRII AEDESGFVMS HGDHNHYFFK   450
KDLTEEQIKA AQKHLEEVKT SHNGLDSLSS HEQDYPGNA              489
(SEQ ID NO : 56)
```

*FIG. 21*

```
MKFSKKYIAA GSAVIVSLSL CAYALNQHRS QENKDNNRVS YVDGSQSSQK SENLTPDQVS    60
QKEGIQAEQI VIKITDQGYV TSHGDHYHYY NGKVPYDALF SEELLMKDPN YQLKDADIVN   120
EVKGGYIIKV DGKYYVYLKD AAHADNVRTK DEINRQKQEH VKDNEKVNSN VAVARSQGRY   180
TTNDGYVFNP ADIIEDTGNA YIVPHGGHYH YIPKSDLSAS ELAAAKAHLA GKNMQPSQLS   240
YSSTASDNNT QSVAKGSTSK PANKSENLQS LLKELYDSPS AQRYSESDGL VFDPAKIISR   300
TPNGVAIPHG DHYHFIPYSK LSALEEKIAR MVPISGTGST VSTNAKPNEV VSSLGSLSSN   360
PSSLTTSKEL SSASDGYIFN PKDIVEETAT AYIVRHGDHF HYIPKSNQIG QPTLPNNSLA   420
TPSPSLPINP GTSHEKHEED GYGFDANRII AEDESGFVMS HGDHNHYFFK KDLTEEQIKA   480
AQKHLEEVKT SHNGLDSLSS HEQDYPGNA   (SEQ ID NO : 57)                509
```

*FIG. 22*

```
DLTEEQIKAA QKHLEEVKTS HNGLDSLSSH EQDYPGNAKE MKDLDKKIEE    50
KIAGIMKQYG VKRESIVVNK EKNAIIYPHG DHHHADPIDE HKPVGIGHSH   100
SNYELFKPEE GVAKKEGNKV YTGEELTNVV NLLKNSTFNN QNFTLANGQK   150
RVSFSFPPEL EKKLGINMLV KLITPDGKVL EKVSGKVPGE GVGNIANFEL   200
DQPYLPGQTF KYTIASKDYP EVSYDGTFTV PTSLAYKMAS QTIFYPFHAG   250
DTYLRVNPQF AVPKGTDALV RVFDEFHGNA YLENNYKVGE IKLPIPKLNQ   300
GTTRTAGNKI PVTFMANAYL DNQSTYIVEV PILEKENQTD KPSILPQFKR   350
NKAQENSKLD EKVEEPKTSE KVEKEKLSET GNSTSNSTLE EVPTVDPVQE   400
KVAKFAESYG MKLENVLFNM DGTIELYLPS GEVIKKNMAD FTGEAPQGNG   450
ENKPSENGKV STGTVENQPT ENKPADSLPE APNEKPVKPE NSTDNGMLNP   500
EGNVGSDPML DPALEEAPAV DPVQEKLEKF TASYGLGLDS VIFNMDGTIE   550
LRLPSGEVIK KNLSDFIAKL RYRSNHWVPD SRPEEPSPQP TPEPSPSPQP   600
APNPQPAPSN PIDEKLVKEA VRKVGDGYVF EENGVSRYIP AKNLSAETAA   650
GIDSKLAKQE SLSHKLGAKK TDLPSSDREF YNKAYDLLAR IHQDLLDNKG   700
RQVDFEALDN LLERLKDVSS DKVKLVDDIL AFLAPIRHPE RLGKPNAQIT   750
YTDDEIQVAK LAGKYTTEDG YIFDPRDITS DEGDAYVTPH MTHSHWIKKD   800
SLSEAERAAA QAYAKEKGLT PPSTDHQDSG NTEAKGAEAI YNRVKAAKKV   850
PLDRMPYNLQ YTVEVKNGSL IIPHYDHYHN IKFEWFDEGL YEAPKGYTLE   900
DLLATVKYYV EHPNERPHSD NGFGNASDHV QRNKNGQADT NQTEKPSEEK   950
PQTEKPEEET PREEKPQSEK PESPKPTEEP EEESPEESEE PQVETEKVEE  1000
KLREAEDLLG KIQDPIIKSN AKETLTGLKN NLLFGTQDNN TIMAEAEKLL  1050
ALLKESK   (SEQ ID NO : 58)                              1057
```

*FIG. 23*

```
CAYALNQHRS QENKDNNRVS YVDGSQSSQK SENLTPDQVS QKEGIQAEQI    50
VIKITDQGYV TSHGDHYHYY NGKVPYDALF SEELLMKDPN YQLKDADIVN   100
EVKGGYIIKV DGKYYVYLKD AAHADNVRTK DEINRQKQEH VKDNEKVNSN   150
VAVARSQGRY TTNDGYVFNP ADIIEDTGNA YIVPHGGHYH YIPKSDLSAS   200
ELAAA      (SEQ ID NO : 59)                             205
```

FIG. 24

```
CAYELGLHQA QTVKENNRVS YIDGKQATQK TENLTPDEVS KREGINAEQI    50
VIKITDQGYV TSHGDHYHYY NGKVPYDAII SEELLMKDPN YQLKDSDIVN   100
EIKGGYVIKV NGKYYVYLKD AAHADNVRTK EEINRQKQEH SQHREGGTSA   150
NDGAVAFARS QGRYTTDDGY IFNASDIIED TGDAYIVPHG DHYHYIPKNE   200
LSASELAAAE AFLSGRENLS NLRTYRRQNS DNTPRTNWVP SVSNPGTTNT   250
NTSNNSNTNS QASQSNDIDS LLKQLYKLPL SQRHVESDGL IFDPAQITSR   300
TARGVAVPHG NHYHFIPYEQ MSELEKRIAR IIPLRYRSNH WVPDSRPEEP   350
SPQPTPEPSP SPQPAPNPQP APSNPIDEKL VKEAVRKVGD GYVFEENGVS   400
RYIPAKNLSA ETAAGIDSKL AKQESLSHKL GAKKTDLPSS DREFYNKAYD   450
LLARIHQDLL DNKGRQVDFE ALDNLLERLK DVSSDKVKLV DDILAFLAPI   500
RHPERLGKPN AQITYTDDEI QVAKLAGKYT TEDGYIFDPR DITSDEGDAY   550
VTPHMTHSHW IKKDSLSEAE RAAAQAYAKE KGLTPPSTDH QDSGNTEAKG   600
AEAIYNRVKA AKKVPLDRMP YNLQYTVEVK NGSLIIPHYD HYHNIKFEWF   650
DEGLYEAPKG YTLEDLLATV KYYVEHPNER PHSDNGFGNA SDHVQRNKNG   700
QADTNQTEKP SEEKPQTEKP EEETPREEKP QSEKPESPKP TEEPEEESPE   750
ESEEPQVETE KVEEKLREAE DLLGKIQDPI IKSNAKETLT GLKNNLLFGT   800
QDNNTIMAEA EKLLALLKES K        ((SEQ ID NO : 60)        821
```

FIG. 25

```
CAYELGLHQA QTVKENNRVS YIDGKQATQK TENLTPDEVS KREGINAEQI    50
VIKITDQGYV TSHGDHYHYY NGKVPYDAII SEELLMKDPN YQLKDSDIVN   100
EIKGGYVIKV NGKYYVYLKD AAHADNVRTK EEINRQKQEH SQHREGGTSA   150
NDGAVAFARS QGRYTTDDGY IFNASDIIED TGDAYIVPHG DHYHYIPKNE   200
LSASELAAAE AFLSGRENLS NLRTYRRQNS DNTPRTNWVP SVSNPGTTNT   250
NTSNNSNTNS QASQSNDIDS LLKQLYKLPL SQRHVESDGL IFDPAQITSR   300
TARGVAVPHG NHYHFIPYEQ MSELEKRIAR IIPL                   334
(SEQ ID NO : 61)
```

FIG. 26

```
RYRSNHWVPD SRPEEPSPQP TPEPSPSPQP APNPQPAPSN PIDEKLVKEA    50
VRKVGDYVF  EENGVSRYIP AKNLSAETAA GIDSKLAKQE SLSHKLGAKK   100
TDLPSSDREF YNKAYDLLAR IHQDLLDNKG RQVDFEALDN LLERLKDVSS   150
DKVKLVDDIL AFLAPIRHPE RLGKPNAQIT YTDDEIQVAK LAGKYTTEDG   200
YIFDPRDITS DEGDAYVTPH MTHSHWIKKD SLSEAERAAA QAYAKEKGLT   250
PPSTDHQDSG NTEAKGAEAI YNRVKAAKKV PLDRMPYNLQ YTVEVKNGSL   300
IIPHYDHYHN IKFEWFDEGL YEAPKGYTLE DLLATVKYYV EHPNERPHSD   350
NGFGNASDHV QRNKNGQADT NQTEKPSEEK PQTEKPEEET PREEKPQSEK   400
PESPKPTEEP EEESPEESEE PQVETEKVEE KLREAEDLLG KIQDPIIKSN   450
AKETLTGLKN NLLFGTQDNN TIMAEAEKLL ALLKESK                487
(SEQ ID NO : 62)
```

FIG. 27

| | | | | | |
|---|---|---|---|---|---|
| AEAFLSGREN | LSNLRTYRRQ | NSDNTPRTNW | VPSVSNPGTT | NTNTSNNSNT | 50 |
| NSQASQSNDI | DSLLKQLYKL | PLSQRHVESD | GLIFDPAQIT | SRTARGVAVP | 100 |
| HGNHYHFIPY | EQMSELEKRI | ARIIPLRYRS | NHWVPDSRPE | EPSPQPTPEP | 150 |
| SPSPQPAPNP | QPAPSNPIDE | KLVKEAVRKV | GDGYVFEENG | VSRYIPAKNL | 200 |
| SAETAAGIDS | KLAKQESLSH | KLGAKKTDLP | SSDREFYNKA | YDLLARIHQD | 250 |
| LLDNKGRQVD | FEALDNLLER | LKDVSSDKVK | LVDDILAFLA | PIRHPERLGK | 300 |
| PNAQITYTDD | EIQVAKLAGK | YTTEDGYIFD | PRDITSDEGD | AYVTPHMTHS | 350 |
| HWIKKDSLSE | AERAAAQAYA | KEKGLTPPST | DHQDSGNTEA | KGAEAIYNRV | 400 |
| KAAKKVPLDR | MPYNLQYTVE | VKNGSLIIPH | YDHYHNIKFE | WFDEGLYEAP | 450 |
| KGYTLEDLLA | TVKYYVEHPN | ERPHSDNGFG | NASDHVQRNK | NGQADTNQTE | 500 |
| KPSEEKPQTE | KPEEETPREE | KPQSEKPESP | KPTEEPEEES | PEESEEPQVE | 550 |
| TEKVEEKLRE | AEDLLGKIQD | PIIKSNAKET | LTGLKNNLLF | GTQDNNTIMA | 600 |
| EAEKLLALLK | ESK | (SEQ ID NO : 63) | | | 613 |

FIG. 28

| | | | | | |
|---|---|---|---|---|---|
| DLTEEQIKAA | QKHLEEVKTS | HNGLDSLSSH | EQDYPGNAKE | MKDLDKKIEE | 50 |
| KIAGIMKQYG | VKRESIVVNK | EKNAIIYPHG | DHHHADPIDE | HKPVGIGHSH | 100 |
| SNYELFKPEE | GVAKKEGNKV | YTGEELTNVV | NLLKNSTFNN | QNFTLANGQK | 150 |
| RVSFSFPPEL | EKKLGINMLV | KLITPDGKVL | EKVSGKVFGE | GVGNIANFEL | 200 |
| DQPYLPGQTF | KYTIASKDYP | EVSYDGTFTV | PTSLAYKMAS | QTIFYPFHAG | 250 |
| DTYLRVNPQF | AVPKGTDALV | RVFDEFHGNA | YLENNYKVGE | IKLPIPKLNQ | 300 |
| GTTRTAGNKI | PVTFMANAYL | DNQSTYIVEV | PILEKENQTD | KPSILPQFKR | 350 |
| NKAQENSKLD | EKVEEPKTSE | KVEKEKLSET | GNSTSNSTLE | EVPTVDPVQE | 400 |
| KVAKFAESYG | MKLENVLFNM | DGTIELYLPS | GEVIKKNMAD | FTGEAPQGNG | 450 |
| ENKPSENGKV | STGTVENQPT | ENKPADSLPE | APNEKPVKPE | NSTDNGMLNP | 500 |
| EGNVGSDPML | DPALEEAPAV | DPVQEKLEKF | TASYGLGLDS | VIFNMDGTIE | 550 |
| LRLPSGEVIK | KNLSDFIA | (SEQ ID NO : 64) | | | 568 |

FIG. 29

| | | | | | |
|---|---|---|---|---|---|
| DLTEEQIKAA | QKHLEEVKTS | HNGLDSLSSH | EQDYPGNAKE | MKDLDKKIEE | 50 |
| KIAGIMKQYG | VKRESIVVNK | EKNAIIYPHG | DHHHADPIDE | HKPVGIGHSH | 100 |
| SNYELFKPEE | GVAKKEGNKV | YTGEELTNVV | NLLKNSTFNN | QNFTLANGQK | 150 |
| RVSFSFPPEL | EKKLGINMLV | KLITPDGKVL | EKVSGKVFGE | GVGNIANFEL | 200 |
| DQPYLPGQTF | KYTIASKDYP | EVSYDGTFTV | PTSLAYKMAS | QTIFYPFHAG | 250 |
| DTYLRVNPQF | AVPKGTDALV | RVFDEFHGNA | YLENNYKVGE | IKLPIPKLNQ | 300 |
| GTTRTAGNKI | PVTFMANAYL | DNQSTYIVE | (SEQ ID NO : 65) | | 329 |

FIG. 30

```
EVPILEKENQ  TDKPSILPQF  KRNKAQENSK  LDEKVEEPKT  SEKVEKEKLS     50
ETGNSTSNST  LEEVPTVDPV  QEKVAKFAES  YGMKLENVLF  NMDGTIELYL    100
PSGEVIKKNM  ADFTGEAPQG  NGENKPSENG  KVSTGTVENQ  PTENKPADSL    150
PEAPNEKPVK  PENSTDNGML  NPEGNVGSDP  MLDPALEEAP  AVDPVQEKLE    200
KFTASYGLGL  DSVIFNMDGT  IELRLPSGEV  IKKNLSDFIA                240
(SEQ ID NO : 66)
```

*FIG. 31*

```
DIDSLLKQLY  KLPLSQRHVE  SDGLIFDPAQ  ITSRTARGVA  VPHGNHYHFI     50
PYEQMSELEK  RIARIIPLRY  RSNHWVPDSR  PEEPSPQPTP  EPSPSPQPAP    100
NPQPAPSNPI  DEKLVKEAVR  KVGDGYVFEE  NGVSRYIPAK  NLSAETAAGI    150
DSKLAKQESL  SHKLGAKKTD  LPSSDREFYN  KAYDLLARIH  QDLLDNKGRQ    200
VDFEALDNLL  ERLKDVSSDK  VKLVDDILAF  LAPIRHPERL  GKPNAQITYT    250
DDEIQVAKLA  GKYTTEDGYI  FDPRDITSDE  GDAYVTPHMT  HSHWIKKDSL    300
SEAERAAAQA  YAKEKGLTPP  STDHQDSGNT  EAKGAEAIYN  RVKAAKKVPL    350
DRMPYNLQYT  VEVKNGSLII  PHYDHYHNIK  FEWFDEGLYE  APKGYTLEDL    400
LATVKYYVEH  PNERPHSDNG  FGNASDHVQR  NKNGQADTNQ  TEKPSEEKPQ    450
TEKPEEETPR  EEKPQSEKPE  SPKPTEEPEE  ESPEESEEPQ  VETEKVEEKL    500
REAEDLLGKI  QDPIIKSNAK  ETLTGLKNNL  LFGTQDNNTI  MAEAEKLLAL    550
LKESK   (SEQ ID NO : 67)                                      555
```

*FIG. 32*

```
DIDSLLKQLY  KLPLSQRHVE  SDGLIFDPAQ  ITSRTARGVA  VPHGNHYHFI     50
PYEQMSELEK  RIARIIPLRY  RSNHWVPDSR  PEEPSPQPTP  EPSPSPQPAP    100
NPQPAPSNPI  DEKLVKEAVR  KVGDGYVFEE  NGVSRYIPAK  NLSAETAAGI    150
DSKLAKQESL  SHKLGAKKTD  LPSSDREFYN  KAYDLLARIH  QDLLDNKGRQ    200
VDFEALDNLL  ERLKDVSSDK  VKLVDDILAF  LAPIRHPERL  GKPNAQITYT    250
DDEIQVAKLA  GKYTTEDGYI  FDPRDITSDE  GDAYVTPHMT  HSHWIKKDSL    300
SEAERAAAQA  YAKEKGLTPP  STDHQDSGNT  EAKGAEAIYN  RVKAAKKVPL    350
DRMPYNLQYT  VEVKNGSLII  PHYDHYHNIK  FEWFDEGLYE  APKGYTLEDL    400
LATVKYYVEH  PNERPHSDNG  FGNASDHV    (SEQ ID NO : 68)          428
```

*FIG. 33*

```
GLYEAPKGYT  LEDLLATVKY  YVEHPNERPH  SDNGFGNASD  HVQRNKNGQA     50
DTNQTEKPSE  EKPQTEKPEE  ETPREEKPQS  EKPESPKPTE  EPEEESPEES    100
EEPQVETEKV  EEKLREAEDL  L    (SEQ ID NO : 69)                 121
```

*FIG. 34*

```
ASDHVQRNKN  GQADTNQTEK  PSEEKPQTEK  PEEETPREEK  PQSEKPESPK     50
PTEEPEEESP  EESEEPQVET  EKVEEKLREA  EDLLGKIQDP  IIKSNAKETL    100
TGLKNNLLFG  TQDNNTIMAE  AEKLLALLKE  SK                        132
(SEQ ID NO : 70)
```

*FIG. 35*

```
DIDSLLKQLY  KLPLSQRHVE  SDGLIFDPAQ  ITSRTARGVA  VPHGNHYHFI         50
PYEQMSELEK  RIARIIPLRY  RSNHWVPDSR  PEEPSPQPTP  EPSPSPQPAP        100
NPQPAPSNPI  DEKLVKEAVR  KVGDGYVFEE  NGVSRYIPAK  NLSAETAAGI        150
DSKLAKQESL  SHKLGAKKTD  LPSSDREFYN  KAYDLLARIH  QDLLDNKGRQ        200
VDFEALDNLL  ERLKDVSSDK  VKLVDD      (SEQ ID NO : 71)              226
```

*FIG. 36*

```
DILAFLAPIR  HPERLGKPNA  QITYTDDEIQ  VAKLAGKYTT  EDGYIFDPRD         50
ITSDEGDAYV  TPHMTHSHWI  KKDSLSEAER  AAAQAYAKEK  GLTPPSTDHQ        100
DSGNTEAKGA  EAIYNRVKAA  KKVPLDRMPY  NLQYTVEVKN  GSLIIPHYDH        150
YHNIKFEWFD  EGLYEAPKGY  TLEDLLATVK  YYVEHPNERP  HSDNGFGNAS        200
DHV         (SEQ ID NO : 72)                                      203
```

*FIG. 37*

```
CSYELGRHQA  GQVKKESNRV  SYIDGDQAGQ  KAENLTPDEV  SKREGINAEQ         50
IVIKITDQGY  VTSHGDHYHY  YNGKVPYDAI  ISEELLMKDP  NYQLKDSDIV        100
NEIKGGYVIK  VDGKYYVYLK  DAAHADNIRT  KEEIKRQKQE  HSHNHNSRAD        150
NAVAAARAQG  RYTTDDGYIF  NASDIIEDTG  DAYIVPHGDH  YHYIPKNELS        200
ASELAAAEAY  WNGKQGSRPS  SSSSYNANPV  QPRLSENHNL  TVTPTYHQNQ        250
GENISSLLRE  LYAKPLSERH  VESDGLIFDP  AQITSRTARG  VAVPHGNHYH        300
FIPYEQMSEL  EKRIARIIPL  RYRSNHWVPD  SRPEQPSPQS  TPEPSPSLQP        350
APNPQPAPSN  PIDEKLVKEA  VRKVGDGYVF  EENGVSRYIP  AKDLSAETAA        400
GIDSKLAKQE  SLSHKLGAKK  TDLPSSDREF  YNKAYDLLAR  IHQDLLDNKG        450
RQVDFEVLDN  LLERLKDVSS  DKVKLVDDIL  AFLAPIRHPE  RLGKPNAQIT        500
YTDDEIQVAK  LAGKYTTEDG  YIFDPRDITS  DEGDAYVTPH  MTHSHWIKKD        550
SLSEAERAAA  QAYAKEKGLT  PPSTDHQDSG  NTEAKGAEAI  YNRVKAAKKV        600
PLDRMPYNLQ  YTVEVKNGSL  IIPHYDHYHN  IKFEWFDEGL  YEAPKGYSLE        650
DLLATVKYYV  EHPNERPHSD  NGFGNASDHV  RKNKADQDSK  PDEDKEHDEV        700
SEPTHPESDE  KENHAGLNPS  ADNLYKPSTD  TEETEEEAED  TTDEAEIPQV        750
ENSVINAKIA  DAEALLEKVT  DPSIRQNAME  TLTGLKSSLL  LGTKDNNTIS        800
AEVDSLLALL  KESQPAPIQ   (SEQ ID NO : 73)                          819
```

*FIG. 38*

```
ENISSLLREL  YAKPLSERHV  ESDGLIFDPA  QITSRTARGV  AVPHGNHYHF         50
IPYEQMSELE  KRIARIIPLR  YRSNHWVPDS  RPEQPSPQST  PEPSPSLQPA        100
PNPQPAPSNP  IDEKLVKEAV  RKVGDGYVFE  ENGVSRYIPA  KDLSAETAAG        150
IDSKLAKQES  LSHKLGAKKT  DLPSSDREFY  NKAYDLLARI  HQDLLDNKGR        200
QVDFEVLDNL  LERLKDVSSD  KVKLVDDILA  FLAPIRHPER  LGKPNAQITY        250
TDDEIQVAKL  AGKYTTEDGY  IFDPRDITSD  EGDAYVTPHM  THSHWIKKDS        300
LSEAERAAAQ  AYAKEKGLTP  PSTDHQDSGN  TEAKGAEAIY  NRVKAAKKVP        350
LDRMPYNLQY  TVEVKNGSLI  IPHYDHYHNI  KFEWFDEGLY  EAPKGYSLED        400
LLATVKYYVE  HPNERPHSDN  GFGNASDHVR  KNKADQDSKP  DEDKEHDEVS        450
EPTHPESDEK  ENHAGLNPSA  DNLYKPSTDT  EETEEEAEDT  TDEAEIPQVE        500
NSVINAKIAD  AEALLEKVTD  PSIRQNAMET  LTGLKSSLLL  GTKDNNTISA        550
EVDSLLALLK  ESQPAPIQ    (SEQ ID NO : 74)                          568
```

*FIG. 39*

```
VRKNKADQDS KPDEDKEHDE VSEPTHPESD EKENHAGLNP SADNLYKPST    50
DTEETEEEAE DTTDEAEIPQ VENSVINAKI ADAEALLEKV TDPSIRQNAM   100
ETLTGLKSSL LLGTKDNNTI SAEVDSLLAL LKESQPAPIQ             140
(SEQ ID NO : 75)
```

*FIG. 40*

```
GACTTGACAG AAGAGCAAAT TAAGGCTGCG CAAAAACATT TAGAGGAAGT    50
TAAAACTAGT CATAATGGAT TAGATTCTTT GTCATCTCAT GAACAGGATT   100
ATCCAGGTAA TGCCAAAGAA ATGAAAGATT TAGATAAAAA AATCGAAGAA   150
AAAATTGCTG GCATTATGAA ACAATATGGT GTCAAACGTG AAAGTATTGT   200
CGTGAATAAA GAAAAAAATG CGATTATTTA TCCGCATGGA GATCACCATC   250
ATGCAGATCC GATTGATGAA CATAAACCGG TTGGAATTGG TCATTCTCAC   300
AGTAACTATG AACTGTTTAA ACCCGAAGAA GGAGTTGCTA AAAAAGAAGG   350
GAATAAAGTT TATACTGGAG AAGAATTAAC GAATGTTGTT AATTTGTTAA   400
AAAATAGTAC GTTAATAAT CAAAACTTTA CTCTAGCCAA TGGTCAAAAA    450
CGCGTTTCTT TTAGTTTTCC GCCTGAATTG GAGAAAAAAT TAGGTATCAA   500
TATGCTAGTA AAATTAATAA CACCAGATGG AAAAGTATTG GAGAAAGTAT   550
CTGGTAAAGT ATTTGGAGAA GGAGTAGGGA ATATTGCAAA CTTTGAATTA   600
GATCAACCTT ATTTACCAGG ACAAACATTT AAGTATACTA TCGCTTCAAA   650
AGATTATCCA GAAGTAAGTT ATGATGGTAC ATTTACAGTT CCAACCTCTT   700
TAGCTTACAA AATGGCCAGT CAAACGATTT CTATCCTTT CCATGCAGGG    750
GATACTTATT TAAGAGTGAA CCCTCAATTT GCAGTGCCTA AAGGAACTGA   800
TGCTTTAGTC AGAGTGTTTG ATGAATTTCA TGGAAATGCT TATTTAGAAA   850
ATAACTATAA AGTTGGTGAA ATCAAATTAC CGATTCCGAA ATTAAACCAA   900
GGAACAACCA GAACGGCCGG AAATAAAATT CCTGTAACCT TCATGGCAAA   950
TGCTTATTTG ACAATCAAT CGACTTATAT TGTGGAAGTA CCTATCTTGG   1000
AAAAAGAAAA TCAAACTGAT AAACCAAGTA TTCTACCACA ATTTAAAAGG   1050
AATAAAGCAC AAGAAACTC AAAACTTGAT GAAAAGGTAG AAGAACCAAA   1100
GACTAGTGAG AAGGTAGAAA AAGAAAAACT TTCTGAAACT GGGAATAGTA   1150
CTAGTAATTC AACGTTAGAA GAAGTTCCTA CAGTGGATCC TGTACAAGAA   1200
AAAGTAGCAA AATTTGCTGA AGTTATGGG ATGAAGCTAG AAAATGTCTT    1250
GTTTAATATG GACGGAACAA TTGAATTATA TTTACCATCA GGAGAAGTCA   1300
TTAAAAAGAA TATGGCAGAT TTTACAGGAG AAGCACCTCA AGGAAATGGT   1350
GAAAATAAAC CATCTGAAAA TGGAAAAGTA TCTACTGGAA CAGTTGAGAA   1400
CCAACCAACA GAAAATAAAC CAGCAGATTC TTTACCAGAG GCACCAAACG   1450
AAAAACCTGT AAAACCAGAA AACTCAACGG ATAATGGAAT GTTGAATCCA   1500
GAAGGGAATG TGGGGAGTGA CCCTATGTTA GATCCAGCAT TAGAGGAAGC   1550
TCCAGCAGTA GATCCTGTAC AAGAAAAATT AGAAAAATTT ACAGCTAGTT   1600
ACGGATTAGG CTTAGATAGT GTTATATTCA ATATGGATGG AACGATTGAA   1650
TTAAGATTGC CAAGTGGAGA AGTGATAAAA AAGAATTTAT CTGATTTCAT   1700
AGCGAAGCTT CGTTATCGTT CAAACCATTG GGTACCAGAT TCAAGACCAG   1750
AAGAACCAAG TCCACAACCG ACTCCAGAAC CTAGTCCAAG TCCGCAACCT   1800
GCACCAAATC CTCAACCAGC TCCAAGCAAT CCAATTGATG AGAAATTGGT   1850
CAAAGAAGCT GTTCGAAAAG TAGGCGATGG TTATGTCTTT GAGGAGAATG   1900
GAGTTTCTCG TTATATCCCA GCCAAGAATC TTTCAGCAGA AACAGCAGCA   1950
GGCATTGATA GCAAACTGGC CAAGCAGGAA AGTTATCTC ATAAGCTAGG    2000
AGCTAAGAAA ACTGACCTCC CATCTAGTGA TCGAGAATTT ACAATAAGG    2050
CTTATGACTT ACTAGCAAGA ATTCACCAAG ATTTACTTGA TAATAAAGGT   2100
CGACAAGTTG ATTTTGAGGC TTTGGATAAC CTGTTGGAAC GACTCAAGGA   2150
TGTCTCAAGT GATAAAGTCA AGTTAGTGGA TGATATTCTT GCCTTCTTAG   2200
CTCCGATTCG TCATCCAGAA CGTTTAGGAA AACCAAATGC GCAAATTACC   2250
TACACTGATG ATGAGATTCA AGTAGCCAAG TTGGCAGGCA AGTACACAAC   2300
AGAAGACGGT TATATCTTTG ATCCTCGTGA TATAACCAGT GATGAGGGGG   2350
ATGCCTATGT AACTCCACAT ATGACCCATA GCCACTGGAT TAAAAAAGAT   2400
AGTTTGTCTG AAGCTGAGAG AGCGGCAGCC CAGGCTTATG CTAAAGAGAA   2450
AGGTTTGACC CCTCCTTCGA CAGACCATCA GGATTCAGGA AATACTGAGG   2500
CAAAAGGAGC AGAAGCTATC TACAACCGCG TGAAAGCAGC TAAGAAGGTG   2550
```

*FIG. 41A*

```
CCACTTGATC GTATGCCTTA CAATCTTCAA TATACTGTAG AAGTCAAAAA    2600
CGGTAGTTTA ATCATACCTC ATTATGACCA TTACCATAAC ATCAAATTTG    2650
AGTGGTTTGA CGAAGGCCTT TATGAGGCAC CTAAGGGGTA TACTCTTGAG    2700
GATCTTTTGG CGACTGTCAA GTACTATGTC GAACATCCAA ACGAACGTCC    2750
GCATTCAGAT AATGGTTTTG GTAACGCTAG CGACCATGTT CAAAGAAACA    2800
AAAATGGTCA AGCTGATACC AATCAAACGG AAAAACCAAG CGAGGAGAAA    2850
CCTCAGACAG AAAAACCTGA GGAAGAAACC CCTCGAGAAG AGAAACCACA    2900
AAGCGAGAAA CCAGAGTCTC CAAAACCAAC AGAGGAACCA GAAGAAGAAT    2950
CACCAGAGGA ATCAGAAGAA CCTCAGGTCG AGACTGAAAA GGTTGAAGAA    3000
AAACTGAGAG AGGCTGAAGA TTTACTTGGA AAAATCCAGG ATCCAATTAT    3050
CAAGTCCAAT GCCAAGAGA CTCTCACAGG ATTAAAAAAT AATTTACTAT    3100
TTGGCACCCA GGACAACAAT ACTATTATGG CAGAAGCTGA AAAACTATTG    3150
GCTTTATTAA AGGAGAGTAA G    (SEQ ID NO : 76)                3171
```

FIG. 41B

```
EAYWNGKQGS RPSSSSSYNA NPVQPRLSEN HNLTVTPTYH QNQGENISSL     50
LRELYAKPLS ERHVESDGLI FDPAQITSRT ARGVAPHGN HYHFIPYEQM     100
SELEKRIARI IPLRYRSNHW VPDSRPEQPS PQSTPEPSPS LQPAPNPQPA    150
PSNPIDEKLV KEAVRKVGDG YVFEENGVSR YIPAKDLSAE TAAGIDSKLA    200
KQESLSHKLG AKKTDLPSSD REFYNKAYDL LARIHQDLLD NKGRQVDFEV    250
LDNLLERLKD VSSDKVKLVD DILAFLAPIR HPERLGKPNA QITYTDDEIQ    300
VAKLAGKYTT EDGYIFDPRD ITSDEGDAYV TPHMTHSHWI KKDSLSEAER    350
AAAQAYAKEK GLTPPSTDHQ DSGNTEAKGA EAIYNRVKAA KKVPLDRMPY    400
NLQYTVEVKN GSLIIPHYDH YHNIKFEWFD EGLYEAPKGY SLEDLLATVK    450
YYVEHPNERP HSDNGFGNAS DHV    (SEQ ID NO : 77)             473
```

FIG. 42

```
CAYALNQHRS QENKDNNRVS YVDGSQSSQK SENLTPDQVS QKEGIQAEQI      50
VIKITDQGYV TSHGDHYHYY NGKVPYDALF SEELLMKDPN YQLKDADIVN     100
EVKGGYIIKV DGKYYVYLKD AAHADNVRTK DEINRQKQEH VKDNEKVNSN     150
VAVARSQGRY TTNDGYVFNP ADIIEDTGNA YIVPHGGHYH YIPKSDLSAS     200
ELAAAKAHLA GKNMQPSQLS YSSTASDNNT QSVAKGSTSK PANKSENLQS     250
LLKELYDSPS AQRYSESDGL VFDPAKIISR TPNGVAIPHG DHYHFIPYSK     300
LSALEEKIAR MVPISGTGST VSTNAKPNEV VSSLGSLSSN PSSLTTSKEL     350
SSASDGYIFN PKDIVEETAT AYIVRHGDHF HYIPKSNQIG QPTLPNNSLA     400
TPSPSLPINP GTSHEKHEED GYGFDANRII AEDESGFVMS HGDHNHYFFK     450
KDLTEEQIKA AQKHLEEVKT SHNGLDSLSS HEQDYPGNAK EMKDLDKKIE     500
EKIAGIMKQY GVKRESIVVN KEKNAIIYPH GDHHHADPID EHKPVGIGHS     550
HSNYELFKPE EGVAKKEGNK VYTGEELTNV VNLLKNSTFN NQNFTLANGQ     600
KRVSFSFPPE LEKKLGINML VKLITPDGKV LEKVSGKVFG EGVGNIANFE     650
LDQPYLPGQT FKYTIASKDY PEVSYDGTFT VPTSLAYKMA SQTIFYPFHA     700
GDTYLRVNPQ FAVPKGTDAL VRVFDEFHGN AYLENNYKVG EIKLPIPKLN     750
QGTTRTAGNK IPVTFMANAY LDNQSTYIVE      (SEQ ID NO : 78)    780
```

FIG. 43

```
CAYELGLHQA QTVKENNRVS YIDGKQATQK TENLTPDEVS KREGINAEQI      50
VIKITDQGYV TSHGDHYHYY NGKVPYDAII SEELLMKDPN YQLKDSDIVN     100
EIKGGYVIKV NGKYYVYLKD AAHADNVRTK EEINRQKQEH SQHREGGTSA     150
NDGAVAFARS QGRYTTDDGY IFNASDIIED TGDAYIVPHG DHYHYIPKNE     200
LSASELAAAE AFLSGRENLS NLRTYRRQNS DNTPRTNWVP SVSNPGTTNT     250
NTSNNSNTNS QASQSNDIDS LLKQLYKLPL SQRHVESDGL IFDPAQITSR     300
TARGVAVPHG NHYHFIPYEQ MSELEKRIAR IIPLRYRSNH WVPDSRPEEP     350
SPQPTPEPSP SPQPAPNPQP APSNPIDEKL VKEAVRKVGD GYVFEENGVS     400
RYIPAKNLSA ETAAGIDSKL AKQESLSHKL GAKKTDLPSS DREFYNKAYD     450
LLARIHQDLL DNKGRQVDFE ALDNLLERLK DVSSDKVKLV DDILAFLAPI     500
RHPERLGKPN AQITYTDDEI QVAKLAGKYT TEDGYIFDPR DITSDEGDAY     550
VTPHMTHSHW IKKDSLSEAE RAAAQAYAKE KGLTPPSTDH QDSGNTEAKG     600
AEAIYNRVKA AKKVPLDRMP YNLQYTVEVK NGSLIIPHYD HYHNIKFEWF     650
DEGLYEAPKG YTLEDLLATV KYYVEHPNER PHSDNGFGNA               690
(SEQ ID NO : 79)
```

FIG. 44

```
GTGAAGAAAA CATATGGTTA TATCGGCTCA GTTGCTGCCA TTTTACTAGC TACTCATATT      60
GGAAGTTACC AACTTGGTAA GCATCATATG GGTCTAGCAA CAAAGGACAA TCAGATTGCC     120
TATATTGATG ACAGCAAAGG TAAGGCAAAA GCCCCTAAAA CAAACAAAAC GATGGATCAA     180
ATCAGTGCTG AAGAAGGCAT CTCTGCTGAA CAGATCGTAG TCAAAATTAC TGACCAAGGC     240
TATGTGACCT CACACGGTGA CCATTATCAT TTTTACAATG GAAAGTTCC TTATGATGCG      300
ATTATTAGTG AAGAGTTGTT GATGACGGAT CCTAATTACC GTTTTAAACA ATCAGACGTT     360
ATCAATGAAA TCTTAGACGG TTACGTTATT AAAGTCAATG GCAACTATTA TGTTTACCTC     420
AAGCCAGGTA GTAAGCGCAA AAACATTCGA ACCAAACAAC AAATTGCTGA GCAAGTAGCC     480
AAAGGAACTA AAGAAGCTAA AGAAAAAGGT TTAGCTCAAG TGGCCCATCT CAGTAAAGAA     540
GAAGTTGCGG CAGTCAATGA AGCAAAAAGA CAAGGACGCT ATACTACAGA CGATGGCTAT     600
ATTTTTAGTC CGACAGATAT CATTGATGAT TTAGGAGATG CTTATTTAGT ACCTCATGGT     660
AATCACTATC ATTATATTCC TAAAAAGGAT TTGTCTCCAA GTGAGCTAGC TGCTGCACAA     720
GCCTACTGGA GTCAAAAACA AGGTCGAGGT GCTAGACCGT CTGATTACCG CCCGACACCA     780
GCCCCAGGTC GTAGGAAAGC CCCAATTCCT GATGTGACGC CTAACCCTGG ACAAGGTCAT     840
CAGCCAGATA ACGGTGGCTA TCATCCAGCG CCTCCTAGGC CAAATGATGC GTCACAAAAC     900
AAACACCAAA GAGATGAGTT TAAAGGAAAA ACCTTTAAGG AACTTTTAGA TCAACTACAC     960
CGTCTTGATT TGAAATACCG TCATGTGGAA GAAGATGGGT TGATTTTTGA ACCGACTCAA    1020
GTGATCAAAT CAAACGCTTT TGGGTATGTG GTGCCTCATG GAGATCATTA TCATATTATC    1080
CCAAGAAGTC AGTTATCACC TCTTGAAATG GAATTAGCAG ATCGATACTT AGCTGGCCAA    1140
ACTGAGGACA ATGACTCAGG TTCAGAGCAC TCAAAACCAT CAGATAAAGA AGTGACACAT    1200
ACCTTTCTTG GTCATCGCAT CAAAGCTTAC GGAAAAGGCT TAGATGGTAA ACCATATGAT    1260
ACGAGTGATG CTTATGTTTT TAGTAAAGAA TCCATTCATT CAGTGGATAA ATCAGGAGTT    1320
ACAGCTAAAC ACGGAGATCA TTTCCACTAT ATAGGATTTG GAGAACTTGA ACAATATGAG    1380
TTGGATGAGG TCGCTAACTG GGTGAAAGCA AAGGTCAAG CTGATGAGCT TGCTGCTGCT     1440
TTGGATCAGG AACAAGGCAA AGAAAAACCA CTCTTTGACA CTAAAAAGT GAGTCGCAAA     1500
GTAACAAAAG ATGGTAAAGT GGGCTATATG ATGCCAAAAG ATGGTAAGGA CTATTTCTAT    1560
GCTCGTGATC AACTTGATTT GACTCAGATT GCCTTTGCCG AACAAGAACT AATGCTTAAA    1620
GATAAGAAGC ATTACCGTTA TGACATTGTT GACACAGGTA TTGAGCCACG ACTTGCTGTA    1680
GATGTGTCAA GTCTGCCGAT GCATGCTGGT AATGCTACTT ACGATACTGG AAGTTCGTTT    1740
GTTATCCCAC ATATTGATCA TATCCATGTC GTTCCGTATT CATGGTTGAC GCGCGATCAG    1800
ATTGCAACAG TCAAGTATGT GATGCAACAC CCCGAAGTTC GTCCGGATGT ATGGTCTAAG    1860
CCAGGGCATG AAGAGTCAGG TTCGGTCATT CCAAATGTTA CGCCTCTTGA TAAACGTGCT    1920
GGTATGCCAA ACTGGCAAAT TATCCATTCT GCTGAAGAAG TTCAAAAAGC CCTAGCAGAA    1980
GGTCGTTTTG CAACACCAGA CGGCTATATT TTCGATCCAC GAGATGTTTT GGCCAAAGAA    2040
ACTTTTGTAT GGAAAGATGG CTCCTTTAGC ATCCCAAGAG CAGATGGCAG TTCATTGAGA    2100
ACCATTAATA AATCTGATCT ATCCCAAGCT GAGTGGCAAC AAGCTCAAGA GTTATTGGCA    2160
AAGAAAAATA CTGGTGATGC TACTGATACG GATAAACCCA AGAAAAGCA ACAGGCAGAT     2220
AAGAGCAATG AAAACCAACA GCCAAGTGAA GCCAGTAAAG AAGAAAAAGA ATCAGATGAC    2280
TTTATAGACA GTTTACCAGA CTATGGTCTA GATAGAGCAA CCCTAGAAGA TCATATCAAT    2340
CAATTAGCAC AAAAAGCTAA TATCGATCCT AAGTATCTCA TTTTCCAACC AGAAGGTGTC    2400
CAATTTTATA ATAAAAATGG TGAATTGGTA ACTTATGATA TCAAGACACT TCAACAAATA    2460
AACCCTTAA   (SEQ ID NO : 80)                                        2469
```

FIG. 45

```
VKKTYGYIGS VAAILLATHI GSYQLGKHHM GLATKDNQIA YIDDSKGKAK        50
APKTNKTMDQ ISAEEGISAE QIVVKITDQG YVTSHGDHYH FYNGKVPYDA       100
IISEELLMTD PNYRFKQSDV INEILDGYVI KVNGNYYVYL KPGSKRKNIR       150
TKQQIAEQVA KGTKEAKEKG LAQVAHLSKE EVAAVNEAKR QGRYTTDDGY       200
IFSPTDIIDD LGDAYLVPHG NHYHYIPKKD LSPSELAAAQ AYWSQKQGRG       250
ARPSDYRPTP APGRRKAPIP DVTPNPGQGH QPDNGGYHPA PPRPNDASQN       300
KHQRDEFKGK TFKELLDQLH RLDLKYRHVE EDGLIFEPTQ VIKSNAFGYV       350
VPHGDHYHII PRSQLSPLEM ELADRYLAGQ TEDNDSGSEH SKPSDKEVTH       400
TFLGHRIKAY GKGLDGKPYD TSDAYVFSKE SIHSVDKSGV TAKHGDHFHY       450
IGFGELEQYE LDEVANWVKA KGQADELAAA LDQEQGKEKP LFDTKKVSRK       500
VTKDGKVGYM MPKDGKDYFY ARDQLDLTQI AFAEQELMLK DKKHYRYDIV       550
DTGIEPRLAV DVSSLPMHAG NATYDTGSSF VIPHIDHIHV VPYSWLTRDQ       600
IATVKYVMQH PEVRPDVWSK PGHEESGSVI PNVTPLDKRA GMPNWQIIHS       650
AEEVQKALAE GRFATPDGYI FDPRDVLAKE TFVWKDGSFS IPRADGSSLR       700
TINKSDLSQA EWQQAQELLA KKNTGDATDT DKPKEKQQAD KSNENQQPSE       750
ASKEEKESDD FIDSLPDYGL DRATLEDHIN QLAQKANIDP KYLIFQPEGV       800
QFYNKNGELV TYDIKTLQQI NPP       (SEQ ID NO : 81)            823
```

*FIG. 46*

```
GTGAAGAAAA CATATGGTTA TATCGGCTCA GTTGCTGCCA TTTTACTAGC TACTCATATT      60
GGAAGTTACC AACTTGGTAA GCATCATATG GGTCTAGCAA CAAAGGACAA TCAGATTGCC     120
TATATTGATG ATAGCAAAGG TAAGGCAAAA GCCCCTAAAA CAAACAAAAC GATGGATCAA     180
ATCAGTGCTG AAGAAGGCAT CTCTGCTGAA CAGATCGTAG TCAAAATTAC TGACCAAGGT     240
TATGTGACCT CACACGGTGA CCATTATCAT TTTTACAATG GGAAAGTTCC TTATGATGCG     300
ATTATTAGTG AAGAGTTGTT GATGACGGAT CCTAATTACC ATTTTAAACA ATCAGACGTT     360
ATCAATGAAA TCTTAGACGG TTACGTTATT AAAGTCAATG GCAACTATTA TGTTTACCTC     420
AAGCCAGGTA GTAAGCGCAA AAACATTCGA ACCAAACAAC AAATTGCTGA GCAAGTAGCC     480
AAAGGAACTA AGAAGCTAA AGAAAAAGGT TTAGCTCAAG TGGCCCATCT CAGTAAAGAA     540
GAAGTTGCGG CAGTCAATGA AGCAAAAAGA CAAGGACGCT ATACTACAGA CGATGGCTAT     600
ATTTTTAGTC CGACAGATAT CATTGATGAT TTAGGAGACG CTTATTTAGT ACCTCATGGT     660
AATCACTATC ATTATATTCC TAAAAAAGAT TTGTCTCCAA GTGAGCTAGC TGCTGCACAA     720
GCTTACTGGA GTCAAAAACA AGGTCGAGGT GCTAGACCGT CTGATTACCG CCCGACACCA     780
GCCCCAGGTC GTAGGAAAGC TCCAATTCCT GATGTGACGC CTAACCCTGG ACAAGGTCAT     840
CAGCCAGATA ACGGTGGCTA TCATCCAGCG CCTCCTAGGC CAAATGATGC GTCACAAAAC     900
AAACACCAAA GAGATGAGTT TAAAGGAAAA ACCTTTAAGG AACTTTTAGA TCAACTACAC     960
CGTCTTGATT TGAAATACCG TCATGTGGAA GAAGATGGGT TGATTTTTGA ACCGACTCAA    1020
GTGATCAAAT CAAACGCTTT TGGGTATGTG GTGCCTCATG GAGATCATTA TCATATTATC    1080
CCAAGAAGTC AGTTATCACC TCTTGAAATG GAATTAGCAG ATCGATACTT AGCCGGTCAA    1140
ACTGAGGACA ATGATTCAGG TTCAGATCAC TCAAAACCAT CAGATAAAGA AGTGACACAT    1200
ACCTTTCTTG GTCATCGCAT CAAAGCTTAC GGAAAAGGCT TAGATGGTAA ACCATATGAT    1260
ACGAGTGATG CTTATGTTTT TAGTAAAGAA TCCATTCATT CAGTGGATAA ATCAGGAGTT    1320
ACAGCTAAAC ACGGAGATCA TTTCCACTAT ATAGGATTTG GAGAACTTGA ACAATATGAG    1380
TTGGATGAGG TCGCTAACTG GGTGAAAGCA AAAGGTCAAG CTGATGAGCT TGCTGCTGCT    1440
TTGGATCAGG AACAAGGCAA AGAAAAACCA CTCTTTGACA CTAAAAAAGT GAGTCGCAAA    1500
GTAACAAAAG ATGGTAAAGT GGGCTATATT ATGCCAAAAG ATGGCAAGGA CTATTTCTAT    1560
GCTCGTGATC AACTTGATTT GACTCAGATT GCCTTTGCCG AACAAGAACT AATGCTTAAA    1620
GATAAGAACC ATTACCGTTA TGACATTGTT GACACAGGTA TTGAGCCACG ACTTGCTGTA    1680
GATGTGTCAA GTCTGCCGAT GCATGCTGGT AATGCTACTT ACGATACTGG AAGTTCGTTT    1740
GTTATCCCTC ATATTGATCA TATCCATGTC GTTCCGTATT CATGGTTGAC GCGCGATCAG    1800
ATTGCAACAA TCAAGTATGT GATGCAACAC CCCGAAGTTC GTCCAGATGT ATGGTCTAAG    1860
CCAGGGCATG AAGAGTCAGG TTCGGTCATT CCAAATGTTA CGCCTCTTGA TAAACGTGCT    1920
GGTATGCCAA ATTGGCAAAT CATCCATTCT GCTGAAGAAG TTCAAAAAGC CCTAGCAGAA    1980
GGTCGTTTTG CAACACCAGA CGGCTATATT TTCGATCCAC GAGATGTTTT GGCCAAAGAA    2040
ACTTTTGTAT GGAAAGATGG CTCCTTTAGC ATCCCAAGAG CAGATGGCAG TTCATTGAGA    2100
ACCATTAATA AATCTGATCT ATCCCAAGCT GAGTGGCAAC AAGCTCAAGA GTTATTGGCA    2160
AAGAAAAACG CTGGTGATGC TACTGATACG GATAAACCCA AGAAAAGCA ACAGGCAGAT    2220
AAGAGCAATG AAAACCAACA GCCAAGTGAA GCCAGTAAAG AAGAAGAAAA AGAATCAGAT    2280
GACTTTATAG ACAGTTTACC AGACTATGGT CTAGATAGAG CAACCCTAGA AGATCATATC    2340
AATCAATTAG CACAAAAAGC TAATATCGAT CCTAAGTATC TCATTTTCCA ACCAGAAGGT    2400
GTCCAATTTT ATAATAAAAA TGGTGAATTA GTAACTTATG ATATCAAGAC GCTTCAACAA    2460
ATAAACCCTT AA    (SEQ ID NO : 82)                                    2472
```

*FIG. 47*

```
VKKTYGYIGS  VAAILLATHI  GSYQLGKHHM  GLATKDNQIA  YIDDSKGKAK         50
APKTNKTMDQ  ISAEEGISAE  QIVVKITDQG  YVTSHGDHYH  FYNGKVPYDA        100
IISEELLMTD  PNYHFKQSDV  INEILDGYVI  KVNGNYYVYL  KPGSKRKNIR        150
TKQQIAEQVA  KGTKEAKEKG  LAQVAHLSKE  EVAAVNEAKR  QGRYTTDDGY        200
IFSPTDIIDD  LGDAYLVPHG  NHYHYIPKKD  LSPSELAAAQ  AYWSQKQGRG        250
ARPSDYRPTP  APGRRKAPIP  DVTPNPGQGH  QPDNGGYHPA  PPRPNDASQN        300
KHQRDEFKGK  TFKELLDQLH  RLDLKYRHVE  EDGLIFEPTQ  VIKSNAFGYV        350
VPHGDHYHII  PRSQLSPLEM  ELADRYLAGQ  TEDNDSGSDH  SKPSDKEVTH        400
TFLGHRIKAY  GKGLDGKPYD  TSDAYVFSKE  SIHSVDKSGV  TAKHGDHFHY        450
IGFGELEQYE  LDEVANWVKA  KGQADELAAA  LDQEQGKEKP  LFDTKKVSRK        500
VTKDGKVGYI  MPKDGKDYFY  ARDQLDLTQI  AFAEQELMLK  DKNHYRYDIV        550
DTGIEPRLAV  DVSSLPMHAG  NATYDTGSSF  VIPHIDHIHV  VPYSWLTRDQ        600
IATIKYVMQH  PEVRPDVWSK  PGHEESGSVI  PNVTPLDKRA  GMPNWQIIHS        650
AEEVQKALAE  GRFATPDGYI  FDPRDVLAKE  TFVWKDGSFS  IPRADGSSLR        700
TINKSDLSQA  EWQQAQELLA  KKNAGDATDT  DKPKEKQQAD  KSNENQQPSE        750
ASKEEEKESD  DFIDSLPDYG  LDRATLEDHI  NQLAQKANID  PKYLIFQPEG        800
VQFYNKNGEL  VTYDIKTLQQ  INPP      (SEQ ID NO : 83)               824
```

*FIG. 48*

SEQUENCE LISTING

<160> NUMBER OF SEQ ID NOS: 102

<210> SEQ ID NO 1
<211> LENGTH: 3120
<212> TYPE: DNA
<213> ORGANISM: S. pneumoniae

<400> SEQUENCE: 1

| | | | | | |
|---|---|---|---|---|---|
| atgaaattta | gtaaaaaata | tatagcagct | ggatcagctg | ttatcgtatc | cttgagtcta | 60 |
| tgtgcctatg | cactaaacca | gcatcgttcg | caggaaaata | aggacaataa | tcgtgtctct | 120 |
| tatgtggatg | gcagccagtc | aagtcagaaa | agtgaaaact | tgacaccaga | ccaggttagc | 180 |
| cagaaagaag | gaattcaggc | tgagcaaatt | gtaatcaaaa | ttacagatca | gggctatgta | 240 |
| acgtcacacg | gtgaccacta | tcattactat | aatgggaaag | ttccttatga | tgccctcttt | 300 |
| agtgaagaac | tcttgatgaa | ggatccaaac | tatcaactta | aagacgctga | tattgtcaat | 360 |
| gaagtcaagg | gtggttatat | catcaaggtc | gatgaaaat | attatgtcta | cctgaaagat | 420 |
| gcagctcatg | ctgataatgt | tcgaactaaa | gatgaaatca | atcgtcaaaa | acaagaacat | 480 |
| gtcaaagata | atgagaaggt | taactctaat | gttgctgtag | caaggtctca | gggacgatat | 540 |
| acgacaaatg | atggttatgt | ctttaatcca | gctgatatta | tcgaagatac | gggtaatgct | 600 |
| tatatcgttc | ctcatggagg | tcactatcac | tacattccca | aaagcgattt | atctgctagt | 660 |
| gaattagcag | cagctaaagc | acatctggct | ggaaaaaata | tgcaaccgag | tcagttaagc | 720 |
| tattcttcaa | cagctagtga | caataacacg | caatctgtag | caaaaggatc | aactagcaag | 780 |
| ccagcaaata | aatctgaaaa | tctccagagt | cttttgaagg | aactctatga | ttcacctagc | 840 |
| gcccaacgtt | acagtgaatc | agatggcctg | gtctttgacc | ctgctaagat | tatcagtcgt | 900 |
| acaccaaatg | gagttgcgat | tccgcatggc | gaccattacc | actttattcc | ttacagcaag | 960 |
| cttctctgctt | tagaagaaaa | gattgccaga | atggtgccta | tcagtggaac | tggttctaca | 1020 |
| gtttctacaa | atgcaaaacc | taatgaagta | gtgtctagtc | taggcagtct | ttcaagcaat | 1080 |
| ccttcttctt | taacgacaag | taaggagctc | tcttcagcat | ctgatggtta | tatttttaat | 1140 |
| ccaaaagata | tcgttgaaga | aacggctaca | gcttatattg | taagacatgg | tgatcatttc | 1200 |
| cattacattc | caaaatcaaa | tcaaattggg | caaccgactc | ttccaaacaa | tagtctagca | 1260 |
| acaccttctc | catctcttcc | aatcaatcca | ggaacttcac | atgagaaaca | tgaagaagat | 1320 |
| ggatacggat | ttgatgctaa | tcgtattatc | gctgaagatg | aatcaggttt | tgtcatgagt | 1380 |
| cacggagacc | acaatcatta | tttcttcaag | aaggacttga | cagaagagca | aattaaggct | 1440 |
| gcgcaaaaac | atttagagga | agttaaaact | agtcataatg | gattagattc | tttgtcatct | 1500 |
| catgaacagg | attatccagg | taatgccaaa | gaaatgaaag | atttagataa | aaaaatcgaa | 1560 |
| gaaaaaattg | ctggcattat | gaaacaatat | ggtgtcaaac | gtgaaagtat | tgtcgtgaat | 1620 |
| aaagaaaaaa | atgcgattat | ttatccgcat | ggagatcacc | atcatgcaga | tccgattgat | 1680 |
| gaacataaac | cggttggaat | tggtcattct | cacagtaact | atgaactgtt | taaacccgaa | 1740 |
| gaaggagttg | ctaaaaaaga | agggaataaa | gtttatactg | gagaagaatt | aacgaatgtt | 1800 |
| gttaatttgt | taaaaaatag | tacgtttaat | aatcaaaact | ttactctagc | caatggtcaa | 1860 |

-continued

```
aaacgcgttt cttttagttt tccgcctgaa ttggagaaaa aattaggtat caatatgcta    1920
gtaaaattaa taacaccaga tggaaaagta ttggagaaag tatctggtaa agtatttgga    1980
gaaggagtag ggaatattgc aaactttgaa ttagatcaac cttatttacc aggacaaaca    2040
tttaagtata ctatcgcttc aaaagattat ccagaagtaa gttatgatgg tacatttaca    2100
gttccaacct ctttagctta caaaatggcc agtcaaacga ttttctatcc tttccatgca    2160
ggggatactt atttaagagt gaaccctcaa tttgcagtgc ctaaaggaac tgatgcttta    2220
gtcagagtgt ttgatgaatt tcatggaaat gcttatttag aaaataacta taaagttggt    2280
gaaatcaaat taccgattcc gaaattaaac caaggaacaa ccagaacggc cggaaataaa    2340
attcctgtaa ccttcatggc aaatgcttat ttggacaatc aatcgactta tattgtggaa    2400
gtacctatct tggaaaaaga aaatcaaact gataaaccaa gtattctacc acaatttaaa    2460
aggaataaag cacaagaaaa actcaaaactt gatgaaaagg tagaagaacc aaagactagt    2520
gagaaggtag aaaagaaaa actttctgaa actgggaata gtactagtaa ttcaacgtta    2580
gaagaagttc ctacagtgga tcctgtacaa gaaaaagtag caaaatttgc tgaaagttat    2640
gggatgaagc tagaaaatgt cttgtttaat atggacggaa caattgaatt atatttacca    2700
tcaggagaag tcattaaaaa gaatatggca gattttacag gagaagcacc tcaaggaaat    2760
ggtgaaaata aaccatctga aaatggaaaa gtatctactg aacagttga aaccaacca    2820 acagaaaata aaccagcaga ttcttttacca gaggcaccaa acgaaaaacc tgtaaaacca    2880
gaaaactcaa cggataatgg aatgttgaat ccagaaggga atgtggggag tgaccctatg    2940
ttagatccag cattagagga agctccagca gtagatcctg tacaagaaaa attagaaaaa    3000
tttacagcta gttacggatt aggcttagat agtgttatat tcaatatgga tggaacgatt    3060
gaattaagat tgccaagtgg agaagtgata aaaagaatt tatctgattt catagcgtaa    3120
```

<210> SEQ ID NO 2
<211> LENGTH: 1039
<212> TYPE: PRT
<213> ORGANISM: S. pneumoniae

<400> SEQUENCE: 2

```
Met Lys Phe Ser Lys Lys Tyr Ile Ala Ala Gly Ser Ala Val Ile Val
  1               5                  10                  15

Ser Leu Ser Leu Cys Ala Tyr Ala Leu Asn Gln His Arg Ser Gln Glu
             20                  25                  30

Asn Lys Asp Asn Asn Arg Val Ser Tyr Val Asp Gly Ser Gln Ser Ser
         35                  40                  45

Gln Lys Ser Glu Asn Leu Thr Pro Asp Gln Val Ser Gln Lys Glu Gly
     50                  55                  60

Ile Gln Ala Glu Gln Ile Val Ile Lys Ile Thr Asp Gln Gly Tyr Val
 65                  70                  75                  80

Thr Ser His Gly Asp His Tyr His Tyr Tyr Asn Gly Lys Val Pro Tyr
                 85                  90                  95

Asp Ala Leu Phe Ser Glu Glu Leu Leu Met Lys Asp Pro Asn Tyr Gln
            100                 105                 110

Leu Lys Asp Ala Asp Ile Val Asn Glu Val Lys Gly Gly Tyr Ile Ile
        115                 120                 125

Lys Val Asp Gly Lys Tyr Tyr Val Tyr Leu Lys Asp Ala Ala His Ala
    130                 135                 140

Asp Asn Val Arg Thr Lys Asp Glu Ile Asn Arg Gln Lys Gln Glu His
145                 150                 155                 160
```

```
Val Lys Asp Asn Glu Lys Val Asn Ser Asn Val Ala Val Ala Arg Ser
                165                 170                 175
Gln Gly Arg Tyr Thr Thr Asn Asp Gly Tyr Val Phe Asn Pro Ala Asp
            180                 185                 190
Ile Ile Glu Asp Thr Gly Asn Ala Tyr Ile Val Pro His Gly Gly His
        195                 200                 205
Tyr His Tyr Ile Pro Lys Ser Asp Leu Ser Ala Ser Glu Leu Ala Ala
    210                 215                 220
Ala Lys Ala His Leu Ala Gly Lys Asn Met Gln Pro Ser Gln Leu Ser
225                 230                 235                 240
Tyr Ser Ser Thr Ala Ser Asp Asn Asn Thr Gln Ser Val Ala Lys Gly
                245                 250                 255
Ser Thr Ser Lys Pro Ala Asn Lys Ser Glu Asn Leu Gln Ser Leu Leu
            260                 265                 270
Lys Glu Leu Tyr Asp Ser Pro Ser Ala Gln Arg Tyr Ser Glu Ser Asp
        275                 280                 285
Gly Leu Val Phe Asp Pro Ala Lys Ile Ile Ser Arg Thr Pro Asn Gly
    290                 295                 300
Val Ala Ile Pro His Gly Asp His Tyr His Phe Ile Pro Tyr Ser Lys
305                 310                 315                 320
Leu Ser Ala Leu Glu Glu Lys Ile Ala Arg Met Val Pro Ile Ser Gly
                325                 330                 335
Thr Gly Ser Thr Val Ser Thr Asn Ala Lys Pro Asn Glu Val Val Ser
            340                 345                 350
Ser Leu Gly Ser Leu Ser Ser Asn Pro Ser Ser Leu Thr Thr Ser Lys
        355                 360                 365
Glu Leu Ser Ser Ala Ser Asp Gly Tyr Ile Phe Asn Pro Lys Asp Ile
    370                 375                 380
Val Glu Glu Thr Ala Thr Ala Tyr Ile Val Arg His Gly Asp His Phe
385                 390                 395                 400
His Tyr Ile Pro Lys Ser Asn Gln Ile Gly Gln Pro Thr Leu Pro Asn
                405                 410                 415
Asn Ser Leu Ala Thr Pro Ser Pro Ser Leu Pro Ile Asn Pro Gly Thr
            420                 425                 430
Ser His Glu Lys His Glu Glu Asp Gly Tyr Gly Phe Asp Ala Asn Arg
        435                 440                 445
Ile Ile Ala Glu Asp Glu Ser Gly Phe Val Met Ser His Gly Asp His
    450                 455                 460
Asn His Tyr Phe Phe Lys Lys Asp Leu Thr Glu Glu Gln Ile Lys Ala
465                 470                 475                 480
Ala Gln Lys His Leu Glu Glu Val Lys Thr Ser His Asn Gly Leu Asp
                485                 490                 495
Ser Leu Ser Ser His Glu Gln Tyr Pro Gly Asn Ala Lys Glu Met
        500                 505                 510
Lys Asp Leu Asp Lys Lys Ile Glu Glu Lys Ile Ala Gly Ile Met Lys
        515                 520                 525
Gln Tyr Gly Val Lys Arg Glu Ser Ile Val Val Asn Lys Glu Lys Asn
    530                 535                 540
Ala Ile Ile Tyr Pro His Gly Asp His His Ala Asp Pro Ile Asp
545                 550                 555                 560
Glu His Lys Pro Val Gly Ile Gly His Ser His Ser Asn Tyr Glu Leu
                565                 570                 575
```

-continued

```
Phe Lys Pro Glu Glu Gly Val Ala Lys Lys Glu Gly Asn Lys Val Tyr
            580                 585                 590

Thr Gly Glu Glu Leu Thr Asn Val Val Asn Leu Leu Lys Asn Ser Thr
        595                 600                 605

Phe Asn Asn Gln Asn Phe Thr Leu Ala Asn Gly Gln Lys Arg Val Ser
    610                 615                 620

Phe Ser Phe Pro Pro Glu Leu Glu Lys Lys Leu Gly Ile Asn Met Leu
625                 630                 635                 640

Val Lys Leu Ile Thr Pro Asp Gly Lys Val Leu Glu Lys Val Ser Gly
                645                 650                 655

Lys Val Phe Gly Glu Gly Val Gly Asn Ile Ala Asn Phe Glu Leu Asp
            660                 665                 670

Gln Pro Tyr Leu Pro Gly Gln Thr Phe Lys Tyr Thr Ile Ala Ser Lys
        675                 680                 685

Asp Tyr Pro Glu Val Ser Tyr Asp Gly Thr Phe Thr Val Pro Thr Ser
    690                 695                 700

Leu Ala Tyr Lys Met Ala Ser Gln Thr Ile Phe Tyr Pro Phe His Ala
705                 710                 715                 720

Gly Asp Thr Tyr Leu Arg Val Asn Pro Gln Phe Ala Val Pro Lys Gly
                725                 730                 735

Thr Asp Ala Leu Val Arg Val Phe Asp Glu Phe His Gly Asn Ala Tyr
            740                 745                 750

Leu Glu Asn Asn Tyr Lys Val Gly Glu Ile Lys Leu Pro Ile Pro Lys
        755                 760                 765

Leu Asn Gln Gly Thr Thr Arg Thr Ala Gly Asn Lys Ile Pro Val Thr
    770                 775                 780

Phe Met Ala Asn Ala Tyr Leu Asp Asn Gln Ser Thr Tyr Ile Val Glu
785                 790                 795                 800

Val Pro Ile Leu Glu Lys Glu Asn Gln Thr Asp Lys Pro Ser Ile Leu
                805                 810                 815

Pro Gln Phe Lys Arg Asn Lys Ala Gln Glu Asn Ser Lys Leu Asp Glu
            820                 825                 830

Lys Val Glu Glu Pro Lys Thr Ser Glu Lys Val Glu Lys Glu Lys Leu
        835                 840                 845

Ser Glu Thr Gly Asn Ser Thr Ser Asn Ser Thr Leu Glu Glu Val Pro
    850                 855                 860

Thr Val Asp Pro Val Gln Glu Lys Val Ala Lys Phe Ala Glu Ser Tyr
865                 870                 875                 880

Gly Met Lys Leu Glu Asn Val Leu Phe Asn Met Asp Gly Thr Ile Glu
                885                 890                 895

Leu Tyr Leu Pro Ser Gly Glu Val Ile Lys Lys Asn Met Ala Asp Phe
            900                 905                 910

Thr Gly Glu Ala Pro Gln Gly Asn Gly Glu Asn Lys Pro Ser Glu Asn
        915                 920                 925

Gly Lys Val Ser Thr Gly Thr Val Glu Asn Gln Pro Thr Glu Asn Lys
    930                 935                 940

Pro Ala Asp Ser Leu Pro Glu Ala Pro Asn Glu Lys Pro Val Lys Pro
945                 950                 955                 960

Glu Asn Ser Thr Asp Asn Gly Met Leu Asn Pro Glu Gly Asn Val Gly
                965                 970                 975

Ser Asp Pro Met Leu Asp Pro Ala Leu Glu Glu Ala Pro Ala Val Asp
            980                 985                 990

Pro Val Gln Glu Lys Leu Glu Lys Phe Thr Ala Ser Tyr Gly Leu Gly
```

```
                995              1000              1005
Leu Asp Ser Val Ile Phe Asn Met Asp Gly Thr Ile Glu Leu Arg Leu
    1010              1015              1020

Pro Ser Gly Glu Val Ile Lys Lys Asn Leu Ser Asp Phe Ile Ala
1025              1030              1035

<210> SEQ ID NO 3
<211> LENGTH: 2523
<212> TYPE: DNA
<213> ORGANISM: S. pneumoniae
<220> FEATURE:
<221> NAME/KEY: CDS
<222> LOCATION: (1)...(2520)
<223> OTHER INFORMATION: Coding region of BVH-11 gene

<400> SEQUENCE: 3 atg aaa atc aat aaa aaa tat cta gct ggg tca gta gct aca ctt gtt       48
Met Lys Ile Asn Lys Lys Tyr Leu Ala Gly Ser Val Ala Thr Leu Val
  1               5                  10                  15 tta agt gtc tgt gct tat gaa cta ggt ttg cat caa gct caa act gta       96
Leu Ser Val Cys Ala Tyr Glu Leu Gly Leu His Gln Ala Gln Thr Val
             20                  25                  30 aaa gaa aat aat cgt gtt tcc tat ata gat gga aaa caa gcg acg caa      144
Lys Glu Asn Asn Arg Val Ser Tyr Ile Asp Gly Lys Gln Ala Thr Gln
         35                  40                  45 aaa acg gag aat ttg act cct gat gag gtt agc aag cgt gaa gga atc      192
Lys Thr Glu Asn Leu Thr Pro Asp Glu Val Ser Lys Arg Glu Gly Ile
     50                  55                  60 aac gcc gaa caa atc gtc atc aag att acg gat caa ggt tat gtg acc      240
Asn Ala Glu Gln Ile Val Ile Lys Ile Thr Asp Gln Gly Tyr Val Thr
 65                  70                  75                  80 tct cat gga gac cat tat cat tac tat aat ggc aag gtc cct tat gat      288
Ser His Gly Asp His Tyr His Tyr Tyr Asn Gly Lys Val Pro Tyr Asp
                 85                  90                  95 gcc atc atc agt gaa gag ctc ctc atg aaa gat ccg aat tat cag ttg      336
Ala Ile Ile Ser Glu Glu Leu Leu Met Lys Asp Pro Asn Tyr Gln Leu
            100                 105                 110 aag gat tca gac att gtc aat gaa atc aag ggt ggt tat gtc att aag      384
Lys Asp Ser Asp Ile Val Asn Glu Ile Lys Gly Gly Tyr Val Ile Lys
        115                 120                 125 gta aac ggt aaa tac tat gtt tac ctt aag gat gca gct cat gcg gat      432
Val Asn Gly Lys Tyr Tyr Val Tyr Leu Lys Asp Ala Ala His Ala Asp
    130                 135                 140 aat gtc cgt aca aaa gaa gaa atc aat cgg caa aaa caa gaa cat agt      480
Asn Val Arg Thr Lys Glu Glu Ile Asn Arg Gln Lys Gln Glu His Ser
145                 150                 155                 160 cag cat cgt gaa gga ggg act tca gca aac gat ggt gcg gta gcc ttt      528
Gln His Arg Glu Gly Gly Thr Ser Ala Asn Asp Gly Ala Val Ala Phe
                165                 170                 175 gca cgt tca cag gga cgc tac acc aca gat gat ggt tat atc ttc aat      576
Ala Arg Ser Gln Gly Arg Tyr Thr Thr Asp Asp Gly Tyr Ile Phe Asn
            180                 185                 190 gca tct gat atc atc gaa gat acg ggc gat gcc tat atc gtt cct cat      624
Ala Ser Asp Ile Ile Glu Asp Thr Gly Asp Ala Tyr Ile Val Pro His
        195                 200                 205 gga gat cat tac cat tac att cct aag aat gag tta tca gct agc gag      672
Gly Asp His Tyr His Tyr Ile Pro Lys Asn Glu Leu Ser Ala Ser Glu
    210                 215                 220 ttg gct gct gca gaa gcc ttc cta tct ggt cgg gaa aat ctg tca aat      720
Leu Ala Ala Ala Glu Ala Phe Leu Ser Gly Arg Glu Asn Leu Ser Asn
225                 230                 235                 240
```

```
tta aga acc tat cgc cga caa aat agc gat aac act cca aga aca aac       768
Leu Arg Thr Tyr Arg Arg Gln Asn Ser Asp Asn Thr Pro Arg Thr Asn
                245                 250                 255 tgg gta cct tct gta agc aat cca gga act aca aat act aac aca agc       816
Trp Val Pro Ser Val Ser Asn Pro Gly Thr Thr Asn Thr Asn Thr Ser
        260                 265                 270 aac aac agc aac act aac agt caa gca agt caa agt aat gac att gat       864
Asn Asn Ser Asn Thr Asn Ser Gln Ala Ser Gln Ser Asn Asp Ile Asp
                275                 280                 285 agt ctc ttg aaa cag ctc tac aaa ctg cct ttg agt caa cgc cat gta       912
Ser Leu Leu Lys Gln Leu Tyr Lys Leu Pro Leu Ser Gln Arg His Val
        290                 295                 300 gaa tct gat ggc ctt att ttc gac cca gcg caa atc aca agt cga acc       960
Glu Ser Asp Gly Leu Ile Phe Asp Pro Ala Gln Ile Thr Ser Arg Thr
305                 310                 315                 320 gcc aga ggt gta gct gtc cct cat ggt aac cat tac cac ttt atc cct      1008
Ala Arg Gly Val Ala Val Pro His Gly Asn His Tyr His Phe Ile Pro
                325                 330                 335 tat gaa caa atg tct gaa ttg gaa aaa cga att gct cgt att att ccc      1056
Tyr Glu Gln Met Ser Glu Leu Glu Lys Arg Ile Ala Arg Ile Ile Pro
        340                 345                 350 ctt cgt tat cgt tca aac cat tgg gta cca gat tca aga cca gaa gaa      1104
Leu Arg Tyr Arg Ser Asn His Trp Val Pro Asp Ser Arg Pro Glu Glu
                355                 360                 365 cca agt cca caa ccg act cca gaa cct agt cca agt ccg caa cct gca      1152
Pro Ser Pro Gln Pro Thr Pro Glu Pro Ser Pro Ser Pro Gln Pro Ala
        370                 375                 380 cca aat cct caa cca gct cca agc aat cca att gat gag aaa ttg gtc      1200
Pro Asn Pro Gln Pro Ala Pro Ser Asn Pro Ile Asp Glu Lys Leu Val
385                 390                 395                 400 aaa gaa gct gtt cga aaa gta ggc gat ggt tat gtc ttt gag gag aat      1248
Lys Glu Ala Val Arg Lys Val Gly Asp Gly Tyr Val Phe Glu Glu Asn
                405                 410                 415 gga gtt tct cgt tat atc cca gcc aag aat ctt tca gca gaa aca gca      1296
Gly Val Ser Arg Tyr Ile Pro Ala Lys Asn Leu Ser Ala Glu Thr Ala
        420                 425                 430 gca ggc att gat agc aaa ctg gcc aag cag gaa agt tta tct cat aag      1344
Ala Gly Ile Asp Ser Lys Leu Ala Lys Gln Glu Ser Leu Ser His Lys
                435                 440                 445 cta gga gct aag aaa act gac ctc cca tct agt gat cga gaa ttt tac      1392
Leu Gly Ala Lys Lys Thr Asp Leu Pro Ser Ser Asp Arg Glu Phe Tyr
        450                 455                 460 aat aag gct tat gac tta cta gca aga att cac caa gat tta ctt gat      1440
Asn Lys Ala Tyr Asp Leu Leu Ala Arg Ile His Gln Asp Leu Leu Asp
465                 470                 475                 480 aat aaa ggt cga caa gtt gat ttt gag gct ttg gat aac ctg ttg gaa      1488
Asn Lys Gly Arg Gln Val Asp Phe Glu Ala Leu Asp Asn Leu Leu Glu
                485                 490                 495 cga ctc aag gat gtc tca agt gat aaa gtc aag tta gtg gat gat att      1536
Arg Leu Lys Asp Val Ser Ser Asp Lys Val Lys Leu Val Asp Asp Ile
        500                 505                 510 ctt gcc ttc tta gct ccg att cgt cat cca gaa cgt tta gga aaa cca      1584
Leu Ala Phe Leu Ala Pro Ile Arg His Pro Glu Arg Leu Gly Lys Pro
                515                 520                 525 aat gcg caa att acc tac act gat gat gag att caa gta gcc aag ttg      1632
Asn Ala Gln Ile Thr Tyr Thr Asp Asp Glu Ile Gln Val Ala Lys Leu
530                 535                 540 gca ggc aag tac aca aca gaa gac ggt tat atc ttt gat cct cgt gat      1680
Ala Gly Lys Tyr Thr Thr Glu Asp Gly Tyr Ile Phe Asp Pro Arg Asp
```

```
                    545                 550                 555                 560
ata acc agt gat gag ggg gat gcc tat gta act cca cat atg acc cat        1728
Ile Thr Ser Asp Glu Gly Asp Ala Tyr Val Thr Pro His Met Thr His
                    565                 570                 575 agc cac tgg att aaa aaa gat agt ttg tct gaa gct gag aga gcg gca        1776
Ser His Trp Ile Lys Lys Asp Ser Leu Ser Glu Ala Glu Arg Ala Ala
                580                 585                 590 gcc cag gct tat gct aaa gag aaa ggt ttg acc cct cct tcg aca gac        1824
Ala Gln Ala Tyr Ala Lys Glu Lys Gly Leu Thr Pro Pro Ser Thr Asp
            595                 600                 605 cat cag gat tca gga aat act gag gca aaa gga gca gaa gct atc tac        1872
His Gln Asp Ser Gly Asn Thr Glu Ala Lys Gly Ala Glu Ala Ile Tyr
        610                 615                 620 aac cgc gtg aaa gca gct aag aag gtg cca ctt gat cgt atg cct tac        1920
Asn Arg Val Lys Ala Ala Lys Lys Val Pro Leu Asp Arg Met Pro Tyr
625                 630                 635                 640 aat ctt caa tat act gta gaa gtc aaa aac ggt agt tta atc ata cct        1968
Asn Leu Gln Tyr Thr Val Glu Val Lys Asn Gly Ser Leu Ile Ile Pro
                645                 650                 655 cat tat gac cat tac cat aac atc aaa ttt gag tgg ttt gac gaa ggc        2016
His Tyr Asp His Tyr His Asn Ile Lys Phe Glu Trp Phe Asp Glu Gly
            660                 665                 670 ctt tat gag gca cct aag ggg tat act ctt gag gat ctt ttg gcg act        2064
Leu Tyr Glu Ala Pro Lys Gly Tyr Thr Leu Glu Asp Leu Leu Ala Thr
        675                 680                 685 gtc aag tac tat gtc gaa cat cca aac gaa cgt ccg cat tca gat aat        2112
Val Lys Tyr Tyr Val Glu His Pro Asn Glu Arg Pro His Ser Asp Asn
690                 695                 700 ggt ttt ggt aac gct agc gac cat gtt caa aga aac aaa aat ggt caa        2160
Gly Phe Gly Asn Ala Ser Asp His Val Gln Arg Asn Lys Asn Gly Gln
705                 710                 715                 720 gct gat acc aat caa acg gaa aaa cca agc gag gag aaa cct cag aca        2208
Ala Asp Thr Asn Gln Thr Glu Lys Pro Ser Glu Glu Lys Pro Gln Thr
                725                 730                 735 gaa aaa cct gag gaa gaa acc cct cga gaa gag aaa cca caa agc gag        2256
Glu Lys Pro Glu Glu Glu Thr Pro Arg Glu Glu Lys Pro Gln Ser Glu
            740                 745                 750 aaa cca gag tct cca aaa cca aca gag gaa cca gaa gaa gaa tca cca        2304
Lys Pro Glu Ser Pro Lys Pro Thr Glu Glu Pro Glu Glu Glu Ser Pro
        755                 760                 765 gag gaa tca gaa gaa cct cag gtc gag act gaa aag gtt gaa gaa aaa        2352
Glu Glu Ser Glu Glu Pro Gln Val Glu Thr Glu Lys Val Glu Glu Lys
    770                 775                 780 ctg aga gag gct gaa gat tta ctt gga aaa atc cag gat cca att atc        2400
Leu Arg Glu Ala Glu Asp Leu Leu Gly Lys Ile Gln Asp Pro Ile Ile
785                 790                 795                 800 aag tcc aat gcc aaa gag act ctc aca gga tta aaa aat aat tta cta        2448
Lys Ser Asn Ala Lys Glu Thr Leu Thr Gly Leu Lys Asn Asn Leu Leu
                805                 810                 815 ttt ggc acc cag gac aac aat act att atg gca gaa gct gaa aaa cta        2496
Phe Gly Thr Gln Asp Asn Asn Thr Ile Met Ala Glu Ala Glu Lys Leu
            820                 825                 830 ttg gct tta tta aag gag agt aag taa                                    2523
Leu Ala Leu Leu Lys Glu Ser Lys
        835                 840

<210> SEQ ID NO 4
<211> LENGTH: 840
<212> TYPE: PRT
<213> ORGANISM: S. pneumoniae
```

<400> SEQUENCE: 4

```
Met Lys Ile Asn Lys Lys Tyr Leu Ala Gly Ser Val Ala Thr Leu Val
 1               5                  10                  15
Leu Ser Val Cys Ala Tyr Glu Leu Gly Leu His Gln Ala Gln Thr Val
                20                  25                  30
Lys Glu Asn Asn Arg Val Ser Tyr Ile Asp Gly Lys Gln Ala Thr Gln
            35                  40                  45
Lys Thr Glu Asn Leu Thr Pro Asp Glu Val Ser Lys Arg Glu Gly Ile
 50                  55                  60
Asn Ala Glu Gln Ile Val Ile Lys Ile Thr Asp Gln Gly Tyr Val Thr
 65                  70                  75                  80
Ser His Gly Asp His Tyr His Tyr Tyr Asn Gly Lys Val Pro Tyr Asp
                85                  90                  95
Ala Ile Ile Ser Glu Glu Leu Leu Met Lys Asp Pro Asn Tyr Gln Leu
                100                 105                 110
Lys Asp Ser Asp Ile Val Asn Glu Ile Lys Gly Gly Tyr Val Ile Lys
            115                 120                 125
Val Asn Gly Lys Tyr Tyr Val Tyr Leu Lys Asp Ala Ala His Ala Asp
        130                 135                 140
Asn Val Arg Thr Lys Glu Glu Ile Asn Arg Gln Lys Gln Glu His Ser
145                 150                 155                 160
Gln His Arg Glu Gly Gly Thr Ser Ala Asn Asp Gly Ala Val Ala Phe
                165                 170                 175
Ala Arg Ser Gln Gly Arg Tyr Thr Thr Asp Asp Gly Tyr Ile Phe Asn
            180                 185                 190
Ala Ser Asp Ile Ile Glu Asp Thr Gly Asp Ala Tyr Ile Val Pro His
        195                 200                 205
Gly Asp His Tyr His Tyr Ile Pro Lys Asn Glu Leu Ser Ala Ser Glu
    210                 215                 220
Leu Ala Ala Ala Glu Ala Phe Leu Ser Gly Arg Glu Asn Leu Ser Asn
225                 230                 235                 240
Leu Arg Thr Tyr Arg Arg Gln Asn Ser Asp Asn Thr Pro Arg Thr Asn
                245                 250                 255
Trp Val Pro Ser Val Ser Asn Pro Gly Thr Thr Asn Thr Asn Thr Ser
            260                 265                 270
Asn Asn Ser Asn Thr Asn Ser Gln Ala Ser Gln Ser Asn Asp Ile Asp
        275                 280                 285
Ser Leu Leu Lys Gln Leu Tyr Lys Leu Pro Leu Ser Gln Arg His Val
    290                 295                 300
Glu Ser Asp Gly Leu Ile Phe Asp Pro Ala Gln Ile Thr Ser Arg Thr
305                 310                 315                 320
Ala Arg Gly Val Ala Val Pro His Gly Asn His Tyr His Phe Ile Pro
                325                 330                 335
Tyr Glu Gln Met Ser Glu Leu Glu Lys Arg Ile Ala Arg Ile Ile Pro
            340                 345                 350
Leu Arg Tyr Arg Ser Asn His Trp Val Pro Asp Ser Arg Pro Glu Glu
        355                 360                 365
Pro Ser Pro Gln Pro Thr Pro Glu Pro Ser Pro Gln Pro Ala
    370                 375                 380
Pro Asn Pro Gln Pro Ala Pro Ser Asn Pro Ile Asp Glu Lys Leu Val
385                 390                 395                 400
Lys Glu Ala Val Arg Lys Val Gly Asp Gly Tyr Val Phe Glu Glu Asn
```

-continued

```
                405                 410                 415
Gly Val Ser Arg Tyr Ile Pro Ala Lys Asn Leu Ser Ala Glu Thr Ala
                420                 425                 430
Ala Gly Ile Asp Ser Lys Leu Ala Lys Gln Glu Ser Leu Ser His Lys
            435                 440                 445
Leu Gly Ala Lys Lys Thr Asp Leu Pro Ser Ser Asp Arg Glu Phe Tyr
        450                 455                 460
Asn Lys Ala Tyr Asp Leu Leu Ala Arg Ile His Gln Asp Leu Leu Asp
465                 470                 475                 480
Asn Lys Gly Arg Gln Val Asp Phe Glu Ala Leu Asp Asn Leu Leu Glu
                485                 490                 495
Arg Leu Lys Asp Val Ser Ser Asp Lys Val Lys Leu Val Asp Asp Ile
            500                 505                 510
Leu Ala Phe Leu Ala Pro Ile Arg His Pro Glu Arg Leu Gly Lys Pro
        515                 520                 525
Asn Ala Gln Ile Thr Tyr Thr Asp Asp Glu Ile Gln Val Ala Lys Leu
        530                 535                 540
Ala Gly Lys Tyr Thr Thr Glu Asp Gly Tyr Ile Phe Asp Pro Arg Asp
545                 550                 555                 560
Ile Thr Ser Asp Glu Gly Asp Ala Tyr Val Thr Pro His Met Thr His
                565                 570                 575
Ser His Trp Ile Lys Lys Asp Ser Leu Ser Glu Ala Glu Arg Ala Ala
            580                 585                 590
Ala Gln Ala Tyr Ala Lys Glu Lys Gly Leu Thr Pro Pro Ser Thr Asp
        595                 600                 605
His Gln Asp Ser Gly Asn Thr Glu Ala Lys Gly Ala Glu Ala Ile Tyr
    610                 615                 620
Asn Arg Val Lys Ala Ala Lys Lys Val Pro Leu Asp Arg Met Pro Tyr
625                 630                 635                 640
Asn Leu Gln Tyr Thr Val Glu Val Lys Asn Gly Ser Leu Ile Ile Pro
                645                 650                 655
His Tyr Asp His Tyr His Asn Ile Lys Phe Glu Trp Phe Asp Glu Gly
            660                 665                 670
Leu Tyr Glu Ala Pro Lys Gly Tyr Thr Leu Glu Asp Leu Leu Ala Thr
        675                 680                 685
Val Lys Tyr Tyr Val Glu His Pro Asn Glu Arg Pro His Ser Asp Asn
    690                 695                 700
Gly Phe Gly Asn Ala Ser Asp His Val Gln Arg Asn Lys Asn Gly Gln
705                 710                 715                 720
Ala Asp Thr Asn Gln Thr Glu Lys Pro Ser Glu Glu Lys Pro Gln Thr
                725                 730                 735
Glu Lys Pro Glu Glu Glu Thr Pro Arg Glu Glu Lys Pro Gln Ser Glu
            740                 745                 750
Lys Pro Glu Ser Pro Lys Pro Thr Glu Glu Pro Glu Glu Glu Ser Pro
        755                 760                 765
Glu Glu Ser Glu Glu Pro Gln Val Glu Thr Glu Lys Val Glu Glu Lys
    770                 775                 780
Leu Arg Glu Ala Glu Asp Leu Leu Gly Lys Ile Gln Asp Pro Ile Ile
785                 790                 795                 800
Lys Ser Asn Ala Lys Glu Thr Leu Thr Gly Leu Lys Asn Asn Leu Leu
                805                 810                 815
Phe Gly Thr Gln Asp Asn Asn Thr Ile Met Ala Glu Ala Glu Lys Leu
            820                 825                 830
```

Leu Ala Leu Leu Lys Glu Ser Lys
        835              840

<210> SEQ ID NO 5
<211> LENGTH: 1581
<212> TYPE: DNA
<213> ORGANISM: S. pneumoniae
<220> FEATURE:
<221> NAME/KEY: CDS
<222> LOCATION: (1)...(1578)

<400> SEQUENCE: 5

| | |
|---|---|
| atg gag aat ata gac atg ttt aaa tca aat cat gag cga aga atg cgt<br>Met Glu Asn Ile Asp Met Phe Lys Ser Asn His Glu Arg Arg Met Arg<br>1               5                  10                 15 | 48 |
| tat tcc att cgt aaa ttt agt gta gga gta gct agc gta gct gtt gcc<br>Tyr Ser Ile Arg Lys Phe Ser Val Gly Val Ala Ser Val Ala Val Ala<br>            20                  25                 30 | 96 |
| agt ctt ttt atg gga agt gtt gta cat gcg aca gag aaa gag gga agt<br>Ser Leu Phe Met Gly Ser Val Val His Ala Thr Glu Lys Glu Gly Ser<br>        35                  40                 45 | 144 |
| acc caa gca gcc act tct ttt aat agg gga aat gga agt cag gca gaa<br>Thr Gln Ala Ala Thr Ser Phe Asn Arg Gly Asn Gly Ser Gln Ala Glu<br>    50                  55                 60 | 192 |
| caa cgt gga gaa ctc gat tta gaa cga gat aag gca atg aaa gcg gtc<br>Gln Arg Gly Glu Leu Asp Leu Glu Arg Asp Lys Ala Met Lys Ala Val<br>65                  70                 75                 80 | 240 |
| agt gaa tat gta gga aaa atg gtg aga gat gcc tat gta aaa tca gat<br>Ser Glu Tyr Val Gly Lys Met Val Arg Asp Ala Tyr Val Lys Ser Asp<br>                85                  90                 95 | 288 |
| aga aaa cga cat aaa aat act gta gct cta gtt aac cag ttg gga aac<br>Arg Lys Arg His Lys Asn Thr Val Ala Leu Val Asn Gln Leu Gly Asn<br>            100                 105                110 | 336 |
| att aag aac agg tat ttg aat gaa ata gtt cat tca acc tca aaa agc<br>Ile Lys Asn Arg Tyr Leu Asn Glu Ile Val His Ser Thr Ser Lys Ser<br>        115                 120                125 | 384 |
| caa cta cag gaa ctg atg atg aag agt caa tca gaa gta gat gaa gct<br>Gln Leu Gln Glu Leu Met Met Lys Ser Gln Ser Glu Val Asp Glu Ala<br>    130                 135                140 | 432 |
| gtg tct aaa ttt gaa aag gac tca ttt tct tcg tca agt tca gga tcc<br>Val Ser Lys Phe Glu Lys Asp Ser Phe Ser Ser Ser Ser Ser Gly Ser<br>145                 150                 155                160 | 480 |
| tcc act aaa cca gaa act ccg cag ccg gaa aat cca gag cat caa aaa<br>Ser Thr Lys Pro Glu Thr Pro Gln Pro Glu Asn Pro Glu His Gln Lys<br>                165                 170                175 | 528 |
| cca aca act cca tct ccg gat acc aaa cca agc cct caa cca gaa ggc<br>Pro Thr Thr Pro Ser Pro Asp Thr Lys Pro Ser Pro Gln Pro Glu Gly<br>            180                 185                190 | 576 |
| aag aaa cca agc gta cca gac att aat cag gaa aaa gaa aaa gct aag<br>Lys Lys Pro Ser Val Pro Asp Ile Asn Gln Glu Lys Glu Lys Ala Lys<br>        195                 200                205 | 624 |
| ctt gct gta gta acc tac atg agc aag att tta gat gat ata caa aaa<br>Leu Ala Val Val Thr Tyr Met Ser Lys Ile Leu Asp Asp Ile Gln Lys<br>    210                 215                220 | 672 |
| cat cat ctg cag aaa gaa aaa cat cgt cag att gtt gct ctt att aag<br>His His Leu Gln Lys Glu Lys His Arg Gln Ile Val Ala Leu Ile Lys<br>225                 230                 235                240 | 720 |
| gag ctt gat gag ctt aaa aag caa gct ctt tct gaa att gat aat gta<br>Glu Leu Asp Glu Leu Lys Lys Gln Ala Leu Ser Glu Ile Asp Asn Val<br>                245                 250                255 | 768 |

| | | | | | | | | | | | | | | | |
|---|---|---|---|---|---|---|---|---|---|---|---|---|---|---|---|
| aat | acc | aaa | gta | gaa | att | gaa | aat | aca | gtc | cac | aag | ata | ttt | gca | gac | 816 |
| Asn | Thr | Lys | Val | Glu | Ile | Glu | Asn | Thr | Val | His | Lys | Ile | Phe | Ala | Asp |
| | | 260 | | | | | 265 | | | | | 270 | | | |
| atg | gat | gca | gtt | gtg | act | aaa | ttc | aaa | aaa | ggc | tta | act | cag | gac | aca | 864 |
| Met | Asp | Ala | Val | Val | Thr | Lys | Phe | Lys | Lys | Gly | Leu | Thr | Gln | Asp | Thr |
| | | | 275 | | | | | 280 | | | | | 285 | | |
| cca | aaa | gaa | cca | ggt | aac | aaa | aaa | cca | tct | gct | cca | aaa | cca | ggt | atg | 912 |
| Pro | Lys | Glu | Pro | Gly | Asn | Lys | Lys | Pro | Ser | Ala | Pro | Lys | Pro | Gly | Met |
| | 290 | | | | | 295 | | | | | 300 | | | | |
| caa | cca | agt | cct | caa | cca | gag | gtt | aaa | ccg | cag | ctg | gaa | aaa | cca | aaa | 960 |
| Gln | Pro | Ser | Pro | Gln | Pro | Glu | Val | Lys | Pro | Gln | Leu | Glu | Lys | Pro | Lys |
| 305 | | | | | 310 | | | | | 315 | | | | | 320 |
| cca | gag | gtt | aaa | ccg | caa | cca | gaa | aaa | cca | aaa | cca | gag | gtt | aaa | ccg | 1008 |
| Pro | Glu | Val | Lys | Pro | Gln | Pro | Glu | Lys | Pro | Lys | Pro | Glu | Val | Lys | Pro |
| | | | 325 | | | | | 330 | | | | | 335 | | |
| cag | ccg | gaa | aaa | cca | aaa | cca | gag | gtt | aaa | ccg | cag | ccg | gaa | aaa | cca | 1056 |
| Gln | Pro | Glu | Lys | Pro | Lys | Pro | Glu | Val | Lys | Pro | Gln | Pro | Glu | Lys | Pro |
| | | | 340 | | | | | 345 | | | | | 350 | | |
| aaa | cca | gag | gtt | aaa | ccg | cag | ccg | gaa | aaa | cca | aaa | cca | gag | gtt | aaa | 1104 |
| Lys | Pro | Glu | Val | Lys | Pro | Gln | Pro | Glu | Lys | Pro | Lys | Pro | Glu | Val | Lys |
| | | 355 | | | | | 360 | | | | | 365 | | | |
| ccg | cag | ccg | gaa | aaa | cca | aaa | cca | gag | gtt | aaa | ccg | cag | ccg | gaa | aaa | 1152 |
| Pro | Gln | Pro | Glu | Lys | Pro | Lys | Pro | Glu | Val | Lys | Pro | Gln | Pro | Glu | Lys |
| 370 | | | | | 375 | | | | | 380 | | | | | |
| cca | aaa | cca | gag | gtt | aaa | ccg | cag | ccg | gaa | aaa | cca | aaa | cca | gag | gtt | 1200 |
| Pro | Lys | Pro | Glu | Val | Lys | Pro | Gln | Pro | Glu | Lys | Pro | Lys | Pro | Glu | Val |
| 385 | | | | | 390 | | | | | 395 | | | | | 400 |
| aaa | ccg | cag | ccg | gaa | aaa | cca | aaa | cca | gag | gtt | aaa | ccg | cag | ccg | gaa | 1248 |
| Lys | Pro | Gln | Pro | Glu | Lys | Pro | Lys | Pro | Glu | Val | Lys | Pro | Gln | Pro | Glu |
| | | | 405 | | | | | 410 | | | | | 415 | | |
| aaa | cca | aaa | cca | gag | gtt | aaa | ccg | cag | ccg | gaa | aaa | cca | aaa | cca | gag | 1296 |
| Lys | Pro | Lys | Pro | Glu | Val | Lys | Pro | Gln | Pro | Glu | Lys | Pro | Lys | Pro | Glu |
| | | 420 | | | | | 425 | | | | | 430 | | | |
| gtt | aaa | ccg | caa | cca | gaa | aaa | cca | aaa | cca | gag | gtt | aaa | ccg | caa | cca | 1344 |
| Val | Lys | Pro | Gln | Pro | Glu | Lys | Pro | Lys | Pro | Glu | Val | Lys | Pro | Gln | Pro |
| | | 435 | | | | | 440 | | | | | 445 | | | |
| gaa | aaa | cca | aaa | cca | gat | aat | agc | aag | cca | caa | gca | gat | gat | aag | aag | 1392 |
| Glu | Lys | Pro | Lys | Pro | Asp | Asn | Ser | Lys | Pro | Gln | Ala | Asp | Asp | Lys | Lys |
| 450 | | | | | 455 | | | | | 460 | | | | | |
| cca | tca | act | aca | aat | aat | tta | agc | aag | gac | aag | caa | cct | tct | aac | caa | 1440 |
| Pro | Ser | Thr | Thr | Asn | Asn | Leu | Ser | Lys | Asp | Lys | Gln | Pro | Ser | Asn | Gln |
| 465 | | | | | 470 | | | | | 475 | | | | | 480 |
| gct | tca | aca | aac | gaa | aaa | gca | aca | aat | aaa | ccg | aag | aag | tca | ttg | cca | 1488 |
| Ala | Ser | Thr | Asn | Glu | Lys | Ala | Thr | Asn | Lys | Pro | Lys | Lys | Ser | Leu | Pro |
| | | | | 485 | | | | | 490 | | | | | 495 | |
| tca | act | gga | tct | att | tca | aat | cta | gca | ctt | gaa | att | gca | ggt | ctt | ctt | 1536 |
| Ser | Thr | Gly | Ser | Ile | Ser | Asn | Leu | Ala | Leu | Glu | Ile | Ala | Gly | Leu | Leu |
| | | | 500 | | | | | 505 | | | | | 510 | | |
| acc | ttg | gcg | ggg | gca | acc | att | ctt | gct | aag | aaa | aga | atg | aaa | | | 1578 |
| Thr | Leu | Ala | Gly | Ala | Thr | Ile | Leu | Ala | Lys | Lys | Arg | Met | Lys | | |
| | | | 515 | | | | | 520 | | | | | 525 | | |
| tag | | | | | | | | | | | | | | | | 1581 |

<210> SEQ ID NO 6
<211> LENGTH: 526
<212> TYPE: PRT
<213> ORGANISM: S. pneumoniae

<400> SEQUENCE: 6

Met Glu Asn Ile Asp Met Phe Lys Ser Asn His Glu Arg Arg Met Arg

-continued

```
  1               5                  10                 15
Tyr Ser Ile Arg Lys Phe Ser Val Gly Val Ala Ser Val Ala Val Ala
             20                 25                 30

Ser Leu Phe Met Gly Ser Val Val His Ala Thr Glu Lys Glu Gly Ser
         35                 40                 45

Thr Gln Ala Ala Thr Ser Phe Asn Arg Gly Asn Gly Ser Gln Ala Glu
     50                 55                 60

Gln Arg Gly Glu Leu Asp Leu Glu Arg Asp Lys Ala Met Lys Ala Val
 65                 70                 75                 80

Ser Glu Tyr Val Gly Lys Met Val Arg Asp Ala Tyr Val Lys Ser Asp
                 85                 90                 95

Arg Lys Arg His Lys Asn Thr Val Ala Leu Val Asn Gln Leu Gly Asn
             100                105                110

Ile Lys Asn Arg Tyr Leu Asn Glu Ile Val His Ser Thr Ser Lys Ser
         115                120                125

Gln Leu Gln Glu Leu Met Met Lys Ser Gln Ser Glu Val Asp Glu Ala
     130                135                140

Val Ser Lys Phe Glu Lys Asp Ser Phe Ser Ser Ser Ser Gly Ser
145                150                155                160

Ser Thr Lys Pro Glu Thr Pro Gln Pro Glu Asn Pro Glu His Gln Lys
                 165                170                175

Pro Thr Thr Pro Ser Pro Asp Thr Lys Pro Ser Pro Gln Pro Glu Gly
             180                185                190

Lys Lys Pro Ser Val Pro Asp Ile Asn Gln Glu Lys Glu Lys Ala Lys
         195                200                205

Leu Ala Val Val Thr Tyr Met Ser Lys Ile Leu Asp Asp Ile Gln Lys
     210                215                220

His His Leu Gln Lys Glu Lys His Arg Gln Ile Val Ala Leu Ile Lys
225                230                235                240

Glu Leu Asp Glu Leu Lys Lys Gln Ala Leu Ser Glu Ile Asp Asn Val
                 245                250                255

Asn Thr Lys Val Glu Ile Glu Asn Thr Val His Lys Ile Phe Ala Asp
             260                265                270

Met Asp Ala Val Val Thr Lys Phe Lys Lys Gly Leu Thr Gln Asp Thr
         275                280                285

Pro Lys Glu Pro Gly Asn Lys Lys Pro Ser Ala Pro Lys Pro Gly Met
     290                295                300

Gln Pro Ser Pro Gln Pro Glu Val Lys Pro Gln Leu Glu Lys Pro Lys
305                310                315                320

Pro Glu Val Lys Pro Gln Pro Glu Lys Pro Lys Pro Glu Val Lys Pro
                 325                330                335

Gln Pro Glu Lys Pro Lys Pro Glu Val Lys Pro Gln Pro Glu Lys Pro
             340                345                350

Lys Pro Glu Val Lys Pro Gln Pro Glu Lys Pro Lys Pro Glu Val Lys
         355                360                365

Pro Gln Pro Glu Lys Pro Lys Pro Glu Val Lys Pro Gln Pro Glu Lys
     370                375                380

Pro Lys Pro Glu Val Lys Pro Gln Pro Glu Lys Pro Lys Pro Glu Val
385                390                395                400

Lys Pro Gln Pro Glu Lys Pro Lys Pro Glu Val Lys Pro Gln Pro Glu
                 405                410                415

Lys Pro Lys Pro Glu Val Lys Pro Gln Pro Glu Lys Pro Lys Pro Glu
             420                425                430
```

```
Val Lys Pro Gln Pro Glu Lys Pro Lys Pro Glu Val Lys Pro Gln Pro
            435                 440                 445

Glu Lys Pro Lys Pro Asp Asn Ser Lys Pro Gln Ala Asp Asp Lys Lys
        450                 455                 460

Pro Ser Thr Thr Asn Asn Leu Ser Lys Asp Lys Gln Pro Ser Asn Gln
465                 470                 475                 480

Ala Ser Thr Asn Glu Lys Ala Thr Asn Lys Pro Lys Lys Ser Leu Pro
                485                 490                 495

Ser Thr Gly Ser Ile Ser Asn Leu Ala Leu Glu Ile Ala Gly Leu Leu
            500                 505                 510

Thr Leu Ala Gly Ala Thr Ile Leu Ala Lys Lys Arg Met Lys
            515                 520                 525

<210> SEQ ID NO 7
<211> LENGTH: 1455
<212> TYPE: DNA
<213> ORGANISM: S. pneumoniae
<220> FEATURE:
<221> NAME/KEY: CDS
<222> LOCATION: (1)...(1452)

<400> SEQUENCE: 7 atg aaa ttt agt aaa aaa tat ata gca gct gga tca gct gtt atc gta      48
Met Lys Phe Ser Lys Lys Tyr Ile Ala Ala Gly Ser Ala Val Ile Val
 1               5                  10                  15 tcc ttg agt cta tgt gcc tat gca cta aac cag cat cgt tcg cag gaa      96
Ser Leu Ser Leu Cys Ala Tyr Ala Leu Asn Gln His Arg Ser Gln Glu
                20                  25                  30 aat aag gac aat aat cgt gtc tct tat gtg gat ggc agc cag tca agt     144
Asn Lys Asp Asn Asn Arg Val Ser Tyr Val Asp Gly Ser Gln Ser Ser
            35                  40                  45 cag aaa agt gaa aac ttg aca cca gac cag gtt agc cag aaa gaa gga     192
Gln Lys Ser Glu Asn Leu Thr Pro Asp Gln Val Ser Gln Lys Glu Gly
        50                  55                  60 att cag gct gag caa att gta atc aaa att aca gat cag ggc tat gta     240
Ile Gln Ala Glu Gln Ile Val Ile Lys Ile Thr Asp Gln Gly Tyr Val
 65                  70                  75                  80 acg tca cac ggt gac cac tat cat tac tat aat ggg aaa gtt cct tat     288
Thr Ser His Gly Asp His Tyr His Tyr Tyr Asn Gly Lys Val Pro Tyr
                85                  90                  95 gat gcc ctc ttt agt gaa gaa ctc ttg atg aag gat cca aac tat caa     336
Asp Ala Leu Phe Ser Glu Glu Leu Leu Met Lys Asp Pro Asn Tyr Gln
            100                 105                 110 ctt aaa gac gct gat att gtc aat gaa gtc aag ggt ggt tat atc atc     384
Leu Lys Asp Ala Asp Ile Val Asn Glu Val Lys Gly Gly Tyr Ile Ile
        115                 120                 125 aag gtc gat gga aaa tat tat gtc tac ctg aaa gat gca gct cat gct     432
Lys Val Asp Gly Lys Tyr Tyr Val Tyr Leu Lys Asp Ala Ala His Ala
    130                 135                 140 gat aat gtt cga act aaa gat gaa atc aat cgt caa aaa caa gaa cat     480
Asp Asn Val Arg Thr Lys Asp Glu Ile Asn Arg Gln Lys Gln Glu His
145                 150                 155                 160 gtc aaa gat aat gag aag gtt aac tct aat gtt gct gta gca agg tct     528
Val Lys Asp Asn Glu Lys Val Asn Ser Asn Val Ala Val Ala Arg Ser
                165                 170                 175 cag gga cga tat acg aca aat gat ggt tat gtc ttt aat cca gct gat     576
Gln Gly Arg Tyr Thr Thr Asn Asp Gly Tyr Val Phe Asn Pro Ala Asp
            180                 185                 190 att atc gaa gat acg ggt aat gct tat atc gtt cct cat gga ggt cac     624
Ile Ile Glu Asp Thr Gly Asn Ala Tyr Ile Val Pro His Gly Gly His
```

```
Ile Ile Glu Asp Thr Gly Asn Ala Tyr Ile Val Pro His Gly Gly His
            195                 200                 205 tat cac tac att ccc aaa agc gat tta tct gct agt gaa tta gca gca       672
Tyr His Tyr Ile Pro Lys Ser Asp Leu Ser Ala Ser Glu Leu Ala Ala
210                 215                 220 gct aaa gca cat ctg gct gga aaa aat atg caa ccg agt cag tta agc       720
Ala Lys Ala His Leu Ala Gly Lys Asn Met Gln Pro Ser Gln Leu Ser
225                 230                 235                 240 tat tct tca aca gct agt gac aat aac acg caa tct gta gca aaa gga       768
Tyr Ser Ser Thr Ala Ser Asp Asn Asn Thr Gln Ser Val Ala Lys Gly
            245                 250                 255 tca act agc aag cca gca aat aaa tct gaa aat ctc cag agt ctt ttg       816
Ser Thr Ser Lys Pro Ala Asn Lys Ser Glu Asn Leu Gln Ser Leu Leu
            260                 265                 270 aag gaa ctc tat gat tca cct agc gcc caa cgt tac agt gaa tca gat       864
Lys Glu Leu Tyr Asp Ser Pro Ser Ala Gln Arg Tyr Ser Glu Ser Asp
            275                 280                 285 ggc ctg gtc ttt gac cct gct aag att atc agt cgt aca cca aat gga       912
Gly Leu Val Phe Asp Pro Ala Lys Ile Ile Ser Arg Thr Pro Asn Gly
            290                 295                 300 gtt gcg att ccg cat ggc gac cat tac cac ttt att cct tac agc aag       960
Val Ala Ile Pro His Gly Asp His Tyr His Phe Ile Pro Tyr Ser Lys
305                 310                 315                 320 ctt tct gct tta gaa gaa aag att gcc aga atg gtg cct atc agt gga      1008
Leu Ser Ala Leu Glu Glu Lys Ile Ala Arg Met Val Pro Ile Ser Gly
            325                 330                 335 act ggt tct aca gtt tct aca aat gca aaa cct aat gaa gta gtg tct      1056
Thr Gly Ser Thr Val Ser Thr Asn Ala Lys Pro Asn Glu Val Val Ser
            340                 345                 350 agt cta ggc agt ctt tca agc aat cct tct tct tta acg aca agt aag      1104
Ser Leu Gly Ser Leu Ser Ser Asn Pro Ser Ser Leu Thr Thr Ser Lys
            355                 360                 365 gag ctc tct tca gca tct gat ggt tat att ttt aat cca aaa gat atc      1152
Glu Leu Ser Ser Ala Ser Asp Gly Tyr Ile Phe Asn Pro Lys Asp Ile
370                 375                 380 gtt gaa gaa acg gct aca gct tat att gta aga cat ggt gat cat ttc      1200
Val Glu Glu Thr Ala Thr Ala Tyr Ile Val Arg His Gly Asp His Phe
385                 390                 395                 400 cat tac att cca aaa tca aat caa att ggg caa ccg act ctt cca aac      1248
His Tyr Ile Pro Lys Ser Asn Gln Ile Gly Gln Pro Thr Leu Pro Asn
            405                 410                 415 aat agt cta gca aca cct tct cca tct ctt cca atc aat cca gga act      1296
Asn Ser Leu Ala Thr Pro Ser Pro Ser Leu Pro Ile Asn Pro Gly Thr
            420                 425                 430 tca cat gag aaa cat gaa gaa gat gga tac gga ttt gat gct aat cgt      1344
Ser His Glu Lys His Glu Glu Asp Gly Tyr Gly Phe Asp Ala Asn Arg
            435                 440                 445 att atc gct gaa gat gaa tca ggt ttt gtc atg agt cac gga gac cac      1392
Ile Ile Ala Glu Asp Glu Ser Gly Phe Val Met Ser His Gly Asp His
            450                 455                 460 aat cat tat ttc ttc aag aag gac ttg aca gaa gag caa att aag gtg      1440
Asn His Tyr Phe Phe Lys Lys Asp Leu Thr Glu Glu Gln Ile Lys Val
465                 470                 475                 480 cgc aaa aac att tag                                                  1455
Arg Lys Asn Ile <210> SEQ ID NO 8
<211> LENGTH: 484
<212> TYPE: PRT
<213> ORGANISM: S. pneumoniae
```

<400> SEQUENCE: 8

```
Met Lys Phe Ser Lys Lys Tyr Ile Ala Ala Gly Ser Ala Val Ile Val
1               5                   10                  15
Ser Leu Ser Leu Cys Ala Tyr Ala Leu Asn Gln His Arg Ser Gln Glu
            20                  25                  30
Asn Lys Asp Asn Asn Arg Val Ser Tyr Val Asp Gly Ser Gln Ser Ser
        35                  40                  45
Gln Lys Ser Glu Asn Leu Thr Pro Asp Gln Val Ser Gln Lys Glu Gly
    50                  55                  60
Ile Gln Ala Glu Gln Ile Val Ile Lys Ile Thr Asp Gln Gly Tyr Val
65                  70                  75                  80
Thr Ser His Gly Asp His Tyr His Tyr Tyr Asn Gly Lys Val Pro Tyr
                85                  90                  95
Asp Ala Leu Phe Ser Glu Glu Leu Leu Met Lys Asp Pro Asn Tyr Gln
            100                 105                 110
Leu Lys Asp Ala Asp Ile Val Asn Glu Val Lys Gly Gly Tyr Ile Ile
        115                 120                 125
Lys Val Asp Gly Lys Tyr Tyr Val Tyr Leu Lys Asp Ala Ala His Ala
    130                 135                 140
Asp Asn Val Arg Thr Lys Asp Glu Ile Asn Arg Gln Lys Gln Glu His
145                 150                 155                 160
Val Lys Asp Asn Glu Lys Val Asn Ser Asn Val Ala Val Ala Arg Ser
                165                 170                 175
Gln Gly Arg Tyr Thr Thr Asn Asp Gly Tyr Val Phe Asn Pro Ala Asp
            180                 185                 190
Ile Ile Glu Asp Thr Gly Asn Ala Tyr Ile Val Pro His Gly Gly His
        195                 200                 205
Tyr His Tyr Ile Pro Lys Ser Asp Leu Ser Ala Ser Glu Leu Ala Ala
    210                 215                 220
Ala Lys Ala His Leu Ala Gly Lys Asn Met Gln Pro Ser Gln Leu Ser
225                 230                 235                 240
Tyr Ser Ser Thr Ala Ser Asp Asn Asn Thr Gln Ser Val Ala Lys Gly
                245                 250                 255
Ser Thr Ser Lys Pro Ala Asn Lys Ser Glu Asn Leu Gln Ser Leu Leu
            260                 265                 270
Lys Glu Leu Tyr Asp Ser Pro Ser Ala Gln Arg Tyr Ser Glu Ser Asp
        275                 280                 285
Gly Leu Val Phe Asp Pro Ala Lys Ile Ile Ser Arg Thr Pro Asn Gly
    290                 295                 300
Val Ala Ile Pro His Gly Asp His Tyr His Phe Ile Pro Tyr Ser Lys
305                 310                 315                 320
Leu Ser Ala Leu Glu Glu Lys Ile Ala Arg Met Val Pro Ile Ser Gly
                325                 330                 335
Thr Gly Ser Thr Val Ser Thr Asn Ala Lys Pro Asn Glu Val Val Ser
            340                 345                 350
Ser Leu Gly Ser Leu Ser Ser Asn Pro Ser Ser Leu Thr Ser Lys
            355                 360                 365
Glu Leu Ser Ser Ala Ser Asp Gly Tyr Ile Phe Asn Pro Lys Asp Ile
        370                 375                 380
Val Glu Glu Thr Ala Thr Ala Tyr Ile Val Arg His Gly Asp His Phe
385                 390                 395                 400
His Tyr Ile Pro Lys Ser Asn Gln Ile Gly Gln Pro Thr Leu Pro Asn
```

```
                     405                 410                 415
Asn Ser Leu Ala Thr Pro Ser Pro Ser Leu Pro Ile Asn Pro Gly Thr
            420                 425                 430

Ser His Glu Lys His Glu Glu Asp Gly Tyr Gly Phe Asp Ala Asn Arg
            435                 440                 445

Ile Ile Ala Glu Asp Glu Ser Gly Phe Val Met Ser His Gly Asp His
            450                 455                 460

Asn His Tyr Phe Phe Lys Lys Asp Leu Thr Glu Gln Ile Lys Val
465                 470                 475                 480

Arg Lys Asn Ile

<210> SEQ ID NO 9
<211> LENGTH: 1587
<212> TYPE: DNA
<213> ORGANISM: S pneumoniae
<220> FEATURE:
<221> NAME/KEY: CDS
<222> LOCATION: (1)...(1584)

<400> SEQUENCE: 9 atg aaa gat tta gat aaa aaa atc gaa gaa aaa att gct ggc att atg        48
Met Lys Asp Leu Asp Lys Lys Ile Glu Glu Lys Ile Ala Gly Ile Met
1               5                   10                  15 aaa caa tat ggt gtc aaa cgt gaa agt att gtc gtg aat aaa gaa aaa        96
Lys Gln Tyr Gly Val Lys Arg Glu Ser Ile Val Val Asn Lys Glu Lys
            20                  25                  30 aat gcg att att tat ccg cat gga gat cac cat cat gca gat ccg att       144
Asn Ala Ile Ile Tyr Pro His Gly Asp His His His Ala Asp Pro Ile
        35                  40                  45 gat gaa cat aaa ccg gtt gga att ggt cat tct cac agt aac tat gaa       192
Asp Glu His Lys Pro Val Gly Ile Gly His Ser His Ser Asn Tyr Glu
    50                  55                  60 ctg ttt aaa ccc gaa gaa gga gtt gct aaa aaa gaa ggg aat aaa gtt       240
Leu Phe Lys Pro Glu Glu Gly Val Ala Lys Lys Glu Gly Asn Lys Val
65                  70                  75                  80 tat act gga gaa gaa tta acg aat gtt gtt aat ttg tta aaa aat agt       288
Tyr Thr Gly Glu Glu Leu Thr Asn Val Val Asn Leu Leu Lys Asn Ser
                85                  90                  95 acg ttt aat aat caa aac ttt act cta gcc aat ggt caa aaa cgc gtt       336
Thr Phe Asn Asn Gln Asn Phe Thr Leu Ala Asn Gly Gln Lys Arg Val
            100                 105                 110 tct ttt agt ttt ccg cct gaa ttg gag aaa aaa tta ggt atc aat atg       384
Ser Phe Ser Phe Pro Pro Glu Leu Glu Lys Lys Leu Gly Ile Asn Met
        115                 120                 125 cta gta aaa tta ata aca cca gat gga aaa gta ttg gag aaa gta tct       432
Leu Val Lys Leu Ile Thr Pro Asp Gly Lys Val Leu Glu Lys Val Ser
    130                 135                 140 ggt aaa gta ttt gga gaa gga gta ggg aat att gca aac ttt gaa tta       480
Gly Lys Val Phe Gly Glu Gly Val Gly Asn Ile Ala Asn Phe Glu Leu
145                 150                 155                 160 gat caa cct tat tta cca gga caa aca ttt aag tat act atc gct tca       528
Asp Gln Pro Tyr Leu Pro Gly Gln Thr Phe Lys Tyr Thr Ile Ala Ser
                165                 170                 175 aaa gat tat cca gaa gta agt tat gat ggt aca ttt aca gtt cca acc       576
Lys Asp Tyr Pro Glu Val Ser Tyr Asp Gly Thr Phe Thr Val Pro Thr
            180                 185                 190 tct tta gct tac aaa atg gcc agt caa acg att ttc tat cct ttc cat       624
Ser Leu Ala Tyr Lys Met Ala Ser Gln Thr Ile Phe Tyr Pro Phe His
        195                 200                 205
```

```
gca ggg gat act tat tta aga gtg aac cct caa ttt gca gtg cct aaa          672
Ala Gly Asp Thr Tyr Leu Arg Val Asn Pro Gln Phe Ala Val Pro Lys
    210                 215                 220 gga act gat gct tta gtc aga gtg ttt gat gaa ttt cat gga aat gct          720
Gly Thr Asp Ala Leu Val Arg Val Phe Asp Glu Phe His Gly Asn Ala
225                 230                 235                 240 tat tta gaa aat aac tat aaa gtt ggt gaa atc aaa tta ccg att ccg          768
Tyr Leu Glu Asn Asn Tyr Lys Val Gly Glu Ile Lys Leu Pro Ile Pro
                245                 250                 255 aaa tta aac caa gga aca acc aga acg gcc gga aat aaa att cct gta          816
Lys Leu Asn Gln Gly Thr Thr Arg Thr Ala Gly Asn Lys Ile Pro Val
            260                 265                 270 acc ttc atg gca aat gct tat ttg gac aat caa tcg act tat att gtg          864
Thr Phe Met Ala Asn Ala Tyr Leu Asp Asn Gln Ser Thr Tyr Ile Val
        275                 280                 285 gaa gta cct atc ttg gaa aaa gaa aat caa act gat aaa cca agt att          912
Glu Val Pro Ile Leu Glu Lys Glu Asn Gln Thr Asp Lys Pro Ser Ile
    290                 295                 300 cta cca caa ttt aaa agg aat aaa gca caa gaa aac tca aaa ctt gat          960
Leu Pro Gln Phe Lys Arg Asn Lys Ala Gln Glu Asn Ser Lys Leu Asp
305                 310                 315                 320 gaa aag gta gaa gaa cca aag act agt gag aag gta gaa aaa gaa aaa         1008
Glu Lys Val Glu Glu Pro Lys Thr Ser Glu Lys Val Glu Lys Glu Lys
                325                 330                 335 ctt tct gaa act ggg aat agt act agt aat tca acg tta gaa gaa gtt         1056
Leu Ser Glu Thr Gly Asn Ser Thr Ser Asn Ser Thr Leu Glu Glu Val
            340                 345                 350 cct aca gtg gat cct gta caa gaa aaa gta gca aaa ttt gct gaa agt         1104
Pro Thr Val Asp Pro Val Gln Glu Lys Val Ala Lys Phe Ala Glu Ser
        355                 360                 365 tat ggg atg aag cta gaa aat gtc ttg ttt aat atg gac gga aca att         1152
Tyr Gly Met Lys Leu Glu Asn Val Leu Phe Asn Met Asp Gly Thr Ile
    370                 375                 380 gaa tta tat tta cca tca gga gaa gtc att aaa aag aat atg gca gat         1200
Glu Leu Tyr Leu Pro Ser Gly Glu Val Ile Lys Lys Asn Met Ala Asp
385                 390                 395                 400 ttt aca gga gaa gca cct caa gga aat ggt gaa aat aaa cca tct gaa         1248
Phe Thr Gly Glu Ala Pro Gln Gly Asn Gly Glu Asn Lys Pro Ser Glu
                405                 410                 415 aat gga aaa gta tct act gga aca gtt gag aac caa cca aca gaa aat         1296
Asn Gly Lys Val Ser Thr Gly Thr Val Glu Asn Gln Pro Thr Glu Asn
            420                 425                 430 aaa cca gca gat tct tta cca gag gca cca aac gaa aaa cct gta aaa         1344
Lys Pro Ala Asp Ser Leu Pro Glu Ala Pro Asn Glu Lys Pro Val Lys
        435                 440                 445 cca gaa aac tca acg gat aat gga atg ttg aat cca gaa ggg aat gtg         1392
Pro Glu Asn Ser Thr Asp Asn Gly Met Leu Asn Pro Glu Gly Asn Val
    450                 455                 460 ggg agt gac cct atg tta gat cca gca tta gag gaa gct cca gca gta         1440
Gly Ser Asp Pro Met Leu Asp Pro Ala Leu Glu Glu Ala Pro Ala Val
465                 470                 475                 480 gat cct gta caa gaa aaa tta gaa aaa ttt aca gct agt tac gga tta         1488
Asp Pro Val Gln Glu Lys Leu Glu Lys Phe Thr Ala Ser Tyr Gly Leu
                485                 490                 495 ggc tta gat agt gtt ata ttc aat atg gat gga acg att gaa tta aga         1536
Gly Leu Asp Ser Val Ile Phe Asn Met Asp Gly Thr Ile Glu Leu Arg
            500                 505                 510 ttg cca agt gga gaa gtg ata aaa aag aat tta tct gat ttc ata gcg         1584
Leu Pro Ser Gly Glu Val Ile Lys Lys Asn Leu Ser Asp Phe Ile Ala
        515                 520                 525
``` taa                                                                                    1587

<210> SEQ ID NO 10
<211> LENGTH: 528
<212> TYPE: PRT
<213> ORGANISM: S pneumoniae

<400> SEQUENCE: 10

Met Lys Asp Leu Asp Lys Lys Ile Glu Glu Lys Ile Ala Gly Ile Met
1               5                   10                  15

Lys Gln Tyr Gly Val Lys Arg Glu Ser Ile Val Val Asn Lys Glu Lys
            20                  25                  30

Asn Ala Ile Ile Tyr Pro His Gly Asp His His Ala Asp Pro Ile
        35                  40                  45

Asp Glu His Lys Pro Val Gly Ile Gly His Ser His Ser Asn Tyr Glu
    50                  55                  60

Leu Phe Lys Pro Glu Glu Gly Val Ala Lys Glu Gly Asn Lys Val
65                  70                  75                  80

Tyr Thr Gly Glu Glu Leu Thr Asn Val Val Asn Leu Leu Lys Asn Ser
                85                  90                  95

Thr Phe Asn Asn Gln Asn Phe Thr Leu Ala Asn Gly Gln Lys Arg Val
            100                 105                 110

Ser Phe Ser Phe Pro Pro Glu Leu Glu Lys Leu Gly Ile Asn Met
            115                 120                 125

Leu Val Lys Leu Ile Thr Pro Asp Gly Lys Val Leu Glu Lys Val Ser
    130                 135                 140

Gly Lys Val Phe Gly Glu Gly Val Gly Asn Ile Ala Asn Phe Glu Leu
145                 150                 155                 160

Asp Gln Pro Tyr Leu Pro Gly Gln Thr Phe Lys Tyr Thr Ile Ala Ser
                165                 170                 175

Lys Asp Tyr Pro Glu Val Ser Tyr Asp Gly Thr Phe Thr Val Pro Thr
            180                 185                 190

Ser Leu Ala Tyr Lys Met Ala Ser Gln Thr Ile Phe Tyr Pro Phe His
        195                 200                 205

Ala Gly Asp Thr Tyr Leu Arg Val Asn Pro Gln Phe Ala Val Pro Lys
    210                 215                 220

Gly Thr Asp Ala Leu Val Arg Val Phe Asp Glu Phe His Gly Asn Ala
225                 230                 235                 240

Tyr Leu Glu Asn Asn Tyr Lys Val Gly Glu Ile Lys Leu Pro Ile Pro
                245                 250                 255

Lys Leu Asn Gln Gly Thr Thr Arg Thr Ala Gly Asn Lys Ile Pro Val
            260                 265                 270

Thr Phe Met Ala Asn Ala Tyr Leu Asp Asn Gln Ser Thr Tyr Ile Val
        275                 280                 285

Glu Val Pro Ile Leu Glu Lys Glu Asn Gln Thr Asp Lys Pro Ser Ile
    290                 295                 300

Leu Pro Gln Phe Lys Arg Asn Lys Ala Gln Glu Asn Ser Lys Leu Asp
305                 310                 315                 320

Glu Lys Val Glu Glu Pro Lys Thr Ser Glu Lys Val Glu Lys Glu Lys
                325                 330                 335

Leu Ser Glu Thr Gly Asn Ser Thr Ser Asn Ser Thr Leu Glu Glu Val
            340                 345                 350

Pro Thr Val Asp Pro Val Gln Glu Lys Val Ala Lys Phe Ala Glu Ser
        355                 360                 365

```
Tyr Gly Met Lys Leu Glu Asn Val Leu Phe Asn Met Asp Gly Thr Ile
    370                 375                 380
Glu Leu Tyr Leu Pro Ser Gly Glu Val Ile Lys Lys Asn Met Ala Asp
385                 390                 395                 400
Phe Thr Gly Glu Ala Pro Gln Gly Asn Gly Asn Lys Pro Ser Glu
                    405                 410                 415
Asn Gly Lys Val Ser Thr Gly Thr Val Glu Asn Gln Pro Thr Glu Asn
                420                 425                 430
Lys Pro Ala Asp Ser Leu Pro Glu Ala Pro Glu Lys Pro Val Lys
                435                 440                 445
Pro Glu Asn Ser Thr Asp Asn Gly Met Leu Asn Pro Glu Gly Asn Val
                450                 455                 460
Gly Ser Asp Pro Met Leu Asp Pro Ala Leu Glu Ala Pro Ala Val
465                 470                 475                 480
Asp Pro Val Gln Glu Lys Leu Glu Lys Phe Thr Ala Ser Tyr Gly Leu
                    485                 490                 495
Gly Leu Asp Ser Val Ile Phe Asn Met Asp Gly Thr Ile Glu Leu Arg
                500                 505                 510
Leu Pro Ser Gly Glu Val Ile Lys Lys Asn Leu Ser Asp Phe Ile Ala
                515                 520                 525

<210> SEQ ID NO 11
<211> LENGTH: 5048
<212> TYPE: DNA
<213> ORGANISM: S. pneumoniae

<400> SEQUENCE: 11
aattccttgt cgggtaagtt ccgacccgca cgaaaggcgt aatgatttgg gcactgtctc      60
aacgagagac tcggtgaaat tttagtacct gtgaagatgc aggttacccg cgacaggacg     120
gaaagacccc atggagcttt actgcagttt gatattgagt gtctgtacca catgtacagg     180
ataggtagga gtctaagaga tcgggacgcc agtttcgaag agacgctgt tgggatacta      240 cccttgtgtt atggccactc taacccagat aggtgatccc tatcggagac agtgtctgac     300
gggcagtttg actggggcgg tcgcctccta aaaggtaacg gaggcgccca aggttccct      360 cagaatggtt ggaaatcatt cgcagagtgt aaaggtataa gggagcttga ctgcgagagc     420
tacaactcga gcagggacga aagtcgggct tagtgatccg gtggttccgt atggaagggc    480
catcgctcaa cggataaaag ctaccctggg gataacaggc ttatctcccc caagagttca    540
catcgacggg gaggtttggc acctcgatgt cggctcgtcg catcctgggg ctgtagtcgg    600
tcccaagggt tgggctgttc gcccattaaa gcggcacgcg agctgggttc agaacgtcgt    660
gagacagttc ggtccctatc cgtcgcgggc gtaggaaatt tgagaggatc tgctcctagt    720
acgagaggac cagagtggac ttaccgctgg tgtaccagtt gtcttgccaa aggcatcgct    780
gggtagctat gtagggaagg gataaacgct gaaagcatct aagtgtgaaa cccacctcaa    840
gatgagattt cccatgatta tatcagta agagccctga gagatgatca ggtagatagg      900
ttagaagtgg aagtgtggcg acacatgtag cggactaata ctaatagctc gaggacttat    960
ccaaagtaac tgagaatatg aaagcgaacg gttttcttaa attgaataga tattcaattt   1020
tgagtaggta ttactcagag ttaagtgacg atagcctagg agatacacct gtacccatgc   1080
cgaacacaga agttaagccc tagaacgccg gaagtagttg ggggttgccc cctgtgagat   1140
agggaagtcg cttagctcta gggagtttag ctcagctggg agagcatctg ccttacaagc   1200
```

```
agagggtcag cggttcgatc ccgttaactc ccaaaggtcc cgtagtgtag cggttatcac   1260
gtcgccctgt cacggcgaag atcgcgggtt cgattcccgt cgggaccgtt taaggtaacg   1320
caagttattt tagactcgtt agctcagttg gtagagcaat tgacttttaa tcaatgggtc   1380
actggttcga gcccagtacg ggtcatatat gcgggtttgg cggaattcta atctctttga   1440
aatcatcttc tctcactttc caaaactcta ttacctctta ttataccaca tttcaatctt   1500
caacttccca gtaatataag cacctctggc gaaagaagtt tcaatgtcct aaagtaataa   1560
gtgaatccaa ttcaggaact ccaagaacaa aagaaacatc tggtgtcaca agtattggat   1620
ggcacagagt cacgtggtag tctgaccta gcagaaattt taaatagtaa actatttact   1680
ggttaattaa atggttaaat aaccggttta gaaaactatt taataaagta aagaagttg    1740
agaaaaaact tcatcattta ttgaaatgag ggatttatga aatttagtaa aaaatatata   1800
gcagctggat cagctgttat cgtatccttg agtctatgtg cctatgcact aaaccagcat   1860
cgttcgcagg aaaataagga caataatcgt gtctcttatg tggatggcag ccagtcaagt   1920
cagaaaagtg aaaacttgac accagaccag gttagccaga agaaggaat tcaggctgag    1980
caaattgtaa tcaaaattac agatcagggc tatgtaacgt cacacggtga ccactatcat   2040
tactataatg ggaaagttcc ttatgatgcc ctctttagtg aagaactctt gatgaaggat   2100
ccaaactatc aacttaaaga cgctgatatt gtcaatgaag tcaagggtgg ttatatcatc   2160
aaggtcgatg gaaaatatta tgtctacctg aaagatgcag ctcatgctga taatgttcga   2220
actaaagatg aaatcaatcg tcaaaaacaa gaacatgtca agataatga gaaggttaac    2280
tctaatgttg ctgtagcaag gtctcaggga cgatatacga caaatgatgg ttatgtcttt   2340
aatccagctg atattatcga agatacgggt aatgcttata tcgttcctca tggaggtcac   2400
tatcactaca ttcccaaaag cgatttatct gctagtgaat tagcagcagc taaagcacat   2460
ctggctggaa aaaatatgca accgagtcag ttaagctatt cttcaacagc tagtgacaat   2520
aacacgcaat ctgtagcaaa aggatcaact agcaagccag caaataaatc tgaaaatctc   2580
cagagtcttt tgaaggaact ctatgattca cctagcgccc aacgttacag tgaatcagat   2640
ggcctggtct ttgaccctgc taagattatc agtcgtacac caaatggagt tgcgattccg   2700
catggcgacc attaccactt tattccttac agcaagcttt ctgctttaga agaaaagatt   2760
gccagaatgg tgcctatcag tggaactggt tctacagttt ctacaaatgc aaaacctaat   2820
gaagtagtgt ctagtctagg cagtcttca  agcaatcctt cttctttaac gacaagtaag   2880
gagctctctt cagcatctga tggttatatt tttaatccaa aagatatcgt tgaagaaacg   2940
gctacagctt atattgtaag acatggtgat catttccatt acattccaaa atcaaatcaa   3000
attgggcaac cgactcttcc aaacaatagt ctagcaacac cttctccatc tcttccaatc   3060
aatccaggaa cttcacatga gaaacatgaa gaagatggat acggatttga tgctaatcgt   3120
attatcgctg aagatgaatc aggttttgtc atgagtcacg gagaccacaa tcattatttc   3180
ttcaagaagg acttgacaga agagcaaatt aaggctgcgc aaaaacattt agaggaagtt   3240
aaaactagtc ataatggatt agattctttg tcatctcatg aacaggatta tccaggtaat   3300
gccaaagaaa tgaaagattt agataaaaaa atcgaagaaa aaattgctgg cattatgaaa   3360
caatatggtg tcaaacgtga aagtattgtc gtgaataaag aaaaaaatgc gattatttat   3420
ccgcatggag atcaccatca tgcagatccg attgatgaac ataaaccggt tggaattggt   3480
cattctcaca gtaactatga actgttaaa  cccgaagaag gagttgctaa aaaagaaggg   3540
aataaagttt atactggaga agaattaacg aatgttgtta atttgttaaa aaatagtacg   3600
```

```
tttaataatc aaaactttac tctagccaat ggtcaaaaac gcgtttcttt tagttttccg   3660
cctgaattgg agaaaaaatt aggtatcaat atgctagtaa aattaataac accagatgga   3720
aaagtattgg agaaagtatc tggtaaagta tttggagaag gagtagggaa tattgcaaac   3780
tttgaattag atcaacctta tttaccagga caaacattta agtatactat cgcttcaaaa   3840
gattatccag aagtaagtta tgatggtaca tttacagttc caacctcttt agcttacaaa   3900
atggccagtc aaacgatttt ctatcctttc catgcagggg atacttattt aagagtgaac   3960
cctcaatttg cagtgcctaa aggaactgat gctttagtca gagtgtttga tgaatttcat   4020
ggaaatgctt atttagaaaa aactataaa gttggtgaaa tcaaattacc gattccgaaa   4080
ttaaaccaag gaacaaccag aacggccgga aataaaattc ctgtaacctt catggcaaat   4140
gcttatttgg acaatcaatc gacttatatt gtggaagtac ctatcttgga aaaagaaaat   4200
caaactgata aaccaagtat tctaccacaa tttaaaagga ataaagcaca agaaaactca   4260
aaacttgatg aaaaggtaga agaaccaaag actagtgaga aggtagaaaa agaaaaactt   4320
tctgaaactg gaatagtac tagtaattca acgttagaag aagttcctac agtggatcct   4380
gtacaagaaa aagtagcaaa atttgctgaa agttatggga tgaagctaga aaatgtcttg   4440
tttaatatgg acggaacaat tgaattatat ttaccatcag gagaagtcat taaaaagaat   4500
atggcagatt ttacaggaga agcacctcaa ggaaatggtg aaaataaacc atctgaaaat   4560
ggaaaagtat ctactggaac agttgagaac caaccaacag aaaataaacc agcagattct   4620
ttaccagagg caccaaacga aaaacctgta aaaccagaaa actcaacgga taatggaatg   4680
ttgaatccag aagggaatgt ggggagtgac cctatgttag atccagcatt agaggaagct   4740
ccagcagtag atcctgtaca agaaaaatta gaaaaattta cagctagtta cggattaggc   4800
ttagatagtg ttatattcaa tatggatgga acgattgaat taagattgcc aagtggagaa   4860
gtgataaaaa agaatttatc tgatttcata gcgtaaggaa tagcagtaga aaaagtctga   4920
atcaaaaatg aagttctctc aaaagttaga aataaaactc tgactttggg agaatttcat   4980
tttattatta atatataaaa tttcttgaca tacaacttaa aaagaggtgg aatatttact   5040
agttaatt                                                            5048
```

<210> SEQ ID NO 12
<211> LENGTH: 2647
<212> TYPE: DNA
<213> ORGANISM: S. pneumoniae

<400> SEQUENCE: 12

```
cagagatctt agtgaatcaa atatacttaa gaaaagagga agaatgaaa atcaataaaa     60 aatatctagc tgggtcagta gctacacttg ttttaagtgt ctgtgcttat gaactaggtt    120
tgcatcaagc tcaaactgta aaagaaaata atcgtgtttc ctatatagat ggaaaacaag   180
cgacgcaaaa aacggagaat tgactcctg atgaggttag caagcgtgaa ggaatcaacg    240
ccgaacaaat cgtcatcaag attacggatc aaggttatgt gacctctcat ggagaccatt    300
atcattacta taatggcaag gtcccttatg atgccatcat cagtgaagag ctcctcatga    360
aagatccgaa ttatcagttg aaggattcag acattgtcaa tgaaatcaag ggtggttatg    420
tcattaaggt aaacggtaaa tactatgttt accttaagga tgcagctcat gcggataatg    480
tccgtacaaa agaagaaatc aatcggcaaa acaagaaca tagtcagcat cgtgaaggag    540
ggacttcagc aaacgatggt gcggtagcct ttgcacgttc acagggacgc tacaccacag    600
```

-continued

```
atgatggtta tatcttcaat gcatctgata tcatcgaaga tacgggcgat gcctatatcg    660
ttcctcatgg agatcattac cattacattc ctaagaatga gttatcagct agcgagttgg    720
ctgctgcaga agccttccta tctggtcggg aaaatctgtc aaatttaaga acctatcgcc    780
gacaaaatag cgataacact ccaagaacaa actgggtacc ttctgtaagc aatccaggaa    840
ctacaaatac taacacaagc aacaacagca acactaacag tcaagcaagt caaagtaatg    900
acattgatag tctcttgaaa cagctctaca aactgccttt gagtcaacgc catgtagaat    960
ctgatggcct tattttcgac ccagcgcaaa tcacaagtcg aaccgccaga ggtgtagctg    1020
tccctcatgg taaccattac cactttatcc cttatgaaca aatgtctgaa ttggaaaaac    1080
gaattgctcg tattattccc cttcgttatc gttcaaacca ttgggtacca gattcaagac    1140
cagaagaacc aagtccacaa ccgactccag aacctagtcc aagtccgcaa cctgcaccaa    1200
atcctcaacc agctccaagc aatccaattg atgagaaatt ggtcaaagaa gctgttcgaa    1260
aagtaggcga tggttatgtc tttgaggaga atggagtttc tcgttatatc ccagccaaga    1320
atctttcagc agaaacagca gcaggcattg atagcaaact ggccaagcag aaagtttat    1380 ctcataagct aggagctaag aaaactgacc tcccatctag tgatcgagaa ttttacaata    1440
aggcttatga cttactagca agaattcacc aagatttact tgataataaa ggtcgacaag    1500
ttgattttga ggctttggat aacctgttgg aacgactcaa ggatgtctca agtgataaag    1560
tcaagttagt ggatgatatt cttgccttct tagctccgat tcgtcatcca aacgtttag    1620 gaaaaccaaa tgcgcaaatt acctacactg atgatgagat tcaagtagcc aagttggcag    1680
gcaagtacac aacagaagac ggttatatct ttgatcctcg tgatataacc agtgatgagg    1740
gggatgccta tgtaactcca catatgaccc atagccactg gattaaaaaa gatagtttgt    1800
ctgaagctga gagagcggca gcccaggctt atgctaaaga gaaaggtttg acccctcctt    1860
cgacagacca tcaggattca ggaaatactg aggcaaaagg agcagaagct atctacaacc    1920
gcgtgaaagc agctaagaag gtgccacttg atcgtatgcc ttacaatctt caatatactg    1980
tagaagtcaa aaacggtagt ttaatcatac ctcattatga ccattaccat aacatcaaat    2040
ttgagtggtt tgacgaaggc ctttatgagg cacctaaggg gtatactctt gaggatcttt    2100
tggcgactgt caagtactat gtcgaacatc aaacgaacg tccgcattca gataatggtt    2160
ttggtaacgc tagcgaccat gttcaaagaa acaaaaatgg tcaagctgat accaatcaaa    2220
cggaaaaacc aagcgaggag aaacctcaga cagaaaaacc tgaggaagaa acccctcgag    2280
aagagaaacc acaaagcgag aaaccagagt ctccaaaacc aacagaggaa ccagaagaag    2340
aatcaccaga ggaatcagaa gaacctcagg tcgagactga aaaggttgaa gaaaaactga    2400
gagaggctga agatttactt ggaaaaatcc aggatccaat tatcaagtcc aatgccaaag    2460
agactctcac aggattaaaa aataatttac tatttggcac ccaggacaac aatactatta    2520
tggcagaagc tgaaaaacta ttggctttat taaggagag taagtaaagg tagcagcatt    2580
ttctaactcc taaaaacagg ataggagaac gggaaaacga aaaatgagag cagaatgtga    2640
gttctag                                                             2647
```

<210> SEQ ID NO 13
<211> LENGTH: 2639
<212> TYPE: DNA
<213> ORGANISM: S. pneumoniae
<220> FEATURE:
<221> NAME/KEY: CDS
<222> LOCATION: (114)...(2627)

<400> SEQUENCE: 13

```
gggtcttaaa actctgaatc ctttagaggc agacccacaa aatgacaaga cctatttaga      60
aaatctggaa gaaaatatga gtgttctagc agaagaatta aagtgaggaa aga atg        116
                                                             Met
                                                              1 aaa atc aat aaa aaa tat cta gca ggt tca gtg gca gtc ctt gcc cta       164
Lys Ile Asn Lys Lys Tyr Leu Ala Gly Ser Val Ala Val Leu Ala Leu
          5                  10                  15 agt gtt tgt tcc tat gaa ctt ggt cgt cac caa gct ggt cag gtt aag       212
Ser Val Cys Ser Tyr Glu Leu Gly Arg His Gln Ala Gly Gln Val Lys
     20                  25                  30 aaa gag tct aat cga gtt tct tat ata gat ggt gat cag gct ggt caa       260
Lys Glu Ser Asn Arg Val Ser Tyr Ile Asp Gly Asp Gln Ala Gly Gln
 35                  40                  45 aag gca gaa aat ttg aca cca gat gaa gtc agt aag aga gag ggg atc       308
Lys Ala Glu Asn Leu Thr Pro Asp Glu Val Ser Lys Arg Glu Gly Ile
 50                  55                  60                  65 aac gcc gaa caa att gtt atc aag att acg gat caa ggt tat gtg acc       356
Asn Ala Glu Gln Ile Val Ile Lys Ile Thr Asp Gln Gly Tyr Val Thr
                 70                  75                  80 tct cat gga gac cat tat cat tac tat aat ggc aag gtt cct tat gat       404
Ser His Gly Asp His Tyr His Tyr Tyr Asn Gly Lys Val Pro Tyr Asp
             85                  90                  95 gcc atc atc agt gaa gaa ctt ctc atg aaa gat ccg aat tat cag ttg       452
Ala Ile Ile Ser Glu Glu Leu Leu Met Lys Asp Pro Asn Tyr Gln Leu
        100                 105                 110 aag gat tca gac att gtc aat gaa atc aag ggt ggc tat gtg att aag       500
Lys Asp Ser Asp Ile Val Asn Glu Ile Lys Gly Gly Tyr Val Ile Lys
    115                 120                 125 gta gac gga aaa tac tat gtt tac ctt aaa gat gcg gcc cat gcg gac       548
Val Asp Gly Lys Tyr Tyr Val Tyr Leu Lys Asp Ala Ala His Ala Asp
130                 135                 140                 145 aat att cgg aca aaa gaa gag att aaa cgt cag aag cag gaa cac agt       596
Asn Ile Arg Thr Lys Glu Glu Ile Lys Arg Gln Lys Gln Glu His Ser
                150                 155                 160 cat aat cat aac tca aga gca gat aat gct gtt gct gca gcc aga gcc       644
His Asn His Asn Ser Arg Ala Asp Asn Ala Val Ala Ala Ala Arg Ala
            165                 170                 175 caa gga cgt tat aca acg gat gat ggg tat atc ttc aat gca tct gat       692
Gln Gly Arg Tyr Thr Thr Asp Asp Gly Tyr Ile Phe Asn Ala Ser Asp
        180                 185                 190 atc att gag gac acg ggt gat gct tat atc gtt cct cac ggc gac cat       740
Ile Ile Glu Asp Thr Gly Asp Ala Tyr Ile Val Pro His Gly Asp His
    195                 200                 205 tac cat tac att cct aag aat gag tta tca gct agc gag tta gct gct       788
Tyr His Tyr Ile Pro Lys Asn Glu Leu Ser Ala Ser Glu Leu Ala Ala
210                 215                 220                 225 gca gaa gcc tat tgg aat ggg aag cag gga tct cgt cct tct tca agt       836
Ala Glu Ala Tyr Trp Asn Gly Lys Gln Gly Ser Arg Pro Ser Ser Ser
                230                 235                 240 tct agt tat aat gca aat cca gtt caa cca aga ttg tca gag aac cac       884
Ser Ser Tyr Asn Ala Asn Pro Val Gln Pro Arg Leu Ser Glu Asn His
            245                 250                 255 aat ctg act gtc act cca act tat cat caa aat caa ggg gaa aac att       932
Asn Leu Thr Val Thr Pro Thr Tyr His Gln Asn Gln Gly Glu Asn Ile
        260                 265                 270 tca agc ctt tta cgt gaa ttg tat gct aaa ccc tta tca gaa cgc cat       980
Ser Ser Leu Leu Arg Glu Leu Tyr Ala Lys Pro Leu Ser Glu Arg His
    275                 280                 285
```

```
                                              -continued
gta gaa tct gat ggc ctt att ttc gac cca gcg caa atc aca agt cga      1028
Val Glu Ser Asp Gly Leu Ile Phe Asp Pro Ala Gln Ile Thr Ser Arg
290             295                 300                 305 acc gcc aga ggt gta gct gtc cct cat ggt aac cat tac cac ttt atc      1076
Thr Ala Arg Gly Val Ala Val Pro His Gly Asn His Tyr His Phe Ile
            310                 315                 320 cct tat gaa caa atg tct gaa ttg gaa aaa cga att gct cgt att att      1124
Pro Tyr Glu Gln Met Ser Glu Leu Glu Lys Arg Ile Ala Arg Ile Ile
325                 330                 335 ccc ctt cgt tat cgt tca aac cat tgg gta cca gat tca aga cca gaa      1172
Pro Leu Arg Tyr Arg Ser Asn His Trp Val Pro Asp Ser Arg Pro Glu
        340                 345                 350 caa cca agt cca caa tcg act ccg gaa cct agt cca agt ctg caa cct      1220
Gln Pro Ser Pro Gln Ser Thr Pro Glu Pro Ser Pro Ser Leu Gln Pro
355                 360                 365 gca cca aat cct caa cca gct cca agc aat cca att gat gag aaa ttg      1268
Ala Pro Asn Pro Gln Pro Ala Pro Ser Asn Pro Ile Asp Glu Lys Leu
370                 375                 380                 385 gtc aaa gaa gct gtt cga aaa gta ggc gat ggt tat gtc ttt gag gag      1316
Val Lys Glu Ala Val Arg Lys Val Gly Asp Gly Tyr Val Phe Glu Glu
            390                 395                 400 aat gga gtt tct cgt tat atc cca gcc aag gat ctt tca gca gaa aca      1364
Asn Gly Val Ser Arg Tyr Ile Pro Ala Lys Asp Leu Ser Ala Glu Thr
            405                 410                 415 gca gca ggc att gat agc aaa ctg gcc aag cag gaa agt tta tct cat      1412
Ala Ala Gly Ile Asp Ser Lys Leu Ala Lys Gln Glu Ser Leu Ser His
            420                 425                 430 aag cta gga gct aag aaa act gac ctc cca tct agt gat cga gaa ttt      1460
Lys Leu Gly Ala Lys Lys Thr Asp Leu Pro Ser Ser Asp Arg Glu Phe
435                 440                 445 tac aat aag gct tat gac tta cta gca aga att cac caa gat tta ctt      1508
Tyr Asn Lys Ala Tyr Asp Leu Leu Ala Arg Ile His Gln Asp Leu Leu
450                 455                 460                 465 gat aat aaa ggt cga caa gtt gat ttt gag gtt ttg gat aac ctg ttg      1556
Asp Asn Lys Gly Arg Gln Val Asp Phe Glu Val Leu Asp Asn Leu Leu
            470                 475                 480 gaa cga ctc aag gat gtc tca agt gat aaa gtc aag tta gtg gat gat      1604
Glu Arg Leu Lys Asp Val Ser Ser Asp Lys Val Lys Leu Val Asp Asp
            485                 490                 495 att ctt gcc ttc tta gct ccg att cgt cat cca gaa cgt tta gga aaa      1652
Ile Leu Ala Phe Leu Ala Pro Ile Arg His Pro Glu Arg Leu Gly Lys
            500                 505                 510 cca aat gcg caa att acc tac act gat gat gag att caa gta gcc aag      1700
Pro Asn Ala Gln Ile Thr Tyr Thr Asp Asp Glu Ile Gln Val Ala Lys
515                 520                 525 ttg gca ggc aag tac aca aca gaa gac ggt tat atc ttt gat cct cgt      1748
Leu Ala Gly Lys Tyr Thr Thr Glu Asp Gly Tyr Ile Phe Asp Pro Arg
530                 535                 540                 545 gat ata acc agt gat gag ggg gat gcc tat gta act cca cat atg acc      1796
Asp Ile Thr Ser Asp Glu Gly Asp Ala Tyr Val Thr Pro His Met Thr
            550                 555                 560 cat agc cac tgg att aaa aaa gat agt ttg tct gaa gct gag aga gcg      1844
His Ser His Trp Ile Lys Lys Asp Ser Leu Ser Glu Ala Glu Arg Ala
            565                 570                 575 gca gcc cag gct tat gct aaa gag aaa ggt ttg acc cct cct tcg aca      1892
Ala Ala Gln Ala Tyr Ala Lys Glu Lys Gly Leu Thr Pro Pro Ser Thr
            580                 585                 590 gac cac cag gat tca gga aat act gag gca aaa gga gca gaa gct atc      1940
Asp His Gln Asp Ser Gly Asn Thr Glu Ala Lys Gly Ala Glu Ala Ile
595                 600                 605
```

```
tac aac cgc gtg aaa gca gct aag aag gtg cca ctt gat cgt atg cct      1988
Tyr Asn Arg Val Lys Ala Ala Lys Lys Val Pro Leu Asp Arg Met Pro
610                 615                 620                 625 tac aat ctt caa tat act gta gaa gtc aaa aac ggt agt tta atc ata      2036
Tyr Asn Leu Gln Tyr Thr Val Glu Val Lys Asn Gly Ser Leu Ile Ile
                630                 635                 640 cct cat tat gac cat tac cat aac atc aaa ttt gag tgg ttt gac gaa      2084
Pro His Tyr Asp His Tyr His Asn Ile Lys Phe Glu Trp Phe Asp Glu
            645                 650                 655 ggc ctt tat gag gca cct aag ggg tat agt ctt gag gat ctt ttg gcg      2132
Gly Leu Tyr Glu Ala Pro Lys Gly Tyr Ser Leu Glu Asp Leu Leu Ala
        660                 665                 670 act gtc aag tac tat gtc gaa cat cca aac gaa cgt ccg cat tca gat      2180
Thr Val Lys Tyr Tyr Val Glu His Pro Asn Glu Arg Pro His Ser Asp
    675                 680                 685 aat ggt ttt ggt aac gct agt gac cat gtt cgt aaa aat aag gca gac      2228
Asn Gly Phe Gly Asn Ala Ser Asp His Val Arg Lys Asn Lys Ala Asp
690                 695                 700                 705 caa gat agt aaa cct gat gaa gat aag gaa cat gat gaa gta agt gag      2276
Gln Asp Ser Lys Pro Asp Glu Asp Lys Glu His Asp Glu Val Ser Glu
                710                 715                 720 cca act cac cct gaa tct gat gaa aaa gag aat cac gct ggt tta aat      2324
Pro Thr His Pro Glu Ser Asp Glu Lys Glu Asn His Ala Gly Leu Asn
            725                 730                 735 cct tca gca gat aat ctt tat aaa cca agc act gat acg gaa gag aca      2372
Pro Ser Ala Asp Asn Leu Tyr Lys Pro Ser Thr Asp Thr Glu Glu Thr
        740                 745                 750 gag gaa gaa gct gaa gat acc aca gat gag gct gaa att cct caa gta      2420
Glu Glu Glu Ala Glu Asp Thr Thr Asp Glu Ala Glu Ile Pro Gln Val
    755                 760                 765 gag aat tct gtt att aac gct aag ata gca gat gcg gag gcc ttg cta      2468
Glu Asn Ser Val Ile Asn Ala Lys Ile Ala Asp Ala Glu Ala Leu Leu
770                 775                 780                 785 gaa aaa gta aca gat cct agt att aga caa aat gct atg gag aca ttg      2516
Glu Lys Val Thr Asp Pro Ser Ile Arg Gln Asn Ala Met Glu Thr Leu
                790                 795                 800 act ggt cta aaa agt agt ctt ctt ctc gga acg aaa gat aat aac act      2564
Thr Gly Leu Lys Ser Ser Leu Leu Leu Gly Thr Lys Asp Asn Asn Thr
            805                 810                 815 att tca gca gaa gta gat agt ctc ttg gct ttg tta aaa gaa agt caa      2612
Ile Ser Ala Glu Val Asp Ser Leu Leu Ala Leu Leu Lys Glu Ser Gln
        820                 825                 830 ccg gct cct ata cag tagtaaaatg aa                                    2639
Pro Ala Pro Ile Gln
    835

<210> SEQ ID NO 14
<211> LENGTH: 838
<212> TYPE: PRT
<213> ORGANISM: S. pneumoniae

<400> SEQUENCE: 14

Met Lys Ile Asn Lys Lys Tyr Leu Ala Gly Ser Val Ala Val Leu Ala
 1               5                  10                  15

Leu Ser Val Cys Ser Tyr Glu Leu Gly Arg His Gln Ala Gly Gln Val
                20                  25                  30

Lys Lys Glu Ser Asn Arg Val Ser Tyr Ile Asp Gly Asp Gln Ala Gly
            35                  40                  45

Gln Lys Ala Glu Asn Leu Thr Pro Asp Glu Val Ser Lys Arg Glu Gly
```

-continued

```
            50                  55                  60
Ile Asn Ala Glu Gln Ile Val Ile Lys Ile Thr Asp Gln Gly Tyr Val
 65                  70                  75                  80
Thr Ser His Gly Asp His Tyr His Tyr Tyr Asn Gly Lys Val Pro Tyr
                 85                  90                  95
Asp Ala Ile Ile Ser Glu Glu Leu Leu Met Lys Asp Pro Asn Tyr Gln
                100                 105                 110
Leu Lys Asp Ser Asp Ile Val Asn Glu Ile Lys Gly Gly Tyr Val Ile
                115                 120                 125
Lys Val Asp Gly Lys Tyr Tyr Val Tyr Leu Lys Asp Ala Ala His Ala
130                 135                 140
Asp Asn Ile Arg Thr Lys Glu Glu Ile Lys Arg Gln Lys Gln Glu His
145                 150                 155                 160
Ser His Asn His Asn Ser Arg Ala Asp Asn Ala Val Ala Ala Ala Arg
                165                 170                 175
Ala Gln Gly Arg Tyr Thr Thr Asp Asp Gly Tyr Ile Phe Asn Ala Ser
                180                 185                 190
Asp Ile Ile Glu Asp Thr Gly Asp Ala Tyr Ile Val Pro His Gly Asp
                195                 200                 205
His Tyr His Tyr Ile Pro Lys Asn Glu Leu Ser Ala Ser Glu Leu Ala
                210                 215                 220
Ala Ala Glu Ala Tyr Trp Asn Gly Lys Gln Gly Ser Arg Pro Ser Ser
225                 230                 235                 240
Ser Ser Ser Tyr Asn Ala Asn Pro Val Gln Pro Arg Leu Ser Glu Asn
                245                 250                 255
His Asn Leu Thr Val Thr Pro Thr Tyr His Gln Asn Gln Gly Glu Asn
                260                 265                 270
Ile Ser Ser Leu Leu Arg Glu Leu Tyr Ala Lys Pro Leu Ser Glu Arg
                275                 280                 285
His Val Glu Ser Asp Gly Leu Ile Phe Asp Pro Ala Gln Ile Thr Ser
                290                 295                 300
Arg Thr Ala Arg Gly Val Ala Val Pro His Gly Asn His Tyr His Phe
305                 310                 315                 320
Ile Pro Tyr Glu Gln Met Ser Glu Leu Glu Lys Arg Ile Ala Arg Ile
                325                 330                 335
Ile Pro Leu Arg Tyr Arg Ser Asn His Trp Val Pro Asp Ser Arg Pro
                340                 345                 350
Glu Gln Pro Ser Pro Gln Ser Thr Pro Glu Pro Ser Pro Ser Leu Gln
                355                 360                 365
Pro Ala Pro Asn Pro Gln Pro Ala Pro Ser Asn Pro Ile Asp Glu Lys
                370                 375                 380
Leu Val Lys Glu Ala Val Arg Lys Val Gly Asp Gly Tyr Val Phe Glu
385                 390                 395                 400
Glu Asn Gly Val Ser Arg Tyr Ile Pro Ala Lys Asp Leu Ser Ala Glu
                405                 410                 415
Thr Ala Ala Gly Ile Asp Ser Lys Leu Ala Lys Gln Glu Ser Leu Ser
                420                 425                 430
His Lys Leu Gly Ala Lys Lys Thr Asp Leu Pro Ser Ser Asp Arg Glu
                435                 440                 445
Phe Tyr Asn Lys Ala Tyr Asp Leu Leu Ala Arg Ile His Gln Asp Leu
                450                 455                 460
Leu Asp Asn Lys Gly Arg Gln Val Asp Phe Glu Val Leu Asp Asn Leu
465                 470                 475                 480
```

Leu Glu Arg Leu Lys Asp Val Ser Ser Asp Lys Val Lys Leu Val Asp
            485                 490                 495

Asp Ile Leu Ala Phe Leu Ala Pro Ile Arg His Pro Glu Arg Leu Gly
            500                 505                 510

Lys Pro Asn Ala Gln Ile Thr Tyr Thr Asp Asp Glu Ile Gln Val Ala
            515                 520                 525

Lys Leu Ala Gly Lys Tyr Thr Thr Glu Asp Gly Tyr Ile Phe Asp Pro
        530                 535                 540

Arg Asp Ile Thr Ser Asp Glu Gly Asp Ala Tyr Val Thr Pro His Met
545                 550                 555                 560

Thr His Ser His Trp Ile Lys Lys Asp Ser Leu Ser Glu Ala Glu Arg
                565                 570                 575

Ala Ala Ala Gln Ala Tyr Ala Lys Glu Lys Gly Leu Thr Pro Pro Ser
            580                 585                 590

Thr Asp His Gln Asp Ser Gly Asn Thr Glu Ala Lys Gly Ala Glu Ala
            595                 600                 605

Ile Tyr Asn Arg Val Lys Ala Ala Lys Lys Val Pro Leu Asp Arg Met
        610                 615                 620

Pro Tyr Asn Leu Gln Tyr Thr Val Glu Val Lys Asn Gly Ser Leu Ile
625                 630                 635                 640

Ile Pro His Tyr Asp His Tyr His Asn Ile Lys Phe Glu Trp Phe Asp
                645                 650                 655

Glu Gly Leu Tyr Glu Ala Pro Lys Gly Tyr Ser Leu Glu Asp Leu Leu
            660                 665                 670

Ala Thr Val Lys Tyr Tyr Val Glu His Pro Asn Glu Arg Pro His Ser
        675                 680                 685

Asp Asn Gly Phe Gly Asn Ala Ser Asp His Val Arg Lys Asn Lys Ala
        690                 695                 700

Asp Gln Asp Ser Lys Pro Asp Glu Asp Lys Glu His Asp Glu Val Ser
705                 710                 715                 720

Glu Pro Thr His Pro Glu Ser Asp Glu Lys Glu Asn His Ala Gly Leu
                725                 730                 735

Asn Pro Ser Ala Asp Asn Leu Tyr Lys Pro Ser Thr Asp Thr Glu Glu
            740                 745                 750

Thr Glu Glu Glu Ala Glu Asp Thr Thr Asp Glu Ala Glu Ile Pro Gln
            755                 760                 765

Val Glu Asn Ser Val Ile Asn Ala Lys Ile Ala Asp Ala Glu Ala Leu
        770                 775                 780

Leu Glu Lys Val Thr Asp Pro Ser Ile Arg Gln Asn Ala Met Glu Thr
785                 790                 795                 800

Leu Thr Gly Leu Lys Ser Ser Leu Leu Leu Gly Thr Lys Asp Asn Asn
                805                 810                 815

Thr Ile Ser Ala Glu Val Asp Ser Leu Leu Ala Leu Leu Lys Glu Ser
            820                 825                 830

Gln Pro Ala Pro Ile Gln
        835

<210> SEQ ID NO 15
<211> LENGTH: 2528
<212> TYPE: DNA
<213> ORGANISM: S. pneumoniae
<220> FEATURE:
<221> NAME/KEY: CDS
<222> LOCATION: (1)...(2520)

<400> SEQUENCE: 15

```
tgt gcc tat gca cta aac cag cat cgt tcg cag gaa aat aag gac aat      48
Cys Ala Tyr Ala Leu Asn Gln His Arg Ser Gln Glu Asn Lys Asp Asn
1               5                   10                  15 aat cgt gtc tct tat gtg gat ggc agc cag tca agt cag aaa agt gaa      96
Asn Arg Val Ser Tyr Val Asp Gly Ser Gln Ser Ser Gln Lys Ser Glu
            20                  25                  30 aac ttg aca cca gac cag gtt agc cag aaa gaa gga att cag gct gag     144
Asn Leu Thr Pro Asp Gln Val Ser Gln Lys Glu Gly Ile Gln Ala Glu
        35                  40                  45 caa att gta atc aaa att aca gat cag ggc tat gta acg tca cac ggt     192
Gln Ile Val Ile Lys Ile Thr Asp Gln Gly Tyr Val Thr Ser His Gly
    50                  55                  60 gat cac tat cat tac tat aat ggg aaa gtt cct tat gat gcc ctc ttt     240
Asp His Tyr His Tyr Tyr Asn Gly Lys Val Pro Tyr Asp Ala Leu Phe
65                  70                  75                  80 agt gaa gaa ctc ttg atg aag gat cca aac tat caa ctt aaa gac gct     288
Ser Glu Glu Leu Leu Met Lys Asp Pro Asn Tyr Gln Leu Lys Asp Ala
                85                  90                  95 gat att gtc aat gaa gtc aag ggt ggt tat atc atc aag gtc gat gga     336
Asp Ile Val Asn Glu Val Lys Gly Gly Tyr Ile Ile Lys Val Asp Gly
            100                 105                 110 aaa tat tat gtc tac ctg aaa gat gca gct cat gct gat aat gtt cga     384
Lys Tyr Tyr Val Tyr Leu Lys Asp Ala Ala His Ala Asp Asn Val Arg
        115                 120                 125 act aaa gat gaa atc aat cgt caa aaa caa gaa cat gtc aaa gat aat     432
Thr Lys Asp Glu Ile Asn Arg Gln Lys Gln Glu His Val Lys Asp Asn
    130                 135                 140 gag aag gtt aac tct aat gtt gct gta gca agg tct cag gga cga tat     480
Glu Lys Val Asn Ser Asn Val Ala Val Ala Arg Ser Gln Gly Arg Tyr
145                 150                 155                 160 acg aca aat gat ggt tat gtc ttt aat cca gct gat att atc gaa gat     528
Thr Thr Asn Asp Gly Tyr Val Phe Asn Pro Ala Asp Ile Ile Glu Asp
                165                 170                 175 acg ggt aat gct tat atc gtt cct cat gga ggt cac tat cac tac att     576
Thr Gly Asn Ala Tyr Ile Val Pro His Gly Gly His Tyr His Tyr Ile
            180                 185                 190 ccc aaa agc gat tta tct gct agt gaa tta gca gca gct aaa gca cat     624
Pro Lys Ser Asp Leu Ser Ala Ser Glu Leu Ala Ala Ala Lys Ala His
        195                 200                 205 ctg gct gga aaa aat atg caa ccg agt cag tta agc tat tct tca aca     672
Leu Ala Gly Lys Asn Met Gln Pro Ser Gln Leu Ser Tyr Ser Ser Thr
    210                 215                 220 cct tct cca tct ctt cca atc aat cca gga act tca cat gag aaa cat     720
Pro Ser Pro Ser Leu Pro Ile Asn Pro Gly Thr Ser His Glu Lys His
225                 230                 235                 240 gaa gaa gat gga tac gga ttt gat gct aat cgt att atc gct gaa gat     768
Glu Glu Asp Gly Tyr Gly Phe Asp Ala Asn Arg Ile Ile Ala Glu Asp
                245                 250                 255 gaa tca ggt ttt gtc atg agt cac gga gac cac aat cat tat ttc ttc     816
Glu Ser Gly Phe Val Met Ser His Gly Asp His Asn His Tyr Phe Phe
            260                 265                 270 aag aag gac ttg aca gaa gag caa att aag gct gcg caa aaa cat tta     864
Lys Lys Asp Leu Thr Glu Glu Gln Ile Lys Ala Ala Gln Lys His Leu
        275                 280                 285 gag gaa gtt aaa act agt cat aat gga tta gat tct ttg tca tct cat     912
Glu Glu Val Lys Thr Ser His Asn Gly Leu Asp Ser Leu Ser Ser His
    290                 295                 300 gaa cag gat tat cca agt aat gcc aaa gaa atg aaa gat tta gat aaa     960
```

```
Glu Gln Asp Tyr Pro Ser Asn Ala Lys Glu Met Lys Asp Leu Asp Lys
305                 310                 315                 320 aaa atc gaa gaa aaa att gct ggc att atg aaa caa tat ggt gtc aaa        1008
Lys Ile Glu Glu Lys Ile Ala Gly Ile Met Lys Gln Tyr Gly Val Lys
                325                 330                 335 cgt gaa agt att gtc gtg aat aaa gaa aaa aat gcg att att tat ccg        1056
Arg Glu Ser Ile Val Val Asn Lys Glu Lys Asn Ala Ile Ile Tyr Pro
            340                 345                 350 cat gga gat cac cat cat gca gat ccg att gat gaa cat aaa ccg gtt        1104
His Gly Asp His His His Ala Asp Pro Ile Asp Glu His Lys Pro Val
        355                 360                 365 gga att ggt cat tct cac agt aac tat gaa ctg ttt aaa ccc gaa gaa        1152
Gly Ile Gly His Ser His Ser Asn Tyr Glu Leu Phe Lys Pro Glu Glu
    370                 375                 380 gga gtt gct aaa aaa gaa ggg aat aaa gtt tat act gga gaa gaa tta        1200
Gly Val Ala Lys Lys Glu Gly Asn Lys Val Tyr Thr Gly Glu Glu Leu
385                 390                 395                 400 acg aat gtt gtt aat ttg tta aaa aat agt acg ttt aat aat caa aac        1248
Thr Asn Val Val Asn Leu Leu Lys Asn Ser Thr Phe Asn Asn Gln Asn
                405                 410                 415 ttt act cta gcc aat ggt caa aaa cgc gtt tct ttt agt ttt ccg cct        1296
Phe Thr Leu Ala Asn Gly Gln Lys Arg Val Ser Phe Ser Phe Pro Pro
            420                 425                 430 gaa ttg gag aaa aaa tta ggt atc aat atg cta gta aaa tta ata aca        1344
Glu Leu Glu Lys Lys Leu Gly Ile Asn Met Leu Val Lys Leu Ile Thr
        435                 440                 445 cca gat gga aaa gta ttg gag aaa gta tct ggt aaa gta ttt gga gaa        1392
Pro Asp Gly Lys Val Leu Glu Lys Val Ser Gly Lys Val Phe Gly Glu
    450                 455                 460 gga gta ggg aat att gca aac ttt gaa tta gat caa cct tat tta cca        1440
Gly Val Gly Asn Ile Ala Asn Phe Glu Leu Asp Gln Pro Tyr Leu Pro
465                 470                 475                 480 gga caa aca ttt aag tat act atc gct tca aaa gat tat cca gaa gta        1488
Gly Gln Thr Phe Lys Tyr Thr Ile Ala Ser Lys Asp Tyr Pro Glu Val
                485                 490                 495 agt tat gat ggt aca ttt aca gtt cca acc tct tta gct tac aaa atg        1536
Ser Tyr Asp Gly Thr Phe Thr Val Pro Thr Ser Leu Ala Tyr Lys Met
            500                 505                 510 gcc agt caa acg att ttc tat cct ttc cat gca ggg gat act tat tta        1584
Ala Ser Gln Thr Ile Phe Tyr Pro Phe His Ala Gly Asp Thr Tyr Leu
        515                 520                 525 aga gtg aac cct caa ttt gca gtg cct aaa gga act gat gct tta gtc        1632
Arg Val Asn Pro Gln Phe Ala Val Pro Lys Gly Thr Asp Ala Leu Val
    530                 535                 540 aga gtg ttt gat gaa ttt cat gga aat gct tat tta gaa aat aac tat        1680
Arg Val Phe Asp Glu Phe His Gly Asn Ala Tyr Leu Glu Asn Asn Tyr
545                 550                 555                 560 aaa gtt ggt gaa atc aaa tta ccg att ccg aaa tta aac caa gga aca        1728
Lys Val Gly Glu Ile Lys Leu Pro Ile Pro Lys Leu Asn Gln Gly Thr
                565                 570                 575 acc aga acg gcc gga aat aaa att cct gta acc ttc atg gca aat gct        1776
Thr Arg Thr Ala Gly Asn Lys Ile Pro Val Thr Phe Met Ala Asn Ala
            580                 585                 590 tat ttg gac aat caa tcg act tat att gtg gaa gta cct atc ttg gaa        1824
Tyr Leu Asp Asn Gln Ser Thr Tyr Ile Val Glu Val Pro Ile Leu Glu
        595                 600                 605 aaa gaa aat caa act gat aaa cca agt att cta cca caa ttt aaa agg        1872
Lys Glu Asn Gln Thr Asp Lys Pro Ser Ile Leu Pro Gln Phe Lys Arg
    610                 615                 620
```

```
aat aaa gca caa gaa aac tca aaa ctt gat gaa aag gta gaa gaa cca      1920
Asn Lys Ala Gln Glu Asn Ser Lys Leu Asp Glu Lys Val Glu Glu Pro
625                 630                 635                 640 aag act agt gag aag gta gaa aaa gaa aaa ctt tct gaa act ggg aat      1968
Lys Thr Ser Glu Lys Val Glu Lys Glu Lys Leu Ser Glu Thr Gly Asn
            645                 650                 655 agt act agt aat tca acg tta gaa gaa gtt cct aca gtg gat cct gta      2016
Ser Thr Ser Asn Ser Thr Leu Glu Glu Val Pro Thr Val Asp Pro Val
        660                 665                 670 caa gaa aaa gta gca aaa ttt gct gaa agt tat ggg atg aag cta gaa      2064
Gln Glu Lys Val Ala Lys Phe Ala Glu Ser Tyr Gly Met Lys Leu Glu
    675                 680                 685 aat gtc ttg ttt aat atg gac gga aca att gaa tta tat tta cca tcg      2112
Asn Val Leu Phe Asn Met Asp Gly Thr Ile Glu Leu Tyr Leu Pro Ser
690                 695                 700 gga gaa gtc att aaa aag aat atg gca gat ttt aca gga gaa gca cct      2160
Gly Glu Val Ile Lys Lys Asn Met Ala Asp Phe Thr Gly Glu Ala Pro
705                 710                 715                 720 caa gga aat ggt gaa aat aaa cca tct gaa aat gga aaa gta tct act      2208
Gln Gly Asn Gly Glu Asn Lys Pro Ser Glu Asn Gly Lys Val Ser Thr
            725                 730                 735 gga aca gtt gag aac caa cca aca gaa aat aaa cca gca gat tct tta      2256
Gly Thr Val Glu Asn Gln Pro Thr Glu Asn Lys Pro Ala Asp Ser Leu
        740                 745                 750 cca gag gca cca aac gaa aaa cct gta aaa cca gaa aac tca acg gat      2304
Pro Glu Ala Pro Asn Glu Lys Pro Val Lys Pro Glu Asn Ser Thr Asp
    755                 760                 765 aat gga atg ttg aat cca gaa ggg aat gtg ggg agt gac cct atg tta      2352
Asn Gly Met Leu Asn Pro Glu Gly Asn Val Gly Ser Asp Pro Met Leu
770                 775                 780 gat tca gca tta gag gaa gct cca gca gta gat cct gta caa gaa aaa      2400
Asp Ser Ala Leu Glu Glu Ala Pro Ala Val Asp Pro Val Gln Glu Lys
785                 790                 795                 800 tta gaa aaa ttt aca gct agt tac gga tta ggc tta gat agt gtt ata      2448
Leu Glu Lys Phe Thr Ala Ser Tyr Gly Leu Gly Leu Asp Ser Val Ile
            805                 810                 815 ttc aat atg gat gga acg att gaa tta aga ttg cca agt gga gaa gtg      2496
Phe Asn Met Asp Gly Thr Ile Glu Leu Arg Leu Pro Ser Gly Glu Val
        820                 825                 830 ata aaa aag aat tta ttg atc tca tagcgtaa                             2528
Ile Lys Lys Asn Leu Leu Ile Ser
    835                 840

<210> SEQ ID NO 16
<211> LENGTH: 840
<212> TYPE: PRT
<213> ORGANISM: S. pneumoniae

<400> SEQUENCE: 16

Cys Ala Tyr Ala Leu Asn Gln His Arg Ser Gln Glu Asn Lys Asp Asn
1               5                   10                  15

Asn Arg Val Ser Tyr Val Asp Gly Ser Gln Ser Ser Gln Lys Ser Glu
            20                  25                  30

Asn Leu Thr Pro Asp Gln Val Ser Gln Lys Glu Gly Ile Gln Ala Glu
        35                  40                  45

Gln Ile Val Ile Lys Ile Thr Asp Gln Gly Tyr Val Thr Ser His Gly
    50                  55                  60

Asp His Tyr His Tyr Tyr Asn Gly Lys Val Pro Tyr Asp Ala Leu Phe
65                  70                  75                  80
```

-continued

```
Ser Glu Glu Leu Leu Met Lys Asp Pro Asn Tyr Gln Leu Lys Asp Ala
             85                  90                  95

Asp Ile Val Asn Glu Val Lys Gly Gly Tyr Ile Ile Lys Val Asp Gly
            100                 105                 110

Lys Tyr Tyr Val Tyr Leu Lys Asp Ala Ala His Ala Asp Asn Val Arg
            115                 120                 125

Thr Lys Asp Glu Ile Asn Arg Gln Lys Gln Glu His Val Lys Asp Asn
130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Gly His Tyr His Tyr Ile
            180                 185                 190

Pro Lys Ser Asp Leu Ser Ala Ser Glu Leu Ala Ala Lys Ala His
            195                 200                 205

Leu Ala Gly Lys Asn Met Gln Pro Ser Gln Leu Ser Tyr Ser Ser Thr
210                 215                 220

Pro Ser Pro Ser Leu Pro Ile Asn Pro Gly Thr Ser His Glu Lys His
225                 230                 235                 240

Glu Glu Asp Gly Tyr Gly Phe Asp Ala Asn Arg Ile Ile Ala Glu Asp
                245                 250                 255

Glu Ser Gly Phe Val Met Ser His Gly Asp His Asn His Tyr Phe Phe
            260                 265                 270

Lys Lys Asp Leu Thr Glu Glu Gln Ile Lys Ala Ala Gln Lys His Leu
            275                 280                 285

Glu Glu Val Lys Thr Ser His Asn Gly Leu Asp Ser Leu Ser Ser His
            290                 295                 300

Glu Gln Asp Tyr Pro Ser Asn Ala Lys Glu Met Lys Asp Leu Asp Lys
305                 310                 315                 320

Lys Ile Glu Glu Lys Ile Ala Gly Ile Met Lys Gln Tyr Gly Val Lys
                325                 330                 335

Arg Glu Ser Ile Val Val Asn Lys Glu Lys Asn Ala Ile Ile Tyr Pro
            340                 345                 350

His Gly Asp His His His Ala Asp Pro Ile Asp Glu His Lys Pro Val
            355                 360                 365

Gly Ile Gly His Ser His Ser Asn Tyr Glu Leu Phe Lys Pro Glu Glu
            370                 375                 380

Gly Val Ala Lys Lys Glu Gly Asn Lys Val Tyr Thr Gly Glu Glu Leu
385                 390                 395                 400

Thr Asn Val Val Asn Leu Leu Lys Asn Ser Thr Phe Asn Asn Gln Asn
                405                 410                 415

Phe Thr Leu Ala Asn Gly Gln Lys Arg Val Ser Phe Ser Phe Pro Pro
            420                 425                 430

Glu Leu Glu Lys Lys Leu Gly Ile Asn Met Leu Val Lys Leu Ile Thr
            435                 440                 445

Pro Asp Gly Lys Val Leu Glu Lys Val Ser Gly Lys Val Phe Gly Glu
            450                 455                 460

Gly Val Gly Asn Ile Ala Asn Phe Glu Leu Asp Gln Pro Tyr Leu Pro
465                 470                 475                 480

Gly Gln Thr Phe Lys Tyr Thr Ile Ala Ser Lys Asp Tyr Pro Glu Val
                485                 490                 495

Ser Tyr Asp Gly Thr Phe Thr Val Pro Thr Ser Leu Ala Tyr Lys Met
```

```
                500             505             510
Ala Ser Gln Thr Ile Phe Tyr Pro Phe His Ala Gly Asp Thr Tyr Leu
        515                 520                 525

Arg Val Asn Pro Gln Phe Ala Val Pro Lys Gly Thr Asp Ala Leu Val
        530                 535                 540

Arg Val Phe Asp Glu Phe His Gly Asn Ala Tyr Leu Glu Asn Asn Tyr
545                 550                 555                 560

Lys Val Gly Glu Ile Lys Leu Pro Ile Pro Lys Leu Asn Gln Gly Thr
                565                 570                 575

Thr Arg Thr Ala Gly Asn Lys Ile Pro Val Thr Phe Met Ala Asn Ala
                580                 585                 590

Tyr Leu Asp Asn Gln Ser Thr Tyr Ile Val Glu Val Pro Ile Leu Glu
        595                 600                 605

Lys Glu Asn Gln Thr Asp Lys Pro Ser Ile Leu Pro Gln Phe Lys Arg
        610                 615                 620

Asn Lys Ala Gln Glu Asn Ser Lys Leu Asp Glu Lys Val Glu Glu Pro
625                 630                 635                 640

Lys Thr Ser Glu Lys Val Glu Lys Glu Lys Leu Ser Glu Thr Gly Asn
                645                 650                 655

Ser Thr Ser Asn Ser Thr Leu Glu Glu Val Pro Thr Val Asp Pro Val
                660                 665                 670

Gln Glu Lys Val Ala Lys Phe Ala Glu Ser Tyr Gly Met Lys Leu Glu
        675                 680                 685

Asn Val Leu Phe Asn Met Asp Gly Thr Ile Glu Leu Tyr Leu Pro Ser
        690                 695                 700

Gly Glu Val Ile Lys Lys Asn Met Ala Asp Phe Thr Gly Glu Ala Pro
705                 710                 715                 720

Gln Gly Asn Gly Glu Asn Lys Pro Ser Glu Asn Gly Lys Val Ser Thr
                725                 730                 735

Gly Thr Val Glu Asn Gln Pro Thr Glu Asn Lys Pro Ala Asp Ser Leu
                740                 745                 750

Pro Glu Ala Pro Asn Glu Lys Pro Val Lys Pro Glu Asn Ser Thr Asp
        755                 760                 765

Asn Gly Met Leu Asn Pro Glu Gly Asn Val Gly Ser Asp Pro Met Leu
        770                 775                 780

Asp Ser Ala Leu Glu Glu Ala Pro Ala Val Asp Pro Val Gln Glu Lys
785                 790                 795                 800

Leu Glu Lys Phe Thr Ala Ser Tyr Gly Leu Gly Leu Asp Ser Val Ile
                805                 810                 815

Phe Asn Met Asp Gly Thr Ile Glu Leu Arg Leu Pro Ser Gly Glu Val
                820                 825                 830

Ile Lys Lys Asn Leu Leu Ile Ser
        835                 840

<210> SEQ ID NO 17
<211> LENGTH: 27
<212> TYPE: DNA
<213> ORGANISM: Artificial Sequence
<220> FEATURE:
<223> OTHER INFORMATION: PCR oligonucleotide primer

<400> SEQUENCE: 17
cagtagatct gtgcctatgc actaaac                                      27

<210> SEQ ID NO 18
```

```
<211> LENGTH: 33
<212> TYPE: DNA
<213> ORGANISM: Artificial Sequence
<220> FEATURE:
<223> OTHER INFORMATION: PCR oligonucleotide primer

<400> SEQUENCE: 18
gatctctaga ctactgctat tccttacgct atg                           33

<210> SEQ ID NO 19
<211> LENGTH: 30
<212> TYPE: DNA
<213> ORGANISM: Artificial Sequence
<220> FEATURE:
<223> OTHER INFORMATION: PCR oligonucleotide primer

<400> SEQUENCE: 19
atcactcgag cattacctgg ataatcctgt                               30

<210> SEQ ID NO 20
<211> LENGTH: 26
<212> TYPE: DNA
<213> ORGANISM: Artificial Sequence
<220> FEATURE:
<223> OTHER INFORMATION: PCR oligonucleotide primer

<400> SEQUENCE: 20
ctgctaagct tatgaaagat ttagat                                   26

<210> SEQ ID NO 21
<211> LENGTH: 24
<212> TYPE: DNA
<213> ORGANISM: Artificial Sequence
<220> FEATURE:
<223> OTHER INFORMATION: PCR oligonucleotide primer

<400> SEQUENCE: 21
gatactcgag ctgctattcc ttac                                     24

<210> SEQ ID NO 22
<211> LENGTH: 28
<212> TYPE: DNA
<213> ORGANISM: Artificial Sequence
<220> FEATURE:
<223> OTHER INFORMATION: PCR oligonucleotide primer

<400> SEQUENCE: 22
gaatctcgag ttaagctgct gctaattc                                 28

<210> SEQ ID NO 23
<211> LENGTH: 32
<212> TYPE: DNA
<213> ORGANISM: Artificial Sequence
<220> FEATURE:
<223> OTHER INFORMATION: PCR oligonucleotide primer

<400> SEQUENCE: 23
gacgctcgag cgctatgaaa tcagataaat tc                            32

<210> SEQ ID NO 24
<211> LENGTH: 37
<212> TYPE: DNA
<213> ORGANISM: Artificial Sequence
<220> FEATURE:
<223> OTHER INFORMATION: PCR oligonucleotide primer

<400> SEQUENCE: 24
```

```
gacgctcgag ggcattacct ggataatcct gttcatg                                      37

<210> SEQ ID NO 25
<211> LENGTH: 33
<212> TYPE: DNA
<213> ORGANISM: Artificial Sequence
<220> FEATURE:
<223> OTHER INFORMATION: PCR oligonucleotide primer

<400> SEQUENCE: 25
cagtagatct cttcatcatt tattgaaaag agg                                          33

<210> SEQ ID NO 26
<211> LENGTH: 40
<212> TYPE: DNA
<213> ORGANISM: Artificial Sequence
<220> FEATURE:
<223> OTHER INFORMATION: PCR oligonucleotide primer

<400> SEQUENCE: 26
ttatttcttc catatggact tgacagaaga gcaaattaag                                   40

<210> SEQ ID NO 27
<211> LENGTH: 32
<212> TYPE: DNA
<213> ORGANISM: Artificial Sequence
<220> FEATURE:
<223> OTHER INFORMATION: PCR oligonucleotide primer

<400> SEQUENCE: 27
cgccaagctt cgctatgaaa tcagataaat tc                                           32

<210> SEQ ID NO 28
<211> LENGTH: 34
<212> TYPE: DNA
<213> ORGANISM: Artificial Sequence
<220> FEATURE:
<223> OTHER INFORMATION: PCR oligonucleotide primer

<400> SEQUENCE: 28
cgccaagctt ttccacaata taagtcgatt gatt                                         34

<210> SEQ ID NO 29
<211> LENGTH: 40
<212> TYPE: DNA
<213> ORGANISM: Artificial Sequence
<220> FEATURE:
<223> OTHER INFORMATION: PCR oligonucleotide primer

<400> SEQUENCE: 29
ttatttcttc catatggaag tacctatctt ggaaaaagaa                                   40

<210> SEQ ID NO 30
<211> LENGTH: 37
<212> TYPE: DNA
<213> ORGANISM: Artificial Sequence
<220> FEATURE:
<223> OTHER INFORMATION: PCR oligonucleotide primer

<400> SEQUENCE: 30
ttatttcttc catatggtgc ctatgcacta aaccagc                                      37

<210> SEQ ID NO 31
<211> LENGTH: 40
<212> TYPE: DNA
```

```
<213> ORGANISM: Artificial Sequence
<220> FEATURE:
<223> OTHER INFORMATION: PCR oligonucleotide primer

<400> SEQUENCE: 31
ataagaatgc ggccgcttcc acaatataag tcgattgatt                    40

<210> SEQ ID NO 32
<211> LENGTH: 31
<212> TYPE: DNA
<213> ORGANISM: Artificial Sequence
<220> FEATURE:
<223> OTHER INFORMATION: PCR oligonucleotide primer

<400> SEQUENCE: 32
cagtagatct gtgcttatga actaggtttg c                             31

<210> SEQ ID NO 33
<211> LENGTH: 32
<212> TYPE: DNA
<213> ORGANISM: Artificial Sequence
<220> FEATURE:
<223> OTHER INFORMATION: PCR oligonucleotide primer

<400> SEQUENCE: 33
gatcaagctt gctgctacct ttacttactc tc                            32

<210> SEQ ID NO 34
<211> LENGTH: 26
<212> TYPE: DNA
<213> ORGANISM: Artificial Sequence
<220> FEATURE:
<223> OTHER INFORMATION: PCR oligonucleotide primer

<400> SEQUENCE: 34
ctgagatatc cgttatcgtt caaacc                                   26

<210> SEQ ID NO 35
<211> LENGTH: 28
<212> TYPE: DNA
<213> ORGANISM: Artificial Sequence
<220> FEATURE:
<223> OTHER INFORMATION: PCR oligonucleotide primer

<400> SEQUENCE: 35
ctgcaagctt ttaaagggga ataatacg                                 28

<210> SEQ ID NO 36
<211> LENGTH: 29
<212> TYPE: DNA
<213> ORGANISM: Artificial Sequence
<220> FEATURE:
<223> OTHER INFORMATION: PCR oligonucleotide primer

<400> SEQUENCE: 36
cagtagatct gcagaagcct tcctatctg                                29

<210> SEQ ID NO 37
<211> LENGTH: 33
<212> TYPE: DNA
<213> ORGANISM: Artificial Sequence
<220> FEATURE:
<223> OTHER INFORMATION: PCR oligonucleotide primer

<400> SEQUENCE: 37
tcgccaagct tcgttatcgt tcaaaccatt ggg                           33
```

<210> SEQ ID NO 38
<211> LENGTH: 45
<212> TYPE: DNA
<213> ORGANISM: Artificial Sequence
<220> FEATURE:
<223> OTHER INFORMATION: PCR oligonucleotide primer

<400> SEQUENCE: 38
ataagaatgc ggccgcctta ctctccttta ataaagccaa tagtt                45

<210> SEQ ID NO 39
<211> LENGTH: 34
<212> TYPE: DNA
<213> ORGANISM: Artificial Sequence
<220> FEATURE:
<223> OTHER INFORMATION: PCR oligonucleotide primer

<400> SEQUENCE: 39
catgccatgg acattgatag tctcttgaaa cagc                            34

<210> SEQ ID NO 40
<211> LENGTH: 37
<212> TYPE: DNA
<213> ORGANISM: Artificial Sequence
<220> FEATURE:
<223> OTHER INFORMATION: PCR oligonucleotide primer

<400> SEQUENCE: 40
cgccaagctt cttactctcc tttaataaag ccaatag                         37

<210> SEQ ID NO 41
<211> LENGTH: 31
<212> TYPE: DNA
<213> ORGANISM: Artificial Sequence
<220> FEATURE:
<223> OTHER INFORMATION: PCR oligonucleotide primer

<400> SEQUENCE: 41
cgacaagctt aacatggtcg ctagcgttac c                               31

<210> SEQ ID NO 42
<211> LENGTH: 30
<212> TYPE: DNA
<213> ORGANISM: Artificial Sequence
<220> FEATURE:
<223> OTHER INFORMATION: PCR oligonucleotide primer

<400> SEQUENCE: 42
cataccatgg gcctttatga ggcacctaag                                 30

<210> SEQ ID NO 43
<211> LENGTH: 34
<212> TYPE: DNA
<213> ORGANISM: Artificial Sequence
<220> FEATURE:
<223> OTHER INFORMATION: PCR oligonucleotide primer

<400> SEQUENCE: 43
cgacaagctt aagtaaatct tcagcctctc tcag                            34

<210> SEQ ID NO 44
<211> LENGTH: 31
<212> TYPE: DNA
<213> ORGANISM: Artificial Sequence
<220> FEATURE:

```
<223> OTHER INFORMATION: PCR oligonucleotide primer

<400> SEQUENCE: 44
gataccatgg ctagcgacca tgttcaaaga a                           31

<210> SEQ ID NO 45
<211> LENGTH: 36
<212> TYPE: DNA
<213> ORGANISM: Artificial Sequence
<220> FEATURE:
<223> OTHER INFORMATION: PCR oligonucleotide primer

<400> SEQUENCE: 45
cgccaagctt atcatccact aacttgactt tatcac                      36

<210> SEQ ID NO 46
<211> LENGTH: 33
<212> TYPE: DNA
<213> ORGANISM: Artificial Sequence
<220> FEATURE:
<223> OTHER INFORMATION: PCR oligonucleotide primer

<400> SEQUENCE: 46
cataccatgg atattcttgc cttcttagct ccg                         33

<210> SEQ ID NO 47
<211> LENGTH: 30
<212> TYPE: DNA
<213> ORGANISM: Artificial Sequence
<220> FEATURE:
<223> OTHER INFORMATION: PCR oligonucleotide primer

<400> SEQUENCE: 47
catgccatgg tgcttatgaa ctaggtttgc                             30

<210> SEQ ID NO 48
<211> LENGTH: 32
<212> TYPE: DNA
<213> ORGANISM: Artificial Sequence
<220> FEATURE:
<223> OTHER INFORMATION: PCR oligonucleotide primer

<400> SEQUENCE: 48
cgccaagctt tagcgttacc aaaaccatta tc                          32

<210> SEQ ID NO 49
<211> LENGTH: 36
<212> TYPE: DNA
<213> ORGANISM: Artificial Sequence
<220> FEATURE:
<223> OTHER INFORMATION: PCR oligonucleotide primer

<400> SEQUENCE: 49
gtattagatc tgttcctatg aacttggtcg tcacca                      36

<210> SEQ ID NO 50
<211> LENGTH: 28
<212> TYPE: DNA
<213> ORGANISM: Artificial Sequence
<220> FEATURE:
<223> OTHER INFORMATION: PCR oligonucleotide primer

<400> SEQUENCE: 50
cgcctctaga ctactgtata ggagccgg                               28
```

-continued

<210> SEQ ID NO 51
<211> LENGTH: 34
<212> TYPE: DNA
<213> ORGANISM: Artificial Sequence
<220> FEATURE:
<223> OTHER INFORMATION: PCR oligonucleotide primer

<400> SEQUENCE: 51
catgccatgg aaaacatttc aagccttta cgtg                               34

<210> SEQ ID NO 52
<211> LENGTH: 34
<212> TYPE: DNA
<213> ORGANISM: Artificial Sequence
<220> FEATURE:
<223> OTHER INFORMATION: PCR oligonucleotide primer

<400> SEQUENCE: 52
cgacaagctt ctgtatagga gccggttgac tttc                              34

<210> SEQ ID NO 53
<211> LENGTH: 34
<212> TYPE: DNA
<213> ORGANISM: Artificial Sequence
<220> FEATURE:
<223> OTHER INFORMATION: PCR oligonucleotide primer

<400> SEQUENCE: 53
catgccatgg ttcgtaaaaa taaggcagac caag                              34

<210> SEQ ID NO 54
<211> LENGTH: 30
<212> TYPE: DNA
<213> ORGANISM: Artificial Sequence
<220> FEATURE:
<223> OTHER INFORMATION: PCR oligonucleotide primer

<400> SEQUENCE: 54
catgccatgg aagcctattg gaatgggaag                                   30

<210> SEQ ID NO 55
<211> LENGTH: 1019
<212> TYPE: PRT
<213> ORGANISM: S. pneumoniae

<400> SEQUENCE: 55

Cys Ala Tyr Ala Leu Asn Gln His Arg Ser Gln Glu Asn Lys Asp Asn
 1               5                  10                  15

Asn Arg Val Ser Tyr Val Asp Gly Ser Gln Ser Ser Gln Lys Ser Glu
            20                  25                  30

Asn Leu Thr Pro Asp Gln Val Ser Gln Lys Glu Gly Ile Gln Ala Glu
        35                  40                  45

Gln Ile Val Ile Lys Ile Thr Asp Gln Gly Tyr Val Thr Ser His Gly
    50                  55                  60

Asp His Tyr His Tyr Tyr Asn Gly Lys Val Pro Tyr Asp Ala Leu Phe
65                  70                  75                  80

Ser Glu Glu Leu Leu Met Lys Asp Pro Asn Tyr Gln Leu Lys Asp Ala
                85                  90                  95

Asp Ile Val Asn Glu Val Lys Gly Gly Tyr Ile Ile Lys Val Asp Gly
            100                 105                 110

Lys Tyr Tyr Val Tyr Leu Lys Asp Ala Ala His Ala Asp Asn Val Arg
        115                 120                 125

-continued

```
Thr Lys Asp Glu Ile Asn Arg Gln Lys Gln Glu His Val Lys Asp Asn
    130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Gly His Tyr His Tyr Ile
            180                 185                 190

Pro Lys Ser Asp Leu Ser Ala Ser Glu Leu Ala Ala Lys Ala His
            195                 200                 205

Leu Ala Gly Lys Asn Met Gln Pro Ser Gln Leu Ser Tyr Ser Ser Thr
    210                 215                 220

Ala Ser Asp Asn Asn Thr Gln Ser Val Ala Lys Gly Ser Thr Ser Lys
225                 230                 235                 240

Pro Ala Asn Lys Ser Glu Asn Leu Gln Ser Leu Lys Glu Leu Tyr
                245                 250                 255

Asp Ser Pro Ser Ala Gln Arg Tyr Ser Glu Ser Asp Gly Leu Val Phe
                260                 265                 270

Asp Pro Ala Lys Ile Ile Ser Arg Thr Pro Asn Gly Val Ala Ile Pro
    275                 280                 285

His Gly Asp His Tyr His Phe Ile Pro Tyr Ser Lys Leu Ser Ala Leu
    290                 295                 300

Glu Lys Ile Ala Arg Met Val Pro Ile Ser Gly Thr Gly Ser Thr
305                 310                 315                 320

Val Ser Thr Asn Ala Lys Pro Asn Glu Val Val Ser Ser Leu Gly Ser
                325                 330                 335

Leu Ser Ser Asn Pro Ser Ser Leu Thr Thr Ser Lys Glu Leu Ser Ser
                340                 345                 350

Ala Ser Asp Gly Tyr Ile Phe Asn Pro Lys Asp Ile Val Glu Glu Thr
            355                 360                 365

Ala Thr Ala Tyr Ile Val Arg His Gly Asp His Phe His Tyr Ile Pro
    370                 375                 380

Lys Ser Asn Gln Ile Gly Gln Pro Thr Leu Pro Asn Asn Ser Leu Ala
385                 390                 395                 400

Thr Pro Ser Pro Ser Leu Pro Ile Asn Pro Gly Thr Ser His Glu Lys
                405                 410                 415

His Glu Glu Asp Gly Tyr Gly Phe Asp Ala Asn Arg Ile Ile Ala Glu
                420                 425                 430

Asp Glu Ser Gly Phe Val Met Ser His Gly Asp His Asn His Tyr Phe
    435                 440                 445

Phe Lys Lys Asp Leu Thr Glu Glu Gln Ile Lys Ala Ala Gln Lys His
    450                 455                 460

Leu Glu Glu Val Lys Thr Ser His Asn Gly Leu Asp Ser Leu Ser Ser
465                 470                 475                 480

His Glu Gln Asp Tyr Pro Gly Asn Ala Lys Glu Met Lys Asp Leu Asp
                485                 490                 495

Lys Lys Ile Glu Glu Lys Ile Ala Gly Ile Met Lys Gln Tyr Gly Val
            500                 505                 510

Lys Arg Glu Ser Ile Val Val Asn Lys Glu Lys Asn Ala Ile Ile Tyr
    515                 520                 525

Pro His Gly Asp His His Ala Asp Pro Ile Asp Glu His Lys Pro
    530                 535                 540

Val Gly Ile Gly His Ser His Ser Asn Tyr Glu Leu Phe Lys Pro Glu
```

-continued

```
         545                 550                 555                 560
    Glu Gly Val Ala Lys Lys Glu Gly Asn Lys Val Tyr Thr Gly Glu Glu
                    565                 570                 575
    Leu Thr Asn Val Val Asn Leu Leu Lys Asn Ser Thr Phe Asn Asn Gln
                580                 585                 590
    Asn Phe Thr Leu Ala Asn Gly Gln Lys Arg Val Ser Phe Ser Phe Pro
                595                 600                 605
    Pro Glu Leu Glu Lys Lys Leu Gly Ile Asn Met Leu Val Lys Leu Ile
                610                 615                 620
    Thr Pro Asp Gly Lys Val Leu Glu Lys Val Ser Gly Lys Val Phe Gly
    625                 630                 635                 640
    Glu Gly Val Gly Asn Ile Ala Asn Phe Glu Leu Asp Gln Pro Tyr Leu
                    645                 650                 655
    Pro Gly Gln Thr Phe Lys Tyr Thr Ile Ala Ser Lys Asp Tyr Pro Glu
                    660                 665                 670
    Val Ser Tyr Asp Gly Thr Phe Thr Val Pro Thr Ser Leu Ala Tyr Lys
                675                 680                 685
    Met Ala Ser Gln Thr Ile Phe Tyr Pro Phe His Ala Gly Asp Thr Tyr
                690                 695                 700
    Leu Arg Val Asn Pro Gln Phe Ala Val Pro Lys Gly Thr Asp Ala Leu
    705                 710                 715                 720
    Val Arg Val Phe Asp Glu Phe His Gly Asn Ala Tyr Leu Glu Asn Asn
                    725                 730                 735
    Tyr Lys Val Gly Glu Ile Lys Leu Pro Ile Pro Lys Leu Asn Gln Gly
                    740                 745                 750
    Thr Thr Arg Thr Ala Gly Asn Lys Ile Pro Val Thr Phe Met Ala Asn
                755                 760                 765
    Ala Tyr Leu Asp Asn Gln Ser Thr Tyr Ile Val Glu Val Pro Ile Leu
                770                 775                 780
    Glu Lys Glu Asn Gln Thr Asp Lys Pro Ser Ile Leu Pro Gln Phe Lys
    785                 790                 795                 800
    Arg Asn Lys Ala Gln Glu Asn Ser Lys Leu Asp Glu Lys Val Glu Glu
                    805                 810                 815
    Pro Lys Thr Ser Glu Lys Val Glu Lys Glu Lys Leu Ser Glu Thr Gly
                    820                 825                 830
    Asn Ser Thr Ser Asn Ser Thr Leu Glu Glu Val Pro Thr Val Asp Pro
                835                 840                 845
    Val Gln Glu Lys Val Ala Lys Phe Ala Glu Ser Tyr Gly Met Lys Leu
                850                 855                 860
    Glu Asn Val Leu Phe Asn Met Asp Gly Thr Ile Glu Leu Tyr Leu Pro
    865                 870                 875                 880
    Ser Gly Glu Val Ile Lys Lys Asn Met Ala Asp Phe Thr Gly Glu Ala
                    885                 890                 895
    Pro Gln Gly Asn Gly Glu Asn Lys Pro Ser Glu Asn Gly Lys Val Ser
                    900                 905                 910
    Thr Gly Thr Val Glu Asn Gln Pro Thr Glu Asn Lys Pro Ala Asp Ser
                915                 920                 925
    Leu Pro Glu Ala Pro Asn Glu Lys Pro Val Lys Pro Glu Asn Ser Thr
                930                 935                 940
    Asp Asn Gly Met Leu Asn Pro Glu Gly Asn Val Gly Ser Asp Pro Met
    945                 950                 955                 960
    Leu Asp Pro Ala Leu Glu Glu Ala Pro Ala Val Asp Pro Val Gln Glu
                    965                 970                 975
```

```
Lys Leu Glu Lys Phe Thr Ala Ser Tyr Gly Leu Gly Leu Asp Ser Val
            980                 985                 990

Ile Phe Asn Met Asp Gly Thr Ile Glu Leu Arg Leu Pro Ser Gly Glu
            995                 1000                1005

Val Ile Lys Lys Asn Leu Ser Asp Phe Ile Ala
        1010                1015

<210> SEQ ID NO 56
<211> LENGTH: 489
<212> TYPE: PRT
<213> ORGANISM: S. pneumoniae

<400> SEQUENCE: 56

Cys Ala Tyr Ala Leu Asn Gln His Arg Ser Gln Glu Asn Lys Asp Asn
1               5                   10                  15

Asn Arg Val Ser Tyr Val Asp Gly Ser Gln Ser Gln Lys Ser Glu
            20                  25                  30

Asn Leu Thr Pro Asp Gln Val Ser Gln Lys Glu Gly Ile Gln Ala Glu
        35                  40                  45

Gln Ile Val Ile Lys Ile Thr Asp Gln Gly Tyr Val Thr Ser His Gly
50                  55                  60

Asp His Tyr His Tyr Tyr Asn Gly Lys Val Pro Tyr Asp Ala Leu Phe
65                  70                  75                  80

Ser Glu Glu Leu Leu Met Lys Asp Pro Asn Tyr Gln Leu Lys Asp Ala
                85                  90                  95

Asp Ile Val Asn Glu Val Lys Gly Gly Tyr Ile Ile Lys Val Asp Gly
            100                 105                 110

Lys Tyr Tyr Val Tyr Leu Lys Asp Ala Ala His Ala Asp Asn Val Arg
        115                 120                 125

Thr Lys Asp Glu Ile Asn Arg Gln Lys Gln Glu His Val Lys Asp Asn
130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Gly Gly His Tyr His Tyr Ile
            180                 185                 190

Pro Lys Ser Asp Leu Ser Ala Ser Glu Leu Ala Ala Lys Ala His
        195                 200                 205

Leu Ala Gly Lys Asn Met Gln Pro Ser Gln Leu Ser Tyr Ser Ser Thr
210                 215                 220

Ala Ser Asp Asn Thr Gln Ser Val Ala Lys Gly Ser Thr Ser Lys
225                 230                 235                 240

Pro Ala Asn Lys Ser Glu Asn Leu Gln Ser Leu Leu Lys Glu Leu Tyr
                245                 250                 255

Asp Ser Pro Ser Ala Gln Arg Tyr Ser Glu Ser Asp Gly Leu Val Phe
            260                 265                 270

Asp Pro Ala Lys Ile Ile Ser Arg Thr Pro Asn Gly Val Ala Ile Pro
        275                 280                 285

His Gly Asp His Tyr His Phe Ile Pro Tyr Ser Lys Leu Ser Ala Leu
290                 295                 300

Glu Glu Lys Ile Ala Arg Met Val Pro Ile Ser Gly Thr Gly Ser Thr
305                 310                 315                 320

Val Ser Thr Asn Ala Lys Pro Asn Glu Val Val Ser Ser Leu Gly Ser
```

```
                325                 330                 335
Leu Ser Ser Asn Pro Ser Ser Leu Thr Thr Ser Lys Glu Leu Ser Ser
            340                 345                 350

Ala Ser Asp Gly Tyr Ile Phe Asn Pro Lys Asp Ile Val Glu Glu Thr
        355                 360                 365

Ala Thr Ala Tyr Ile Val Arg His Gly Asp His Phe His Tyr Ile Pro
    370                 375                 380

Lys Ser Asn Gln Ile Gly Gln Pro Thr Leu Pro Asn Asn Ser Leu Ala
385                 390                 395                 400

Thr Pro Ser Pro Ser Leu Pro Ile Asn Pro Gly Thr Ser His Glu Lys
                405                 410                 415

His Glu Glu Asp Gly Tyr Gly Phe Asp Ala Asn Arg Ile Ile Ala Glu
            420                 425                 430

Asp Glu Ser Gly Phe Val Met Ser His Gly Asp His Asn His Tyr Phe
        435                 440                 445

Phe Lys Lys Asp Leu Thr Glu Glu Gln Ile Lys Ala Ala Gln Lys His
    450                 455                 460

Leu Glu Glu Val Lys Thr Ser His Asn Gly Leu Asp Ser Leu Ser Ser
465                 470                 475                 480

His Glu Gln Asp Tyr Pro Gly Asn Ala
                485

<210> SEQ ID NO 57
<211> LENGTH: 509
<212> TYPE: PRT
<213> ORGANISM: S. pneumoniae

<400> SEQUENCE: 57

Met Lys Phe Ser Lys Lys Tyr Ile Ala Ala Gly Ser Ala Val Ile Val
1               5                   10                  15

Ser Leu Ser Leu Cys Ala Tyr Ala Leu Asn Gln His Arg Ser Gln Glu
            20                  25                  30

Asn Lys Asp Asn Asn Arg Val Ser Tyr Val Asp Gly Ser Gln Ser Ser
        35                  40                  45

Gln Lys Ser Glu Asn Leu Thr Pro Asp Gln Val Ser Gln Lys Glu Gly
    50                  55                  60

Ile Gln Ala Glu Gln Ile Val Lys Ile Thr Asp Gln Gly Tyr Val
65                  70                  75                  80

Thr Ser His Gly Asp His Tyr His Tyr Asn Gly Lys Val Pro Tyr
                85                  90                  95

Asp Ala Leu Phe Ser Glu Glu Leu Leu Met Lys Asp Pro Asn Tyr Gln
            100                 105                 110

Leu Lys Asp Ala Asp Ile Val Asn Glu Val Lys Gly Tyr Ile Ile
        115                 120                 125

Lys Val Asp Gly Lys Tyr Tyr Val Tyr Leu Lys Asp Ala Ala His Ala
    130                 135                 140

Asp Asn Val Arg Thr Lys Asp Glu Ile Asn Arg Gln Lys Gln Glu His
145                 150                 155                 160

Val Lys Asp Asn Glu Lys Val Asn Ser Asn Val Ala Val Ala Arg Ser
                165                 170                 175

Gln Gly Arg Tyr Thr Thr Asn Asp Gly Tyr Val Phe Asn Pro Ala Asp
            180                 185                 190

Ile Ile Glu Asp Thr Gly Asn Ala Tyr Ile Val Pro His Gly Gly His
        195                 200                 205
```

Tyr His Tyr Ile Pro Lys Ser Asp Leu Ser Ala Ser Glu Leu Ala Ala
210                 215                 220

Ala Lys Ala His Leu Ala Gly Lys Asn Met Gln Pro Ser Gln Leu Ser
225                 230                 235                 240

Tyr Ser Ser Thr Ala Ser Asp Asn Asn Thr Gln Ser Val Ala Lys Gly
            245                 250                 255

Ser Thr Ser Lys Pro Ala Asn Lys Ser Glu Asn Leu Gln Ser Leu Leu
        260                 265                 270

Lys Glu Leu Tyr Asp Ser Pro Ser Ala Gln Arg Tyr Ser Glu Ser Asp
    275                 280                 285

Gly Leu Val Phe Asp Pro Ala Lys Ile Ile Ser Arg Thr Pro Asn Gly
290                 295                 300

Val Ala Ile Pro His Gly Asp His Tyr His Phe Ile Pro Tyr Ser Lys
305                 310                 315                 320

Leu Ser Ala Leu Glu Glu Lys Ile Ala Arg Met Val Pro Ile Ser Gly
            325                 330                 335

Thr Gly Ser Thr Val Ser Thr Asn Ala Lys Pro Asn Glu Val Val Ser
        340                 345                 350

Ser Leu Gly Ser Leu Ser Asn Pro Ser Ser Leu Thr Thr Ser Lys
    355                 360                 365

Glu Leu Ser Ser Ala Ser Asp Gly Tyr Ile Phe Asn Pro Lys Asp Ile
370                 375                 380

Val Glu Glu Thr Ala Thr Ala Tyr Ile Val Arg His Gly Asp His Phe
385                 390                 395                 400

His Tyr Ile Pro Lys Ser Asn Gln Ile Gly Gln Pro Thr Leu Pro Asn
            405                 410                 415

Asn Ser Leu Ala Thr Pro Ser Pro Ser Leu Pro Ile Asn Pro Gly Thr
        420                 425                 430

Ser His Glu Lys His Glu Glu Asp Gly Tyr Gly Phe Asp Ala Asn Arg
    435                 440                 445

Ile Ile Ala Glu Asp Glu Ser Gly Phe Val Met Ser His Gly Asp His
450                 455                 460

Asn His Tyr Phe Phe Lys Lys Asp Leu Thr Glu Gln Ile Lys Ala
465                 470                 475                 480

Ala Gln Lys His Leu Glu Glu Val Lys Thr Ser His Asn Gly Leu Asp
            485                 490                 495

Ser Leu Ser Ser His Glu Gln Asp Tyr Pro Gly Asn Ala
        500                 505

<210> SEQ ID NO 58
<211> LENGTH: 1057
<212> TYPE: PRT
<213> ORGANISM: S. pneumoniae

<400> SEQUENCE: 58

Asp Leu Thr Glu Glu Gln Ile Lys Ala Ala Gln Lys His Leu Glu Glu
1               5                   10                  15

Val Lys Thr Ser His Asn Gly Leu Asp Ser Leu Ser Ser His Glu Gln
                20                  25                  30

Asp Tyr Pro Gly Asn Ala Lys Glu Met Lys Asp Leu Asp Lys Lys Ile
            35                  40                  45

Glu Glu Lys Ile Ala Gly Ile Met Lys Gln Tyr Gly Val Lys Arg Glu
    50                  55                  60

Ser Ile Val Val Asn Lys Glu Lys Asn Ala Ile Ile Tyr Pro His Gly
65                  70                  75                  80

```
Asp His His His Ala Asp Pro Ile Asp Glu His Lys Pro Val Gly Ile
            85                  90                  95

Gly His Ser His Ser Asn Tyr Glu Leu Phe Lys Pro Glu Glu Gly Val
            100                 105                 110

Ala Lys Lys Glu Gly Asn Lys Val Tyr Thr Gly Glu Leu Thr Asn
            115                 120                 125

Val Val Asn Leu Leu Lys Asn Ser Thr Phe Asn Gln Asn Phe Thr
            130                 135                 140

Leu Ala Asn Gly Gln Lys Arg Val Ser Phe Ser Phe Pro Pro Glu Leu
145                 150                 155                 160

Glu Lys Lys Leu Gly Ile Asn Met Leu Val Lys Leu Ile Thr Pro Asp
            165                 170                 175

Gly Lys Val Leu Glu Lys Val Ser Lys Val Phe Gly Glu Gly Val
            180                 185                 190

Gly Asn Ile Ala Asn Phe Glu Leu Asp Gln Pro Tyr Leu Pro Gly Gln
            195                 200                 205

Thr Phe Lys Tyr Thr Ile Ala Ser Lys Asp Tyr Pro Glu Val Ser Tyr
            210                 215                 220

Asp Gly Thr Phe Thr Val Pro Thr Ser Leu Ala Tyr Lys Met Ala Ser
225                 230                 235                 240

Gln Thr Ile Phe Tyr Pro Phe His Ala Gly Asp Thr Tyr Leu Arg Val
            245                 250                 255

Asn Pro Gln Phe Ala Val Pro Lys Gly Thr Asp Ala Leu Val Arg Val
            260                 265                 270

Phe Asp Glu Phe His Gly Asn Ala Tyr Leu Glu Asn Asn Tyr Lys Val
            275                 280                 285

Gly Glu Ile Lys Leu Pro Ile Pro Lys Leu Asn Gln Gly Thr Thr Arg
            290                 295                 300

Thr Ala Gly Asn Lys Ile Pro Val Thr Phe Met Ala Asn Ala Tyr Leu
305                 310                 315                 320

Asp Asn Gln Ser Thr Tyr Ile Val Glu Val Pro Ile Leu Glu Lys Glu
            325                 330                 335

Asn Gln Thr Asp Lys Pro Ser Ile Leu Pro Gln Phe Lys Arg Asn Lys
            340                 345                 350

Ala Gln Glu Asn Ser Lys Leu Asp Glu Lys Val Glu Glu Pro Lys Thr
            355                 360                 365

Ser Glu Lys Val Glu Lys Glu Lys Leu Ser Glu Thr Gly Asn Ser Thr
            370                 375                 380

Ser Asn Ser Thr Leu Glu Glu Val Pro Thr Val Asp Pro Val Gln Glu
385                 390                 395                 400

Lys Val Ala Lys Phe Ala Glu Ser Tyr Gly Met Lys Leu Glu Asn Val
            405                 410                 415

Leu Phe Asn Met Asp Gly Thr Ile Glu Leu Tyr Leu Pro Ser Gly Glu
            420                 425                 430

Val Ile Lys Lys Asn Met Ala Asp Phe Thr Gly Glu Ala Pro Gln Gly
            435                 440                 445

Asn Gly Glu Asn Lys Pro Ser Glu Asn Gly Lys Val Ser Thr Gly Thr
            450                 455                 460

Val Glu Asn Gln Pro Thr Glu Asn Lys Pro Ala Asp Ser Leu Pro Glu
465                 470                 475                 480

Ala Pro Asn Glu Lys Pro Val Lys Pro Glu Asn Ser Thr Asp Asn Gly
            485                 490                 495
```

-continued

```
Met Leu Asn Pro Glu Gly Asn Val Gly Ser Asp Pro Met Leu Asp Pro
            500                 505                 510
Ala Leu Glu Glu Ala Pro Ala Val Asp Pro Val Gln Glu Lys Leu Glu
        515                 520                 525
Lys Phe Thr Ala Ser Tyr Gly Leu Gly Leu Asp Ser Val Ile Phe Asn
    530                 535                 540
Met Asp Gly Thr Ile Glu Leu Arg Leu Pro Ser Gly Glu Val Ile Lys
545                 550                 555                 560
Lys Asn Leu Ser Asp Phe Ile Ala Lys Leu Arg Tyr Arg Ser Asn His
            565                 570                 575
Trp Val Pro Asp Ser Arg Pro Glu Glu Pro Ser Pro Gln Pro Thr Pro
        580                 585                 590
Glu Pro Ser Pro Ser Pro Gln Pro Ala Pro Asn Pro Gln Pro Ala Pro
    595                 600                 605
Ser Asn Pro Ile Asp Glu Lys Leu Val Lys Glu Ala Val Arg Lys Val
    610                 615                 620
Gly Asp Gly Tyr Val Phe Glu Glu Asn Gly Val Ser Arg Tyr Ile Pro
625                 630                 635                 640
Ala Lys Asn Leu Ser Ala Glu Thr Ala Ala Gly Ile Asp Ser Lys Leu
            645                 650                 655
Ala Lys Gln Glu Ser Leu Ser His Lys Leu Gly Ala Lys Lys Thr Asp
        660                 665                 670
Leu Pro Ser Ser Asp Arg Glu Phe Tyr Asn Lys Ala Tyr Asp Leu Leu
    675                 680                 685
Ala Arg Ile His Gln Asp Leu Leu Asp Asn Lys Gly Arg Gln Val Asp
    690                 695                 700
Phe Glu Ala Leu Asp Asn Leu Leu Glu Arg Leu Lys Asp Val Ser Ser
705                 710                 715                 720
Asp Lys Val Lys Leu Val Asp Asp Ile Leu Ala Phe Leu Ala Pro Ile
            725                 730                 735
Arg His Pro Glu Arg Leu Gly Lys Pro Asn Ala Gln Ile Thr Tyr Thr
        740                 745                 750
Asp Asp Glu Ile Gln Val Ala Lys Leu Ala Gly Lys Tyr Thr Thr Glu
    755                 760                 765
Asp Gly Tyr Ile Phe Asp Pro Arg Asp Ile Thr Ser Asp Glu Gly Asp
    770                 775                 780
Ala Tyr Val Thr Pro His Met Thr His Ser His Trp Ile Lys Lys Asp
785                 790                 795                 800
Ser Leu Ser Glu Ala Glu Arg Ala Ala Ala Gln Ala Tyr Ala Lys Glu
            805                 810                 815
Lys Gly Leu Thr Pro Pro Ser Thr Asp His Gln Asp Ser Gly Asn Thr
        820                 825                 830
Glu Ala Lys Gly Ala Glu Ala Ile Tyr Asn Arg Val Lys Ala Ala Lys
    835                 840                 845
Lys Val Pro Leu Asp Arg Met Pro Tyr Asn Leu Gln Tyr Thr Val Glu
    850                 855                 860
Val Lys Asn Gly Ser Leu Ile Ile Pro His Tyr Asp His Tyr His Asn
865                 870                 875                 880
Ile Lys Phe Glu Trp Phe Asp Glu Gly Leu Tyr Glu Ala Pro Lys Gly
            885                 890                 895
Tyr Thr Leu Glu Asp Leu Leu Ala Thr Val Lys Tyr Tyr Val Glu His
        900                 905                 910
Pro Asn Glu Arg Pro His Ser Asp Asn Gly Phe Gly Asn Ala Ser Asp
```

```
                915                 920                 925
His Val Gln Arg Asn Lys Asn Gly Gln Ala Asp Thr Asn Gln Thr Glu
    930                 935                 940

Lys Pro Ser Glu Glu Lys Pro Gln Thr Glu Lys Pro Glu Glu Glu Thr
945                 950                 955                 960

Pro Arg Glu Glu Lys Pro Gln Ser Glu Lys Pro Glu Ser Pro Lys Pro
                965                 970                 975

Thr Glu Glu Pro Glu Glu Ser Pro Glu Glu Ser Glu Glu Pro Gln
            980                 985                 990

Val Glu Thr Glu Lys Val Glu Glu Lys Leu Arg Glu Ala Glu Asp Leu
            995                1000                1005

Leu Gly Lys Ile Gln Asp Pro Ile Ile Lys Ser Asn Ala Lys Glu Thr
        1010                1015                1020

Leu Thr Gly Leu Lys Asn Asn Leu Leu Phe Gly Thr Gln Asp Asn Asn
1025                1030                1035                1040

Thr Ile Met Ala Glu Ala Glu Lys Leu Leu Ala Leu Leu Lys Glu Ser
                1045                1050                1055

Lys

<210> SEQ ID NO 59
<211> LENGTH: 205
<212> TYPE: PRT
<213> ORGANISM: S. pneumoniae

<400> SEQUENCE: 59

Cys Ala Tyr Ala Leu Asn Gln His Arg Ser Gln Glu Asn Lys Asp Asn
1               5                  10                  15

Asn Arg Val Ser Tyr Val Asp Gly Ser Gln Ser Ser Gln Lys Ser Glu
            20                  25                  30

Asn Leu Thr Pro Asp Gln Val Ser Gln Lys Glu Gly Ile Gln Ala Glu
        35                  40                  45

Gln Ile Val Ile Lys Ile Thr Asp Gln Gly Tyr Val Thr Ser His Gly
    50                  55                  60

Asp His Tyr His Tyr Tyr Asn Gly Lys Val Pro Tyr Asp Ala Leu Phe
65                  70                  75                  80

Ser Glu Glu Leu Leu Met Lys Asp Pro Asn Tyr Gln Leu Lys Asp Ala
                85                  90                  95

Asp Ile Val Asn Glu Val Lys Gly Gly Tyr Ile Ile Lys Val Asp Gly
            100                 105                 110

Lys Tyr Tyr Val Tyr Leu Lys Asp Ala Ala His Ala Asp Asn Val Arg
        115                 120                 125

Thr Lys Asp Glu Ile Asn Arg Gln Lys Gln Glu His Val Lys Asp Asn
    130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Gly Gly His Tyr His Tyr Ile
            180                 185                 190

Pro Lys Ser Asp Leu Ser Ala Ser Glu Leu Ala Ala Ala
        195                 200                 205

<210> SEQ ID NO 60
<211> LENGTH: 821
<212> TYPE: PRT
```

<213> ORGANISM: S. pneumoniae

<400> SEQUENCE: 60

| | | | | | | | | | | | | | | |
|---|---|---|---|---|---|---|---|---|---|---|---|---|---|---|
| Cys | Ala | Tyr | Glu | Leu | Gly | Leu | His | Gln | Ala | Gln | Thr | Val | Lys | Glu | Asn |
| 1 | | | | 5 | | | | | 10 | | | | | 15 | |
| Asn | Arg | Val | Ser | Tyr | Ile | Asp | Gly | Lys | Gln | Ala | Thr | Gln | Lys | Thr | Glu |
| | | | 20 | | | | | 25 | | | | | 30 | | |
| Asn | Leu | Thr | Pro | Asp | Glu | Val | Ser | Lys | Arg | Glu | Gly | Ile | Asn | Ala | Glu |
| | | | 35 | | | | | 40 | | | | | 45 | | |
| Gln | Ile | Val | Ile | Lys | Ile | Thr | Asp | Gln | Gly | Tyr | Val | Thr | Ser | His | Gly |
| | 50 | | | | | 55 | | | | | 60 | | | | |
| Asp | His | Tyr | His | Tyr | Tyr | Asn | Gly | Lys | Val | Pro | Tyr | Asp | Ala | Ile | Ile |
| 65 | | | | | 70 | | | | | 75 | | | | | 80 |
| Ser | Glu | Glu | Leu | Leu | Met | Lys | Asp | Pro | Asn | Tyr | Gln | Leu | Lys | Asp | Ser |
| | | | | 85 | | | | | 90 | | | | | 95 | |
| Asp | Ile | Val | Asn | Glu | Ile | Lys | Gly | Gly | Tyr | Val | Ile | Lys | Val | Asn | Gly |
| | | | 100 | | | | | 105 | | | | | 110 | | |
| Lys | Tyr | Tyr | Val | Tyr | Leu | Lys | Asp | Ala | Ala | His | Ala | Asp | Asn | Val | Arg |
| | | 115 | | | | | 120 | | | | | 125 | | | |
| Thr | Lys | Glu | Glu | Ile | Asn | Arg | Gln | Lys | Gln | Glu | His | Ser | Gln | His | Arg |
| 130 | | | | | 135 | | | | | 140 | | | | | |
| Glu | Gly | Gly | Thr | Ser | Ala | Asn | Asp | Gly | Ala | Val | Ala | Phe | Ala | Arg | Ser |
| 145 | | | | | 150 | | | | | 155 | | | | | 160 |
| Gln | Gly | Arg | Tyr | Thr | Thr | Asp | Asp | Gly | Tyr | Ile | Phe | Asn | Ala | Ser | Asp |
| | | | | 165 | | | | | 170 | | | | | 175 | |
| Ile | Ile | Glu | Asp | Thr | Gly | Asp | Ala | Tyr | Ile | Val | Pro | His | Gly | Asp | His |
| | | | 180 | | | | | 185 | | | | | 190 | | |
| Tyr | His | Tyr | Ile | Pro | Lys | Asn | Glu | Leu | Ser | Ala | Ser | Glu | Leu | Ala | Ala |
| | | 195 | | | | | 200 | | | | | 205 | | | |
| Ala | Glu | Ala | Phe | Leu | Ser | Gly | Arg | Glu | Asn | Leu | Ser | Asn | Leu | Arg | Thr |
| 210 | | | | | 215 | | | | | 220 | | | | | |
| Tyr | Arg | Arg | Gln | Asn | Ser | Asp | Asn | Thr | Pro | Arg | Thr | Asn | Trp | Val | Pro |
| 225 | | | | | 230 | | | | | 235 | | | | | 240 |
| Ser | Val | Ser | Asn | Pro | Gly | Thr | Thr | Asn | Thr | Asn | Thr | Ser | Asn | Asn | Ser |
| | | | | 245 | | | | | 250 | | | | | 255 | |
| Asn | Thr | Asn | Ser | Gln | Ala | Ser | Gln | Ser | Asn | Asp | Ile | Asp | Ser | Leu | Leu |
| | | | 260 | | | | | 265 | | | | | 270 | | |
| Lys | Gln | Leu | Tyr | Lys | Leu | Pro | Leu | Ser | Gln | Arg | His | Val | Glu | Ser | Asp |
| | | 275 | | | | | 280 | | | | | 285 | | | |
| Gly | Leu | Ile | Phe | Asp | Pro | Ala | Gln | Ile | Thr | Ser | Arg | Thr | Ala | Arg | Gly |
| 290 | | | | | 295 | | | | | 300 | | | | | |
| Val | Ala | Val | Pro | His | Gly | Asn | His | Tyr | His | Phe | Ile | Pro | Tyr | Glu | Gln |
| 305 | | | | | 310 | | | | | 315 | | | | | 320 |
| Met | Ser | Glu | Leu | Glu | Lys | Arg | Ile | Ala | Arg | Ile | Ile | Pro | Leu | Arg | Tyr |
| | | | | 325 | | | | | 330 | | | | | 335 | |
| Arg | Ser | Asn | His | Trp | Val | Pro | Asp | Ser | Arg | Pro | Glu | Glu | Pro | Ser | Pro |
| | | | 340 | | | | | 345 | | | | | 350 | | |
| Gln | Pro | Thr | Pro | Glu | Pro | Ser | Pro | Gln | Pro | Ala | Pro | Asn | Pro | | |
| | | 355 | | | | | 360 | | | | | 365 | | | |
| Gln | Pro | Ala | Pro | Ser | Asn | Pro | Ile | Asp | Glu | Lys | Leu | Val | Lys | Glu | Ala |
| | | 370 | | | | | 375 | | | | | 380 | | | |
| Val | Arg | Lys | Val | Gly | Asp | Gly | Tyr | Val | Phe | Glu | Glu | Asn | Gly | Val | Ser |
| 385 | | | | | 390 | | | | | 395 | | | | | 400 |

-continued

```
Arg Tyr Ile Pro Ala Lys Asn Leu Ser Ala Glu Thr Ala Ala Gly Ile
            405                 410                 415

Asp Ser Lys Leu Ala Lys Gln Glu Ser Leu Ser His Lys Leu Gly Ala
            420                 425                 430

Lys Lys Thr Asp Leu Pro Ser Ser Asp Arg Glu Phe Tyr Asn Lys Ala
            435                 440                 445

Tyr Asp Leu Leu Ala Arg Ile His Gln Asp Leu Leu Asp Asn Lys Gly
        450                 455                 460

Arg Gln Val Asp Phe Glu Ala Leu Asp Asn Leu Leu Glu Arg Leu Lys
465                 470                 475                 480

Asp Val Ser Ser Asp Lys Val Lys Leu Val Asp Ile Leu Ala Phe
                485                 490                 495

Leu Ala Pro Ile Arg His Pro Glu Arg Leu Gly Lys Pro Asn Ala Gln
                500                 505                 510

Ile Thr Tyr Thr Asp Asp Glu Ile Gln Val Ala Lys Leu Ala Gly Lys
                515                 520                 525

Tyr Thr Thr Glu Asp Gly Tyr Ile Phe Asp Pro Arg Asp Ile Thr Ser
        530                 535                 540

Asp Glu Gly Asp Ala Tyr Val Thr Pro His Met Thr His Ser His Trp
545                 550                 555                 560

Ile Lys Lys Asp Ser Leu Ser Glu Ala Glu Arg Ala Ala Ala Gln Ala
                565                 570                 575

Tyr Ala Lys Glu Lys Gly Leu Thr Pro Pro Ser Thr Asp His Gln Asp
                580                 585                 590

Ser Gly Asn Thr Glu Ala Lys Gly Ala Glu Ala Ile Tyr Asn Arg Val
                595                 600                 605

Lys Ala Ala Lys Lys Val Pro Leu Asp Arg Met Pro Tyr Asn Leu Gln
            610                 615                 620

Tyr Thr Val Glu Val Lys Asn Gly Ser Leu Ile Ile Pro His Tyr Asp
625                 630                 635                 640

His Tyr His Asn Ile Lys Phe Glu Trp Phe Asp Gly Leu Tyr Glu
                645                 650                 655

Ala Pro Lys Gly Tyr Thr Leu Glu Asp Leu Leu Ala Thr Val Lys Tyr
                660                 665                 670

Tyr Val Glu His Pro Asn Glu Arg Pro His Ser Asp Asn Gly Phe Gly
                675                 680                 685

Asn Ala Ser Asp His Val Gln Arg Asn Lys Asn Gly Gln Ala Asp Thr
            690                 695                 700

Asn Gln Thr Glu Lys Pro Ser Glu Glu Lys Pro Gln Thr Glu Lys Pro
705                 710                 715                 720

Glu Glu Glu Thr Pro Arg Glu Glu Lys Pro Gln Ser Glu Lys Pro Glu
                725                 730                 735

Ser Pro Lys Pro Thr Glu Glu Pro Glu Glu Ser Pro Glu Glu Ser
                740                 745                 750

Glu Glu Pro Gln Val Glu Thr Glu Lys Val Glu Glu Lys Leu Arg Glu
            755                 760                 765

Ala Glu Asp Leu Leu Gly Lys Ile Gln Asp Pro Ile Ile Lys Ser Asn
            770                 775                 780

Ala Lys Glu Thr Leu Thr Gly Leu Lys Asn Asn Leu Leu Phe Gly Thr
785                 790                 795                 800

Gln Asp Asn Asn Thr Ile Met Ala Glu Ala Glu Lys Leu Leu Ala Leu
                805                 810                 815

Leu Lys Glu Ser Lys
```

<210> SEQ ID NO 61
<211> LENGTH: 334
<212> TYPE: PRT
<213> ORGANISM: S. pneumoniae

<400> SEQUENCE: 61

Cys Ala Tyr Glu Leu Gly Leu His Gln Ala Gln Thr Val Lys Glu Asn
1               5                   10                  15

Asn Arg Val Ser Tyr Ile Asp Gly Lys Gln Ala Thr Gln Lys Thr Glu
            20                  25                  30

Asn Leu Thr Pro Asp Glu Val Ser Lys Arg Glu Gly Ile Asn Ala Glu
        35                  40                  45

Gln Ile Val Ile Lys Ile Thr Asp Gln Gly Tyr Val Thr Ser His Gly
    50                  55                  60

Asp His Tyr His Tyr Tyr Asn Gly Lys Val Pro Tyr Asp Ala Ile Ile
65                  70                  75                  80

Ser Glu Glu Leu Leu Met Lys Asp Pro Asn Tyr Gln Leu Lys Asp Ser
                85                  90                  95

Asp Ile Val Asn Glu Ile Lys Gly Gly Tyr Val Ile Lys Val Asn Gly
            100                 105                 110

Lys Tyr Tyr Val Tyr Leu Lys Asp Ala Ala His Ala Asp Asn Val Arg
        115                 120                 125

Thr Lys Glu Glu Ile Asn Arg Gln Lys Gln Glu His Ser Gln His Arg
    130                 135                 140

Glu Gly Gly Thr Ser Ala Asn Asp Gly Ala Val Ala Phe Ala Arg Ser
145                 150                 155                 160

Gln Gly Arg Tyr Thr Thr Asp Asp Gly Tyr Ile Phe Asn Ala Ser Asp
                165                 170                 175

Ile Ile Glu Asp Thr Gly Asp Ala Tyr Ile Val Pro His Gly Asp His
            180                 185                 190

Tyr His Tyr Ile Pro Lys Asn Glu Leu Ser Ala Ser Glu Leu Ala Ala
        195                 200                 205

Ala Glu Ala Phe Leu Ser Gly Arg Glu Asn Leu Ser Asn Leu Arg Thr
    210                 215                 220

Tyr Arg Arg Gln Asn Ser Asp Asn Thr Pro Arg Thr Asn Trp Val Pro
225                 230                 235                 240

Ser Val Ser Asn Pro Gly Thr Thr Asn Thr Asn Thr Ser Asn Asn Ser
                245                 250                 255

Asn Thr Asn Ser Gln Ala Ser Gln Ser Asn Asp Ile Asp Ser Leu Leu
            260                 265                 270

Lys Gln Leu Tyr Lys Leu Pro Leu Ser Gln Arg His Val Glu Ser Asp
        275                 280                 285

Gly Leu Ile Phe Asp Pro Ala Gln Ile Thr Ser Arg Thr Ala Arg Gly
    290                 295                 300

Val Ala Val Pro His Gly Asn His Tyr His Phe Ile Pro Tyr Glu Gln
305                 310                 315                 320

Met Ser Glu Leu Glu Lys Arg Ile Ala Arg Ile Ile Pro Leu
                325                 330

<210> SEQ ID NO 62
<211> LENGTH: 487
<212> TYPE: PRT
<213> ORGANISM: S. pneumoniae

<400> SEQUENCE: 62

```
Arg Tyr Arg Ser Asn His Trp Val Pro Asp Ser Arg Pro Glu Glu Pro
1               5                   10                  15
Ser Pro Gln Pro Thr Pro Glu Pro Ser Pro Ser Pro Gln Pro Ala Pro
            20                  25                  30
Asn Pro Gln Pro Ala Pro Ser Asn Pro Ile Asp Glu Lys Leu Val Lys
        35                  40                  45
Glu Ala Val Arg Lys Val Gly Asp Gly Tyr Val Phe Glu Glu Asn Gly
    50                  55                  60
Val Ser Arg Tyr Ile Pro Ala Lys Asn Leu Ser Ala Glu Thr Ala Ala
65                  70                  75                  80
Gly Ile Asp Ser Lys Leu Ala Lys Gln Glu Ser Leu Ser His Lys Leu
                85                  90                  95
Gly Ala Lys Lys Thr Asp Leu Pro Ser Ser Asp Arg Glu Phe Tyr Asn
            100                 105                 110
Lys Ala Tyr Asp Leu Leu Ala Arg Ile His Gln Asp Leu Leu Asp Asn
        115                 120                 125
Lys Gly Arg Gln Val Asp Phe Glu Ala Leu Asp Asn Leu Leu Glu Arg
    130                 135                 140
Leu Lys Asp Val Ser Ser Asp Lys Val Lys Leu Val Asp Asp Ile Leu
145                 150                 155                 160
Ala Phe Leu Ala Pro Ile Arg His Pro Glu Arg Leu Gly Lys Pro Asn
                165                 170                 175
Ala Gln Ile Thr Tyr Thr Asp Asp Glu Ile Gln Val Ala Lys Leu Ala
            180                 185                 190
Gly Lys Tyr Thr Thr Glu Asp Gly Tyr Ile Phe Asp Pro Arg Asp Ile
        195                 200                 205
Thr Ser Asp Glu Gly Asp Ala Tyr Val Thr Pro His Met Thr His Ser
    210                 215                 220
His Trp Ile Lys Lys Asp Ser Leu Ser Glu Ala Glu Arg Ala Ala Ala
225                 230                 235                 240
Gln Ala Tyr Ala Lys Glu Lys Gly Leu Thr Pro Pro Ser Thr Asp His
                245                 250                 255
Gln Asp Ser Gly Asn Thr Glu Ala Lys Gly Ala Glu Ala Ile Tyr Asn
            260                 265                 270
Arg Val Lys Ala Ala Lys Lys Val Pro Leu Asp Arg Met Pro Tyr Asn
        275                 280                 285
Leu Gln Tyr Thr Val Glu Val Lys Asn Gly Ser Leu Ile Ile Pro His
    290                 295                 300
Tyr Asp His Tyr His Asn Ile Lys Phe Glu Trp Phe Asp Glu Gly Leu
305                 310                 315                 320
Tyr Glu Ala Pro Lys Gly Tyr Thr Leu Glu Asp Leu Leu Ala Thr Val
                325                 330                 335
Lys Tyr Tyr Val Glu His Pro Asn Glu Arg Pro His Ser Asp Asn Gly
            340                 345                 350
Phe Gly Asn Ala Ser Asp His Val Gln Arg Asn Lys Asn Gly Gln Ala
        355                 360                 365
Asp Thr Asn Gln Thr Glu Lys Pro Ser Glu Lys Pro Gln Thr Glu
    370                 375                 380
Lys Pro Glu Glu Glu Thr Pro Arg Glu Glu Lys Pro Gln Ser Glu Lys
385                 390                 395                 400
Pro Glu Ser Pro Lys Pro Thr Glu Glu Pro Glu Glu Ser Pro Glu
                405                 410                 415
```

```
Glu Ser Glu Glu Pro Gln Val Glu Thr Glu Lys Val Glu Lys Leu
            420                 425                 430

Arg Glu Ala Glu Asp Leu Leu Gly Lys Ile Gln Asp Pro Ile Ile Lys
            435                 440                 445

Ser Asn Ala Lys Glu Thr Leu Thr Gly Leu Lys Asn Asn Leu Leu Phe
    450                 455                 460

Gly Thr Gln Asp Asn Asn Thr Ile Met Ala Glu Ala Glu Lys Leu Leu
465                 470                 475                 480

Ala Leu Leu Lys Glu Ser Lys
                485

<210> SEQ ID NO 63
<211> LENGTH: 613
<212> TYPE: PRT
<213> ORGANISM: S. pneumoniae

<400> SEQUENCE: 63

Ala Glu Ala Phe Leu Ser Gly Arg Glu Asn Leu Ser Asn Leu Arg Thr
1               5                   10                  15

Tyr Arg Arg Gln Asn Ser Asp Asn Thr Pro Arg Thr Asn Trp Val Pro
            20                  25                  30

Ser Val Ser Asn Pro Gly Thr Thr Asn Thr Asn Thr Ser Asn Asn Ser
        35                  40                  45

Asn Thr Asn Ser Gln Ala Ser Gln Ser Asn Asp Ile Asp Ser Leu Leu
    50                  55                  60

Lys Gln Leu Tyr Lys Leu Pro Leu Ser Gln Arg His Val Glu Ser Asp
65                  70                  75                  80

Gly Leu Ile Phe Asp Pro Ala Gln Ile Thr Ser Arg Thr Ala Arg Gly
                85                  90                  95

Val Ala Val Pro His Gly Asn His Tyr His Phe Ile Pro Tyr Glu Gln
            100                 105                 110

Met Ser Glu Leu Glu Lys Arg Ile Ala Arg Ile Ile Pro Leu Arg Tyr
        115                 120                 125

Arg Ser Asn His Trp Val Pro Asp Ser Arg Pro Glu Glu Pro Ser Pro
    130                 135                 140

Gln Pro Thr Pro Glu Pro Ser Pro Ser Pro Gln Pro Ala Pro Asn Pro
145                 150                 155                 160

Gln Pro Ala Pro Ser Asn Pro Ile Asp Glu Lys Leu Val Lys Glu Ala
                165                 170                 175

Val Arg Lys Val Gly Asp Gly Tyr Val Phe Glu Glu Asn Gly Val Ser
            180                 185                 190

Arg Tyr Ile Pro Ala Lys Asn Leu Ser Ala Glu Thr Ala Ala Gly Ile
        195                 200                 205

Asp Ser Lys Leu Ala Lys Gln Glu Ser Leu Ser His Lys Leu Gly Ala
    210                 215                 220

Lys Lys Thr Asp Leu Pro Ser Ser Asp Arg Glu Phe Tyr Asn Lys Ala
225                 230                 235                 240

Tyr Asp Leu Leu Ala Arg Ile His Gln Asp Leu Leu Asp Asn Lys Gly
                245                 250                 255

Arg Gln Val Asp Phe Glu Ala Leu Asp Asn Leu Leu Glu Arg Leu Lys
            260                 265                 270

Asp Val Ser Ser Asp Lys Val Lys Leu Val Asp Ile Leu Ala Phe
        275                 280                 285

Leu Ala Pro Ile Arg His Pro Glu Arg Leu Gly Lys Pro Asn Ala Gln
```

-continued

```
                290                 295                 300
Ile Thr Tyr Thr Asp Asp Glu Ile Gln Val Ala Lys Leu Ala Gly Lys
305                 310                 315                 320

Tyr Thr Thr Glu Asp Gly Tyr Ile Phe Asp Pro Arg Asp Ile Thr Ser
                325                 330                 335

Asp Glu Gly Asp Ala Tyr Val Thr Pro His Met Thr His Ser His Trp
                340                 345                 350

Ile Lys Lys Asp Ser Leu Ser Glu Ala Glu Arg Ala Ala Ala Gln Ala
                355                 360                 365

Tyr Ala Lys Glu Lys Gly Leu Thr Pro Pro Ser Thr Asp His Gln Asp
370                 375                 380

Ser Gly Asn Thr Glu Ala Lys Gly Ala Glu Ala Ile Tyr Asn Arg Val
385                 390                 395                 400

Lys Ala Ala Lys Lys Val Pro Leu Asp Arg Met Pro Tyr Asn Leu Gln
                405                 410                 415

Tyr Thr Val Glu Val Lys Asn Gly Ser Leu Ile Ile Pro His Tyr Asp
                420                 425                 430

His Tyr His Asn Ile Lys Phe Glu Trp Phe Asp Glu Gly Leu Tyr Glu
                435                 440                 445

Ala Pro Lys Gly Tyr Thr Leu Glu Asp Leu Leu Ala Thr Val Lys Tyr
450                 455                 460

Tyr Val Glu His Pro Asn Glu Arg Pro His Ser Asp Asn Gly Phe Gly
465                 470                 475                 480

Asn Ala Ser Asp His Val Gln Arg Asn Lys Asn Gly Gln Ala Asp Thr
                485                 490                 495

Asn Gln Thr Glu Lys Pro Ser Glu Glu Lys Pro Gln Thr Glu Lys Pro
                500                 505                 510

Glu Glu Glu Thr Pro Arg Glu Glu Lys Pro Gln Ser Glu Lys Pro Glu
                515                 520                 525

Ser Pro Lys Pro Thr Glu Glu Pro Glu Glu Ser Pro Glu Glu Ser
530                 535                 540

Glu Glu Pro Gln Val Glu Thr Glu Lys Val Glu Glu Lys Leu Arg Glu
545                 550                 555                 560

Ala Glu Asp Leu Leu Gly Lys Ile Gln Asp Pro Ile Ile Lys Ser Asn
                565                 570                 575

Ala Lys Glu Thr Leu Thr Gly Leu Lys Asn Asn Leu Leu Phe Gly Thr
                580                 585                 590

Gln Asp Asn Asn Thr Ile Met Ala Glu Ala Lys Leu Leu Ala Leu
                595                 600                 605

Leu Lys Glu Ser Lys
    610

<210> SEQ ID NO 64
<211> LENGTH: 568
<212> TYPE: PRT
<213> ORGANISM: S. pneumoniae

<400> SEQUENCE: 64

Asp Leu Thr Glu Glu Gln Ile Lys Ala Ala Gln Lys His Leu Glu Glu
1               5                   10                  15

Val Lys Thr Ser His Asn Gly Leu Asp Ser Leu Ser Ser His Glu Gln
                20                  25                  30

Asp Tyr Pro Gly Asn Ala Lys Glu Met Lys Asp Leu Asp Lys Lys Ile
                35                  40                  45
```

-continued

Glu Glu Lys Ile Ala Gly Ile Met Lys Gln Tyr Gly Val Lys Arg Glu
 50                  55                  60

Ser Ile Val Val Asn Lys Glu Lys Asn Ala Ile Ile Tyr Pro His Gly
 65                  70                  75                  80

Asp His His His Ala Asp Pro Ile Asp Glu His Lys Pro Val Gly Ile
                 85                  90                  95

Gly His Ser His Ser Asn Tyr Glu Leu Phe Lys Pro Glu Glu Gly Val
             100                 105                 110

Ala Lys Lys Glu Gly Asn Lys Val Tyr Thr Gly Glu Glu Leu Thr Asn
         115                 120                 125

Val Val Asn Leu Leu Lys Asn Ser Thr Phe Asn Asn Gln Asn Phe Thr
130                 135                 140

Leu Ala Asn Gly Gln Lys Arg Val Ser Phe Ser Phe Pro Pro Glu Leu
145                 150                 155                 160

Glu Lys Lys Leu Gly Ile Asn Met Leu Val Lys Leu Ile Thr Pro Asp
                 165                 170                 175

Gly Lys Val Leu Glu Lys Val Ser Gly Lys Val Phe Gly Glu Gly Val
             180                 185                 190

Gly Asn Ile Ala Asn Phe Glu Leu Asp Gln Pro Tyr Leu Pro Gly Gln
         195                 200                 205

Thr Phe Lys Tyr Thr Ile Ala Ser Lys Asp Tyr Pro Glu Val Ser Tyr
210                 215                 220

Asp Gly Thr Phe Thr Val Pro Thr Ser Leu Ala Tyr Lys Met Ala Ser
225                 230                 235                 240

Gln Thr Ile Phe Tyr Pro Phe His Ala Gly Asp Thr Tyr Leu Arg Val
                 245                 250                 255

Asn Pro Gln Phe Ala Val Pro Lys Gly Thr Asp Ala Leu Val Arg Val
             260                 265                 270

Phe Asp Glu Phe His Gly Asn Ala Tyr Leu Glu Asn Asn Tyr Lys Val
         275                 280                 285

Gly Glu Ile Lys Leu Pro Ile Pro Lys Leu Asn Gln Gly Thr Thr Arg
290                 295                 300

Thr Ala Gly Asn Lys Ile Pro Val Thr Phe Met Ala Asn Ala Tyr Leu
305                 310                 315                 320

Asp Asn Gln Ser Thr Tyr Ile Val Glu Val Pro Ile Leu Glu Lys Glu
                 325                 330                 335

Asn Gln Thr Asp Lys Pro Ser Ile Leu Pro Gln Phe Lys Arg Asn Lys
             340                 345                 350

Ala Gln Glu Asn Ser Lys Leu Asp Glu Lys Val Glu Pro Lys Thr
         355                 360                 365

Ser Glu Lys Val Glu Lys Glu Lys Leu Ser Glu Thr Gly Asn Ser Thr
370                 375                 380

Ser Asn Ser Thr Leu Glu Glu Val Pro Thr Val Asp Pro Val Gln Glu
385                 390                 395                 400

Lys Val Ala Lys Phe Ala Glu Ser Tyr Gly Met Lys Leu Glu Asn Val
                 405                 410                 415

Leu Phe Asn Met Asp Gly Thr Ile Glu Leu Tyr Leu Pro Ser Gly Glu
             420                 425                 430

Val Ile Lys Lys Asn Met Ala Asp Phe Thr Gly Glu Ala Pro Gln Gly
         435                 440                 445

Asn Gly Glu Asn Lys Pro Ser Glu Asn Gly Lys Val Ser Thr Gly Thr
450                 455                 460

Val Glu Asn Gln Pro Thr Glu Asn Lys Pro Ala Asp Ser Leu Pro Glu

```
                465                 470                 475                 480
Ala Pro Asn Glu Lys Pro Val Lys Pro Glu Asn Ser Thr Asp Asn Gly
                    485                 490                 495

Met Leu Asn Pro Glu Gly Asn Val Gly Ser Asp Pro Met Leu Asp Pro
                500                 505                 510

Ala Leu Glu Glu Ala Pro Ala Val Asp Pro Val Gln Glu Lys Leu Glu
                515                 520                 525

Lys Phe Thr Ala Ser Tyr Gly Leu Gly Leu Asp Ser Val Ile Phe Asn
            530                 535                 540

Met Asp Gly Thr Ile Glu Leu Arg Leu Pro Ser Gly Glu Val Ile Lys
545                 550                 555                 560

Lys Asn Leu Ser Asp Phe Ile Ala
                565

<210> SEQ ID NO 65
<211> LENGTH: 329
<212> TYPE: PRT
<213> ORGANISM: S. pneumoniae

<400> SEQUENCE: 65

Asp Leu Thr Glu Glu Gln Ile Lys Ala Ala Gln Lys His Leu Glu Glu
 1               5                  10                  15

Val Lys Thr Ser His Asn Gly Leu Asp Ser Leu Ser Ser His Glu Gln
            20                  25                  30

Asp Tyr Pro Gly Asn Ala Lys Glu Met Lys Asp Leu Asp Lys Lys Ile
        35                  40                  45

Glu Glu Lys Ile Ala Gly Ile Met Lys Gln Tyr Gly Val Lys Arg Glu
    50                  55                  60

Ser Ile Val Val Asn Lys Glu Lys Asn Ala Ile Ile Tyr Pro His Gly
65                  70                  75                  80

Asp His His Ala Asp Pro Ile Asp Glu His Lys Pro Val Gly Ile
            85                  90                  95

Gly His Ser His Ser Asn Tyr Glu Leu Phe Lys Pro Glu Glu Gly Val
            100                 105                 110

Ala Lys Lys Glu Gly Asn Lys Val Tyr Thr Gly Glu Glu Leu Thr Asn
        115                 120                 125

Val Val Asn Leu Leu Lys Asn Ser Thr Phe Asn Asn Gln Asn Phe Thr
    130                 135                 140

Leu Ala Asn Gly Gln Lys Arg Val Ser Phe Ser Phe Pro Pro Glu Leu
145                 150                 155                 160

Glu Lys Lys Leu Gly Ile Asn Met Leu Val Lys Leu Ile Thr Pro Asp
                165                 170                 175

Gly Lys Val Leu Glu Lys Val Ser Gly Lys Val Phe Gly Glu Gly Val
            180                 185                 190

Gly Asn Ile Ala Asn Phe Glu Leu Asp Gln Pro Tyr Leu Pro Gly Gln
        195                 200                 205

Thr Phe Lys Tyr Thr Ile Ala Ser Lys Asp Tyr Pro Glu Val Ser Tyr
    210                 215                 220

Asp Gly Thr Phe Thr Val Pro Thr Ser Leu Ala Tyr Lys Met Ala Ser
225                 230                 235                 240

Gln Thr Ile Phe Tyr Pro Phe His Ala Gly Asp Thr Tyr Leu Arg Val
                245                 250                 255

Asn Pro Gln Phe Ala Val Pro Lys Gly Thr Asp Ala Leu Val Arg Val
            260                 265                 270
```

```
Phe Asp Glu Phe His Gly Asn Ala Tyr Leu Glu Asn Tyr Lys Val
        275                 280                 285

Gly Glu Ile Lys Leu Pro Ile Pro Lys Leu Asn Gln Gly Thr Thr Arg
        290                 295                 300

Thr Ala Gly Asn Lys Ile Pro Val Thr Phe Met Ala Asn Ala Tyr Leu
305                 310                 315                 320

Asp Asn Gln Ser Thr Tyr Ile Val Glu
                325

<210> SEQ ID NO 66
<211> LENGTH: 240
<212> TYPE: PRT
<213> ORGANISM: S. pneumoniae

<400> SEQUENCE: 66

Glu Val Pro Ile Leu Glu Lys Glu Asn Gln Thr Asp Lys Pro Ser Ile
1               5                   10                  15

Leu Pro Gln Phe Lys Arg Asn Lys Ala Gln Glu Asn Ser Lys Leu Asp
            20                  25                  30

Glu Lys Val Glu Glu Pro Lys Thr Ser Glu Lys Val Glu Lys Glu Lys
        35                  40                  45

Leu Ser Glu Thr Gly Asn Ser Thr Ser Asn Ser Thr Leu Glu Glu Val
    50                  55                  60

Pro Thr Val Asp Pro Val Gln Glu Lys Val Ala Lys Phe Ala Glu Ser
65                  70                  75                  80

Tyr Gly Met Lys Leu Glu Asn Val Leu Phe Asn Met Asp Gly Thr Ile
                85                  90                  95

Glu Leu Tyr Leu Pro Ser Gly Glu Val Ile Lys Lys Asn Met Ala Asp
            100                 105                 110

Phe Thr Gly Glu Ala Pro Gln Gly Asn Gly Glu Asn Lys Pro Ser Glu
        115                 120                 125

Asn Gly Lys Val Ser Thr Gly Thr Val Glu Asn Gln Pro Thr Glu Asn
    130                 135                 140

Lys Pro Ala Asp Ser Leu Pro Glu Ala Pro Asn Glu Lys Pro Val Lys
145                 150                 155                 160

Pro Glu Asn Ser Thr Asp Asn Gly Met Leu Asn Pro Glu Gly Asn Val
                165                 170                 175

Gly Ser Asp Pro Met Leu Asp Pro Ala Leu Glu Glu Ala Pro Ala Val
            180                 185                 190

Asp Pro Val Gln Glu Lys Leu Gly Lys Phe Thr Ala Ser Tyr Gly Leu
        195                 200                 205

Gly Leu Asp Ser Val Ile Phe Asn Met Asp Gly Thr Ile Glu Leu Arg
    210                 215                 220

Leu Pro Ser Gly Glu Val Ile Lys Lys Asn Leu Ser Asp Phe Ile Ala
225                 230                 235                 240

<210> SEQ ID NO 67
<211> LENGTH: 555
<212> TYPE: PRT
<213> ORGANISM: S. pneumoniae

<400> SEQUENCE: 67

Asp Ile Asp Ser Leu Leu Lys Gln Leu Tyr Lys Leu Pro Leu Ser Gln
1               5                   10                  15

Arg His Val Glu Ser Asp Gly Leu Ile Phe Asp Pro Ala Gln Ile Thr
            20                  25                  30
```

```
Ser Arg Thr Ala Arg Gly Val Ala Val Pro His Gly Asn His Tyr His
        35                  40                  45

Phe Ile Pro Tyr Glu Gln Met Ser Glu Leu Glu Lys Arg Ile Ala Arg
 50                  55                  60

Ile Ile Pro Leu Arg Tyr Arg Ser Asn His Trp Val Pro Asp Ser Arg
65                  70                  75                  80

Pro Glu Glu Pro Ser Pro Gln Pro Thr Pro Glu Pro Ser Pro Ser Pro
                    85                  90                  95

Gln Pro Ala Pro Asn Pro Gln Pro Ala Pro Ser Asn Pro Ile Asp Glu
                100                 105                 110

Lys Leu Val Lys Glu Ala Val Arg Lys Val Gly Asp Gly Tyr Val Phe
                115                 120                 125

Glu Glu Asn Gly Val Ser Arg Tyr Ile Pro Ala Lys Asn Leu Ser Ala
130                 135                 140

Glu Thr Ala Ala Gly Ile Asp Ser Lys Leu Ala Lys Gln Glu Ser Leu
145                 150                 155                 160

Ser His Lys Leu Gly Ala Lys Lys Thr Asp Leu Pro Ser Ser Asp Arg
                165                 170                 175

Glu Phe Tyr Asn Lys Ala Tyr Asp Leu Leu Ala Arg Ile His Gln Asp
                180                 185                 190

Leu Leu Asp Asn Lys Gly Arg Gln Val Asp Phe Glu Ala Leu Asp Asn
                195                 200                 205

Leu Leu Glu Arg Leu Lys Asp Val Ser Ser Asp Lys Val Lys Leu Val
                210                 215                 220

Asp Asp Ile Leu Ala Phe Leu Ala Pro Ile Arg His Pro Glu Arg Leu
225                 230                 235                 240

Gly Lys Pro Asn Ala Gln Ile Thr Tyr Thr Asp Asp Glu Ile Gln Val
                245                 250                 255

Ala Lys Leu Ala Gly Lys Tyr Thr Thr Glu Asp Gly Tyr Ile Phe Asp
                260                 265                 270

Pro Arg Asp Ile Thr Ser Asp Glu Gly Asp Ala Tyr Val Thr Pro His
                275                 280                 285

Met Thr His Ser His Trp Ile Lys Lys Asp Ser Leu Ser Glu Ala Glu
                290                 295                 300

Arg Ala Ala Ala Gln Ala Tyr Ala Lys Glu Lys Gly Leu Thr Pro Pro
305                 310                 315                 320

Ser Thr Asp His Gln Asp Ser Gly Asn Thr Glu Ala Lys Gly Ala Glu
                325                 330                 335

Ala Ile Tyr Asn Arg Val Lys Ala Ala Lys Lys Val Pro Leu Asp Arg
                340                 345                 350

Met Pro Tyr Asn Leu Gln Tyr Thr Val Glu Val Lys Asn Gly Ser Leu
                355                 360                 365

Ile Ile Pro His Tyr Asp His Tyr His Asn Ile Lys Phe Glu Trp Phe
                370                 375                 380

Asp Glu Gly Leu Tyr Glu Ala Pro Lys Gly Tyr Thr Leu Glu Asp Leu
385                 390                 395                 400

Leu Ala Thr Val Lys Tyr Tyr Val Glu His Pro Asn Glu Arg Pro His
                405                 410                 415

Ser Asp Asn Gly Phe Gly Asn Ala Ser Asp His Val Gln Arg Asn Lys
                420                 425                 430

Asn Gly Gln Ala Asp Thr Asn Gln Thr Glu Lys Pro Ser Glu Glu Lys
                435                 440                 445

Pro Gln Thr Glu Lys Pro Glu Glu Glu Thr Pro Arg Glu Glu Lys Pro
```

```
                450               455               460
Gln Ser Glu Lys Pro Glu Ser Lys Pro Thr Glu Glu Pro Glu Glu
465                 470                 475                 480

Glu Ser Pro Glu Glu Ser Glu Glu Pro Gln Val Glu Thr Glu Lys Val
                485                 490                 495

Glu Glu Lys Leu Arg Glu Ala Glu Asp Leu Leu Gly Lys Ile Gln Asp
            500                 505                 510

Pro Ile Ile Lys Ser Asn Ala Lys Glu Thr Leu Thr Gly Leu Lys Asn
        515                 520                 525

Asn Leu Leu Phe Gly Thr Gln Asp Asn Thr Ile Met Ala Glu Ala
    530                 535                 540

Glu Lys Leu Leu Ala Leu Leu Lys Glu Ser Lys
545                 550                 555

<210> SEQ ID NO 68
<211> LENGTH: 428
<212> TYPE: PRT
<213> ORGANISM: S. pneumoniae

<400> SEQUENCE: 68

Asp Ile Asp Ser Leu Leu Lys Gln Leu Tyr Lys Leu Pro Leu Ser Gln
  1               5                  10                  15

Arg His Val Glu Ser Asp Gly Leu Ile Phe Asp Pro Ala Gln Ile Thr
                 20                  25                  30

Ser Arg Thr Ala Arg Gly Val Ala Val Pro His Gly Asn His Tyr His
             35                  40                  45

Phe Ile Pro Tyr Glu Gln Met Ser Glu Leu Glu Lys Arg Ile Ala Arg
         50                  55                  60

Ile Ile Pro Leu Arg Tyr Arg Ser Asn His Trp Val Pro Asp Ser Arg
 65                  70                  75                  80

Pro Glu Glu Pro Ser Pro Gln Pro Thr Pro Glu Pro Ser Pro Ser Pro
                 85                  90                  95

Gln Pro Ala Pro Asn Pro Gln Pro Ala Pro Ser Asn Pro Ile Asp Glu
            100                 105                 110

Lys Leu Val Lys Glu Ala Val Arg Lys Val Gly Asp Gly Tyr Val Phe
        115                 120                 125

Glu Glu Asn Gly Val Ser Arg Tyr Ile Pro Ala Lys Asn Leu Ser Ala
    130                 135                 140

Glu Thr Ala Ala Gly Ile Asp Ser Lys Leu Ala Lys Gln Glu Ser Leu
145                 150                 155                 160

Ser His Lys Leu Gly Ala Lys Lys Thr Asp Leu Pro Ser Ser Asp Arg
                165                 170                 175

Glu Phe Tyr Asn Lys Ala Tyr Asp Leu Leu Ala Arg Ile His Gln Asp
            180                 185                 190

Leu Leu Asp Asn Lys Gly Arg Gln Val Asp Phe Glu Ala Leu Asp Asn
        195                 200                 205

Leu Leu Glu Arg Leu Lys Asp Val Ser Ser Asp Lys Val Lys Leu Val
    210                 215                 220

Asp Asp Ile Leu Ala Phe Leu Ala Pro Ile Arg His Pro Glu Arg Leu
225                 230                 235                 240

Gly Lys Pro Asn Ala Gln Ile Thr Tyr Thr Asp Glu Ile Gln Val
                245                 250                 255

Ala Lys Leu Ala Gly Lys Tyr Thr Thr Glu Asp Gly Tyr Ile Phe Asp
            260                 265                 270
```

```
Pro Arg Asp Ile Thr Ser Asp Glu Gly Asp Ala Tyr Val Thr Pro His
            275                 280                 285

Met Thr His Ser His Trp Ile Lys Lys Asp Ser Leu Ser Glu Ala Glu
        290                 295                 300

Arg Ala Ala Ala Gln Ala Tyr Ala Lys Glu Lys Gly Leu Thr Pro Pro
305                 310                 315                 320

Ser Thr Asp His Gln Asp Ser Gly Asn Thr Glu Ala Lys Gly Ala Glu
            325                 330                 335

Ala Ile Tyr Asn Arg Val Lys Ala Ala Lys Lys Val Pro Leu Asp Arg
            340                 345                 350

Met Pro Tyr Asn Leu Gln Tyr Thr Val Glu Val Lys Asn Gly Ser Leu
            355                 360                 365

Ile Ile Pro His Tyr Asp His Tyr His Asn Ile Lys Phe Glu Trp Phe
            370                 375                 380

Asp Glu Gly Leu Tyr Glu Ala Pro Lys Gly Tyr Thr Leu Glu Asp Leu
385                 390                 395                 400

Leu Ala Thr Val Lys Tyr Tyr Val Glu His Pro Asn Glu Arg Pro His
            405                 410                 415

Ser Asp Asn Gly Phe Gly Asn Ala Ser Asp His Val
            420                 425
```

```
<210> SEQ ID NO 69
<211> LENGTH: 121
<212> TYPE: PRT
<213> ORGANISM: S. pneumoniae

<400> SEQUENCE: 69

Gly Leu Tyr Glu Ala Pro Lys Gly Tyr Thr Leu Glu Asp Leu Leu Ala
1               5                   10                  15

Thr Val Lys Tyr Tyr Val Glu His Pro Asn Glu Arg Pro His Ser Asp
            20                  25                  30

Asn Gly Phe Gly Asn Ala Ser Asp His Val Gln Arg Asn Lys Asn Gly
            35                  40                  45

Gln Ala Asp Thr Asn Gln Thr Glu Lys Pro Ser Glu Glu Lys Pro Gln
50                  55                  60

Thr Glu Lys Pro Glu Glu Glu Thr Pro Arg Glu Glu Lys Pro Gln Ser
65                  70                  75                  80

Glu Lys Pro Glu Ser Pro Lys Pro Thr Glu Glu Pro Glu Glu Glu Ser
            85                  90                  95

Pro Glu Glu Ser Glu Glu Pro Gln Val Glu Thr Glu Lys Val Glu Glu
            100                 105                 110

Lys Leu Arg Glu Ala Glu Asp Leu Leu
            115                 120
```

```
<210> SEQ ID NO 70
<211> LENGTH: 132
<212> TYPE: PRT
<213> ORGANISM: S. pneumoniae

<400> SEQUENCE: 70

Ala Ser Asp His Val Gln Arg Asn Lys Asn Gly Gln Ala Asp Thr Asn
1               5                   10                  15

Gln Thr Glu Lys Pro Ser Glu Glu Lys Pro Gln Thr Glu Lys Pro Glu
            20                  25                  30

Glu Glu Thr Pro Arg Glu Glu Lys Pro Gln Ser Glu Lys Pro Glu Ser
            35                  40                  45
```

```
Pro Lys Pro Thr Glu Glu Pro Glu Glu Ser Pro Glu Glu Ser Glu
    50                  55                  60

Glu Pro Gln Val Glu Thr Glu Lys Val Glu Glu Lys Leu Arg Glu Ala
65                  70                  75                  80

Glu Asp Leu Leu Gly Lys Ile Gln Asp Pro Ile Ile Lys Ser Asn Ala
                    85                  90                  95

Lys Glu Thr Leu Thr Gly Leu Lys Asn Asn Leu Leu Phe Gly Thr Gln
                100                 105                 110

Asp Asn Asn Thr Ile Met Ala Glu Ala Glu Lys Leu Leu Ala Leu Leu
                115                 120                 125

Lys Glu Ser Lys
    130

<210> SEQ ID NO 71
<211> LENGTH: 226
<212> TYPE: PRT
<213> ORGANISM: S. pneumoniae

<400> SEQUENCE: 71

Asp Ile Asp Ser Leu Leu Lys Gln Leu Tyr Lys Leu Pro Leu Ser Gln
1               5                   10                  15
Arg His Val Glu Ser Asp Gly Leu Ile Phe Asp Pro Ala Gln Ile Thr
                20                  25                  30
Ser Arg Thr Ala Arg Gly Val Ala Val Pro His Gly Asn His Tyr His
            35                  40                  45
Phe Ile Pro Tyr Glu Gln Met Ser Glu Leu Glu Lys Arg Ile Ala Arg
    50                  55                  60
Ile Ile Pro Leu Arg Tyr Arg Ser Asn His Trp Val Pro Asp Ser Arg
65                  70                  75                  80
Pro Glu Glu Pro Ser Pro Gln Pro Thr Pro Glu Pro Ser Pro Ser Pro
                85                  90                  95
Gln Pro Ala Pro Asn Pro Gln Pro Ala Pro Ser Asn Pro Ile Asp Glu
                100                 105                 110
Lys Leu Val Lys Glu Ala Val Arg Lys Val Gly Asp Gly Tyr Val Phe
                115                 120                 125
Glu Glu Asn Gly Val Ser Arg Tyr Ile Pro Ala Lys Asn Leu Ser Ala
                130                 135                 140
Glu Thr Ala Ala Gly Ile Asp Ser Lys Leu Ala Lys Gln Glu Ser Leu
145                 150                 155                 160
Ser His Lys Leu Gly Ala Lys Lys Thr Asp Leu Pro Ser Ser Asp Arg
                165                 170                 175
Glu Phe Tyr Asn Lys Ala Tyr Asp Leu Leu Ala Arg Ile His Gln Asp
                180                 185                 190
Leu Leu Asp Asn Lys Gly Arg Gln Val Asp Phe Glu Ala Leu Asp Asn
                195                 200                 205
Leu Leu Glu Arg Leu Lys Asp Val Ser Asp Lys Val Lys Leu Val
210                 215                 220
Asp Asp
225

<210> SEQ ID NO 72
<211> LENGTH: 203
<212> TYPE: PRT
<213> ORGANISM: S. pneumoniae

<400> SEQUENCE: 72

Asp Ile Leu Ala Phe Leu Ala Pro Ile Arg His Pro Glu Arg Leu Gly
1               5                   10                  15

Lys Pro Asn Ala Gln Ile Thr Tyr Thr Asp Asp Glu Ile Gln Val Ala
                20                  25                  30

Lys Leu Ala Gly Lys Tyr Thr Thr Glu Asp Gly Tyr Ile Phe Asp Pro
            35                  40                  45

Arg Asp Ile Thr Ser Asp Glu Gly Asp Ala Tyr Val Thr Pro His Met
    50                  55                  60

Thr His Ser His Trp Ile Lys Lys Asp Ser Leu Ser Glu Ala Glu Arg
65                  70                  75                  80
```

```
Ala Ala Ala Gln Ala Tyr Ala Lys Glu Lys Gly Leu Thr Pro Pro Ser
                85                  90                  95

Thr Asp His Gln Asp Ser Gly Asn Thr Glu Ala Lys Gly Ala Glu Ala
            100                 105                 110

Ile Tyr Asn Arg Val Lys Ala Ala Lys Lys Val Pro Leu Asp Arg Met
        115                 120                 125

Pro Tyr Asn Leu Gln Tyr Thr Val Glu Val Lys Asn Gly Ser Leu Ile
    130                 135                 140

Ile Pro His Tyr Asp His Tyr His Asn Ile Lys Phe Glu Trp Phe Asp
145                 150                 155                 160

Glu Gly Leu Tyr Glu Ala Pro Lys Gly Tyr Thr Leu Glu Asp Leu Leu
                165                 170                 175

Ala Thr Val Lys Tyr Tyr Val Glu His Pro Asn Glu Arg Pro His Ser
                180                 185                 190

Asp Asn Gly Phe Gly Asn Ala Ser Asp His Val
            195                 200

<210> SEQ ID NO 73
<211> LENGTH: 819
<212> TYPE: PRT
<213> ORGANISM: S. pneumoniae

<400> SEQUENCE: 73

Cys Ser Tyr Glu Leu Gly Arg His Gln Ala Gly Gln Val Lys Lys Glu
1               5                   10                  15

Ser Asn Arg Val Ser Tyr Ile Asp Gly Asp Gln Ala Gly Gln Lys Ala
            20                  25                  30

Glu Asn Leu Thr Pro Asp Glu Val Ser Lys Arg Glu Gly Ile Asn Ala
        35                  40                  45

Glu Gln Ile Val Ile Lys Ile Thr Asp Gln Gly Tyr Val Thr Ser His
    50                  55                  60

Gly Asp His Tyr His Tyr Tyr Asn Gly Lys Val Pro Tyr Asp Ala Ile
65                  70                  75                  80

Ile Ser Glu Glu Leu Leu Met Lys Asp Pro Asn Tyr Gln Leu Lys Asp
                85                  90                  95

Ser Asp Ile Val Asn Glu Ile Lys Gly Gly Tyr Val Ile Lys Val Asp
            100                 105                 110

Gly Lys Tyr Tyr Val Tyr Leu Lys Asp Ala Ala His Ala Asp Asn Ile
        115                 120                 125

Arg Thr Lys Glu Glu Ile Lys Arg Gln Lys Gln Glu His Ser His Asn
    130                 135                 140

His Asn Ser Arg Ala Asp Asn Ala Val Ala Ala Arg Ala Gln Gly Arg
145                 150                 155                 160

Arg Tyr Thr Thr Asp Asp Gly Tyr Ile Phe Asn Ala Ser Asp Ile Ile
                165                 170                 175

Glu Asp Thr Gly Asp Ala Tyr Ile Val Pro His Gly Asp His Tyr His
                180                 185                 190

Tyr Ile Pro Lys Asn Glu Leu Ser Ala Ser Glu Leu Ala Ala Ala Glu
            195                 200                 205

Ala Tyr Trp Asn Gly Lys Gln Gly Ser Arg Pro Ser Ser Ser Ser Ser
        210                 215                 220

Tyr Asn Ala Asn Pro Val Gln Pro Arg Leu Ser Glu Asn His Asn Leu
225                 230                 235                 240

Thr Val Thr Pro Thr Tyr His Gln Asn Gln Gly Glu Asn Ile Ser Ser
```

```
                    245                 250                 255
Leu Leu Arg Glu Leu Tyr Ala Lys Pro Leu Ser Glu Arg His Val Glu
            260                 265                 270

Ser Asp Gly Leu Ile Phe Asp Pro Ala Gln Ile Thr Ser Arg Thr Ala
            275                 280                 285

Arg Gly Val Ala Val Pro His Gly Asn His Tyr His Phe Ile Pro Tyr
            290                 295                 300

Glu Gln Met Ser Glu Leu Glu Lys Arg Ile Ala Arg Ile Ile Pro Leu
305                 310                 315                 320

Arg Tyr Arg Ser Asn His Trp Val Pro Asp Ser Arg Pro Glu Gln Pro
                325                 330                 335

Ser Pro Gln Ser Thr Pro Glu Pro Ser Pro Ser Leu Gln Pro Ala Pro
            340                 345                 350

Asn Pro Gln Pro Ala Pro Ser Asn Pro Ile Asp Glu Lys Leu Val Lys
            355                 360                 365

Glu Ala Val Arg Lys Val Gly Asp Gly Tyr Val Phe Glu Glu Asn Gly
            370                 375                 380

Val Ser Arg Tyr Ile Pro Ala Lys Asp Leu Ser Ala Glu Thr Ala Ala
385                 390                 395                 400

Gly Ile Asp Ser Lys Leu Ala Lys Gln Glu Ser Leu Ser His Lys Leu
                405                 410                 415

Gly Ala Lys Lys Thr Asp Leu Pro Ser Ser Asp Arg Glu Phe Tyr Asn
                420                 425                 430

Lys Ala Tyr Asp Leu Leu Ala Arg Ile His Gln Asp Leu Leu Asp Asn
            435                 440                 445

Lys Gly Arg Gln Val Asp Phe Glu Val Leu Asp Asn Leu Leu Glu Arg
            450                 455                 460

Leu Lys Asp Val Ser Ser Asp Lys Val Lys Leu Val Asp Asp Ile Leu
465                 470                 475                 480

Ala Phe Leu Ala Pro Ile Arg His Pro Glu Arg Leu Gly Lys Pro Asn
                485                 490                 495

Ala Gln Ile Thr Tyr Thr Asp Asp Glu Ile Gln Val Ala Lys Leu Ala
            500                 505                 510

Gly Lys Tyr Thr Thr Glu Asp Gly Tyr Ile Phe Asp Pro Arg Asp Ile
            515                 520                 525

Thr Ser Asp Glu Gly Asp Ala Tyr Val Thr Pro His Met Thr His Ser
530                 535                 540

His Trp Ile Lys Lys Asp Ser Leu Ser Glu Ala Glu Arg Ala Ala Ala
545                 550                 555                 560

Gln Ala Tyr Ala Lys Glu Lys Gly Leu Thr Pro Pro Ser Thr Asp His
            565                 570                 575

Gln Asp Ser Gly Asn Thr Glu Ala Lys Gly Ala Glu Ala Ile Tyr Asn
            580                 585                 590

Arg Val Lys Ala Ala Lys Lys Val Pro Leu Asp Arg Met Pro Tyr Asn
            595                 600                 605

Leu Gln Tyr Thr Val Glu Val Lys Asn Gly Ser Leu Ile Ile Pro His
            610                 615                 620

Tyr Asp His Tyr His Asn Ile Lys Phe Glu Trp Phe Asp Glu Gly Leu
625                 630                 635                 640

Tyr Glu Ala Pro Lys Gly Tyr Ser Leu Glu Asp Leu Leu Ala Thr Val
                645                 650                 655

Lys Tyr Tyr Val Glu His Pro Asn Glu Arg Pro His Ser Asp Asn Gly
            660                 665                 670
```

```
Phe Gly Asn Ala Ser Asp His Val Arg Lys Asn Lys Ala Asp Gln Asp
            675                 680                 685

Ser Lys Pro Asp Glu Asp Lys Glu His Asp Glu Val Ser Glu Pro Thr
        690                 695                 700

His Pro Glu Ser Asp Glu Lys Glu Asn His Ala Gly Leu Asn Pro Ser
705                 710                 715                 720

Ala Asp Asn Leu Tyr Lys Pro Ser Thr Asp Thr Glu Glu Thr Glu Glu
                725                 730                 735

Glu Ala Glu Asp Thr Thr Asp Glu Ala Glu Ile Pro Gln Val Glu Asn
            740                 745                 750

Ser Val Ile Asn Ala Lys Ile Ala Asp Ala Glu Ala Leu Leu Glu Lys
        755                 760                 765

Val Thr Asp Pro Ser Ile Arg Gln Asn Ala Met Glu Thr Leu Thr Gly
    770                 775                 780

Leu Lys Ser Ser Leu Leu Leu Gly Thr Lys Asp Asn Asn Thr Ile Ser
785                 790                 795                 800

Ala Glu Val Asp Ser Leu Leu Ala Leu Leu Lys Glu Ser Gln Pro Ala
                805                 810                 815

Pro Ile Gln

<210> SEQ ID NO 74
<211> LENGTH: 568
<212> TYPE: PRT
<213> ORGANISM: S. pneumoniae

<400> SEQUENCE: 74

Glu Asn Ile Ser Ser Leu Leu Arg Glu Leu Tyr Ala Lys Pro Leu Ser
1               5                   10                  15

Glu Arg His Val Glu Ser Asp Gly Leu Ile Phe Asp Pro Ala Gln Ile
            20                  25                  30

Thr Ser Arg Thr Ala Arg Gly Val Ala Val Pro His Gly Asn His Tyr
        35                  40                  45

His Phe Ile Pro Tyr Glu Gln Met Ser Glu Leu Glu Lys Arg Ile Ala
    50                  55                  60

Arg Ile Ile Pro Leu Arg Tyr Arg Ser Asn His Trp Val Pro Asp Ser
65                  70                  75                  80

Arg Pro Glu Gln Pro Ser Pro Gln Ser Thr Pro Glu Pro Ser Pro Ser
                85                  90                  95

Leu Gln Pro Ala Pro Asn Pro Gln Pro Ala Pro Ser Asn Pro Ile Asp
            100                 105                 110

Glu Lys Leu Val Lys Glu Ala Val Arg Lys Val Gly Asp Gly Tyr Val
        115                 120                 125

Phe Glu Glu Asn Gly Val Ser Arg Tyr Ile Pro Ala Lys Asp Leu Ser
    130                 135                 140

Ala Glu Thr Ala Ala Gly Ile Asp Ser Lys Leu Ala Lys Gln Glu Ser
145                 150                 155                 160

Leu Ser His Lys Leu Gly Ala Lys Lys Thr Asp Leu Pro Ser Ser Asp
                165                 170                 175

Arg Glu Phe Tyr Asn Lys Ala Tyr Asp Leu Leu Ala Arg Ile His Gln
            180                 185                 190

Asp Leu Leu Asp Asn Lys Gly Arg Gln Val Asp Phe Glu Val Leu Asp
        195                 200                 205

Asn Leu Leu Glu Arg Leu Lys Asp Val Ser Ser Asp Lys Val Lys Leu
    210                 215                 220
```

Val Asp Asp Ile Leu Ala Phe Leu Ala Pro Ile Arg His Pro Glu Arg
225                 230                 235                 240

Leu Gly Lys Pro Asn Ala Gln Ile Thr Tyr Thr Asp Asp Glu Ile Gln
            245                 250                 255

Val Ala Lys Leu Ala Gly Lys Tyr Thr Thr Glu Asp Gly Tyr Ile Phe
            260                 265                 270

Asp Pro Arg Asp Ile Thr Ser Asp Glu Gly Asp Ala Tyr Val Thr Pro
            275                 280                 285

His Met Thr His Ser His Trp Ile Lys Lys Asp Ser Leu Ser Glu Ala
    290                 295                 300

Glu Arg Ala Ala Ala Gln Ala Tyr Ala Lys Glu Lys Gly Leu Thr Pro
305                 310                 315                 320

Pro Ser Thr Asp His Gln Asp Ser Gly Asn Thr Glu Ala Lys Gly Ala
                325                 330                 335

Glu Ala Ile Tyr Asn Arg Val Lys Ala Ala Lys Lys Val Pro Leu Asp
            340                 345                 350

Arg Met Pro Tyr Asn Leu Gln Tyr Thr Val Glu Val Lys Asn Gly Ser
            355                 360                 365

Leu Ile Ile Pro His Tyr Asp His Tyr His Asn Ile Lys Phe Glu Trp
370                 375                 380

Phe Asp Glu Gly Leu Tyr Glu Ala Pro Lys Gly Tyr Ser Leu Glu Asp
385                 390                 395                 400

Leu Leu Ala Thr Val Lys Tyr Tyr Val Glu His Pro Asn Glu Arg Pro
                405                 410                 415

His Ser Asp Asn Gly Phe Gly Asn Ala Ser Asp His Val Arg Lys Asn
            420                 425                 430

Lys Ala Asp Gln Asp Ser Lys Pro Asp Glu Asp Lys Glu His Asp Glu
            435                 440                 445

Val Ser Glu Pro Thr His Pro Glu Ser Asp Lys Glu Asn His Ala
450                 455                 460

Gly Leu Asn Pro Ser Ala Asp Asn Leu Tyr Lys Pro Ser Thr Asp Thr
465                 470                 475                 480

Glu Glu Thr Glu Glu Glu Ala Glu Asp Thr Thr Asp Glu Ala Glu Ile
                485                 490                 495

Pro Gln Val Glu Asn Ser Val Ile Asn Ala Lys Ile Ala Asp Ala Glu
            500                 505                 510

Ala Leu Leu Glu Lys Val Thr Asp Pro Ser Ile Arg Gln Asn Ala Met
            515                 520                 525

Glu Thr Leu Thr Gly Leu Lys Ser Ser Leu Leu Gly Thr Lys Asp
530                 535                 540

Asn Asn Thr Ile Ser Ala Glu Val Asp Ser Leu Leu Ala Leu Leu Lys
545                 550                 555                 560

Glu Ser Gln Pro Ala Pro Ile Gln
                565

<210> SEQ ID NO 75
<211> LENGTH: 140
<212> TYPE: PRT
<213> ORGANISM: S. pneumoniae

<400> SEQUENCE: 75

Val Arg Lys Asn Lys Ala Asp Gln Asp Ser Lys Pro Asp Glu Asp Lys
1               5                   10                  15

Glu His Asp Glu Val Ser Glu Pro Thr His Pro Glu Ser Asp Glu Lys

|  | 20 |  |  | 25 |  |  | 30 |  |
|---|---|---|---|---|---|---|---|---|

Glu Asn His Ala Gly Leu Asn Pro Ser Ala Asp Asn Leu Tyr Lys Pro
          35                  40                  45

Ser Thr Asp Thr Glu Glu Thr Glu Glu Ala Glu Asp Thr Thr Asp
 50                  55                  60

Glu Ala Glu Ile Pro Gln Val Glu Asn Ser Val Ile Asn Ala Lys Ile
 65                  70                  75                  80

Ala Asp Ala Glu Ala Leu Leu Glu Lys Val Thr Asp Pro Ser Ile Arg
                85                  90                  95

Gln Asn Ala Met Glu Thr Leu Thr Gly Leu Lys Ser Ser Leu Leu Leu
              100                 105                 110

Gly Thr Lys Asp Asn Asn Thr Ile Ser Ala Glu Val Asp Ser Leu Leu
            115                 120                 125

Ala Leu Leu Lys Glu Ser Gln Pro Ala Pro Ile Gln
          130                 135                 140

<210> SEQ ID NO 76
<211> LENGTH: 3171
<212> TYPE: DNA
<213> ORGANISM: S. pneumoniae

<400> SEQUENCE: 76

```
gacttgacag aagagcaaat taaggctgcg caaaaacatt tagaggaagt taaaactagt      60
cataatggat tagattcttt gtcatctcat gaacaggatt atccaggtaa tgccaaagaa     120
atgaaagatt tagataaaaa aatcgaagaa aaaattgctg gcattatgaa acaatatggt     180
gtcaaacgtg aaagtattgt cgtgaataaa gaaaaaatg cgattattta tccgcatgga     240
gatcaccatc atgcagatcc gattgatgaa cataaaccgg ttggaattgg tcattctcac     300
agtaactatg aactgtttaa acccgaagaa ggagttgcta aaaagaagg gaataaagtt     360
tatactggag aagaattaac gaatgttgtt aatttgttaa aaatagtac gtttaataat     420
caaaacttta ctctagccaa tggtcaaaaa cgcgtttctt ttagttttcc gcctgaattg     480
gagaaaaaat taggtatcaa tatgctagta aaattaataa caccagatgg aaaagtattg     540
gagaaagtat ctggtaaagt atttggagaa ggagtaggga atattgcaaa ctttgaatta     600
gatcaacctt atttaccagg acaaacattt aagtatacta tcgcttcaaa agattatcca     660
gaagtaagtt atgatggtac atttacagtt ccaacctctt tagcttacaa aatggccagt     720
caaacgattt tctatccttt ccatgcaggg gatacttatt taagagtgaa ccctcaattt     780
gcagtgccta aaggaactga tgctttagtc agagtgtttg atgaatttca tggaaatgct     840
tatttagaaa ataactataa agttggtgaa atcaaattac cgattccgaa attaaaccaa     900
ggaacaacca gaacggccgg aaataaaatt cctgtaacct tcatggcaaa tgcttatttg     960
gacaatcaat cgactatat tgtggaagta cctatcttgg aaaaagaaaa tcaaactgat    1020
aaaccaagta ttctaccaca atttaaaagg aataaagcac aagaaaactc aaaacttgat    1080
gaaaaggtag aagaaccaaa gactagtgag aaggtagaaa agaaaaaact ttctgaaact    1140
gggaatagta ctagtaattc aacgttagaa gaagttccta cagtggatcc tgtacaagaa    1200
aaagtagcaa aatttgctga agttatgggg atgaagctag aaaatgtctt gtttaatatg    1260
gacggaacaa ttgaattata tttaccatca ggagaagtca ttaaaaagaa tatggcagat    1320
tttacaggag aagcacctca aggaaatggt gaaaataaac catctgaaaa tggaaaagta    1380
tctactggaa cagttgagaa ccaaccaaca gaaaataaac cagcagattc tttaccagag    1440
```

-continued

```
gcaccaaacg aaaaacctgt aaaaccagaa aactcaacgg ataatggaat gttgaatcca   1500
gaagggaatg tggggagtga ccctatgtta gatccagcat tagaggaagc tccagcagta   1560
gatcctgtac aagaaaaatt agaaaaattt acagctagtt acggattagg cttagatagt   1620
gttatattca atatggatgg aacgattgaa ttaagattgc caagtggaga agtgataaaa   1680
aagaatttat ctgatttcat agcgaagctt cgttatcgtt caaaccattg ggtaccagat   1740
tcaagaccag aagaaccaag tccacaaccg actccagaac ctagtccaag tccgcaacct   1800
gcaccaaatc ctcaaccagc tccaagcaat ccaattgatg agaaattggt caaagaagct   1860
gttcgaaaag taggcgatgg ttatgtcttt gaggagaatg gagtttctcg ttatatccca   1920
gccaagaatc tttcagcaga aacagcagca ggcattgata gcaaactggc caagcaggaa   1980
agtttatctc ataagctagg agctaagaaa actgacctcc catctagtga tcgagaattt   2040
tacaataagg cttatgactt actagcaaga attcaccaag atttacttga taataaaggt   2100
cgacaagttg attttgaggc tttggataac ctgttggaac gactcaagga tgtctcaagt   2160
gataaagtca agttagtgga tgatattctt gccttcttag ctccgattcg tcatccagaa   2220
cgtttaggaa aaccaaatgc gcaaattacc tacactgatg atgagattca agtagccaag   2280
ttggcaggca agtacacaac agaagacggt tatatctttg atcctcgtga tataaccagt   2340
gatgaggggg atgcctatgt aactccacat atgacccata gccactggat taaaaaagat   2400
agtttgtctg aagctgagag agcggcagcc caggcttatg ctaaagagaa aggtttgacc   2460
cctccttcga cagaccatca ggattcagga aatactgagg caaaggagc agaagctatc   2520 tacaaccgcg tgaaagcagc taagaaggtg ccacttgatc gtatgcctta caatcttcaa   2580
tatactgtag aagtcaaaaa cggtagttta atcatacctc attatgacca ttaccataac   2640
atcaaatttg agtggtttga cgaaggcctt tatgaggcac ctaaggggta tactcttgag   2700
gatcttttgg cgactgtcaa gtactatgtc gaacatccaa acgaacgtcc gcattcagat   2760
aatggttttg gtaacgctag cgaccatgtt caaagaaaca aaaatggtca agctgatacc   2820
aatcaaacgg aaaaaccaag cgaggagaaa cctcagacag aaaaacctga ggaagaaacc   2880
cctcgagaag agaaaccaca aagcgagaaa ccagagtctc caaaaccaac agaggaacca   2940
gaagaagaat caccagagga atcagaagaa cctcaggtcg agactgaaaa ggttgaagaa   3000
aaactgagag aggctgaaga tttacttgga aaaatccagg atccaattat caagtccaat   3060
gccaaagaga ctctcacagg attaaaaaat aatttactat ttggcaccca ggacaacaat   3120
actattatgg cagaagctga aaactattg gctttattaa aggagagtaa g           3171
```

<210> SEQ ID NO 77
<211> LENGTH: 473
<212> TYPE: PRT
<213> ORGANISM: S. pneumoniae

<400> SEQUENCE: 77

```
Glu Ala Tyr Trp Asn Gly Lys Gln Gly Ser Arg Pro Ser Ser Ser Ser
  1               5                  10                  15

Ser Tyr Asn Ala Asn Pro Val Gln Pro Arg Leu Ser Glu Asn His Asn
             20                  25                  30

Leu Thr Val Thr Pro Thr Tyr His Gln Asn Gln Gly Glu Asn Ile Ser
         35                  40                  45

Ser Leu Leu Arg Glu Leu Tyr Ala Lys Pro Leu Ser Glu Arg His Val
     50                  55                  60

Glu Ser Asp Gly Leu Ile Phe Asp Pro Ala Gln Ile Thr Ser Arg Thr
```

```
            65                  70                  75                  80
Ala Arg Gly Val Ala Val Pro His Gly Asn His Tyr His Phe Ile Pro
                    85                  90                  95
Tyr Glu Gln Met Ser Glu Leu Glu Lys Arg Ile Ala Arg Ile Ile Pro
                100                 105                 110
Leu Arg Tyr Arg Ser Asn His Trp Val Pro Asp Ser Arg Pro Glu Gln
                115                 120                 125
Pro Ser Pro Gln Ser Thr Pro Glu Pro Ser Pro Ser Leu Gln Pro Ala
            130                 135                 140
Pro Asn Pro Gln Pro Ala Pro Ser Asn Pro Ile Asp Glu Lys Leu Val
145                 150                 155                 160
Lys Glu Ala Val Arg Lys Val Gly Asp Gly Tyr Val Phe Glu Asn
                    165                 170                 175
Gly Val Ser Arg Tyr Ile Pro Ala Lys Asp Leu Ser Ala Glu Thr Ala
                180                 185                 190
Ala Gly Ile Asp Ser Lys Leu Ala Lys Gln Glu Ser Leu Ser His Lys
                195                 200                 205
Leu Gly Ala Lys Lys Thr Asp Leu Pro Ser Ser Asp Arg Glu Phe Tyr
            210                 215                 220
Asn Lys Ala Tyr Asp Leu Leu Ala Arg Ile His Gln Asp Leu Leu Asp
225                 230                 235                 240
Asn Lys Gly Arg Gln Val Asp Phe Glu Val Leu Asp Asn Leu Leu Glu
                    245                 250                 255
Arg Leu Lys Asp Val Ser Ser Asp Lys Val Lys Leu Val Asp Asp Ile
                260                 265                 270
Leu Ala Phe Leu Ala Pro Ile Arg His Pro Glu Arg Leu Gly Lys Pro
                275                 280                 285
Asn Ala Gln Ile Thr Tyr Thr Asp Asp Glu Ile Gln Val Ala Lys Leu
            290                 295                 300
Ala Gly Lys Tyr Thr Thr Glu Asp Gly Tyr Ile Phe Asp Pro Arg Asp
305                 310                 315                 320
Ile Thr Ser Asp Glu Gly Asp Ala Tyr Val Thr Pro His Met Thr His
                    325                 330                 335
Ser His Trp Ile Lys Lys Asp Ser Leu Ser Glu Ala Glu Arg Ala Ala
                340                 345                 350
Ala Gln Ala Tyr Ala Lys Glu Lys Gly Leu Thr Pro Pro Ser Thr Asp
            355                 360                 365
His Gln Asp Ser Gly Asn Thr Glu Ala Lys Gly Ala Glu Ala Ile Tyr
            370                 375                 380
Asn Arg Val Lys Ala Ala Lys Lys Val Pro Leu Asp Arg Met Pro Tyr
385                 390                 395                 400
Asn Leu Gln Tyr Thr Val Glu Val Lys Asn Gly Ser Leu Ile Ile Pro
                    405                 410                 415
His Tyr Asp His Tyr His Asn Ile Lys Phe Glu Trp Phe Asp Glu Gly
                420                 425                 430
Leu Tyr Glu Ala Pro Lys Gly Tyr Ser Leu Glu Asp Leu Leu Ala Thr
            435                 440                 445
Val Lys Tyr Tyr Val Glu His Pro Asn Glu Arg Pro His Ser Asp Asn
            450                 455                 460
Gly Phe Gly Asn Ala Ser Asp His Val
465                 470

<210> SEQ ID NO 78
```

```
<211> LENGTH: 780
<212> TYPE: PRT
<213> ORGANISM: S. pneumoniae

<400> SEQUENCE: 78
```

| | | | | | | | | | | | | | | | |
|---|---|---|---|---|---|---|---|---|---|---|---|---|---|---|---|
| Cys | Ala | Tyr | Ala | Leu | Asn | Gln | His | Arg | Ser | Gln | Glu | Asn | Lys | Asp | Asn |
| 1 | | | | 5 | | | | | 10 | | | | | 15 | |
| Asn | Arg | Val | Ser | Tyr | Val | Asp | Gly | Ser | Gln | Ser | Ser | Gln | Lys | Ser | Glu |
| | | | 20 | | | | | 25 | | | | | 30 | | |
| Asn | Leu | Thr | Pro | Asp | Gln | Val | Ser | Gln | Lys | Glu | Gly | Ile | Gln | Ala | Glu |
| | | | | 35 | | | | | 40 | | | | | 45 | |
| Gln | Ile | Val | Ile | Lys | Ile | Thr | Asp | Gln | Gly | Tyr | Val | Thr | Ser | His | Gly |
| | 50 | | | | | 55 | | | | | 60 | | | | |
| Asp | His | Tyr | His | Tyr | Tyr | Asn | Gly | Lys | Val | Pro | Tyr | Asp | Ala | Leu | Phe |
| 65 | | | | | 70 | | | | | 75 | | | | | 80 |
| Ser | Glu | Glu | Leu | Leu | Met | Lys | Asp | Pro | Asn | Tyr | Gln | Leu | Lys | Asp | Ala |
| | | | | 85 | | | | | 90 | | | | | 95 | |
| Asp | Ile | Val | Asn | Glu | Val | Lys | Gly | Gly | Tyr | Ile | Ile | Lys | Val | Asp | Gly |
| | | | 100 | | | | | 105 | | | | | 110 | | |
| Lys | Tyr | Tyr | Val | Tyr | Leu | Lys | Asp | Ala | Ala | His | Ala | Asp | Asn | Val | Arg |
| | | | | 115 | | | | | 120 | | | | | 125 | |
| Thr | Lys | Asp | Glu | Ile | Asn | Arg | Gln | Lys | Gln | Glu | His | Val | Lys | Asp | Asn |
| | 130 | | | | | 135 | | | | | 140 | | | | |
| Glu | Lys | Val | Asn | Ser | Asn | Val | Ala | Val | Ala | Arg | Ser | Gln | Gly | Arg | Tyr |
| 145 | | | | | 150 | | | | | 155 | | | | | 160 |
| Thr | Thr | Asn | Asp | Gly | Tyr | Val | Phe | Asn | Pro | Ala | Asp | Ile | Ile | Glu | Asp |
| | | | | 165 | | | | | 170 | | | | | 175 | |
| Thr | Gly | Asn | Ala | Tyr | Ile | Val | Pro | His | Gly | Gly | His | Tyr | His | Tyr | Ile |
| | | | 180 | | | | | 185 | | | | | 190 | | |
| Pro | Lys | Ser | Asp | Leu | Ser | Ala | Ser | Glu | Leu | Ala | Ala | Ala | Lys | Ala | His |
| | | | | 195 | | | | | 200 | | | | | 205 | |
| Leu | Ala | Gly | Lys | Asn | Met | Gln | Pro | Ser | Gln | Leu | Ser | Tyr | Ser | Ser | Thr |
| | 210 | | | | | 215 | | | | | 220 | | | | |
| Ala | Ser | Asp | Asn | Asn | Thr | Gln | Ser | Val | Ala | Lys | Gly | Ser | Thr | Ser | Lys |
| 225 | | | | | 230 | | | | | 235 | | | | | 240 |
| Pro | Ala | Asn | Lys | Ser | Glu | Asn | Leu | Gln | Ser | Leu | Leu | Lys | Glu | Leu | Tyr |
| | | | | 245 | | | | | 250 | | | | | 255 | |
| Asp | Ser | Pro | Ser | Ala | Gln | Arg | Tyr | Ser | Glu | Ser | Asp | Gly | Leu | Val | Phe |
| | | | 260 | | | | | 265 | | | | | 270 | | |
| Asp | Pro | Ala | Lys | Ile | Ile | Ser | Arg | Thr | Pro | Asn | Gly | Val | Ala | Ile | Pro |
| | | | | 275 | | | | | 280 | | | | | 285 | |
| His | Gly | Asp | His | Tyr | His | Phe | Ile | Pro | Tyr | Ser | Lys | Leu | Ser | Ala | Leu |
| | 290 | | | | | 295 | | | | | 300 | | | | |
| Glu | Glu | Lys | Ile | Ala | Arg | Met | Val | Pro | Ile | Ser | Gly | Thr | Gly | Ser | Thr |
| 305 | | | | | 310 | | | | | 315 | | | | | 320 |
| Val | Ser | Thr | Asn | Ala | Lys | Pro | Asn | Glu | Val | Val | Ser | Ser | Leu | Gly | Ser |
| | | | | 325 | | | | | 330 | | | | | 335 | |
| Leu | Ser | Ser | Asn | Pro | Ser | Ser | Leu | Thr | Thr | Ser | Lys | Glu | Leu | Ser | Ser |
| | | | 340 | | | | | 345 | | | | | 350 | | |
| Ala | Ser | Asp | Gly | Tyr | Ile | Phe | Asn | Pro | Lys | Asp | Ile | Val | Glu | Glu | Thr |
| | | | | 355 | | | | | 360 | | | | | 365 | |
| Ala | Thr | Ala | Tyr | Ile | Val | Arg | His | Gly | Asp | His | Phe | His | Tyr | Ile | Pro |
| | 370 | | | | | 375 | | | | | 380 | | | | |
| Lys | Ser | Asn | Gln | Ile | Gly | Gln | Pro | Thr | Leu | Pro | Asn | Asn | Ser | Leu | Ala |

```
                385                 390                 395                 400
Thr Pro Ser Pro Ser Leu Pro Ile Asn Pro Gly Thr Ser His Glu Lys
                405                 410                 415
His Glu Glu Asp Gly Tyr Gly Phe Asp Ala Asn Arg Ile Ile Ala Glu
            420                 425                 430
Asp Glu Ser Gly Phe Val Met Ser His Gly Asp His Asn His Tyr Phe
            435                 440                 445
Phe Lys Lys Asp Leu Thr Glu Glu Gln Ile Lys Ala Ala Gln Lys His
        450                 455                 460
Leu Glu Glu Val Lys Thr Ser His Asn Gly Leu Asp Ser Leu Ser Ser
465                 470                 475                 480
His Glu Gln Asp Tyr Pro Gly Asn Ala Lys Glu Met Lys Asp Leu Asp
                485                 490                 495
Lys Lys Ile Glu Glu Lys Ile Ala Gly Ile Met Lys Gln Tyr Gly Val
                500                 505                 510
Lys Arg Glu Ser Ile Val Val Asn Lys Glu Lys Asn Ala Ile Ile Tyr
            515                 520                 525
Pro His Gly Asp His His Ala Asp Pro Ile Asp Glu His Lys Pro
        530                 535                 540
Val Gly Ile Gly His Ser His Ser Asn Tyr Glu Leu Phe Lys Pro Glu
545                 550                 555                 560
Glu Gly Val Ala Lys Lys Gly Asn Lys Val Tyr Thr Gly Glu Glu
            565                 570                 575
Leu Thr Asn Val Val Asn Leu Leu Lys Asn Ser Thr Phe Asn Asn Gln
            580                 585                 590
Asn Phe Thr Leu Ala Asn Gly Gln Lys Arg Val Ser Phe Ser Phe Pro
            595                 600                 605
Pro Glu Leu Glu Lys Lys Leu Gly Ile Asn Met Leu Val Lys Leu Ile
        610                 615                 620
Thr Pro Asp Gly Lys Val Leu Glu Lys Val Ser Gly Lys Val Phe Gly
625                 630                 635                 640
Glu Gly Val Gly Asn Ile Ala Asn Phe Glu Leu Asp Gln Pro Tyr Leu
                645                 650                 655
Pro Gly Gln Thr Phe Lys Tyr Thr Ile Ala Ser Lys Asp Tyr Pro Glu
            660                 665                 670
Val Ser Tyr Asp Gly Thr Phe Thr Val Pro Thr Ser Leu Ala Tyr Lys
        675                 680                 685
Met Ala Ser Gln Thr Ile Phe Tyr Pro Phe His Ala Gly Asp Thr Tyr
        690                 695                 700
Leu Arg Val Asn Pro Gln Phe Ala Val Pro Lys Gly Thr Asp Ala Leu
705                 710                 715                 720
Val Arg Val Phe Asp Glu Phe His Gly Asn Ala Tyr Leu Glu Asn Asn
                725                 730                 735
Tyr Lys Val Gly Glu Ile Lys Leu Pro Ile Pro Lys Leu Asn Gln Gly
            740                 745                 750
Thr Thr Arg Thr Ala Gly Asn Lys Ile Pro Val Thr Phe Met Ala Asn
            755                 760                 765
Ala Tyr Leu Asp Asn Gln Ser Thr Tyr Ile Val Glu
        770                 775                 780

<210> SEQ ID NO 79
<211> LENGTH: 690
<212> TYPE: PRT
<213> ORGANISM: S. pneumoniae
```

-continued

<400> SEQUENCE: 79

Cys Ala Tyr Glu Leu Gly Leu His Gln Ala Gln Thr Val Lys Glu Asn
1               5                   10                  15

Asn Arg Val Ser Tyr Ile Asp Gly Lys Gln Ala Thr Gln Lys Thr Glu
            20                  25                  30

Asn Leu Thr Pro Asp Glu Val Ser Lys Arg Glu Gly Ile Asn Ala Glu
        35                  40                  45

Gln Ile Val Ile Lys Ile Thr Asp Gln Gly Tyr Val Thr Ser His Gly
    50                  55                  60

Asp His Tyr His Tyr Asn Gly Lys Val Pro Tyr Asp Ala Ile Ile
65                  70                  75                  80

Ser Glu Glu Leu Leu Met Lys Asp Pro Asn Tyr Gln Leu Lys Asp Ser
                85                  90                  95

Asp Ile Val Asn Glu Ile Lys Gly Gly Tyr Val Ile Lys Val Asn Gly
            100                 105                 110

Lys Tyr Tyr Val Tyr Leu Lys Asp Ala Ala His Ala Asp Asn Val Arg
        115                 120                 125

Thr Lys Glu Glu Ile Asn Arg Gln Lys Gln His Ser Gln His Arg
    130                 135                 140

Glu Gly Gly Thr Ser Ala Asn Asp Gly Ala Val Ala Phe Ala Arg Ser
145                 150                 155                 160

Gln Gly Arg Tyr Thr Thr Asp Asp Gly Tyr Ile Phe Asn Ala Ser Asp
                165                 170                 175

Ile Ile Glu Asp Thr Gly Asp Ala Tyr Ile Val Pro His Gly Asp His
            180                 185                 190

Tyr His Tyr Ile Pro Lys Asn Glu Leu Ser Ala Ser Glu Leu Ala Ala
        195                 200                 205

Ala Glu Ala Phe Leu Ser Gly Arg Glu Asn Leu Ser Asn Leu Arg Thr
    210                 215                 220

Tyr Arg Arg Gln Asn Ser Asp Asn Thr Pro Arg Thr Asn Trp Val Pro
225                 230                 235                 240

Ser Val Ser Asn Pro Gly Thr Thr Asn Thr Asn Ser Asn Asn Ser
                245                 250                 255

Asn Thr Asn Ser Gln Ala Ser Gln Ser Asn Asp Ile Asp Ser Leu Leu
            260                 265                 270

Lys Gln Leu Tyr Lys Leu Pro Leu Ser Gln Arg His Val Glu Ser Asp
        275                 280                 285

Gly Leu Ile Phe Asp Pro Ala Gln Ile Thr Ser Arg Thr Ala Arg Gly
    290                 295                 300

Val Ala Val Pro His Gly Asn His Tyr His Phe Ile Pro Tyr Glu Gln
305                 310                 315                 320

Met Ser Glu Leu Glu Lys Arg Ile Ala Arg Ile Ile Pro Leu Arg Tyr
                325                 330                 335

Arg Ser Asn His Trp Val Pro Asp Ser Arg Pro Glu Glu Pro Ser Pro
            340                 345                 350

Gln Pro Thr Pro Glu Pro Ser Pro Ser Pro Gln Pro Ala Pro Asn Pro
        355                 360                 365

Gln Pro Ala Pro Ser Asn Pro Ile Asp Glu Lys Leu Val Lys Glu Ala
    370                 375                 380

Val Arg Lys Val Gly Asp Gly Tyr Val Phe Glu Glu Asn Gly Val Ser
385                 390                 395                 400

Arg Tyr Ile Pro Ala Lys Asn Leu Ser Ala Glu Thr Ala Ala Gly Ile

```
                405             410             415
Asp Ser Lys Leu Ala Lys Gln Glu Ser Leu Ser His Lys Leu Gly Ala
            420             425             430
Lys Lys Thr Asp Leu Pro Ser Ser Asp Arg Glu Phe Tyr Asn Lys Ala
            435             440             445
Tyr Asp Leu Leu Ala Arg Ile His Gln Asp Leu Leu Asp Asn Lys Gly
            450             455             460
Arg Gln Val Asp Phe Glu Ala Leu Asp Asn Leu Leu Glu Arg Leu Lys
465             470             475             480
Asp Val Ser Ser Asp Lys Val Lys Leu Val Asp Asp Ile Leu Ala Phe
            485             490             495
Leu Ala Pro Ile Arg His Pro Glu Arg Leu Gly Lys Pro Asn Ala Gln
            500             505             510
Ile Thr Tyr Thr Asp Asp Glu Ile Gln Val Ala Lys Leu Ala Gly Lys
            515             520             525
Tyr Thr Thr Glu Asp Gly Tyr Ile Phe Asp Pro Arg Asp Ile Thr Ser
            530             535             540
Asp Glu Gly Asp Ala Tyr Val Thr Pro His Met Thr His Ser His Trp
545             550             555             560
Ile Lys Lys Asp Ser Leu Ser Glu Ala Glu Arg Ala Ala Ala Gln Ala
            565             570             575
Tyr Ala Lys Glu Lys Gly Leu Thr Pro Pro Ser Thr Asp His Gln Asp
            580             585             590
Ser Gly Asn Thr Glu Ala Lys Gly Ala Glu Ala Ile Tyr Asn Arg Val
            595             600             605
Lys Ala Ala Lys Lys Val Pro Leu Asp Arg Met Pro Tyr Asn Leu Gln
            610             615             620
Tyr Thr Val Glu Val Lys Asn Gly Ser Leu Ile Ile Pro His Tyr Asp
625             630             635             640
His Tyr His Asn Ile Lys Phe Glu Trp Phe Asp Glu Gly Leu Tyr Glu
            645             650             655
Ala Pro Lys Gly Tyr Thr Leu Glu Asp Leu Leu Ala Thr Val Lys Tyr
            660             665             670
Tyr Val Glu His Pro Asn Glu Arg Pro His Ser Asp Asn Gly Phe Gly
            675             680             685
Asn Ala
    690

<210> SEQ ID NO 80
<211> LENGTH: 2469
<212> TYPE: DNA
<213> ORGANISM: S. pneumoniae

<400> SEQUENCE: 80
gtgaagaaaa catatggtta tatcggctca gttgctgcca ttttactagc tactcatatt      60
ggaagttacc aacttggtaa gcatcatatg ggtctagcaa caaaggacaa tcagattgcc     120
tatattgatg acagcaaagg taaggcaaaa gcccctaaaa caaacaaaac gatggatcaa     180
atcagtgctg aagaaggcat ctctgctgaa cagatcgtag tcaaaattac tgaccaaggc     240
tatgtgacct cacacggtga ccattatcat ttttacaatg ggaaagttcc ttatgatgcg     300
attattagtg aagagttgtt gatgacggat cctaattacc gttttaaaca atcagacgtt     360
atcaatgaaa tcttagacgg ttacgttatt aaagtcaatg caactattag tgtttacctc     420
aagccaggta gtaagcgcaa aaacattcga accaaacaac aaattgctga gcaagtagcc     480
```

```
aaaggaacta aagaagctaa agaaaaaggt ttagctcaag tggcccatct cagtaaagaa      540
gaagttgcgg cagtcaatga agcaaaaaga caaggacgct atactacaga cgatggctat      600 attttagtc cgacagatat cattgatgat ttaggagatg cttatttagt acctcatggt      660
aatcactatc attatattcc taaaaaggat ttgtctccaa gtgagctagc tgctgcacaa      720
gcctactgga gtcaaaaaca aggtcgaggt gctagaccgt ctgattaccg cccgacacca      780
gccccaggtc gtaggaaagc cccaattcct gatgtgacgc ctaaccctgg acaaggtcat      840
cagccagata acggtggcta tcatccagcg cctcctaggc caaatgatgc gtcacaaaac      900
aaacaccaaa gagatgagtt taaaggaaaa acctttaagg aactttaga tcaactacac       960 cgtcttgatt tgaaataccg tcatgtggaa gaagatgggg tgattttga ccgactcaa       1020 gtgatcaaat caacgctttt gggtatgtg gtgcctcatg gagatcatta tcatattatc      1080
ccaagaagtc agttatcacc tcttgaaatg gaattagcag atcgatactt agctggccaa     1140
actgaggaca atgactcagg ttcagagcac tcaaaaccat cagataaaga agtgacacat     1200
acctttcttg gtcatcgcat caaagcttac ggaaaaggct tagatggtaa accatatgat     1260
acgagtgatg cttatgttt tagtaaagaa tccattcatt cagtggataa atcaggagtt     1320
acagctaaac acggagatca tttccactat ataggatttg gagaacttga acaatatgag     1380
ttggatgagg tcgctaactg ggtgaaagca aaaggtcaag ctgatgagct tgctgctgct     1440
ttggatcagg aacaaggcaa agaaaaacca ctctttgaca ctaaaaaagt gagtcgcaaa     1500
gtaacaaaag atggtaaagt gggctatatg atgccaaaag atggtaagga ctatttctat     1560
gctcgtgatc aacttgattt gactcagatt gcctttgccg aacaagaact aatgcttaaa     1620
gataagaagc attaccgtta tgacattgtt gacacaggta ttgagccacg acttgctgta     1680
gatgtgtcaa gtctgccgat gcatgctggt aatgctactt acgatactgg aagttcgttt     1740
gttatcccac atattgatca tatccatgtc gttccgtatt catggttgac gcgcgatcag     1800
attgcaacag tcaagtatgt gatgcaacac cccgaagttc gtccggatgt atggtctaag     1860
ccagggcatg aagagtcagg ttcggtcatt ccaaatgtta cgcctcttga taaacgtgct     1920
ggtatgccaa actggcaaat tatccattct gctgaagaag ttcaaaaagc cctagcagaa     1980
ggtcgttttg caacaccaga cggctatatt ttcgatccac gagatgtttt ggccaaagaa     2040
acttttgtat ggaaagatgg ctcctttagc atcccaagag cagatggcag ttcattgaga     2100
accattaata aatctgatct atcccaagct gagtggcaac aagctcaaga gttattggca     2160
aagaaaaata ctggtgatgc tactgatacg gataaaccca agaaaagca acaggcagat     2220 aagagcaatg aaaaccaaca gccaagtgaa gccagtaaag aagaaaaaga atcagatgac     2280
tttatagaca gtttaccaga ctatggtcta gatagagcaa ccctagaaga tcatatcaat     2340
caattagcac aaaaagctaa tatcgatcct aagtatctca ttttccaacc agaaggtgtc     2400
caattttata ataaaaatgg tgaattggta acttatgata tcaagacact tcaacaaata     2460
aaccctaa                                                              2469
```

<210> SEQ ID NO 81
<211> LENGTH: 823
<212> TYPE: PRT
<213> ORGANISM: S. pneumoniae

<400> SEQUENCE: 81

```
Val Lys Lys Thr Tyr Gly Tyr Ile Gly Ser Val Ala Ala Ile Leu Leu
 1               5                  10                  15
```

```
Ala Thr His Ile Gly Ser Tyr Gln Leu Gly Lys His His Met Gly Leu
             20                  25                  30
Ala Thr Lys Asp Asn Gln Ile Ala Tyr Ile Asp Ser Lys Gly Lys
         35                  40                  45
Ala Lys Ala Pro Lys Thr Asn Lys Thr Met Asp Gln Ile Ser Ala Glu
         50                  55                  60
Glu Gly Ile Ser Ala Glu Gln Ile Val Val Lys Ile Thr Asp Gln Gly
65                  70                  75                  80
Tyr Val Thr Ser His Gly Asp His Tyr His Phe Tyr Asn Gly Lys Val
                 85                  90                  95
Pro Tyr Asp Ala Ile Ile Ser Glu Glu Leu Leu Met Thr Asp Pro Asn
            100                 105                 110
Tyr Arg Phe Lys Gln Ser Asp Val Ile Asn Glu Ile Leu Asp Gly Tyr
            115                 120                 125
Val Ile Lys Val Asn Gly Asn Tyr Tyr Val Tyr Leu Lys Pro Gly Ser
            130                 135                 140
Lys Arg Lys Asn Ile Arg Thr Lys Gln Gln Ile Ala Glu Gln Val Ala
145                 150                 155                 160
Lys Gly Thr Lys Glu Ala Lys Glu Lys Gly Leu Ala Gln Val Ala His
                165                 170                 175
Leu Ser Lys Glu Glu Val Ala Ala Val Asn Glu Ala Lys Arg Gln Gly
            180                 185                 190
Arg Tyr Thr Thr Asp Asp Gly Tyr Ile Phe Ser Pro Thr Asp Ile Ile
            195                 200                 205
Asp Asp Leu Gly Asp Ala Tyr Leu Val Pro His Gly Asn His Tyr His
210                 215                 220
Tyr Ile Pro Lys Lys Asp Leu Ser Pro Ser Glu Leu Ala Ala Ala Gln
225                 230                 235                 240
Ala Tyr Trp Ser Gln Lys Gln Gly Arg Gly Ala Arg Pro Ser Asp Tyr
                245                 250                 255
Arg Pro Thr Pro Ala Pro Gly Arg Arg Lys Ala Pro Ile Pro Asp Val
            260                 265                 270
Thr Pro Asn Pro Gly Gln Gly His Gln Pro Asp Asn Gly Gly Tyr His
            275                 280                 285
Pro Ala Pro Pro Arg Pro Asn Asp Ala Ser Gln Asn Lys His Gln Arg
290                 295                 300
Asp Glu Phe Lys Gly Lys Thr Phe Lys Glu Leu Leu Asp Gln Leu His
305                 310                 315                 320
Arg Leu Asp Leu Lys Tyr Arg His Val Glu Glu Asp Gly Leu Ile Phe
                325                 330                 335
Glu Pro Thr Gln Val Ile Lys Ser Asn Ala Phe Gly Tyr Val Val Pro
            340                 345                 350
His Gly Asp His Tyr His Ile Ile Pro Arg Ser Gln Leu Ser Pro Leu
            355                 360                 365
Glu Met Glu Leu Ala Asp Arg Tyr Leu Ala Gly Gln Thr Glu Asp Asn
370                 375                 380
Asp Ser Gly Ser Glu His Ser Lys Pro Ser Asp Lys Glu Val Thr His
385                 390                 395                 400
Thr Phe Leu Gly His Arg Ile Lys Ala Tyr Gly Lys Gly Leu Asp Gly
                405                 410                 415
Lys Pro Tyr Asp Thr Ser Asp Ala Tyr Val Phe Ser Lys Glu Ser Ile
            420                 425                 430
```

His Ser Val Asp Lys Ser Gly Val Thr Ala Lys His Gly Asp His Phe
        435                 440                 445

His Tyr Ile Gly Phe Gly Glu Leu Glu Gln Tyr Glu Leu Asp Glu Val
        450                 455                 460

Ala Asn Trp Val Lys Ala Lys Gly Gln Ala Asp Glu Leu Ala Ala Ala
465                 470                 475                 480

Leu Asp Gln Glu Gln Gly Lys Glu Lys Pro Leu Phe Asp Thr Lys Lys
                485                 490                 495

Val Ser Arg Lys Val Thr Lys Asp Gly Lys Val Gly Tyr Met Met Pro
                500                 505                 510

Lys Asp Gly Lys Asp Tyr Phe Tyr Ala Arg Asp Gln Leu Asp Leu Thr
            515                 520                 525

Gln Ile Ala Phe Ala Glu Gln Glu Leu Met Leu Lys Asp Lys Lys His
        530                 535                 540

Tyr Arg Tyr Asp Ile Val Asp Thr Gly Ile Glu Pro Arg Leu Ala Val
545                 550                 555                 560

Asp Val Ser Ser Leu Pro Met His Ala Gly Asn Ala Thr Tyr Asp Thr
                565                 570                 575

Gly Ser Ser Phe Val Ile Pro His Ile Asp His Ile His Val Val Pro
                580                 585                 590

Tyr Ser Trp Leu Thr Arg Asp Gln Ile Ala Thr Val Lys Tyr Val Met
            595                 600                 605

Gln His Pro Glu Val Arg Pro Asp Val Trp Ser Lys Pro Gly His Glu
        610                 615                 620

Glu Ser Gly Ser Val Ile Pro Asn Val Thr Pro Leu Asp Lys Arg Ala
625                 630                 635                 640

Gly Met Pro Asn Trp Gln Ile Ile His Ser Ala Glu Glu Val Gln Lys
                645                 650                 655

Ala Leu Ala Glu Gly Arg Phe Ala Thr Pro Asp Gly Tyr Ile Phe Asp
                660                 665                 670

Pro Arg Asp Val Leu Ala Lys Glu Thr Phe Val Trp Lys Asp Gly Ser
            675                 680                 685

Phe Ser Ile Pro Arg Ala Asp Gly Ser Ser Leu Arg Thr Ile Asn Lys
        690                 695                 700

Ser Asp Leu Ser Gln Ala Glu Trp Gln Gln Ala Gln Glu Leu Leu Ala
705                 710                 715                 720

Lys Lys Asn Thr Gly Asp Ala Thr Asp Thr Asp Lys Pro Lys Glu Lys
                725                 730                 735

Gln Gln Ala Asp Lys Ser Asn Glu Asn Gln Pro Ser Glu Ala Ser
                740                 745                 750

Lys Glu Glu Lys Glu Ser Asp Asp Phe Ile Asp Ser Leu Pro Asp Tyr
            755                 760                 765

Gly Leu Asp Arg Ala Thr Leu Glu Asp His Ile Asn Gln Leu Ala Gln
        770                 775                 780

Lys Ala Asn Ile Asp Pro Lys Tyr Leu Ile Phe Gln Pro Glu Gly Val
785                 790                 795                 800

Gln Phe Tyr Asn Lys Asn Gly Glu Leu Val Thr Tyr Asp Ile Lys Thr
                805                 810                 815

Leu Gln Gln Ile Asn Pro Pro
            820

<210> SEQ ID NO 82
<211> LENGTH: 2472
<212> TYPE: DNA

<213> ORGANISM: S. pneumoniae

<400> SEQUENCE: 82

| | | | | | |
|---|---|---|---|---|---|
| gtgaagaaaa | catatggtta | tatcggctca | gttgctgcca | ttttactagc | tactcatatt | 60 |
| ggaagttacc | aacttggtaa | gcatcatatg | ggtctagcaa | caaaggacaa | tcagattgcc | 120 |
| tatattgatg | atagcaaagg | taaggcaaaa | gcccctaaaa | caaacaaaac | gatggatcaa | 180 |
| atcagtgctg | aagaaggcat | ctctgctgaa | cagatcgtag | tcaaaattac | tgaccaaggt | 240 |
| tatgtgacct | cacacggtga | ccattatcat | ttttacaatg | ggaaagttcc | ttatgatgcg | 300 |
| attattagtg | aagagttgtt | gatgacggat | cctaattacc | attttaaaca | atcagacgtt | 360 |
| atcaatgaaa | tcttagacgg | ttacgttatt | aaagtcaatg | gcaactatta | tgtttacctc | 420 |
| aagccaggta | gtaagcgcaa | aaacattcga | accaaacaac | aaattgctga | gcaagtagcc | 480 |
| aaaggaacta | agaagctaa | agaaaaggt | ttagctcaag | tggcccatct | cagtaaagaa | 540 |
| gaagttgcgg | cagtcaatga | agcaaaaaga | caaggacgct | atactacaga | cgatggctat | 600 |
| attttagtc | cgacagatat | cattgatgat | ttaggagacg | cttatttagt | acctcatggt | 660 |
| aatcactatc | attatattcc | taaaaagat | ttgtctccaa | gtgagctagc | tgctgcacaa | 720 |
| gcttactgga | gtcaaaaaca | aggtcgaggt | gctagaccgt | ctgattaccg | cccgacacca | 780 |
| gccccaggtc | gtaggaaagc | tccaattcct | gatgtgacgc | taaccctgg | acaaggtcat | 840 |
| cagccagata | acggtggcta | tcatccagcg | cctcctaggc | caaatgatgc | gtcacaaaac | 900 |
| aaacaccaaa | gagatgagtt | taaggaaaa | acctttaagg | aacttttaga | tcaactacac | 960 |
| cgtcttgatt | tgaaataccg | tcatgtggaa | gaagatgggt | tgattttga | accgactcaa | 1020 |
| gtgatcaaat | caaacgcttt | tgggtatgtg | gtgcctcatg | gagatcatta | tcatattatc | 1080 |
| ccaagaagtc | agttatcacc | tcttgaaatg | gaattagcag | atcgatactt | agccggtcaa | 1140 |
| actgaggaca | atgattcagg | ttcagatcac | tcaaaaccat | cagataaaga | agtgacacat | 1200 |
| accttttcttg | gtcatcgcat | caaagcttac | ggaaaaggct | tagatggtaa | accatatgat | 1260 |
| acgagtgatg | cttatgtttt | tagtaaagaa | tccattcatt | cagtggataa | atcaggagtt | 1320 |
| acagctaaac | acggagatca | tttccactat | ataggatttg | gagaacttga | acaatatgag | 1380 |
| ttggatgagg | tcgctaactg | ggtgaaagca | aaggtcaag | ctgatgagct | tgctgctgct | 1440 |
| ttggatcagg | aacaaggcaa | agaaaaacca | ctctttgaca | ctaaaaaagt | gagtcgcaaa | 1500 |
| gtaacaaaag | atggtaaagt | gggctatatt | atgccaaaag | atggcaagga | ctatttctat | 1560 |
| gctcgtgatc | aacttgattt | gactcagatt | gcctttgccg | aacaagaact | aatgcttaaa | 1620 |
| gataagaacc | attaccgtta | tgacattgtt | gacacaggta | ttgagccacg | acttgctgta | 1680 |
| gatgtgtcaa | gtctgccgat | gcatgctggt | aatgctactt | acgatactgg | aagttcgttt | 1740 |
| gttatccctc | atattgatca | tatccatgtc | gttccgtatt | catggttgac | gcgcgatcag | 1800 |
| attgcaacaa | tcaagtatgt | gatgcaacac | cccgaagttc | gtccagatgt | atggtctaag | 1860 |
| ccagggcatg | aagagtcagg | ttcggtcatt | ccaaatgtta | cgcctcttga | taaacgtgct | 1920 |
| ggtatgccaa | attggcaaat | catccattct | gctgaagaag | ttcaaaaagc | cctagcagaa | 1980 |
| ggtcgttttg | caacaccaga | cggctatatt | ttcgatccac | gagatgtttt | ggccaaagaa | 2040 |
| acttttgtat | ggaagatgg | ctcctttagc | atcccaagag | cagatggcag | ttcattgaga | 2100 |
| accattaata | aatctgatct | atcccaagct | gagtggcaac | aagctcaaga | gttattggca | 2160 |
| aagaaaaacg | ctggtgatgc | tactgatacg | gataaaccca | agaaaagca | acaggcgat | 2220 |
| aagagcaatg | aaaaccaaca | gccaagtgaa | gccagtaaag | aagaagaaaa | agaatcagat | 2280 |

```
gactttatag acagtttacc agactatggt ctagatagag caaccctaga agatcatatc   2340
aatcaattag cacaaaaagc taatatcgat cctaagtatc tcattttcca accagaaggt   2400
gtccaatttt ataataaaaa tggtgaatta gtaacttatg atatcaagac gcttcaacaa   2460
ataaaccctt aa                                                        2472
```

<210> SEQ ID NO 83
<211> LENGTH: 824
<212> TYPE: PRT
<213> ORGANISM: S. pneumoniae

<400> SEQUENCE: 83

```
Val Lys Lys Thr Tyr Gly Tyr Ile Gly Ser Val Ala Ala Ile Leu Leu
 1               5                   10                  15

Ala Thr His Ile Gly Ser Tyr Gln Leu Gly Lys His His Met Gly Leu
                20                  25                  30

Ala Thr Lys Asp Asn Gln Ile Ala Tyr Ile Asp Asp Ser Lys Gly Lys
            35                  40                  45

Ala Lys Ala Pro Lys Thr Asn Lys Thr Met Asp Gln Ile Ser Ala Glu
        50                  55                  60

Glu Gly Ile Ser Ala Glu Gln Ile Val Val Lys Ile Thr Asp Gln Gly
65                  70                  75                  80

Tyr Val Thr Ser His Gly Asp His Tyr His Phe Tyr Asn Gly Lys Val
                85                  90                  95

Pro Tyr Asp Ala Ile Ile Ser Glu Glu Leu Leu Met Thr Asp Pro Asn
           100                 105                 110

Tyr His Phe Lys Gln Ser Asp Val Ile Asn Glu Ile Leu Asp Gly Tyr
       115                  120                 125

Val Ile Lys Val Asn Gly Asn Tyr Tyr Val Tyr Leu Lys Pro Gly Ser
130                 135                 140

Lys Arg Lys Asn Ile Arg Thr Lys Gln Gln Ile Ala Glu Gln Val Ala
145                 150                 155                 160

Lys Gly Thr Lys Glu Ala Lys Glu Lys Gly Leu Ala Gln Val Ala His
               165                 170                 175

Leu Ser Lys Glu Glu Val Ala Ala Val Asn Glu Ala Lys Arg Gln Gly
           180                 185                 190

Arg Tyr Thr Thr Asp Asp Gly Tyr Ile Phe Ser Pro Thr Asp Ile Ile
       195                 200                 205

Asp Asp Leu Gly Asp Ala Tyr Leu Val Pro His Gly Asn His Tyr His
   210                 215                 220

Tyr Ile Pro Lys Lys Asp Leu Ser Pro Ser Glu Leu Ala Ala Ala Gln
225                 230                 235                 240

Ala Tyr Trp Ser Gln Lys Gln Gly Arg Gly Ala Arg Pro Ser Asp Tyr
               245                 250                 255

Arg Pro Thr Pro Ala Pro Gly Arg Arg Lys Ala Pro Ile Pro Asp Val
           260                 265                 270

Thr Pro Asn Pro Gly Gln Gly His Gln Pro Asp Asn Gly Gly Tyr His
       275                 280                 285

Pro Ala Pro Pro Arg Pro Asn Asp Ala Ser Gln Asn Lys His Gln Arg
   290                 295                 300

Asp Glu Phe Lys Gly Lys Thr Phe Lys Glu Leu Leu Asp Gln Leu His
305                 310                 315                 320

Arg Leu Asp Leu Lys Tyr Arg His Val Glu Glu Asp Gly Leu Ile Phe
               325                 330                 335
```

```
Glu Pro Thr Gln Val Ile Lys Ser Asn Ala Phe Gly Tyr Val Val Pro
                340                 345                 350

His Gly Asp His Tyr His Ile Ile Pro Arg Ser Gln Leu Ser Pro Leu
            355                 360                 365

Glu Met Glu Leu Ala Asp Arg Tyr Leu Ala Gly Gln Thr Glu Asp Asn
        370                 375                 380

Asp Ser Gly Ser Asp His Ser Lys Pro Ser Asp Lys Glu Val Thr His
385                 390                 395                 400

Thr Phe Leu Gly His Arg Ile Lys Ala Tyr Gly Lys Gly Leu Asp Gly
                405                 410                 415

Lys Pro Tyr Asp Thr Ser Asp Ala Tyr Val Phe Ser Lys Glu Ser Ile
            420                 425                 430

His Ser Val Asp Lys Ser Gly Val Thr Ala Lys His Gly Asp His Phe
        435                 440                 445

His Tyr Ile Gly Phe Gly Glu Leu Gln Tyr Glu Leu Asp Glu Val
        450                 455                 460

Ala Asn Trp Val Lys Ala Lys Gly Gln Ala Asp Glu Leu Ala Ala Ala
465                 470                 475                 480

Leu Asp Gln Glu Gln Gly Lys Glu Lys Pro Leu Phe Asp Thr Lys Lys
                485                 490                 495

Val Ser Arg Lys Val Thr Lys Asp Gly Lys Val Gly Tyr Ile Met Pro
            500                 505                 510

Lys Asp Gly Lys Asp Tyr Phe Tyr Ala Arg Asp Gln Leu Asp Leu Thr
        515                 520                 525

Gln Ile Ala Phe Ala Glu Gln Leu Met Leu Lys Asp Lys Asn His
        530                 535                 540

Tyr Arg Tyr Asp Ile Val Asp Thr Gly Ile Glu Pro Arg Leu Ala Val
545                 550                 555                 560

Asp Val Ser Ser Leu Pro Met His Ala Gly Asn Ala Thr Tyr Asp Thr
                565                 570                 575

Gly Ser Ser Phe Val Ile Pro His Ile Asp His Ile His Val Val Pro
            580                 585                 590

Tyr Ser Trp Leu Thr Arg Asp Gln Ile Ala Thr Ile Lys Tyr Val Met
        595                 600                 605

Gln His Pro Glu Val Arg Pro Asp Val Trp Ser Lys Pro Gly His Glu
        610                 615                 620

Glu Ser Gly Ser Val Ile Pro Asn Val Thr Pro Leu Asp Lys Arg Ala
625                 630                 635                 640

Gly Met Pro Asn Trp Gln Ile Ile His Ser Ala Glu Glu Val Gln Lys
                645                 650                 655

Ala Leu Ala Glu Gly Arg Phe Ala Thr Pro Asp Gly Tyr Ile Phe Asp
            660                 665                 670

Pro Arg Asp Val Leu Ala Lys Glu Thr Phe Val Trp Lys Asp Gly Ser
        675                 680                 685

Phe Ser Ile Pro Arg Ala Asp Gly Ser Ser Leu Arg Thr Ile Asn Lys
        690                 695                 700

Ser Asp Leu Ser Gln Ala Glu Trp Gln Gln Ala Gln Glu Leu Leu Ala
705                 710                 715                 720

Lys Lys Asn Ala Gly Asp Ala Thr Asp Thr Lys Pro Lys Glu Lys
                725                 730                 735

Gln Gln Ala Asp Lys Ser Asn Glu Asn Gln Gln Pro Ser Glu Ala Ser
            740                 745                 750
```

```
Lys Glu Glu Lys Glu Ser Asp Asp Phe Ile Asp Ser Leu Pro Asp
            755                 760                 765

Tyr Gly Leu Asp Arg Ala Thr Leu Glu Asp His Ile Asn Gln Leu Ala
            770                 775                 780

Gln Lys Ala Asn Ile Asp Pro Lys Tyr Leu Ile Phe Gln Pro Glu Gly
785                 790                 795                 800

Val Gln Phe Tyr Asn Lys Asn Gly Glu Leu Val Thr Tyr Asp Ile Lys
            805                 810                 815

Thr Leu Gln Gln Ile Asn Pro Pro
            820

<210> SEQ ID NO 84
<211> LENGTH: 1019
<212> TYPE: PRT
<213> ORGANISM: S. pneumoniae

<400> SEQUENCE: 84

Cys Ala Tyr Ala Leu Asn Gln His Arg Ser Gln Glu Asn Lys Asp Asn
1               5                   10                  15

Asn Arg Val Ser Tyr Val Asp Gly Ser Gln Ser Ser Gln Lys Ser Glu
            20                  25                  30

Asn Leu Thr Pro Asp Gln Val Ser Gln Lys Glu Gly Ile Gln Ala Glu
        35                  40                  45

Gln Ile Val Ile Lys Ile Thr Asp Gln Gly Tyr Val Thr Ser His Gly
50                  55                  60

Asp His Tyr His Tyr Tyr Asn Gly Lys Val Pro Tyr Asp Ala Leu Phe
65                  70                  75                  80

Ser Glu Glu Leu Leu Met Lys Asp Pro Asn Tyr Gln Leu Lys Asp Ala
                85                  90                  95

Asp Ile Val Asn Glu Val Lys Gly Gly Tyr Ile Ile Lys Val Asp Gly
            100                 105                 110

Lys Tyr Tyr Val Tyr Leu Lys Asp Ala Ala His Ala Asp Asn Val Arg
        115                 120                 125

Thr Lys Asp Glu Ile Asn Arg Gln Lys Gln Glu His Val Lys Asp Asn
130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Arg Gly His Tyr His Tyr Ile
            180                 185                 190

Pro Lys Ser Asp Leu Ser Ala Ser Glu Leu Ala Ala Lys Ala His
        195                 200                 205

Leu Ala Gly Lys Asn Met Gln Pro Ser Gln Leu Ser Tyr Ser Ser Thr
210                 215                 220

Ala Ser Asp Asn Asn Thr Gln Ser Val Ala Lys Gly Ser Thr Ser Lys
225                 230                 235                 240

Pro Ala Asn Lys Ser Glu Asn Leu Gln Ser Leu Leu Lys Glu Leu Tyr
                245                 250                 255

Asp Ser Pro Ser Ala Gln Arg Tyr Ser Glu Ser Asp Gly Leu Val Phe
            260                 265                 270

Asp Pro Ala Lys Ile Ile Ser Arg Thr Pro Asn Gly Val Ala Ile Pro
        275                 280                 285

His Gly Asp His Tyr His Phe Ile Pro Tyr Ser Lys Leu Ser Ala Leu
290                 295                 300
```

-continued

```
Glu Glu Lys Ile Ala Arg Met Val Pro Ile Ser Gly Thr Gly Ser Thr
305                 310                 315                 320

Val Ser Thr Asn Ala Lys Pro Asn Glu Val Val Ser Ser Leu Gly Ser
                325                 330                 335

Leu Ser Ser Asn Pro Ser Ser Leu Thr Thr Ser Lys Glu Leu Ser Ser
                340                 345                 350

Ala Ser Asp Gly Tyr Ile Phe Asn Pro Lys Asp Ile Val Glu Glu Thr
                355                 360                 365

Ala Thr Ala Tyr Ile Val Arg His Gly Asp His Phe His Tyr Ile Pro
            370                 375                 380

Lys Ser Asn Gln Ile Gly Gln Pro Thr Leu Pro Asn Asn Ser Leu Ala
385                 390                 395                 400

Thr Pro Ser Pro Ser Leu Pro Ile Asn Pro Gly Thr Ser His Glu Lys
                405                 410                 415

His Glu Glu Asp Gly Tyr Gly Phe Asp Ala Asn Arg Ile Ile Ala Glu
                420                 425                 430

Asp Glu Ser Gly Phe Val Met Ser His Gly Asp His Asn His Tyr Phe
                435                 440                 445

Phe Lys Lys Asp Leu Thr Glu Glu Gln Ile Lys Ala Ala Gln Lys His
            450                 455                 460

Leu Glu Glu Val Lys Thr Ser His Asn Gly Leu Asp Ser Leu Ser Ser
465                 470                 475                 480

His Glu Gln Asp Tyr Pro Ser Asn Ala Lys Glu Met Lys Asp Leu Asp
                485                 490                 495

Lys Lys Ile Glu Glu Lys Ile Ala Gly Ile Met Lys Gln Tyr Gly Val
                500                 505                 510

Lys Arg Glu Ser Ile Val Val Asn Lys Glu Lys Asn Ala Ile Ile Tyr
            515                 520                 525

Pro His Gly Asp His His His Ala Asp Pro Ile Asp Glu His Lys Pro
530                 535                 540

Val Gly Ile Gly His Ser His Ser Asn Tyr Glu Leu Phe Lys Pro Glu
545                 550                 555                 560

Glu Gly Val Ala Lys Lys Glu Gly Asn Lys Val Tyr Thr Gly Glu Glu
                565                 570                 575

Leu Thr Asn Val Val Asn Leu Leu Lys Asn Ser Thr Phe Asn Asn Gln
                580                 585                 590

Asn Phe Thr Leu Ala Asn Gly Gln Lys Arg Val Ser Phe Ser Phe Pro
            595                 600                 605

Pro Glu Leu Glu Lys Lys Leu Gly Ile Asn Met Leu Val Lys Leu Ile
            610                 615                 620

Thr Pro Asp Gly Lys Val Leu Glu Lys Val Ser Gly Lys Val Phe Gly
625                 630                 635                 640

Glu Gly Val Gly Asn Ile Ala Asn Phe Glu Leu Asp Gln Pro Tyr Leu
                645                 650                 655

Pro Gly Gln Thr Phe Lys Tyr Thr Ile Ala Ser Lys Asp Tyr Pro Glu
                660                 665                 670

Val Ser Tyr Asp Gly Thr Phe Thr Val Pro Thr Ser Leu Ala Tyr Lys
                675                 680                 685

Met Ala Ser Gln Thr Ile Phe Tyr Pro Phe His Ala Gly Asp Thr Tyr
            690                 695                 700

Leu Arg Val Asn Pro Gln Phe Ala Val Pro Lys Gly Thr Asp Ala Leu
705                 710                 715                 720
```

-continued

```
Val Arg Val Phe Asp Glu Phe His Gly Asn Ala Tyr Leu Glu Asn Asn
            725                 730                 735

Tyr Lys Val Gly Glu Ile Lys Leu Pro Ile Pro Lys Leu Asn Gln Gly
            740                 745                 750

Thr Thr Arg Thr Ala Gly Asn Lys Ile Pro Val Thr Phe Met Ala Asn
            755                 760                 765

Ala Tyr Leu Asp Asn Gln Ser Thr Tyr Ile Val Glu Val Pro Ile Leu
            770                 775                 780

Glu Lys Glu Asn Gln Thr Asp Lys Pro Ser Ile Leu Pro Gln Phe Lys
785                 790                 795                 800

Arg Asn Lys Ala Gln Glu Asn Ser Lys Phe Asp Glu Lys Val Glu Glu
                805                 810                 815

Pro Lys Thr Ser Glu Lys Val Glu Lys Glu Lys Leu Ser Glu Thr Gly
                820                 825                 830

Asn Ser Thr Ser Asn Ser Thr Leu Glu Glu Val Pro Thr Val Asp Pro
            835                 840                 845

Val Gln Glu Lys Val Ala Lys Phe Ala Glu Ser Tyr Gly Met Lys Leu
            850                 855                 860

Glu Asn Val Leu Phe Asn Met Asp Gly Thr Ile Glu Leu Tyr Leu Pro
865                 870                 875                 880

Ser Gly Glu Val Ile Lys Lys Asn Met Ala Asp Phe Thr Gly Glu Ala
                885                 890                 895

Pro Gln Gly Asn Gly Glu Asn Lys Pro Ser Glu Asn Gly Lys Val Ser
                900                 905                 910

Thr Gly Thr Val Glu Asn Gln Pro Thr Glu Asn Lys Pro Ala Asp Ser
            915                 920                 925

Leu Pro Glu Ala Pro Asn Glu Lys Pro Val Lys Pro Glu Asn Ser Thr
            930                 935                 940

Asp Asn Gly Met Leu Asn Pro Glu Gly Asn Val Gly Ser Asp Pro Met
945                 950                 955                 960

Leu Asp Pro Ala Leu Glu Glu Ala Pro Ala Val Asp Pro Val Gln Glu
                965                 970                 975

Lys Leu Glu Lys Phe Thr Ala Ser Tyr Gly Leu Gly Leu Asp Ser Val
                980                 985                 990

Ile Phe Asn Met Asp Gly Thr Ile Glu Leu Arg Leu Pro Ser Gly Glu
            995                 1000                1005

Val Ile Lys Lys Asn Leu Ser Asp Leu Ile Ala
    1010                1015
```

<210> SEQ ID NO 85
<211> LENGTH: 1019
<212> TYPE: PRT
<213> ORGANISM: S. pneumoniae

<400> SEQUENCE: 85

```
Cys Ala Tyr Ala Leu Asn Gln His Arg Ser Gln Glu Asn Lys Asp Asn
1               5                   10                  15

Asn Arg Val Ser Tyr Val Asp Gly Ser Gln Ser Ser Gln Lys Ser Glu
            20                  25                  30

Asn Leu Thr Pro Asp Gln Val Ser Gln Lys Glu Gly Ile Gln Ala Glu
            35                  40                  45

Gln Ile Val Ile Lys Ile Thr Asp Gln Gly Tyr Val Thr Ser His Gly
    50                  55                  60

Asp His Tyr His Tyr Tyr Asn Gly Lys Val Pro Tyr Asp Ala Leu Phe
65                  70                  75                  80
```

-continued

```
Ser Glu Glu Leu Leu Met Lys Asp Pro Asn Tyr Gln Leu Lys Asp Ala
                85                  90                  95

Asp Ile Val Asn Glu Val Lys Gly Gly Tyr Ile Ile Lys Val Asp Gly
            100                 105                 110

Lys Tyr Tyr Val Tyr Leu Lys Asp Ala Ala His Ala Asp Asn Val Arg
            115                 120                 125

Thr Lys Asp Glu Ile Asn Arg Gln Lys Gln His Val Lys Asp Asn
        130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Gly Gly His Tyr His Tyr Ile
            180                 185                 190

Pro Lys Ser Asp Leu Ser Ala Ser Glu Leu Ala Ala Ala Lys Ala His
            195                 200                 205

Leu Ala Gly Lys Asn Met Gln Pro Ser Gln Leu Ser Tyr Ser Ser Thr
    210                 215                 220

Ala Ser Asp Asn Asn Thr Gln Ser Val Ala Lys Gly Ser Thr Ser Lys
225                 230                 235                 240

Pro Ala Asn Lys Ser Glu Asn Leu Gln Ser Leu Leu Lys Glu Leu Tyr
                245                 250                 255

Asp Ser Pro Ser Ala Gln Arg Tyr Ser Glu Ser Asp Gly Leu Val Phe
            260                 265                 270

Asp Pro Ala Lys Ile Ile Ser Arg Thr Pro Asn Gly Val Ala Ile Pro
            275                 280                 285

His Gly Asp His Tyr His Phe Ile Pro Tyr Ser Lys Leu Ser Ala Leu
    290                 295                 300

Glu Glu Lys Ile Ala Arg Arg Val Pro Ile Ser Gly Thr Gly Ser Thr
305                 310                 315                 320

Val Ser Thr Asn Ala Lys Pro Asn Glu Val Val Ser Ser Leu Gly Ser
                325                 330                 335

Leu Ser Ser Asn Pro Ser Ser Leu Thr Thr Ser Lys Glu Leu Ser Ser
            340                 345                 350

Ala Ser Asp Gly Tyr Ile Phe Asn Pro Lys Asp Ile Val Glu Glu Thr
            355                 360                 365

Ala Thr Ala Tyr Ile Val Arg His Gly Asp His Phe His Tyr Ile Pro
    370                 375                 380

Lys Ser Asn Gln Ile Gly Gln Pro Thr Leu Pro Asn Asn Ser Leu Ala
385                 390                 395                 400

Thr Pro Ser Pro Ser Leu Pro Ile Asn Pro Gly Ile Ser His Glu Lys
                405                 410                 415

His Glu Glu Asp Gly Tyr Gly Phe Asp Ala Asn Arg Ile Ile Ala Glu
            420                 425                 430

Asp Glu Ser Gly Phe Ile Met Ser His Gly Asn His Asn His Tyr Phe
        435                 440                 445

Phe Lys Lys Asp Leu Thr Glu Glu Gln Ile Lys Ala Ala Gln Lys His
    450                 455                 460

Leu Glu Glu Val Lys Thr Ser His Asn Gly Leu Asp Ser Leu Ser Ser
465                 470                 475                 480

His Glu Gln Asp Tyr Pro Gly Asn Ala Lys Glu Met Lys Asp Leu Asp
                485                 490                 495
```

```
Lys Lys Ile Glu Glu Lys Ile Ala Gly Ile Met Lys Gln Tyr Gly Val
            500                 505                 510

Lys Arg Glu Ser Ile Val Val Asn Lys Glu Lys Asn Ala Ile Ile Tyr
            515                 520                 525

Pro His Gly Asp His His His Ala Asp Pro Ile Asp Glu His Lys Pro
            530                 535                 540

Val Gly Ile Gly His Ser His Ser Asn Tyr Glu Leu Phe Lys Pro Glu
545                 550                 555                 560

Glu Gly Val Ala Lys Lys Glu Gly Asn Lys Val Tyr Thr Gly Glu Glu
                565                 570                 575

Leu Thr Asn Val Val Asn Leu Leu Lys Asn Ser Thr Phe Asn Asn Gln
            580                 585                 590

Asn Phe Thr Leu Ala Asn Gly Gln Lys Arg Val Ser Phe Ser Phe Pro
            595                 600                 605

Pro Glu Leu Glu Lys Lys Leu Gly Ile Asn Met Leu Val Lys Leu Ile
            610                 615                 620

Thr Pro Asp Gly Lys Val Leu Glu Lys Val Ser Gly Lys Val Phe Gly
625                 630                 635                 640

Glu Gly Val Gly Asn Ile Ala Asn Phe Glu Leu Asp Gln Pro Tyr Leu
                645                 650                 655

Pro Gly Gln Thr Phe Lys Tyr Thr Ile Ala Ser Lys Asp Tyr Pro Glu
            660                 665                 670

Val Ser Tyr Asp Gly Thr Phe Thr Val Pro Thr Ser Leu Ala Tyr Lys
            675                 680                 685

Met Ala Ser Gln Thr Ile Phe Tyr Pro Phe His Ala Gly Asp Thr Tyr
            690                 695                 700

Leu Arg Val Asn Pro Gln Phe Ala Val Pro Lys Gly Thr Asp Ala Leu
705                 710                 715                 720

Val Arg Val Phe Asp Glu Phe His Gly Asn Ala Tyr Leu Glu Asn Asn
                725                 730                 735

Tyr Lys Val Gly Glu Ile Lys Leu Pro Ile Pro Lys Leu Asn Gln Gly
            740                 745                 750

Thr Thr Arg Thr Ala Gly Asn Lys Ile Pro Val Thr Phe Met Ala Asn
            755                 760                 765

Ala Tyr Leu Asp Asn Gln Ser Thr Tyr Ile Val Glu Val Pro Ile Leu
            770                 775                 780

Glu Lys Glu Asn Gln Thr Asp Lys Pro Ser Ile Leu Pro Gln Phe Lys
785                 790                 795                 800

Arg Asn Lys Ala Gln Glu Asn Ser Lys Leu Asp Glu Lys Val Glu Glu
                805                 810                 815

Pro Lys Thr Ser Glu Lys Val Lys Glu Lys Leu Ser Glu Thr Gly
            820                 825                 830

Asn Ser Thr Ser Asn Ser Thr Leu Glu Glu Val Pro Thr Val Asp Pro
            835                 840                 845

Val Gln Glu Lys Val Ala Lys Phe Ala Glu Ser Tyr Gly Met Lys Leu
            850                 855                 860

Glu Asn Val Leu Phe Asn Met Asp Gly Thr Ile Glu Leu Tyr Leu Pro
865                 870                 875                 880

Ser Gly Glu Val Ile Lys Lys Asn Met Ala Asp Phe Thr Gly Glu Ala
                885                 890                 895

Pro Gln Gly Asn Gly Glu Asn Lys Pro Ser Glu Asn Gly Lys Val Ser
            900                 905                 910

Thr Gly Thr Val Glu Asn Gln Pro Thr Glu Asn Lys Pro Ala Asp Ser
```

```
              915                 920                 925
Leu Pro Glu Ala Pro Asn Glu Lys Pro Val Lys Pro Glu Asn Ser Thr
    930                 935                 940

Asp Asn Gly Met Leu Asn Pro Glu Gly Asn Val Gly Ser Asp Pro Met
945                 950                 955                 960

Leu Asp Pro Ala Leu Glu Glu Ala Pro Ala Val Asp Pro Val Gln Glu
                965                 970                 975

Lys Leu Glu Lys Phe Thr Ala Ser Tyr Gly Leu Gly Leu Asp Ser Val
                980                 985                 990

Ile Phe Asn Met Asp Gly Thr Ile Glu Leu Arg Leu Pro Ser Gly Glu
                995                1000                1005

Val Ile Lys Lys Asn Leu Ser Asp Leu Ile Ala
    1010                1015

<210> SEQ ID NO 86
<211> LENGTH: 1019
<212> TYPE: PRT
<213> ORGANISM: S. pneumoniae

<400> SEQUENCE: 86

Cys Ala Tyr Ala Leu Asn Gln His Arg Ser Gln Glu Asn Lys Asp Asn
1               5                   10                  15

Asn Arg Val Ser Tyr Val Asp Gly Ser Gln Ser Gln Lys Ser Glu
            20                  25                  30

Asn Leu Thr Pro Asp Gln Val Ser Gln Lys Glu Gly Ile Gln Ala Glu
        35                  40                  45

Gln Ile Val Ile Lys Ile Thr Asp Gln Gly Tyr Val Thr Ser His Gly
    50                  55                  60

Asp His Tyr His Tyr Tyr Asn Gly Lys Val Pro Tyr Asp Ala Leu Phe
65                  70                  75                  80

Ser Glu Glu Leu Leu Met Lys Asp Pro Asn Tyr Gln Leu Lys Asp Ala
                85                  90                  95

Asp Ile Val Asn Glu Val Lys Gly Gly Tyr Ile Ile Lys Val Asp Gly
            100                 105                 110

Lys Tyr Tyr Val Tyr Leu Lys Asp Ala Ala His Ala Asp Asn Val Arg
        115                 120                 125

Thr Lys Asp Glu Ile Asn Arg Gln Lys Gln Glu His Val Lys Asp Asn
    130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Gly Gly His Tyr His Tyr Ile
            180                 185                 190

Pro Lys Ser Asp Leu Ser Ala Ser Glu Leu Ala Ala Lys Ala His
        195                 200                 205

Leu Ala Gly Lys Asn Met Gln Pro Ser Gln Leu Ser Tyr Ser Ser Thr
    210                 215                 220

Ala Ser Asp Asn Asn Thr Gln Ser Val Ala Lys Gly Ser Thr Ser Lys
225                 230                 235                 240

Pro Ala Asn Lys Ser Glu Asn Leu Gln Ser Leu Leu Lys Glu Leu Tyr
                245                 250                 255

Asp Ser Pro Ser Ala Gln Arg Tyr Ser Glu Ser Asp Gly Leu Val Phe
            260                 265                 270
```

```
Asp Pro Ala Lys Ile Ile Ser Arg Thr Pro Asn Gly Val Ala Ile Pro
        275                 280                 285

His Gly Asp His Tyr His Phe Ile Pro Tyr Ser Lys Leu Ser Ala Leu
        290                 295                 300

Glu Glu Lys Ile Ala Arg Met Val Pro Ile Ser Gly Thr Gly Ser Thr
305                 310                 315                 320

Val Ser Thr Asn Ala Lys Pro Asn Glu Val Val Ser Ser Leu Gly Ser
                325                 330                 335

Leu Ser Ser Asn Pro Ser Ser Leu Thr Thr Ser Lys Glu Leu Ser Ser
                340                 345                 350

Ala Ser Asp Gly Tyr Ile Phe Asn Pro Lys Asp Ile Val Glu Glu Thr
                355                 360                 365

Ala Thr Ala Tyr Ile Val Arg His Gly Asp His Phe His Tyr Ile Pro
        370                 375                 380

Lys Ser Asn Gln Ile Gly Gln Pro Thr Leu Pro Asn Asn Ser Leu Ala
385                 390                 395                 400

Thr Pro Ser Pro Ser Leu Pro Ile Asn Pro Gly Thr Ser His Glu Lys
                405                 410                 415

His Glu Glu Asp Gly Tyr Gly Phe Asp Ala Asn Arg Ile Ile Ala Glu
                420                 425                 430

Asp Glu Ser Gly Phe Val Met Ser His Gly Asp His Asn His Tyr Phe
        435                 440                 445

Phe Lys Lys Asp Leu Thr Glu Glu Gln Ile Lys Ala Ala Gln Lys His
        450                 455                 460

Leu Glu Glu Val Lys Thr Ser His Asn Gly Leu Asp Ser Leu Ser Ser
465                 470                 475                 480

His Glu Gln Asp Tyr Pro Ser Asn Ala Lys Glu Met Lys Asp Leu Asp
                485                 490                 495

Lys Lys Ile Glu Glu Lys Ile Ala Gly Ile Met Lys Gln Tyr Gly Val
                500                 505                 510

Lys Arg Glu Ser Ile Val Val Asn Lys Glu Lys Asn Ala Ile Ile Tyr
                515                 520                 525

Pro His Gly Asp His His Ala Asp Pro Ile Asp Glu His Lys Pro
        530                 535                 540

Val Gly Ile Gly His Ser His Ser Asn Tyr Glu Leu Phe Lys Pro Glu
545                 550                 555                 560

Glu Gly Val Ala Lys Lys Glu Gly Asn Lys Val Tyr Thr Gly Glu Glu
                565                 570                 575

Leu Thr Asn Val Val Asn Leu Leu Lys Asn Ser Thr Phe Asn Asn Gln
                580                 585                 590

Asn Phe Thr Leu Ala Asn Gly Gln Lys Arg Val Ser Phe Ser Phe Pro
        595                 600                 605

Pro Glu Leu Glu Lys Lys Leu Gly Ile Asn Met Leu Val Lys Leu Ile
        610                 615                 620

Thr Pro Asp Gly Lys Val Leu Glu Lys Val Ser Gly Lys Val Phe Gly
625                 630                 635                 640

Glu Gly Val Gly Asn Ile Ala Asn Phe Glu Leu Asp Gln Pro Tyr Leu
                645                 650                 655

Pro Gly Gln Thr Phe Lys Tyr Thr Ile Ala Ser Lys Asp Tyr Pro Glu
                660                 665                 670

Val Ser Tyr Asp Gly Thr Phe Thr Val Pro Thr Ser Leu Ala Tyr Lys
                675                 680                 685

Met Ala Ser Gln Thr Ile Phe Tyr Pro Phe His Ala Gly Asp Thr Tyr
```

```
                690             695             700
Leu Arg Val Asn Pro Gln Phe Ala Val Pro Lys Gly Thr Asp Ala Leu
705                     710                     715                 720

Val Arg Val Phe Asp Glu Phe His Gly Asn Ala Tyr Leu Glu Asn Asn
                    725                     730                 735

Tyr Lys Val Gly Glu Ile Lys Leu Pro Ile Pro Lys Leu Asn Gln Gly
                740                     745                 750

Thr Thr Arg Thr Ala Gly Asn Lys Ile Pro Val Thr Phe Met Ala Asn
                    755                 760                 765

Ala Tyr Leu Asp Asn Gln Ser Thr Tyr Ile Val Glu Val Pro Ile Leu
    770                 775                     780

Glu Lys Glu Asn Gln Thr Asp Lys Pro Ser Ile Leu Pro Gln Phe Lys
785                     790                     795                 800

Arg Asn Lys Ala Gln Glu Asn Leu Lys Leu Asp Glu Lys Val Glu Glu
                    805                 810                     815

Pro Lys Thr Ser Glu Lys Val Glu Lys Leu Ser Glu Thr Gly
                820                     825                 830

Asn Ser Thr Ser Asn Ser Thr Leu Glu Glu Val Pro Thr Val Asp Pro
                835                     840                 845

Val Gln Glu Lys Val Ala Lys Phe Ala Glu Ser Tyr Gly Met Lys Leu
    850                 855                     860

Glu Asn Val Leu Phe Asn Met Asp Gly Thr Ile Glu Leu Tyr Leu Pro
865                     870                     875                 880

Ser Gly Glu Val Ile Lys Lys Asn Met Ala Asp Phe Thr Gly Glu Ala
                    885                 890                     895

Pro Gln Gly Asn Gly Glu Asn Lys Pro Ser Glu Asn Gly Lys Val Ser
                900                     905                 910

Thr Gly Thr Val Glu Asn Gln Pro Thr Glu Asn Lys Pro Ala Asp Ser
                    915                 920                     925

Leu Pro Glu Ala Pro Asn Glu Lys Pro Val Lys Pro Glu Asn Ser Thr
                930                     935                 940

Asp Asn Gly Met Leu Asn Pro Glu Gly Asn Val Gly Ser Asp Pro Met
945                     950                     955                 960

Leu Asp Pro Ala Leu Glu Glu Ala Pro Ala Val Asp Pro Val Gln Glu
                    965                     970                 975

Lys Leu Glu Lys Phe Thr Ala Ser Tyr Gly Leu Gly Leu Asp Ser Val
                980                     985                 990

Ile Phe Asn Met Asp Gly Thr Ile Glu Leu Arg Leu Pro Ser Gly Glu
                    995                     1000                1005

Val Ile Lys Lys Asn Leu Ser Asp Leu Ile Ala
    1010                1015

<210> SEQ ID NO 87
<211> LENGTH: 1019
<212> TYPE: PRT
<213> ORGANISM: S. pneumoniae

<400> SEQUENCE: 87

Cys Ala Tyr Ala Leu Asn Gln His Arg Ser Gln Glu Asn Lys Asp Asn
1               5                   10                  15

Asn Arg Val Ser Tyr Val Asp Gly Ser Gln Ser Gln Lys Ser Glu
                20                  25                  30

Asn Leu Thr Pro Asp Gln Val Ser Gln Lys Glu Gly Ile Gln Ala Glu
                35                  40                  45
```

-continued

```
Gln Ile Val Ile Lys Ile Thr Asp Gln Gly Tyr Val Thr Ser His Gly
 50                  55                  60

Asp His Tyr His Tyr Tyr Asn Gly Lys Val Pro Tyr Asp Ala Leu Phe
 65                  70                  75                  80

Ser Glu Glu Leu Leu Met Lys Asp Pro Asn Tyr Gln Leu Lys Asp Ala
                     85                  90                  95

Asp Ile Val Asn Glu Val Lys Gly Gly Tyr Ile Ile Lys Val Asp Gly
                100                 105                 110

Lys Tyr Tyr Val Tyr Leu Lys Asp Ala Ala His Ala Asp Asn Val Arg
                115                 120                 125

Thr Lys Asp Glu Ile Asn Arg Gln Lys Gln Glu His Val Lys Asp Asn
130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Gly His Tyr His Tyr Ile
                180                 185                 190

Pro Lys Ser Asp Leu Ser Ala Ser Glu Leu Ala Ala Lys Ala His
                195                 200                 205

Leu Ala Gly Lys Asn Met Gln Pro Ser Gln Leu Ser Tyr Ser Ser Thr
210                 215                 220

Ala Ser Asp Asn Asn Thr Gln Ser Val Ala Lys Gly Ser Thr Ser Lys
225                 230                 235                 240

Pro Ala Asn Lys Ser Glu Asn Leu Gln Ser Leu Leu Lys Glu Leu Tyr
                245                 250                 255

Asp Ser Pro Ser Ala Gln Arg Tyr Ser Glu Ser Asp Gly Leu Val Phe
                260                 265                 270

Asp Pro Ala Lys Ile Ile Ser Arg Thr Pro Asn Gly Val Ala Ile Pro
                275                 280                 285

His Gly Asp His Tyr His Phe Ile Pro Tyr Ser Lys Leu Ser Ala Leu
                290                 295                 300

Glu Glu Lys Ile Ala Arg Met Val Pro Ile Ser Gly Thr Gly Ser Thr
305                 310                 315                 320

Val Ser Thr Asn Ala Lys Pro Asn Glu Val Val Ser Ser Leu Gly Ser
                325                 330                 335

Leu Ser Ser Asn Pro Ser Ser Leu Thr Thr Ser Lys Glu Leu Ser Ser
                340                 345                 350

Ala Ser Asp Gly Tyr Ile Phe Asn Pro Lys Asp Ile Val Glu Glu Thr
                355                 360                 365

Ala Thr Ala Tyr Ile Val Arg His Gly Asp His Phe His Tyr Ile Pro
370                 375                 380

Lys Ser Asn Gln Ile Gly Gln Pro Thr Leu Pro Asn Asn Ser Leu Ala
385                 390                 395                 400

Thr Pro Ser Pro Ser Leu Pro Ile Asn Pro Gly Thr Ser His Glu Lys
                405                 410                 415

His Glu Glu Asp Gly Tyr Gly Phe Asp Ala Asn Arg Ile Ile Ala Glu
                420                 425                 430

Asp Glu Ser Gly Phe Val Met Ser His Gly Asp His Asn His Tyr Phe
                435                 440                 445

Phe Lys Lys Asp Leu Thr Glu Glu Gln Ile Lys Ala Ala Gln Lys His
450                 455                 460

Leu Glu Glu Val Lys Thr Ser His Asn Gly Leu Asp Ser Leu Ser Ser
```

-continued

```
              465                 470                 475                 480
        His Glu Gln Asp Tyr Pro Gly Asn Ala Lys Glu Met Lys Asp Leu Asp
                        485                 490                 495
        Lys Lys Ile Glu Glu Lys Ile Ala Gly Ile Met Lys Gln Tyr Gly Val
                    500                 505                 510
        Lys Arg Glu Ser Ile Val Val Asn Lys Glu Lys Asn Ala Ile Ile Tyr
                    515                 520                 525
        Pro His Gly Asp His His Ala Asp Pro Ile Asp Glu His Lys Pro
            530                 535                 540
        Val Gly Ile Gly His Ser His Ser Asn Tyr Glu Leu Phe Lys Pro Glu
        545                 550                 555                 560
        Glu Gly Val Ala Lys Lys Glu Gly Asn Lys Val Tyr Thr Gly Glu Glu
                        565                 570                 575
        Leu Thr Asn Val Val Asn Leu Leu Lys Asn Ser Thr Phe Asn Asn Gln
                    580                 585                 590
        Asn Phe Thr Leu Ala Asn Gly Gln Lys Arg Val Ser Phe Ser Phe Pro
                    595                 600                 605
        Pro Glu Leu Glu Lys Lys Leu Gly Ile Asn Met Leu Val Lys Leu Ile
                610                 615                 620
        Thr Pro Asp Gly Lys Val Leu Glu Lys Val Ser Gly Lys Val Phe Gly
        625                 630                 635                 640
        Glu Gly Val Gly Asn Ile Ala Asn Phe Glu Leu Asp Gln Pro Tyr Leu
                        645                 650                 655
        Pro Gly Gln Thr Phe Lys Tyr Thr Ile Ala Ser Lys Asp Tyr Pro Glu
                    660                 665                 670
        Val Ser Tyr Asp Gly Thr Phe Thr Val Pro Thr Ser Leu Ala Tyr Lys
                    675                 680                 685
        Met Ala Ser Gln Thr Ile Phe Tyr Pro Phe His Ala Gly Asp Thr Tyr
                690                 695                 700
        Leu Arg Val Asn Pro Gln Phe Ala Val Pro Lys Gly Thr Asp Ala Leu
        705                 710                 715                 720
        Val Arg Val Phe Asp Glu Phe His Gly Asn Ala Tyr Leu Glu Asn Asn
                        725                 730                 735
        Tyr Lys Val Gly Glu Ile Lys Leu Pro Ile Pro Lys Leu Asn Gln Gly
                    740                 745                 750
        Thr Thr Arg Thr Ala Gly Asn Lys Ile Pro Val Thr Phe Met Ala Asn
                    755                 760                 765
        Ala Tyr Leu Asp Asn Gln Ser Thr Tyr Ile Val Glu Val Pro Ile Leu
                770                 775                 780
        Glu Lys Glu Asn Gln Thr Asp Lys Pro Ser Ile Leu Pro Gln Phe Lys
        785                 790                 795                 800
        Arg Asn Lys Ala Gln Glu Asn Ser Lys Leu Asp Glu Lys Val Glu Glu
                        805                 810                 815
        Pro Lys Thr Ser Glu Lys Val Glu Lys Leu Ser Glu Thr Gly
                    820                 825                 830
        Asn Ser Thr Ser Asn Ser Thr Leu Glu Glu Val Pro Thr Val Asp Pro
                835                 840                 845
        Val Gln Glu Lys Val Ala Lys Phe Ala Glu Ser Tyr Gly Met Lys Leu
            850                 855                 860
        Glu Asn Val Leu Phe Asn Met Asp Gly Thr Ile Glu Leu Tyr Leu Pro
        865                 870                 875                 880
        Ser Gly Glu Val Ile Lys Lys Asn Met Ala Asp Phe Thr Gly Glu Ala
                        885                 890                 895
```

-continued

Pro Gln Gly Asn Gly Glu Asn Lys Pro Ser Glu Asn Gly Lys Val Ser
            900                 905                 910

Thr Gly Thr Val Glu Asn Gln Pro Thr Glu Asn Lys Pro Ala Asp Ser
            915                 920                 925

Leu Pro Glu Ala Pro Asn Glu Lys Pro Val Lys Pro Glu Asn Ser Thr
            930                 935                 940

Asp Asn Gly Met Leu Asn Pro Glu Gly Asn Val Gly Ser Asp Pro Met
945                 950                 955                 960

Leu Asp Pro Ala Leu Glu Glu Ala Pro Ala Val Asp Pro Val Gln Glu
            965                 970                 975

Lys Leu Glu Lys Phe Thr Ala Ser Tyr Gly Leu Gly Leu Asp Ser Val
            980                 985                 990

Ile Phe Asn Met Asp Gly Thr Ile Glu Leu Arg Leu Pro Ser Gly Glu
            995                 1000                1005

Val Ile Lys Lys Asn Leu Ser Asp Phe Ile Ala
            1010                1015

<210> SEQ ID NO 88
<211> LENGTH: 1019
<212> TYPE: PRT
<213> ORGANISM: S. pneumoniae

<400> SEQUENCE: 88

Cys Ala Tyr Ala Leu Asn Gln His Arg Ser Gln Glu Asn Lys Asp Asn
1               5                   10                  15

Asn Arg Val Ser Tyr Val Asp Gly Ser Gln Ser Ser Gln Lys Ser Glu
            20                  25                  30

Asn Leu Thr Pro Asp Gln Val Ser Gln Lys Glu Gly Ile Gln Ala Glu
            35                  40                  45

Gln Ile Val Ile Lys Ile Thr Asp Gln Gly Tyr Val Thr Ser His Gly
        50                  55                  60

Asp His Tyr His Tyr Tyr Asn Gly Lys Val Pro Tyr Asp Ala Leu Phe
65                  70                  75                  80

Ser Glu Glu Leu Leu Met Lys Asp Pro Asn Tyr Gln Leu Lys Asp Ala
            85                  90                  95

Asp Ile Val Asn Glu Val Lys Gly Gly Tyr Ile Ile Lys Val Asp Gly
            100                 105                 110

Lys Tyr Tyr Val Tyr Leu Lys Asp Ala Ala His Ala Asp Asn Val Arg
            115                 120                 125

Thr Lys Asp Glu Ile Asn Arg Gln Lys Gln Glu His Val Lys Asp Asn
130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
            165                 170                 175

Thr Gly Asn Ala Tyr Ile Val Pro His Arg Gly His Tyr His Tyr Ile
            180                 185                 190

Pro Lys Ser Asp Leu Ser Ala Ser Glu Leu Ala Ala Ala Lys Ala His
            195                 200                 205

Leu Ala Gly Lys Asn Met Gln Pro Ser Gln Leu Ser Tyr Ser Ser Thr
            210                 215                 220

Ala Ser Asp Asn Asn Thr Gln Ser Val Ala Lys Gly Ser Thr Ser Lys
225                 230                 235                 240

Pro Ala Asn Lys Ser Glu Asn Leu Gln Ser Leu Leu Lys Glu Leu Tyr

-continued

```
                    245                 250                 255
Asp Ser Pro Ser Ala Gln Arg Tyr Ser Glu Ser Asp Gly Leu Val Phe
            260                 265                 270
Asp Pro Ala Lys Ile Ile Ser Arg Thr Pro Asn Gly Val Ala Ile Pro
            275                 280                 285
His Gly Asp His Tyr His Phe Ile Pro Tyr Ser Lys Leu Ser Ala Leu
            290                 295                 300
Glu Glu Lys Ile Ala Arg Met Val Pro Ile Ser Gly Thr Gly Ser Thr
305                 310                 315                 320
Val Ser Thr Asn Ala Lys Pro Asn Glu Val Val Ser Ser Leu Gly Ser
                325                 330                 335
Leu Ser Ser Asn Pro Ser Ser Leu Thr Thr Ser Lys Glu Leu Ser Ser
                340                 345                 350
Ala Ser Asp Gly Tyr Ile Phe Asn Pro Lys Asp Ile Val Glu Glu Thr
                355                 360                 365
Ala Thr Ala Tyr Ile Val Arg His Gly Asp His Phe His Tyr Ile Pro
            370                 375                 380
Lys Ser Asn Gln Ile Gly Gln Pro Thr Leu Pro Asn Asn Ser Leu Ala
385                 390                 395                 400
Thr Pro Ser Pro Ser Leu Pro Ile Asn Pro Gly Thr Ser His Glu Lys
                405                 410                 415
His Glu Glu Asp Gly Tyr Gly Phe Asp Ala Asn Arg Ile Ile Ala Glu
                420                 425                 430
Asp Glu Ser Gly Phe Val Met Ser His Gly Asp His Asn His Tyr Phe
            435                 440                 445
Phe Lys Lys Asp Leu Thr Glu Glu Gln Ile Lys Ala Ala Gln Lys His
450                 455                 460
Leu Glu Glu Val Lys Thr Ser His Asn Gly Leu Asp Ser Leu Ser Ser
465                 470                 475                 480
His Glu Gln Asp Tyr Pro Ser Asn Ala Lys Glu Met Lys Asp Leu Asp
                485                 490                 495
Lys Lys Ile Glu Glu Lys Ile Ala Gly Ile Met Lys Gln Tyr Gly Val
                500                 505                 510
Lys Arg Glu Ser Ile Val Val Asn Lys Glu Lys Asn Ala Ile Ile Tyr
            515                 520                 525
Pro His Gly Asp His His His Ala Asp Pro Ile Asp Glu His Lys Pro
            530                 535                 540
Val Gly Ile Gly His Ser His Ser Asn Tyr Glu Leu Phe Lys Pro Glu
545                 550                 555                 560
Glu Gly Val Ala Lys Lys Glu Gly Asn Lys Val Tyr Thr Gly Glu Glu
                565                 570                 575
Leu Thr Asn Val Val Asn Leu Leu Lys Asn Ser Thr Phe Asn Asn Gln
                580                 585                 590
Asn Phe Thr Leu Ala Asn Gly Gln Lys Arg Val Ser Phe Ser Phe Pro
            595                 600                 605
Pro Glu Leu Glu Lys Lys Leu Gly Ile Asn Met Leu Val Lys Leu Ile
            610                 615                 620
Thr Pro Asp Gly Lys Val Leu Glu Lys Val Ser Gly Lys Val Phe Gly
625                 630                 635                 640
Glu Gly Val Gly Asn Ile Ala Asn Phe Glu Leu Asp Gln Pro Tyr Leu
                645                 650                 655
Pro Gly Gln Thr Phe Lys Tyr Thr Ile Ala Ser Lys Asp Tyr Pro Glu
            660                 665                 670
```

```
Val Ser Tyr Asp Gly Thr Phe Thr Val Pro Thr Ser Leu Ala Tyr Lys
        675                 680                 685

Met Ala Ser Gln Thr Ile Phe Tyr Pro Phe His Ala Gly Asp Thr Tyr
    690                 695                 700

Leu Arg Val Asn Pro Gln Phe Ala Val Pro Lys Gly Thr Asp Ala Leu
705                 710                 715                 720

Val Arg Val Phe Asp Glu Phe His Gly Asn Ala Tyr Leu Glu Asn Asn
                725                 730                 735

Tyr Lys Val Gly Glu Ile Lys Leu Pro Ile Pro Lys Leu Asn Gln Gly
            740                 745                 750

Thr Thr Arg Thr Ala Gly Asn Lys Ile Pro Val Thr Phe Met Ala Asn
        755                 760                 765

Ala Tyr Leu Asp Asn Gln Ser Thr Tyr Ile Val Glu Val Pro Ile Leu
    770                 775                 780

Glu Lys Glu Asn Gln Thr Asp Lys Pro Ser Ile Leu Pro Gln Phe Lys
785                 790                 795                 800

Arg Asn Lys Ala Gln Glu Asn Ser Lys Phe Asp Glu Lys Val Glu Glu
                805                 810                 815

Pro Lys Thr Ser Glu Lys Val Glu Lys Leu Ser Glu Thr Gly
            820                 825                 830

Asn Ser Thr Ser Asn Ser Thr Leu Glu Glu Val Pro Thr Val Asp Pro
        835                 840                 845

Val Gln Glu Lys Val Ala Lys Phe Ala Glu Ser Tyr Gly Met Lys Leu
    850                 855                 860

Glu Asn Val Leu Phe Asn Met Asp Gly Thr Ile Glu Leu Tyr Leu Pro
865                 870                 875                 880

Ser Gly Glu Val Ile Lys Lys Asn Met Ala Asp Phe Thr Gly Glu Ala
                885                 890                 895

Pro Gln Gly Asn Gly Glu Asn Lys Pro Ser Glu Asn Gly Lys Val Ser
            900                 905                 910

Thr Gly Thr Val Glu Asn Gln Pro Thr Glu Asn Lys Pro Ala Asp Ser
        915                 920                 925

Leu Pro Glu Ala Pro Asn Glu Lys Pro Val Lys Pro Glu Asn Ser Thr
    930                 935                 940

Asp Asn Gly Met Leu Asn Pro Glu Gly Asn Val Gly Ser Asp Pro Met
945                 950                 955                 960

Leu Asp Pro Ala Leu Glu Glu Ala Pro Ala Val Asp Pro Val Gln Glu
                965                 970                 975

Lys Leu Glu Lys Phe Thr Ala Ser Tyr Gly Leu Gly Leu Asp Ser Val
            980                 985                 990

Ile Phe Asn Met Asp Gly Thr Ile Glu Leu Arg Leu Pro Ser Gly Glu
        995                 1000                1005

Val Ile Lys Lys Asn Leu Ser Asp Leu Ile Ala
    1010                1015

<210> SEQ ID NO 89
<211> LENGTH: 1019
<212> TYPE: PRT
<213> ORGANISM: S. pneumoniae

<400> SEQUENCE: 89

Cys Ala Tyr Ala Leu Asn Gln His Arg Ser Gln Glu Asn Lys Asp Asn
1               5                   10                  15

Asn Arg Val Ser Tyr Val Asp Gly Ser Gln Ser Ser Gln Lys Ser Glu
```

-continued

```
                    20                  25                  30
Asn Leu Thr Pro Asp Gln Val Ser Gln Lys Glu Gly Ile Gln Ala Glu
            35                  40                  45
Gln Ile Val Ile Lys Ile Thr Asp Gln Gly Tyr Val Thr Ser His Gly
        50                  55                  60
Asp His Tyr His Tyr Tyr Asn Gly Lys Val Pro Tyr Asp Ala Leu Phe
65                  70                  75                  80
Ser Glu Glu Leu Leu Met Lys Asp Pro Asn Tyr Gln Leu Lys Asp Ala
                85                  90                  95
Asp Ile Val Asn Glu Val Lys Gly Gly Tyr Ile Ile Lys Val Asp Gly
            100                 105                 110
Lys Tyr Tyr Val Tyr Leu Lys Asp Ala Ala His Ala Asp Asn Val Arg
        115                 120                 125
Thr Lys Asp Glu Ile Asn Arg Gln Lys Gln Glu His Val Lys Asp Asn
        130                 135                 140
Glu Lys Val Asn Ser Asn Val Ala Val Ala Arg Ser Gln Gly Arg Tyr
145                 150                 155                 160
Thr Thr Asn Asp Gly Tyr Val Phe Asn Pro Ala Asp Ile Ile Glu Asp
                165                 170                 175
Thr Gly Asn Ala Tyr Ile Val Pro His Arg Gly His Tyr His Tyr Ile
            180                 185                 190
Pro Lys Ser Asp Leu Ser Ala Ser Glu Leu Ala Ala Lys Ala His
        195                 200                 205
Leu Ala Gly Lys Asn Met Gln Pro Ser Gln Leu Ser Tyr Ser Ser Thr
    210                 215                 220
Ala Ser Asp Asn Asn Thr Gln Ser Val Ala Lys Gly Ser Thr Ser Lys
225                 230                 235                 240
Pro Ala Asn Lys Ser Glu Asn Leu Gln Ser Leu Leu Lys Glu Leu Tyr
                245                 250                 255
Asp Ser Pro Ser Ala Gln Arg Tyr Ser Glu Ser Asp Gly Leu Val Phe
            260                 265                 270
Asp Pro Ala Lys Ile Ile Ser Arg Thr Pro Asn Gly Val Ala Ile Pro
        275                 280                 285
His Gly Asp His Tyr His Phe Ile Pro Tyr Ser Lys Leu Ser Ala Leu
    290                 295                 300
Glu Glu Lys Ile Ala Arg Met Val Pro Ile Ser Gly Thr Gly Ser Thr
305                 310                 315                 320
Val Ser Thr Asn Ala Lys Pro Asn Glu Val Val Ser Ser Leu Gly Ser
                325                 330                 335
Leu Ser Ser Asn Pro Ser Ser Leu Thr Thr Ser Lys Glu Leu Ser Ser
            340                 345                 350
Ala Ser Asp Gly Tyr Ile Phe Asn Pro Lys Asp Ile Val Glu Glu Thr
        355                 360                 365
Ala Thr Ala Tyr Ile Val Arg His Gly Asp His Phe His Tyr Ile Pro
    370                 375                 380
Lys Ser Asn Gln Ile Gly Gln Pro Thr Leu Pro Asn Asn Ser Leu Ala
385                 390                 395                 400
Thr Pro Ser Pro Ser Leu Pro Ile Asn Pro Gly Thr Ser His Glu Lys
                405                 410                 415
His Glu Glu Asp Gly Tyr Gly Phe Asp Ala Asn Arg Ile Ile Ala Glu
            420                 425                 430
Asp Glu Ser Gly Phe Val Met Ser His Gly Asp His Asn His Tyr Phe
        435                 440                 445
```

-continued

```
Phe Lys Lys Asp Leu Thr Glu Glu Gln Ile Lys Ala Ala Gln Lys His
    450                 455                 460
Leu Glu Glu Val Lys Thr Ser His Asn Gly Leu Asp Ser Leu Ser Ser
465                 470                 475                 480
His Glu Gln Asp Tyr Pro Ser Asn Ala Lys Glu Met Lys Asp Leu Asp
                485                 490                 495
Lys Lys Ile Glu Glu Lys Ile Ala Gly Ile Met Lys Gln Tyr Gly Val
            500                 505                 510
Lys Arg Glu Ser Ile Val Val Asn Lys Glu Lys Asn Ala Ile Ile Tyr
        515                 520                 525
Pro His Gly Asp His His Ala Asp Pro Ile Asp Glu His Lys Pro
    530                 535                 540
Val Gly Ile Gly His Ser His Ser Asn Tyr Glu Leu Phe Lys Pro Glu
545                 550                 555                 560
Glu Gly Val Ala Lys Lys Glu Gly Asn Lys Val Tyr Thr Gly Glu Glu
                565                 570                 575
Leu Thr Asn Val Val Asn Leu Leu Lys Asn Ser Thr Phe Asn Asn Gln
            580                 585                 590
Asn Phe Thr Leu Ala Asn Gly Gln Lys Arg Val Ser Phe Ser Phe Pro
        595                 600                 605
Pro Glu Leu Glu Lys Lys Leu Gly Ile Asn Met Leu Val Lys Leu Ile
    610                 615                 620
Thr Pro Asp Gly Lys Val Leu Glu Lys Val Ser Gly Lys Val Phe Gly
625                 630                 635                 640
Glu Gly Val Gly Asn Ile Ala Asn Phe Glu Leu Asp Gln Pro Tyr Leu
                645                 650                 655
Pro Gly Gln Thr Phe Lys Tyr Thr Ile Ala Ser Lys Asp Tyr Pro Glu
            660                 665                 670
Val Ser Tyr Asp Gly Thr Phe Thr Val Pro Thr Ser Leu Ala Tyr Lys
        675                 680                 685
Met Ala Ser Gln Thr Ile Phe Tyr Pro Phe His Ala Gly Asp Thr Tyr
    690                 695                 700
Leu Arg Val Asn Pro Gln Phe Ala Val Pro Lys Gly Thr Asp Ala Leu
705                 710                 715                 720
Val Arg Val Phe Asp Glu Phe His Gly Asn Ala Tyr Leu Glu Asn Asn
                725                 730                 735
Tyr Lys Val Gly Glu Ile Lys Leu Pro Ile Pro Lys Leu Asn Gln Gly
            740                 745                 750
Thr Thr Arg Thr Ala Gly Asn Lys Ile Pro Val Thr Phe Met Ala Asn
        755                 760                 765
Ala Tyr Leu Asp Asn Gln Ser Thr Tyr Ile Val Glu Val Pro Ile Leu
    770                 775                 780
Glu Lys Glu Asn Gln Thr Asp Lys Pro Ser Ile Leu Pro Gln Phe Lys
785                 790                 795                 800
Arg Asn Lys Ala Gln Glu Asn Ser Lys Phe Asp Glu Lys Val Glu Glu
                805                 810                 815
Pro Lys Thr Ser Glu Lys Val Glu Lys Glu Lys Leu Ser Glu Thr Gly
            820                 825                 830
Asn Ser Thr Ser Asn Ser Thr Leu Glu Glu Val Pro Thr Val Asp Pro
        835                 840                 845
Val Gln Glu Lys Val Ala Lys Phe Ala Glu Ser Tyr Gly Met Lys Leu
    850                 855                 860
```

-continued

```
Glu Asn Val Leu Phe Asn Met Asp Gly Thr Ile Glu Leu Tyr Leu Pro
865                 870                 875                 880

Ser Gly Glu Val Ile Lys Lys Asn Met Ala Asp Phe Thr Gly Glu Ala
            885                 890                 895

Pro Gln Gly Asn Gly Glu Asn Lys Pro Ser Glu Asn Gly Lys Val Ser
        900                 905                 910

Thr Gly Thr Val Glu Asn Gln Pro Thr Glu Asn Lys Pro Ala Asp Ser
    915                 920                 925

Leu Pro Glu Ala Pro Asn Glu Lys Pro Val Lys Pro Glu Asn Ser Thr
    930                 935                 940

Asp Asn Gly Met Leu Asn Pro Glu Gly Asn Val Gly Ser Asp Pro Met
945                 950                 955                 960

Leu Asp Pro Ala Leu Glu Glu Ala Pro Ala Val Asp Pro Val Gln Glu
            965                 970                 975

Lys Leu Glu Lys Phe Thr Ala Ser Tyr Gly Leu Gly Leu Asp Ser Val
        980                 985                 990

Ile Phe Asn Met Asp Gly Thr Ile Glu Leu Arg Leu Pro Ser Gly Glu
    995                 1000                1005

Val Ile Lys Lys Asn Leu Ser Asp Leu Ile Ala
    1010                1015

<210> SEQ ID NO 90
<211> LENGTH: 819
<212> TYPE: PRT
<213> ORGANISM: S. pneumoniae

<400> SEQUENCE: 90

Cys Ser Tyr Glu Leu Gly Arg His Gln Ala Gly Gln Val Lys Lys Glu
1               5                   10                  15

Ser Asn Arg Val Ser Tyr Ile Asp Gly Asp Gln Ala Gly Gln Lys Ala
            20                  25                  30

Glu Asn Leu Thr Pro Asp Glu Val Ser Lys Arg Glu Gly Ile Asn Ala
        35                  40                  45

Glu Gln Ile Val Ile Lys Ile Thr Asp Gln Gly Tyr Val Thr Ser His
    50                  55                  60

Gly Asp His Tyr His Tyr Tyr Asn Gly Lys Val Pro Tyr Asp Ala Ile
65                  70                  75                  80

Ile Ser Glu Glu Leu Leu Met Lys Asp Pro Asn Tyr Gln Leu Lys Asp
                85                  90                  95

Ser Asp Ile Val Asn Glu Ile Lys Gly Gly Tyr Val Ile Lys Val Asp
            100                 105                 110

Gly Lys Tyr Tyr Val Tyr Leu Lys Asp Ala Ala His Ala Asp Asn Ile
        115                 120                 125

Arg Thr Lys Glu Glu Ile Lys Arg Gln Lys Gln Glu His Ser His Asn
    130                 135                 140

His Asn Ser Arg Ala Asp Asn Ala Val Ala Ala Ala Arg Ala Gln Gly
145                 150                 155                 160

Arg Tyr Thr Thr Asp Asp Gly Tyr Ile Phe Asn Ala Ser Asp Ile Ile
                165                 170                 175

Glu Asp Thr Gly Asp Ala Tyr Ile Val Pro His Gly Asp His Tyr His
            180                 185                 190

Tyr Ile Pro Lys Asn Glu Leu Ser Ala Ser Glu Leu Ala Ala Ala Glu
        195                 200                 205

Ala Tyr Trp Asn Gly Lys Gln Gly Ser Arg Pro Ser Ser Ser Ser Ser
    210                 215                 220
```

-continued

```
Tyr Asn Ala Asn Pro Val Gln Pro Arg Leu Ser Glu Asn His Asn Leu
225                 230                 235                 240

Thr Val Thr Pro Thr Tyr His Gln Asn Gln Gly Glu Asn Ile Ser Ser
            245                 250                 255

Leu Leu Arg Glu Leu Tyr Ala Lys Pro Leu Ser Glu Arg His Val Glu
                260                 265                 270

Ser Asp Gly Leu Ile Phe Asp Pro Ala Gln Ile Thr Ser Arg Thr Ala
            275                 280                 285

Arg Gly Val Ala Val Pro His Gly Asn His Tyr His Phe Ile Pro Tyr
        290                 295                 300

Glu Gln Met Ser Glu Leu Glu Lys Arg Ile Ala Arg Ile Ile Pro Leu
305                 310                 315                 320

Arg Tyr Arg Ser Asn His Trp Val Pro Asp Ser Arg Pro Glu Gln Pro
                325                 330                 335

Ser Pro Gln Ser Thr Pro Glu Pro Ser Pro Ser Leu Gln Pro Ala Pro
            340                 345                 350

Asn Pro Gln Pro Ala Pro Ser Asn Pro Ile Asp Glu Lys Leu Val Lys
        355                 360                 365

Glu Ala Val Arg Lys Val Gly Asp Gly Tyr Val Phe Glu Glu Asn Gly
370                 375                 380

Val Ser Arg Tyr Ile Pro Ala Lys Asp Leu Ser Ala Glu Thr Ala Ala
385                 390                 395                 400

Gly Ile Asp Ser Lys Leu Ala Lys Gln Glu Ser Leu Ser His Lys Leu
                405                 410                 415

Gly Ala Lys Lys Thr Asp Leu Pro Ser Ser Asp Arg Glu Phe Tyr Asn
            420                 425                 430

Lys Ala Tyr Asp Leu Leu Ala Arg Ile His Gln Asp Leu Leu Asp Asn
        435                 440                 445

Lys Gly Arg Gln Val Asp Phe Glu Val Leu Asp Asn Leu Leu Glu Arg
    450                 455                 460

Leu Lys Asp Val Ser Ser Asp Lys Val Lys Leu Val Asp Asp Ile Leu
465                 470                 475                 480

Ala Phe Leu Ala Pro Ile Arg His Pro Glu Arg Leu Gly Lys Pro Asn
                485                 490                 495

Ala Gln Ile Thr Tyr Thr Asp Asp Glu Ile Gln Val Ala Lys Leu Ala
            500                 505                 510

Gly Lys Tyr Thr Thr Glu Asp Gly Tyr Ile Phe Asp Pro Arg Asp Ile
        515                 520                 525

Thr Ser Asp Glu Gly Asp Ala Tyr Val Thr Pro His Met Thr His Ser
530                 535                 540

His Trp Ile Lys Lys Asp Ser Leu Ser Glu Ala Glu Arg Ala Ala Ala
545                 550                 555                 560

Gln Ala Tyr Ala Lys Glu Lys Gly Leu Thr Pro Pro Ser Thr Asp His
                565                 570                 575

Gln Asp Ser Gly Asn Thr Glu Ala Lys Gly Ala Glu Ala Ile Tyr Asn
            580                 585                 590

Arg Val Lys Ala Ala Lys Lys Val Pro Leu Asp Arg Met Pro Tyr Asn
        595                 600                 605

Leu Gln Tyr Thr Val Glu Val Lys Asn Gly Ser Leu Ile Ile Pro His
    610                 615                 620

Tyr Asp His Tyr His Asn Ile Lys Phe Glu Trp Phe Asp Glu Gly Leu
625                 630                 635                 640
```

```
Tyr Glu Ala Pro Lys Gly Tyr Ser Leu Glu Asp Leu Leu Ala Thr Val
                645                 650                 655

Lys Tyr Tyr Val Glu His Pro Asn Glu Arg Pro His Ser Asp Asn Gly
            660                 665                 670

Phe Gly Asn Ala Ser Asp His Val Arg Lys Asn Lys Ala Asp Gln Asp
            675                 680                 685

Ser Lys Pro Asp Glu Asp Lys Glu His Asp Glu Val Ser Glu Pro Thr
            690                 695                 700

His Pro Glu Ser Asp Glu Lys Glu Asn His Ala Gly Leu Asn Pro Ser
705                 710                 715                 720

Ala Asp Asn Leu Tyr Lys Pro Ser Thr Asp Thr Glu Thr Glu Glu
                725                 730                 735

Glu Ala Glu Asp Thr Thr Asp Glu Ala Glu Ile Pro Gln Val Glu Asn
            740                 745                 750

Ser Val Ile Asn Ala Lys Ile Ala Asp Ala Glu Ala Leu Leu Glu Lys
            755                 760                 765

Val Thr Asp Pro Ser Ile Arg Gln Asn Ala Met Glu Thr Leu Thr Gly
770                 775                 780

Leu Lys Ser Ser Leu Leu Leu Gly Thr Lys Asp Asn Asn Thr Ile Ser
785                 790                 795                 800

Ala Glu Val Asp Ser Leu Leu Ala Leu Leu Lys Glu Ser Gln Pro Ala
                805                 810                 815

Pro Ile Gln

<210> SEQ ID NO 91
<211> LENGTH: 820
<212> TYPE: PRT
<213> ORGANISM: S. pneumoniae

<400> SEQUENCE: 91

Cys Ser Tyr Glu Leu Gly Arg His Gln Ala Gly Gln Val Lys Lys Glu
1               5                   10                  15

Ser Asn Arg Val Ser Tyr Ile Asp Gly Asp Gln Ala Gly Gln Lys Ala
                20                  25                  30

Glu Asn Leu Thr Pro Asp Glu Val Ser Lys Arg Glu Gly Ile Asn Ala
            35                  40                  45

Glu Gln Ile Val Ile Lys Ile Thr Asp Gln Gly Tyr Val Thr Ser His
        50                  55                  60

Gly Asp His Tyr His Tyr Tyr Asn Gly Lys Val Pro Tyr Asp Ala Ile
65              70                  75                  80

Ile Ser Glu Glu Leu Leu Met Lys Asp Pro Asn Tyr Gln Leu Lys Asp
                85                  90                  95

Ser Asp Ile Val Asn Glu Ile Lys Gly Gly Tyr Val Ile Lys Val Asp
            100                 105                 110

Gly Lys Tyr Tyr Val Tyr Leu Lys Asp Ala Ala His Ala Asp Asn Ile
            115                 120                 125

Arg Thr Lys Glu Glu Ile Lys Arg Gln Lys Gln Glu His Ser His Asn
        130                 135                 140

His Gly Gly Gly Ser Asn Asp Gln Ala Val Val Ala Ala Arg Ala Gln
145                 150                 155                 160

Gly Arg Tyr Thr Thr Asp Asp Gly Tyr Ile Phe Asn Ala Ser Asp Ile
                165                 170                 175

Ile Glu Asp Thr Gly Asp Ala Tyr Ile Val Pro His Gly Asp His Tyr
            180                 185                 190
```

-continued

```
His Tyr Ile Pro Lys Asn Glu Leu Ser Ala Ser Glu Leu Ala Ala Ala
        195                 200                 205

Glu Ala Tyr Trp Asn Gly Lys Gln Gly Ser Arg Pro Ser Ser Ser Ser
    210                 215                 220

Ser Tyr Asn Ala Asn Pro Ala Gln Pro Arg Leu Ser Glu Asn His Asn
225                 230                 235                 240

Leu Thr Val Thr Pro Thr Tyr His Gln Asn Gln Gly Glu Asn Ile Ser
                245                 250                 255

Ser Leu Leu Arg Glu Leu Tyr Ala Lys Pro Leu Ser Glu Arg His Val
            260                 265                 270

Glu Ser Asp Gly Leu Ile Phe Asp Pro Ala Gln Ile Thr Ser Arg Thr
        275                 280                 285

Ala Arg Gly Val Ala Val Pro His Gly Asn His Tyr His Phe Ile Pro
    290                 295                 300

Tyr Glu Gln Met Ser Glu Leu Glu Lys Arg Ile Ala Arg Ile Ile Pro
305                 310                 315                 320

Leu Arg Tyr Arg Ser Asn His Trp Val Pro Asp Ser Arg Pro Glu Gln
                325                 330                 335

Pro Ser Pro Gln Ser Thr Pro Glu Pro Ser Pro Ser Gln Pro Ala
            340                 345                 350

Pro Asn Pro Gln Pro Ala Pro Ser Asn Pro Ile Asp Glu Lys Leu Val
        355                 360                 365

Lys Glu Ala Val Arg Lys Val Gly Asp Gly Tyr Val Phe Glu Glu Asn
    370                 375                 380

Gly Val Ser Arg Tyr Ile Pro Ala Lys Asp Leu Ser Ala Glu Thr Ala
385                 390                 395                 400

Ala Gly Ile Asp Ser Lys Leu Ala Lys Gln Glu Ser Leu Ser His Lys
                405                 410                 415

Leu Gly Ala Lys Lys Thr Asp Leu Pro Ser Ser Asp Arg Glu Phe Tyr
            420                 425                 430

Asn Lys Ala Tyr Asp Leu Leu Ala Arg Ile His Gln Asp Leu Leu Asp
        435                 440                 445

Asn Lys Gly Arg Gln Val Asp Phe Glu Ala Leu Asp Asn Leu Leu Glu
    450                 455                 460

Arg Leu Lys Asp Val Pro Ser Asp Lys Val Lys Leu Val Asp Asp Ile
465                 470                 475                 480

Leu Ala Phe Leu Ala Pro Ile Arg His Pro Glu Arg Leu Gly Lys Pro
                485                 490                 495

Asn Ala Gln Ile Thr Tyr Thr Asp Asp Glu Ile Gln Val Ala Lys Leu
            500                 505                 510

Ala Gly Lys Tyr Thr Thr Glu Asp Gly Tyr Ile Phe Asp Pro Arg Asp
        515                 520                 525

Ile Thr Ser Asp Glu Gly Asp Ala Tyr Val Thr Pro His Met Thr His
    530                 535                 540

Ser His Trp Ile Lys Lys Asp Ser Leu Ser Glu Ala Glu Arg Ala Ala
545                 550                 555                 560

Ala Gln Ala Tyr Ala Lys Glu Lys Gly Leu Thr Pro Pro Ser Thr Asp
                565                 570                 575

His Gln Asp Ser Gly Asn Thr Glu Ala Lys Gly Ala Glu Ala Ile Tyr
            580                 585                 590

Asn Arg Val Lys Ala Ala Lys Lys Val Pro Leu Asp Arg Met Pro Tyr
        595                 600                 605

Asn Leu Gln Tyr Thr Val Glu Val Lys Asn Gly Ser Leu Ile Ile Pro
```

```
            610                 615                 620
His Tyr Asp His Tyr His Asn Ile Lys Phe Glu Trp Phe Asp Glu Gly
625                 630                 635                 640

Leu Tyr Glu Ala Pro Lys Gly Tyr Thr Leu Glu Asp Leu Leu Ala Thr
                645                 650                 655

Val Lys Tyr Tyr Val Glu His Pro Asn Glu Arg Pro His Ser Asp Asn
                660                 665                 670

Gly Phe Gly Asn Ala Ser Asp His Val Arg Lys Asn Lys Val Asp Gln
                675                 680                 685

Asp Ser Lys Pro Asp Glu Asp Lys Glu His Asp Glu Val Ser Glu Pro
690                 695                 700

Thr His Pro Glu Ser Asp Glu Lys Glu Asn His Ala Gly Leu Asn Pro
705                 710                 715                 720

Ser Ala Asp Asn Leu Tyr Lys Pro Ser Thr Asp Thr Glu Glu Thr Glu
                725                 730                 735

Glu Glu Ala Glu Asp Thr Thr Asp Glu Ala Ile Pro Gln Val Glu
                740                 745                 750

Asn Ser Val Ile Asn Ala Lys Ile Ala Asp Ala Glu Ala Leu Leu Glu
                755                 760                 765

Lys Val Thr Asp Pro Ser Ile Arg Gln Asn Ala Met Glu Thr Leu Thr
                770                 775                 780

Gly Leu Lys Ser Ser Leu Leu Gly Thr Lys Asp Asn Asn Thr Ile
785                 790                 795                 800

Ser Ala Glu Val Asp Ser Leu Leu Ala Leu Leu Lys Glu Ser Gln Pro
                805                 810                 815

Ala Pro Ile Gln
            820

<210> SEQ ID NO 92
<211> LENGTH: 816
<212> TYPE: PRT
<213> ORGANISM: S. pneumoniae

<400> SEQUENCE: 92

Cys Ser Tyr Glu Leu Gly Arg His Gln Ala Gly Gln Asp Lys Lys Glu
1               5                   10                  15

Ser Asn Arg Val Ala Tyr Ile Asp Gly Asp Gln Ala Gly Gln Lys Ala
                20                  25                  30

Glu Asn Leu Thr Pro Asp Glu Val Ser Lys Arg Glu Gly Ile Asn Ala
                35                  40                  45

Glu Gln Ile Val Ile Lys Ile Thr Asp Gln Gly Tyr Val Thr Ser His
            50                  55                  60

Gly Asp His Tyr His Tyr Tyr Asn Gly Lys Val Pro Tyr Asp Ala Ile
65                  70                  75                  80

Ile Ser Glu Glu Leu Leu Met Lys Asp Pro Asn Tyr Gln Leu Lys Asp
                85                  90                  95

Ser Asp Ile Val Asn Glu Ile Lys Gly Gly Tyr Val Ile Lys Val Asn
                100                 105                 110

Gly Lys Tyr Tyr Val Tyr Leu Lys Asp Ala Ala His Ala Asp Asn Ile
            115                 120                 125

Arg Thr Lys Glu Glu Ile Lys Arg Gln Lys Gln Glu His Ser His Asn
        130                 135                 140

His Gly Gly Gly Ser Asn Asp Gln Ala Val Val Ala Ala Arg Ala Gln
145                 150                 155                 160
```

-continued

```
Gly Arg Tyr Thr Thr Asp Asp Gly Tyr Ile Phe Asn Ala Ser Asp Ile
                165                 170                 175

Ile Glu Asp Thr Gly Asp Ala Tyr Ile Val Pro His Gly Asn His Phe
            180                 185                 190

His Tyr Ile Pro Lys Ser Asp Leu Ser Ala Ser Glu Leu Ala Ala Ala
        195                 200                 205

Gln Ala Tyr Trp Asn Gly Lys Gln Gly Ser Arg Pro Ser Ser Ser Ser
    210                 215                 220

Ser His Asn Ala Asn Pro Ala Gln Pro Arg Leu Ser Glu Asn His Asn
225                 230                 235                 240

Leu Thr Val Thr Pro Thr Tyr His Gln Asn Gln Gly Glu Asn Ile Ser
                245                 250                 255

Ser Leu Leu Arg Glu Leu Tyr Ala Lys Pro Leu Ser Glu Arg His Val
            260                 265                 270

Glu Ser Asp Gly Leu Ile Phe Asp Pro Ala Gln Ile Thr Ser Arg Thr
        275                 280                 285

Ala Arg Gly Val Ala Val Pro His Gly Asn His Tyr His Phe Ile Pro
    290                 295                 300

Tyr Glu Gln Met Ser Glu Leu Glu Glu Arg Ile Ala Arg Ile Ile Pro
305                 310                 315                 320

Leu Arg Tyr Arg Ser Asn His Trp Val Pro Asp Ser Arg Pro Glu Gln
                325                 330                 335

Pro Ser Pro Gln Pro Ser Pro Ser Pro Gln Pro Ala Pro Asn Pro Gln
            340                 345                 350

Pro Ala Pro Ser Asn Pro Ile Asp Glu Lys Leu Val Lys Glu Ala Val
        355                 360                 365

Arg Lys Val Gly Asp Gly Tyr Val Phe Glu Glu Asn Gly Val Ser Arg
    370                 375                 380

Tyr Ile Pro Ala Lys Asp Leu Ser Ala Glu Thr Ala Ala Gly Ile Asp
385                 390                 395                 400

Ser Lys Leu Ala Lys Gln Glu Ser Leu Ser His Lys Leu Gly Thr Lys
                405                 410                 415

Lys Thr Asp Leu Pro Ser Ser Asp Arg Glu Phe Tyr Asn Lys Ala Tyr
            420                 425                 430

Asp Leu Leu Ala Arg Ile His Gln Asp Leu Leu Asp Asn Lys Gly Arg
        435                 440                 445

Gln Val Asp Phe Glu Ala Leu Asp Asn Leu Leu Glu Arg Leu Lys Asp
    450                 455                 460

Val Ser Ser Asp Lys Val Lys Leu Val Glu Asp Ile Leu Ala Phe Leu
465                 470                 475                 480

Ala Pro Ile Arg His Pro Glu Arg Leu Gly Lys Pro Asn Ser Gln Ile
                485                 490                 495

Thr Tyr Thr Asp Asp Glu Ile Gln Val Ala Lys Leu Ala Gly Lys Tyr
            500                 505                 510

Thr Thr Glu Asp Gly Tyr Ile Phe Asp Pro Arg Asp Ile Thr Ser Asp
        515                 520                 525

Glu Gly Asp Ala Tyr Val Thr Pro His Met Thr His Ser His Trp Ile
    530                 535                 540

Lys Lys Asp Ser Leu Ser Glu Ala Glu Arg Ala Ala Gln Ala Tyr
545                 550                 555                 560

Ala Lys Glu Lys Gly Leu Thr Pro Pro Ser Thr Asp His Arg Asp Ser
                565                 570                 575

Gly Asn Thr Glu Ala Lys Gly Ala Glu Ala Ile Tyr Asn Arg Val Lys
```

```
            580                 585                 590
Ala Ala Lys Lys Val Pro Leu Asp Arg Met Pro Tyr Asn Leu Gln Tyr
            595                 600                 605

Thr Val Glu Val Lys Asn Gly Ser Leu Ile Ile Pro His Tyr Asp His
            610                 615                 620

Tyr His Asn Ile Lys Phe Glu Trp Phe Asp Glu Gly Leu Tyr Glu Ala
625                 630                 635                 640

Pro Lys Gly Tyr Thr Leu Glu Asp Leu Leu Ala Thr Val Lys Tyr Tyr
                645                 650                 655

Val Glu His Pro Asn Glu Arg Pro His Ser Asp Asn Gly Phe Gly Asn
            660                 665                 670

Ala Ser Asp His Val Arg Lys Asn Lys Ala Asp Gln Asp Ser Lys Pro
            675                 680                 685

Asp Glu Asp Lys Gly His Asp Glu Val Ser Glu Pro Thr His Pro Glu
            690                 695                 700

Ser Asp Glu Lys Glu Asn His Ala Gly Leu Asn Pro Ser Ala Asp Asn
705                 710                 715                 720

Leu Tyr Lys Pro Ser Thr Asp Thr Glu Glu Thr Glu Glu Glu Ala Glu
                725                 730                 735

Asp Thr Thr Asp Glu Ala Glu Ile Pro Gln Val Glu His Ser Val Ile
            740                 745                 750

Asn Ala Lys Ile Ala Asp Ala Glu Ala Leu Leu Glu Lys Val Thr Asp
            755                 760                 765

Pro Ser Ile Arg Gln Asn Ala Met Glu Thr Leu Thr Gly Leu Lys Ser
            770                 775                 780

Ser Leu Leu Leu Gly Thr Lys Asp Asn Asn Thr Ile Ser Ala Glu Val
785                 790                 795                 800

Asp Ser Leu Leu Ala Leu Leu Lys Lys Ser Gln Pro Ala Pro Ile Gln
                805                 810                 815

<210> SEQ ID NO 93
<211> LENGTH: 816
<212> TYPE: PRT
<213> ORGANISM: S. pneumoniae

<400> SEQUENCE: 93

Cys Ser Tyr Glu Leu Gly Arg His Gln Ala Gly Gln Asp Lys Lys Glu
 1               5                  10                  15

Ser Asn Arg Val Ala Tyr Ile Asp Gly Asp Gln Ala Gly Gln Lys Ala
            20                  25                  30

Glu Asn Leu Thr Pro Asp Glu Val Ser Lys Arg Glu Gly Ile Asn Ala
        35                  40                  45

Glu Gln Ile Val Ile Lys Ile Thr Asp Gln Gly Tyr Val Thr Ser His
    50                  55                  60

Gly Asp His Tyr His Tyr Tyr Asn Gly Lys Val Pro Tyr Asp Ala Ile
65                  70                  75                  80

Ile Ser Glu Glu Leu Leu Met Lys Asp Pro Asn Tyr Gln Leu Lys Asp
                85                  90                  95

Ser Asp Ile Val Asn Glu Ile Lys Gly Gly Tyr Val Ile Lys Val Asn
            100                 105                 110

Gly Lys Tyr Tyr Val Tyr Leu Lys Asp Ala Ala His Ala Asp Asn Ile
        115                 120                 125

Arg Thr Lys Glu Glu Ile Lys Arg Gln Arg Gln Glu His Ser His Asn
    130                 135                 140
```

-continued

```
His Gly Gly Gly Ser Asn Asp Gln Ala Val Val Ala Ala Arg Ala Gln
145                 150                 155                 160

Gly Arg Tyr Thr Thr Asp Asp Gly Tyr Ile Phe Asn Ala Ser Asp Ile
                165                 170                 175

Ile Glu Asp Thr Gly Asp Ala Tyr Ile Val Pro His Gly Asn His Phe
            180                 185                 190

His Tyr Ile Pro Lys Ser Asp Leu Ser Ala Ser Glu Leu Ala Ala Ala
        195                 200                 205

Gln Ala Tyr Trp Asn Gly Lys Gln Gly Ser Arg Pro Ser Ser Ser Ser
210                 215                 220

Ser His Asn Ala Asn Pro Ala Gln Pro Arg Leu Ser Glu Asn His Asn
225                 230                 235                 240

Leu Thr Val Thr Pro Thr Tyr His Gln Asn Gln Gly Glu Asn Ile Ser
                245                 250                 255

Ser Leu Leu Arg Glu Leu Tyr Ala Lys Pro Leu Ser Glu Arg His Val
            260                 265                 270

Glu Ser Asp Gly Leu Ile Phe Asp Pro Ala Gln Ile Thr Ser Arg Thr
        275                 280                 285

Ala Arg Gly Val Ala Val Pro His Gly Asn His Tyr His Phe Ile Pro
290                 295                 300

Tyr Glu Gln Met Ser Glu Leu Glu Arg Ile Ala Arg Ile Pro
305                 310                 315                 320

Leu Arg Tyr Arg Ser Asn His Trp Val Pro Asp Ser Arg Pro Glu Gln
                325                 330                 335

Pro Ser Pro Gln Pro Ser Pro Ser Pro Gln Pro Ala Pro Asn Pro Gln
            340                 345                 350

Pro Ala Pro Ser Asn Pro Ile Asp Glu Lys Leu Val Lys Glu Ala Val
        355                 360                 365

Arg Lys Val Gly Asp Gly Tyr Val Phe Glu Glu Asn Gly Val Ser Arg
370                 375                 380

Tyr Ile Pro Ala Lys Asp Leu Ser Ala Glu Thr Ala Ala Gly Ile Asp
385                 390                 395                 400

Ser Lys Leu Ala Lys Gln Glu Ser Leu Ser His Lys Leu Gly Thr Lys
                405                 410                 415

Lys Thr Asp Leu Pro Ser Ser Asp Arg Glu Phe Tyr Asn Lys Ala Tyr
            420                 425                 430

Asp Leu Leu Ala Arg Ile His Gln Asp Leu Leu Asp Asn Lys Gly Arg
        435                 440                 445

Gln Val Asp Phe Glu Ala Leu Asp Asn Leu Leu Glu Arg Leu Lys Asp
450                 455                 460

Val Ser Ser Asp Lys Val Lys Leu Val Glu Asp Ile Leu Ala Phe Leu
465                 470                 475                 480

Ala Pro Ile Arg His Pro Glu Arg Leu Gly Lys Pro Asn Ser Gln Ile
                485                 490                 495

Thr Tyr Thr Asp Asp Glu Ile Gln Val Ala Lys Leu Ala Gly Lys Tyr
            500                 505                 510

Thr Thr Glu Asp Gly Tyr Ile Phe Asp Pro Arg Asp Ile Thr Ser Asp
        515                 520                 525

Glu Gly Asp Ala Tyr Val Thr Pro His Met Thr His Ser His Trp Ile
530                 535                 540

Lys Lys Asp Ser Leu Ser Glu Ala Glu Arg Ala Ala Gln Ala Tyr
545                 550                 555                 560

Ala Lys Glu Lys Gly Leu Thr Pro Pro Ser Thr Asp His Gln Asp Ser
```

```
                         565                 570                 575
Gly Asn Thr Glu Ala Lys Gly Ala Glu Ala Ile Tyr Asn Arg Val Lys
            580                 585                 590

Ala Ala Lys Lys Val Pro Leu Asp Arg Met Pro Tyr Asn Leu Gln Tyr
            595                 600                 605

Thr Val Glu Val Lys Asn Gly Ser Leu Ile Ile Pro His Tyr Asp His
            610                 615                 620

Tyr His Asn Ile Lys Phe Glu Trp Phe Asp Glu Gly Leu Tyr Glu Ala
625                 630                 635                 640

Pro Lys Gly Tyr Thr Leu Glu Asp Leu Leu Ala Thr Val Lys Tyr Tyr
                645                 650                 655

Val Glu His Pro Asn Glu Arg Pro His Ser Asp Asn Gly Phe Gly Asn
            660                 665                 670

Ala Ser Asp His Val Arg Lys Asn Lys Ala Asp Gln Asp Ser Lys Pro
            675                 680                 685

Asp Glu Asp Lys Gly His Asp Glu Val Ser Glu Pro Thr His Pro Glu
            690                 695                 700

Ser Asp Glu Lys Glu Asn His Ala Gly Leu Asn Pro Ser Ala Asp Asn
705                 710                 715                 720

Leu Tyr Lys Pro Ser Thr Asp Thr Glu Glu Thr Glu Glu Glu Ala Glu
                725                 730                 735

Asp Thr Thr Asp Glu Ala Glu Ile Pro Gln Val Glu His Ser Val Ile
            740                 745                 750

Asn Ala Lys Ile Ala Asp Ala Glu Ala Leu Leu Glu Lys Val Thr Asp
            755                 760                 765

Pro Ser Ile Arg Gln Asn Ala Met Glu Thr Leu Thr Gly Leu Lys Ser
            770                 775                 780

Ser Leu Leu Leu Gly Thr Lys Asp Asn Asn Thr Ile Ser Ala Glu Val
785                 790                 795                 800

Asp Ser Leu Leu Ala Leu Leu Lys Lys Ser Gln Pro Ala Pro Ile Gln
                805                 810                 815

<210> SEQ ID NO 94
<211> LENGTH: 816
<212> TYPE: PRT
<213> ORGANISM: S. pneumoniae

<400> SEQUENCE: 94

Cys Ser Tyr Glu Leu Gly Arg His Gln Ala Gly Gln Asp Lys Lys Glu
1               5                   10                  15

Ser Asn Arg Val Ala Tyr Ile Asp Gly Asp Gln Ala Gly Gln Lys Ala
            20                  25                  30

Glu Asn Leu Thr Pro Asp Glu Val Ser Lys Arg Glu Gly Ile Asn Ala
        35                  40                  45

Glu Gln Ile Val Ile Lys Ile Thr Asp Gln Gly Tyr Val Thr Ser His
    50                  55                  60

Gly Asp His Tyr His Tyr Tyr Asn Gly Lys Val Pro Tyr Asp Ala Ile
65                  70                  75                  80

Ile Ser Glu Glu Leu Leu Met Lys Asp Pro Asn Tyr Gln Leu Lys Asp
                85                  90                  95

Ser Asp Ile Val Asn Glu Ile Lys Gly Gly Tyr Val Ile Lys Val Asn
            100                 105                 110

Gly Lys Tyr Tyr Val Tyr Leu Lys Asp Ala Ala His Ala Asp Asn Ile
        115                 120                 125
```

```
Arg Thr Lys Glu Glu Ile Lys Arg Gln Lys Gln Glu His Ser His Asn
    130                 135                 140

His Gly Gly Gly Ser Asn Asp Gln Ala Val Val Ala Ala Arg Ala Gln
145                 150                 155                 160

Gly Arg Tyr Thr Thr Asp Asp Gly Tyr Ile Phe Asn Ala Ser Asp Ile
                165                 170                 175

Ile Glu Asp Thr Gly Asp Ala Tyr Ile Val Pro Arg Gly Asn His Phe
                180                 185                 190

His Tyr Ile Pro Lys Ser Asp Leu Ser Ala Ser Glu Leu Ala Ala Ala
                195                 200                 205

Gln Ala Tyr Trp Asn Gly Lys Gln Gly Ser Arg Pro Ser Ser Ser Ser
    210                 215                 220

Ser His Asn Ala Asn Pro Ala Gln Pro Arg Leu Ser Glu Asn His Asn
225                 230                 235                 240

Leu Thr Val Thr Pro Thr Tyr His Gln Asn Gln Gly Glu Asn Ile Ser
                245                 250                 255

Ser Leu Leu Arg Glu Leu Tyr Ala Lys Pro Leu Ser Glu Arg Arg Val
                260                 265                 270

Glu Ser Asp Gly Leu Ile Phe Asp Pro Ala Gln Ile Thr Ser Arg Thr
    275                 280                 285

Ala Arg Gly Val Ala Val Pro His Gly Asn His Tyr His Phe Ile Pro
    290                 295                 300

Tyr Glu Gln Met Ser Glu Leu Glu Arg Ile Ala Arg Ile Ile Pro
305                 310                 315                 320

Leu Arg Tyr Arg Ser Asn His Trp Val Pro Asp Ser Arg Pro Glu Gln
                325                 330                 335

Pro Ser Pro Gln Pro Ser Pro Ser Pro Gln Pro Ala Pro Asn Pro Gln
                340                 345                 350

Pro Ala Pro Ser Asn Pro Ile Asp Glu Lys Leu Val Lys Glu Ala Val
                355                 360                 365

Arg Lys Val Gly Asp Gly Tyr Val Phe Glu Glu Asn Gly Val Ser Arg
    370                 375                 380

Tyr Ile Pro Ala Lys Asp Leu Ser Ala Glu Thr Ala Ala Gly Ile Asp
385                 390                 395                 400

Ser Lys Leu Ala Lys Gln Glu Ser Leu Ser His Lys Leu Gly Thr Lys
                405                 410                 415

Lys Thr Asp Leu Pro Ser Ser Asp Arg Glu Phe Tyr Asn Lys Ala Tyr
                420                 425                 430

Asp Leu Leu Ala Arg Ile His Gln Asp Leu Leu Asp Asn Lys Gly Arg
                435                 440                 445

Gln Val Asp Phe Glu Ala Leu Asp Asn Leu Leu Glu Arg Leu Lys Asp
    450                 455                 460

Val Ser Ser Asp Lys Val Lys Leu Val Glu Asp Ile Leu Ala Phe Leu
465                 470                 475                 480

Ala Pro Ile Arg His Pro Glu Arg Leu Gly Lys Pro Asn Ser Gln Ile
                485                 490                 495

Thr Tyr Thr Asp Asp Glu Ile Gln Val Ala Lys Leu Ala Gly Lys Tyr
                500                 505                 510

Thr Thr Glu Asp Gly Tyr Ile Phe Asp Pro Arg Asp Ile Thr Ser Asp
                515                 520                 525

Glu Gly Asp Ala Tyr Val Thr Pro His Met Thr His Ser His Trp Ile
    530                 535                 540

Lys Lys Asp Ser Leu Ser Glu Ala Glu Arg Ala Ala Ala Gln Ala Tyr
```

```
                545                 550                 555                 560
Ala Lys Glu Lys Gly Leu Thr Pro Pro Ser Thr Asp His Gln Asp Ser
                    565                 570                 575
Gly Asn Thr Glu Ala Lys Gly Ala Glu Ala Ile Tyr Asn Arg Val Lys
                580                 585                 590
Ala Ala Lys Lys Val Pro Leu Asp Arg Met Pro Tyr Asn Leu Gln Tyr
                595                 600                 605
Thr Val Glu Val Lys Asn Gly Ser Leu Ile Ile Pro His Tyr Asp His
            610                 615                 620
Tyr His Asn Ile Lys Phe Glu Trp Phe Asp Glu Gly Leu Tyr Glu Ala
625                 630                 635                 640
Pro Lys Gly Tyr Thr Leu Glu Asp Leu Leu Ala Thr Val Lys Tyr Tyr
                    645                 650                 655
Val Glu His Pro Asn Glu Arg Pro His Ser Asp Asn Gly Phe Gly Asn
                660                 665                 670
Ala Ser Asp His Val Arg Lys Asn Lys Ala Asp Gln Asp Ser Lys Pro
            675                 680                 685
Asp Glu Asp Lys Gly His Asp Glu Val Ser Glu Pro Thr His Pro Glu
        690                 695                 700
Ser Asp Glu Lys Glu Asn His Ala Gly Leu Asn Pro Ser Ala Asp Asn
705                 710                 715                 720
Leu Tyr Lys Pro Ser Thr Asp Thr Glu Glu Thr Glu Glu Glu Ala Glu
                    725                 730                 735
Asp Thr Thr Asp Glu Ala Glu Ile Pro Gln Val Glu His Ser Val Ile
                740                 745                 750
Asn Ala Lys Ile Ala Asp Ala Glu Ala Leu Leu Glu Lys Val Thr Asp
            755                 760                 765
Pro Ser Ile Arg Gln Asn Ala Met Glu Thr Leu Thr Gly Leu Lys Ser
        770                 775                 780
Ser Leu Leu Leu Gly Thr Lys Asp Asn Asn Thr Ile Ser Ala Glu Val
785                 790                 795                 800
Asp Ser Leu Leu Ala Leu Leu Lys Lys Ser Gln Pro Ala Pro Ile Gln
                    805                 810                 815

<210> SEQ ID NO 95
<211> LENGTH: 834
<212> TYPE: PRT
<213> ORGANISM: S. pneumoniae

<400> SEQUENCE: 95

Cys Ser Tyr Glu Leu Gly Arg His Gln Ala Gly Gln Val Lys Lys Glu
1               5                   10                  15
Ser Asn Arg Val Ser Tyr Ile Asp Gly Asp Gln Ala Gly Gln Lys Ala
                20                  25                  30
Glu Asn Leu Thr Pro Asp Glu Val Ser Lys Arg Glu Gly Ile Asn Ala
            35                  40                  45
Glu Gln Ile Val Ile Lys Ile Thr Asp Gln Gly Tyr Val Thr Ser His
        50                  55                  60
Gly Asp His Tyr His Tyr Tyr Asn Gly Lys Val Pro Tyr Asp Ala Ile
65                  70                  75                  80
Ile Ser Glu Glu Leu Leu Met Lys Asp Pro Asn Tyr Gln Leu Lys Asp
                    85                  90                  95
Ser Asp Ile Val Asn Glu Ile Lys Gly Gly Tyr Val Ile Lys Val Asp
                100                 105                 110
```

-continued

```
Gly Lys Tyr Tyr Val Tyr Leu Lys Asp Ala Ala His Ala Asp Asn Ile
        115                 120                 125

Arg Thr Lys Glu Glu Ile Lys Arg Gln Lys Gln Glu Arg Ser His Asn
130                 135                 140

His Asn Ser Arg Ala Asp Asn Ala Val Ala Ala Arg Ala Gln Gly
145                 150                 155                 160

Arg Tyr Thr Thr Asp Asp Gly Tyr Ile Phe Asn Ala Ser Asp Ile Ile
                165                 170                 175

Glu Asp Thr Gly Asp Ala Tyr Ile Val Pro His Gly Asp His Tyr His
            180                 185                 190

Tyr Ile Pro Lys Ser Asp Leu Ser Ala Ser Glu Leu Ala Ala Ala Gln
        195                 200                 205

Ala Tyr Trp Asn Gly Lys Gln Gly Ser Arg Pro Ser Ser Ser Ser
    210                 215                 220

His Asn Ala Asn Pro Ala Gln Pro Arg Leu Ser Glu Asn His Asn Leu
225                 230                 235                 240

Thr Val Thr Pro Thr Tyr His Gln Asn Gln Gly Glu Asn Ile Ser Ser
                245                 250                 255

Leu Leu Arg Glu Leu Tyr Ala Lys Pro Leu Ser Glu Arg His Val Glu
            260                 265                 270

Ser Asp Gly Leu Ile Phe Asp Pro Ala Gln Ile Thr Ser Arg Thr Ala
        275                 280                 285

Asn Gly Val Ala Val Pro His Gly Asp His Tyr His Phe Ile Pro Tyr
    290                 295                 300

Ser Gln Leu Ser Pro Leu Glu Glu Lys Leu Ala Arg Ile Ile Pro Leu
305                 310                 315                 320

Arg Tyr Arg Ser Asn His Trp Val Pro Asp Ser Arg Pro Glu Gln Pro
                325                 330                 335

Ser Pro Gln Ser Thr Pro Glu Pro Ser Pro Ser Pro Gln Pro Ala Pro
            340                 345                 350

Asn Pro Gln Pro Ala Pro Ser Asn Pro Ile Asp Glu Lys Leu Val Lys
        355                 360                 365

Glu Ala Val Arg Lys Val Gly Asp Gly Tyr Val Phe Glu Glu Asn Gly
    370                 375                 380

Val Pro Arg Tyr Ile Pro Ala Lys Asp Leu Ser Ala Glu Thr Ala Ala
385                 390                 395                 400

Gly Ile Asp Ser Lys Leu Ala Lys Gln Glu Ser Leu Ser His Lys Leu
                405                 410                 415

Gly Ala Lys Lys Thr Asp Leu Pro Ser Ser Asp Arg Glu Phe Tyr Asn
            420                 425                 430

Lys Ala Tyr Asp Leu Leu Ala Arg Ile His Gln Asp Leu Leu Asp Asn
        435                 440                 445

Lys Gly Arg Gln Val Asp Phe Glu Ala Leu Asp Asn Leu Leu Glu Arg
    450                 455                 460

Leu Lys Asp Val Ser Ser Asp Lys Val Lys Leu Val Asp Asp Ile Leu
465                 470                 475                 480

Ala Phe Leu Ala Pro Ile Arg His Pro Glu Arg Leu Gly Lys Pro Asn
                485                 490                 495

Ala Gln Ile Thr Tyr Thr Asp Glu Ile Gln Val Ala Lys Leu Ala
            500                 505                 510

Gly Lys Tyr Thr Thr Glu Asp Gly Tyr Ile Phe Asp Pro Arg Asp Ile
        515                 520                 525

Thr Ser Asp Glu Gly Asp Ala Tyr Val Thr Pro His Met Thr His Ser
```

```
                530             535             540
His Trp Ile Lys Lys Asp Ser Leu Ser Glu Ala Glu Arg Ala Ala Ala
545                 550                 555                 560

Gln Ala Tyr Ala Lys Glu Lys Gly Leu Thr Pro Pro Ser Thr Asp His
                565                 570                 575

Gln Asp Ser Gly Asn Thr Glu Ala Lys Gly Ala Glu Ala Ile Tyr Asn
                580                 585                 590

Arg Val Lys Ala Ala Lys Val Pro Leu Asp Arg Met Pro Tyr Asn
                595                 600                 605

Leu Gln Tyr Thr Val Glu Val Lys Asn Gly Ser Leu Ile Ile Pro His
610                 615                 620

Tyr Asp His Tyr His Asn Ile Lys Phe Glu Trp Phe Asp Glu Gly Leu
625                 630                 635                 640

Tyr Glu Ala Pro Lys Gly Tyr Ser Leu Glu Asp Leu Leu Ala Thr Val
                645                 650                 655

Lys Tyr Tyr Val Glu His Pro Asn Glu Arg Pro His Ser Asp Asn Gly
                660                 665                 670

Phe Gly Asn Ala Ser Asp His Val Gln Arg Asn Lys Asn Gly Gln Ala
                675                 680                 685

Asp Thr Asn Gln Thr Glu Lys Pro Asn Glu Glu Lys Pro Gln Thr Glu
                690                 695                 700

Lys Pro Glu Glu Asp Lys Glu His Asp Glu Val Ser Glu Pro Thr His
705                 710                 715                 720

Pro Glu Ser Asp Glu Lys Glu Asn His Val Gly Leu Asn Pro Ser Ala
                725                 730                 735

Asp Asn Leu Tyr Lys Pro Ser Thr Asp Thr Glu Glu Thr Glu Glu Glu
                740                 745                 750

Ala Glu Asp Thr Thr Asp Glu Ala Glu Ile Pro Gln Val Glu Tyr Ser
                755                 760                 765

Val Ile Asn Ala Lys Ile Ala Glu Ala Glu Ala Leu Leu Glu Lys Val
                770                 775                 780

Thr Asp Ser Ser Ile Arg Gln Asn Ala Val Glu Thr Leu Thr Gly Leu
785                 790                 795                 800

Lys Ser Ser Leu Leu Leu Gly Thr Lys Asp Asn Asn Thr Ile Ser Ala
                805                 810                 815

Glu Val Asp Ser Leu Leu Ala Leu Leu Lys Glu Ser Gln Pro Ala Pro
                820                 825                 830

Ile Gln

<210> SEQ ID NO 96
<211> LENGTH: 811
<212> TYPE: PRT
<213> ORGANISM: S. pneumoniae

<400> SEQUENCE: 96

Cys Ser Tyr Glu Leu Gly Arg His Gln Ala Gly Gln Asp Lys Lys Glu
1               5                   10                  15

Ser Asn Arg Val Ala Tyr Ile Asp Gly Asp Gln Ala Gly Gln Lys Ala
                20                  25                  30

Glu Asn Leu Thr Pro Asp Glu Val Ser Lys Arg Glu Gly Ile Asn Ala
                35                  40                  45

Glu Gln Ile Val Ile Lys Ile Thr Asp Gln Gly Tyr Val Thr Ser His
                50                  55                  60

Gly Asp His Tyr His Tyr Tyr Asn Gly Lys Val Pro Tyr Asp Ala Ile
```

-continued

```
            65                  70                  75                  80
Ile Ser Glu Glu Leu Leu Met Lys Asp Pro Asn Tyr Gln Leu Lys Asp
                    85                  90                  95
Ser Asp Ile Val Asn Glu Ile Lys Gly Gly Tyr Val Ile Lys Val Asn
                100                 105                 110
Gly Lys Tyr Tyr Val Tyr Leu Lys Asp Ala Ala His Ala Asp Asn Ile
            115                 120                 125
Arg Thr Lys Glu Glu Ile Lys Arg Gln Lys Gln Glu His Ser His Asn
        130                 135                 140
His Gly Gly Gly Ser Asn Asp Gln Ala Val Ala Ala Arg Ala Gln
145                 150                 155                 160
Gly Arg Tyr Thr Thr Asp Asp Gly Tyr Ile Phe Asn Ala Ser Asp Ile
                165                 170                 175
Ile Glu Asp Thr Gly Asp Ala Tyr Ile Val Pro His Gly Asn His Phe
                180                 185                 190
His Tyr Ile Pro Lys Ser Asp Leu Ser Ala Ser Glu Leu Ala Ala Ala
            195                 200                 205
Gln Ala Tyr Trp Asn Gly Lys Gln Gly Ser Arg Pro Ser Ser Ser Ser
        210                 215                 220
Ser His Asn Ala Asn Pro Ala Gln Pro Arg Leu Ser Glu Asn His Asn
225                 230                 235                 240
Leu Thr Val Thr Pro Thr Tyr His Gln Asn Gln Gly Glu Asn Ile Ser
                245                 250                 255
Ser Leu Leu Arg Glu Leu Tyr Ala Lys Pro Leu Ser Glu Arg His Val
                260                 265                 270
Glu Ser Asp Gly Leu Ile Phe Asp Pro Ala Gln Ile Thr Ser Arg Thr
            275                 280                 285
Ala Arg Gly Val Ala Val Pro His Gly Asn His Tyr His Phe Ile Pro
        290                 295                 300
Tyr Glu Gln Met Ser Glu Leu Glu Glu Arg Ile Ala Arg Ile Ile Pro
305                 310                 315                 320
Leu Arg Tyr Arg Ser Asn His Trp Val Pro Asp Ser Arg Pro Glu Gln
                325                 330                 335
Pro Ser Pro Gln Pro Ser Pro Ser Pro Gln Pro Ala Pro Asn Pro Gln
                340                 345                 350
Pro Ala Pro Ser Asn Pro Ile Asp Glu Lys Leu Val Lys Glu Ala Val
            355                 360                 365
Arg Lys Val Gly Asp Gly Tyr Val Phe Glu Glu Asn Gly Val Ser Arg
        370                 375                 380
Tyr Ile Pro Ala Lys Asp Leu Ser Ala Glu Thr Ala Ala Gly Ile Asp
385                 390                 395                 400
Ser Lys Leu Ala Lys Gln Glu Ser Leu Ser His Lys Leu Gly Thr Lys
                405                 410                 415
Lys Thr Asp Leu Pro Ser Ser Asp Arg Glu Phe Tyr Asn Lys Ala Tyr
                420                 425                 430
Asp Leu Leu Ala Arg Ile His Gln Asp Leu Leu Asp Asn Lys Gly Arg
            435                 440                 445
Gln Val Asp Phe Glu Ala Leu Asp Asn Leu Leu Glu Arg Leu Lys Asp
        450                 455                 460
Val Ser Ser Asp Lys Val Lys Leu Val Glu Asp Ile Leu Ala Phe Leu
465                 470                 475                 480
Ala Pro Ile Arg His Pro Glu Arg Leu Gly Lys Pro Asn Ser Gln Ile
                485                 490                 495
```

-continued

Thr Tyr Thr Asp Asp Glu Ile Gln Val Ala Lys Leu Ala Gly Lys Tyr
             500                 505                 510

Thr Thr Glu Asp Gly Tyr Ile Phe Asp Pro Arg Asp Ile Thr Ser Asp
             515                 520                 525

Glu Gly Asp Ala Tyr Val Thr Pro His Met Thr His Ser His Trp Ile
             530                 535                 540

Lys Lys Asp Ser Leu Ser Glu Ala Glu Arg Ala Ala Gln Ala Tyr
545                 550                 555                 560

Ala Lys Glu Lys Gly Leu Thr Pro Pro Ser Thr Asp His Gln Asp Ser
             565                 570                 575

Gly Asn Thr Glu Ala Lys Gly Ala Glu Ala Ile Tyr Asn Arg Val Lys
             580                 585                 590

Ala Ala Lys Lys Val Pro Leu Asp Arg Met Pro Tyr Asn Leu Gln Tyr
             595                 600                 605

Thr Val Glu Val Lys Asn Gly Ser Leu Ile Ile Pro His Tyr Asp His
             610                 615                 620

Tyr His Asn Ile Lys Phe Glu Trp Phe Asp Glu Gly Leu Tyr Glu Ala
625                 630                 635                 640

Pro Lys Gly Tyr Thr Leu Glu Asp Leu Leu Ala Thr Val Lys Tyr Tyr
             645                 650                 655

Val Glu His Pro Asn Glu Arg Pro His Ser Asp Asn Gly Phe Gly Asn
             660                 665                 670

Ala Ser Asp His Val Arg Lys Asn Lys Ala Asp Gln Asp Ser Lys Pro
             675                 680                 685

Asp Glu Asp Lys Gly His Asp Glu Val Ser Glu Pro Thr His Pro Glu
             690                 695                 700

Ser Asp Glu Lys Glu Asn His Ala Gly Leu Asn Pro Ser Ala Asp Asn
705                 710                 715                 720

Leu Tyr Lys Pro Ser Thr Asp Thr Glu Glu Thr Glu Glu Glu Ala Glu
             725                 730                 735

Asp Thr Thr Asp Glu Ala Glu Ile Pro Gln Val Glu His Ser Val Ile
             740                 745                 750

Asn Ala Lys Ile Ala Asp Ala Glu Ala Leu Leu Glu Lys Val Thr Asp
             755                 760                 765

Pro Ser Ile Arg Gln Asn Ala Met Glu Thr Leu Thr Gly Leu Lys Ser
             770                 775                 780

Ser Leu Leu Leu Gly Thr Lys Asp Asn Asn Thr Ile Ser Ala Glu Val
785                 790                 795                 800

Asp Ser Leu Leu Ala Leu Leu Lys Glu Ser Lys
             805                 810

<210> SEQ ID NO 97
<211> LENGTH: 811
<212> TYPE: PRT
<213> ORGANISM: S. pneumoniae

<400> SEQUENCE: 97

Cys Ser Tyr Glu Leu Gly Arg His Gln Ala Gly Gln Asp Lys Lys Glu
1               5                  10                  15

Ser Asn Arg Val Ala Tyr Ile Asp Gly Asp Gln Ala Gly Gln Lys Ala
             20                  25                  30

Glu Asn Leu Thr Pro Asp Glu Val Ser Lys Arg Glu Gly Ile Asn Ala
             35                  40                  45

Glu Gln Ile Val Ile Lys Ile Thr Asp Gln Gly Tyr Val Thr Ser His

-continued

```
              50                  55                  60
Gly Asp His Tyr His Tyr Tyr Asn Gly Lys Val Pro Tyr Asp Ala Ile
 65                  70                  75                  80
Ile Ser Glu Glu Leu Leu Met Lys Asp Pro Asn Tyr Gln Leu Lys Asp
                 85                  90                  95
Ser Asp Ile Val Asn Glu Ile Lys Gly Gly Tyr Val Ile Lys Val Asn
                100                 105                 110
Gly Lys Tyr Tyr Gly Tyr Leu Lys Asp Ala Ala His Ala Asp Asn Ile
                115                 120                 125
Arg Thr Lys Glu Glu Ile Lys Arg Gln Lys Gln Glu His Ser His Asn
                130                 135                 140
His Gly Gly Ser Asn Asp Gln Ala Val Ala Ala Arg Ala Gln
145                 150                 155                 160
Gly Arg Tyr Thr Thr Asp Asp Gly Tyr Ile Phe Asn Ala Ser Asp Ile
                    165                 170                 175
Ile Glu Asp Thr Gly Asp Ala Tyr Ile Val Pro His Gly Asn His Phe
                180                 185                 190
His Tyr Ile Pro Lys Ser Asp Leu Ser Ala Ser Glu Leu Ala Ala Ala
                195                 200                 205
Gln Ala Tyr Trp Asn Gly Lys Gln Gly Ser Arg Pro Ser Ser Ser Ser
210                 215                 220
Ser His Asn Ala Asn Pro Ala Gln Pro Arg Leu Ser Glu Asn His Asn
225                 230                 235                 240
Leu Thr Val Thr Pro Thr Tyr His Gln Asn Gln Gly Glu Asn Ile Ser
                    245                 250                 255
Ser Leu Leu Arg Glu Leu Tyr Ala Lys Pro Leu Ser Glu Arg His Val
                260                 265                 270
Glu Ser Asp Gly Leu Ile Phe Asp Pro Ala Gln Ile Thr Ser Arg Thr
                275                 280                 285
Ala Arg Gly Val Ala Val Pro His Gly Asn His Tyr His Phe Ile Pro
                290                 295                 300
Tyr Glu Gln Met Ser Glu Leu Glu Glu Arg Ile Ala Arg Ile Ile Pro
305                 310                 315                 320
Leu Arg Tyr Arg Ser Asn His Trp Val Pro Asp Ser Arg Pro Glu Gln
                    325                 330                 335
Pro Ser Pro Gln Pro Ser Pro Gln Pro Ala Pro Asn Pro Gln
                340                 345                 350
Pro Ala Pro Ser Asn Pro Ile Asp Glu Lys Leu Val Lys Glu Ala Val
                355                 360                 365
Arg Lys Val Gly Asp Gly Tyr Val Phe Glu Glu Asn Gly Val Ser Arg
370                 375                 380
Tyr Ile Pro Ala Lys Asp Leu Ser Ala Glu Thr Ala Ala Gly Ile Asp
385                 390                 395                 400
Ser Lys Leu Ala Lys Gln Glu Ser Leu Ser His Lys Leu Gly Thr Lys
                    405                 410                 415
Lys Thr Asp Leu Pro Ser Ser Asp Arg Glu Phe Tyr Asn Lys Ala Tyr
                420                 425                 430
Asp Leu Leu Ala Arg Ile His Gln Asp Leu Leu Asp Asn Lys Gly Arg
                435                 440                 445
Gln Val Asp Phe Glu Ala Leu Asp Asn Leu Leu Glu Arg Leu Lys Asp
                450                 455                 460
Val Ser Ser Asp Lys Val Lys Leu Val Glu Asp Ile Leu Ala Phe Leu
465                 470                 475                 480
```

```
Ala Pro Ile Arg His Pro Glu Arg Leu Gly Lys Pro Asn Ser Gln Ile
                485                 490                 495

Thr Tyr Thr Asp Asp Glu Ile Gln Val Ala Lys Leu Ala Gly Lys Tyr
            500                 505                 510

Thr Thr Glu Asp Gly Tyr Ile Phe Asp Pro Arg Asp Ile Thr Ser Asp
            515                 520                 525

Glu Gly Asp Ala Tyr Val Thr Pro His Met Thr His Ser His Trp Ile
            530                 535                 540

Lys Lys Asp Ser Leu Ser Glu Ala Glu Arg Ala Ala Gln Ala Tyr
545                 550                 555                 560

Ala Lys Glu Lys Gly Leu Thr Pro Pro Ser Thr Asp His Gln Asp Ser
                565                 570                 575

Gly Asn Thr Glu Ala Lys Gly Ala Glu Ala Ile Tyr Asn Arg Val Lys
            580                 585                 590

Ala Ala Lys Lys Val Pro Leu Asp Arg Met Pro Tyr Asn Leu Gln Tyr
            595                 600                 605

Thr Val Glu Val Lys Asn Gly Ser Leu Ile Ile Pro His Tyr Asp His
    610                 615                 620

Tyr His Asn Ile Lys Phe Glu Trp Phe Asp Glu Gly Leu Tyr Glu Ala
625                 630                 635                 640

Pro Lys Gly Tyr Thr Leu Glu Asp Leu Leu Ala Thr Val Lys Tyr Tyr
                645                 650                 655

Val Glu His Pro Asn Glu Arg Pro His Ser Asp Asn Gly Phe Gly Asn
            660                 665                 670

Ala Ser Asp His Val Arg Lys Asn Lys Ala Asp Gln Asp Ser Lys Pro
            675                 680                 685

Asp Glu Asp Lys Gly His Asp Glu Val Ser Glu Pro Thr His Pro Glu
    690                 695                 700

Ser Asp Glu Lys Glu Asn His Ala Gly Leu Asn Pro Ser Ala Asp Asn
705                 710                 715                 720

Leu Tyr Lys Pro Ser Thr Asp Thr Glu Thr Glu Glu Ala Glu
                725                 730                 735

Asp Thr Thr Asp Glu Ala Glu Ile Pro Gln Val Glu His Ser Val Ile
            740                 745                 750

Asn Ala Lys Ile Ala Asp Ala Glu Ala Leu Leu Glu Lys Val Thr Asp
            755                 760                 765

Pro Ser Ile Arg Gln Asn Ala Met Glu Thr Leu Thr Gly Leu Lys Ser
            770                 775                 780

Ser Leu Leu Leu Gly Thr Lys Asp Asn Asn Thr Ile Ser Ala Glu Val
785                 790                 795                 800

Asp Ser Leu Leu Ala Leu Leu Lys Glu Ser Lys
                805                 810

<210> SEQ ID NO 98
<211> LENGTH: 811
<212> TYPE: PRT
<213> ORGANISM: S. pneumoniae

<400> SEQUENCE: 98

Cys Ser Tyr Glu Leu Gly Arg His Gln Ala Gly Gln Asp Lys Lys Glu
1               5                   10                  15

Ser Asn Arg Val Ala Tyr Ile Asp Gly Asp Gln Ala Gly Gln Lys Ala
            20                  25                  30

Glu Asn Leu Thr Pro Asp Glu Val Ser Lys Arg Glu Gly Ile Asn Ala
```

-continued

```
                35                  40                  45
Glu Gln Ile Val Ile Lys Ile Thr Asp Gln Gly Tyr Val Thr Ser His
 50                  55                  60

Gly Asp His Tyr His Tyr Tyr Asn Gly Lys Val Pro Tyr Asp Ala Ile
 65                  70                  75                  80

Ile Ser Glu Glu Leu Leu Met Lys Asp Pro Asn Tyr Gln Leu Lys Asp
                 85                  90                  95

Ser Asp Ile Val Asn Glu Ile Lys Gly Tyr Val Ile Lys Val Asn
                100                 105                 110

Gly Lys Tyr Tyr Val Tyr Leu Lys Asp Ala Ala His Ala Asp Asn Ile
            115                 120                 125

Arg Thr Lys Glu Glu Ile Lys Arg Gln Lys Gln Glu His Ser His Asn
        130                 135                 140

His Gly Gly Gly Ser Asn Asp Gln Ala Val Val Ala Ala Arg Ala Gln
145                 150                 155                 160

Gly Arg Tyr Thr Thr Asp Asp Gly Tyr Ile Phe Asn Ala Ser Asp Ile
                165                 170                 175

Ile Glu Asp Thr Gly Asp Ala Tyr Ile Val Pro His Gly Asn His Phe
                180                 185                 190

His Tyr Ile Pro Lys Ser Asp Leu Ser Ala Ser Glu Leu Ala Ala Ala
            195                 200                 205

Gln Ala Tyr Trp Asn Gly Lys Gln Gly Ser Arg Pro Ser Ser Ser Ser
        210                 215                 220

Ser His Asn Ala Asn Pro Ala Gln Pro Arg Leu Ser Glu Asn His Asn
225                 230                 235                 240

Leu Thr Val Thr Pro Thr Tyr His Gln Asn Gln Gly Glu Asn Ile Ser
                245                 250                 255

Ser Leu Leu Arg Glu Leu Tyr Ala Lys Pro Leu Ser Glu Arg His Val
            260                 265                 270

Glu Ser Asp Gly Leu Ile Phe Asp Pro Ala Gln Ile Thr Ser Arg Thr
        275                 280                 285

Ala Arg Gly Val Ala Val Pro His Gly Asn His Tyr His Phe Ile Pro
290                 295                 300

Tyr Glu Gln Met Ser Glu Leu Glu Glu Arg Ile Ala Arg Ile Ile Pro
305                 310                 315                 320

Leu Arg Tyr Arg Ser Asn His Trp Val Pro Asp Ser Arg Pro Glu Gln
                325                 330                 335

Pro Ser Pro Gln Pro Ser Pro Ser Pro Gln Pro Ala Pro Asn Pro Gln
            340                 345                 350

Pro Ala Pro Ser Asn Pro Ile Asp Glu Lys Leu Val Lys Glu Ala Val
        355                 360                 365

Arg Lys Val Gly Asp Gly Tyr Val Phe Glu Glu Asn Gly Val Ser Arg
    370                 375                 380

Tyr Ile Pro Ala Lys Asp Leu Ser Ala Glu Thr Ala Ala Gly Ile Asp
385                 390                 395                 400

Ser Lys Leu Ala Lys Gln Glu Ser Leu Ser His Lys Leu Gly Thr Lys
                405                 410                 415

Lys Thr Asp Leu Pro Ser Ser Asp Arg Glu Phe Tyr Asn Lys Ala Tyr
            420                 425                 430

Asp Leu Leu Ala Arg Ile His Gln Asp Leu Leu Asp Asn Lys Gly Arg
        435                 440                 445

Gln Val Asp Phe Glu Ala Leu Asp Asn Leu Leu Glu Arg Leu Lys Asp
    450                 455                 460
```

Val Ser Ser Asp Lys Val Lys Leu Val Glu Asp Ile Leu Ala Phe Leu
465                 470                 475                 480

Ala Pro Ile Arg His Pro Glu Arg Leu Gly Lys Pro Asn Ser Gln Ile
            485                 490                 495

Thr Tyr Thr Asp Asp Glu Ile Gln Val Ala Lys Leu Ala Gly Lys Tyr
                500                 505                 510

Thr Thr Glu Asp Gly Tyr Ile Phe Asp Pro Arg Asp Ile Thr Ser Asp
            515                 520                 525

Glu Gly Asp Ala Tyr Val Thr Pro His Met Thr His Ser His Trp Ile
530                 535                 540

Lys Lys Asp Ser Leu Ser Glu Ala Glu Arg Ala Ala Gln Ala Tyr
545                 550                 555                 560

Ala Lys Glu Lys Gly Leu Thr Pro Pro Ser Thr Asp His Gln Asp Ser
            565                 570                 575

Gly Asn Thr Glu Ala Lys Gly Ala Glu Ala Ile Tyr Asn Arg Val Lys
                580                 585                 590

Ala Ala Lys Lys Val Pro Leu Asp Arg Met Pro Tyr Asn Leu Gln Tyr
            595                 600                 605

Thr Val Glu Val Lys Asn Gly Ser Leu Ile Ile Pro His Tyr Asp His
            610                 615                 620

Tyr His Asn Ile Lys Phe Glu Trp Phe Asp Gly Leu Tyr Glu Ala
625                 630                 635                 640

Pro Lys Gly Tyr Thr Leu Glu Asp Leu Leu Ala Thr Val Lys Tyr Tyr
                645                 650                 655

Val Glu His Pro Asn Glu Arg Pro His Ser Asp Asn Gly Phe Gly Asn
            660                 665                 670

Ala Ser Asp His Val Arg Lys Asn Lys Ala Asp Gln Asp Ser Lys Pro
            675                 680                 685

Asp Glu Asp Lys Gly His Asp Glu Val Ser Glu Pro Thr His Pro Glu
690                 695                 700

Ser Asp Glu Lys Glu Asn His Ala Gly Leu Asn Pro Ser Ala Asp Asn
705                 710                 715                 720

Leu Tyr Lys Pro Ser Thr Asp Thr Glu Glu Thr Glu Glu Ala Glu
                725                 730                 735

Asp Thr Thr Asp Glu Ala Glu Ile Pro Gln Val Glu His Ser Val Ile
            740                 745                 750

Asn Ala Lys Ile Ala Asp Ala Glu Ala Leu Leu Glu Lys Val Thr Asp
            755                 760                 765

Pro Ser Ile Arg Gln Asn Ala Met Glu Thr Leu Thr Gly Leu Lys Ser
    770                 775                 780

Ser Leu Leu Leu Gly Thr Lys Asp Asn Asn Thr Ile Ser Ala Glu Val
785                 790                 795                 800

Asp Ser Leu Leu Ala Leu Leu Lys Glu Ser Lys
                805                 810

```
<210> SEQ ID NO 99
<211> LENGTH: 811
<212> TYPE: PRT
<213> ORGANISM: S. pneumoniae

<400> SEQUENCE: 99
```

Cys Ser Tyr Glu Leu Gly Arg His Gln Ala Gly Gln Val Lys Lys Glu
1               5                   10                  15

Ser Asn Arg Val Ser Tyr Ile Asp Gly Asp Gln Ala Gly Gln Lys Ala

-continued

```
                20                  25                  30
Glu Asn Leu Thr Pro Asp Glu Val Ser Lys Arg Glu Gly Ile Asn Ala
             35                  40                  45
Glu Gln Ile Val Ile Lys Ile Thr Asp Gln Gly Tyr Val Thr Ser His
 50                  55                  60
Gly Asp His Tyr His Tyr Asn Gly Lys Val Pro Tyr Asp Ala Ile
 65                  70                  75                  80
Ile Ser Glu Glu Leu Leu Met Lys Asp Pro Asn Tyr Gln Leu Lys Asp
             85                  90                  95
Ser Asp Ile Val Asn Glu Ile Lys Gly Gly Tyr Val Ile Lys Val Asp
            100                 105                 110
Gly Lys Tyr Tyr Val Tyr Leu Lys Asp Ala Ala His Ala Asp Asn Ile
            115                 120                 125
Arg Thr Lys Glu Glu Ile Lys Arg Gln Lys Gln Arg Ser His Asn
130                 135                 140
His Asn Ser Arg Ala Asp Asn Ala Val Ala Ala Arg Ala Gln Gly
145                 150                 155                 160
Arg Tyr Thr Thr Asp Asp Gly Tyr Ile Phe Asn Ala Ser Asp Ile Ile
            165                 170                 175
Glu Asp Thr Gly Asp Ala Tyr Ile Val Pro His Gly Asp His Tyr His
            180                 185                 190
Tyr Ile Pro Lys Ser Asp Leu Ser Ala Ser Glu Leu Ala Ala Ala Gln
            195                 200                 205
Ala Tyr Trp Asn Gly Lys Gln Gly Ser Arg Pro Ser Ser Ser Ser Ser
210                 215                 220
His Asn Ala Asn Pro Ala Gln Pro Arg Leu Ser Glu Asn His Asn Leu
225                 230                 235                 240
Thr Val Thr Pro Thr Tyr His Gln Asn Gln Gly Glu Asn Ile Ser Ser
            245                 250                 255
Leu Leu Arg Glu Leu Tyr Ala Lys Pro Leu Ser Glu Arg His Val Glu
            260                 265                 270
Ser Asp Gly Leu Ile Phe Asp Pro Ala Gln Ile Thr Ser Arg Thr Ala
            275                 280                 285
Asn Gly Val Ala Val Pro His Gly Asp His Tyr His Phe Ile Pro Tyr
290                 295                 300
Ser Gln Leu Ser Pro Leu Glu Glu Lys Leu Ala Arg Ile Ile Pro Leu
305                 310                 315                 320
Arg Tyr Arg Ser Asn His Trp Val Pro Asp Ser Arg Pro Glu Gln Pro
            325                 330                 335
Ser Pro Gln Ser Thr Pro Glu Pro Ser Pro Ser Pro Gln Pro Ala Pro
            340                 345                 350
Asn Pro Gln Pro Ala Pro Ser Asn Pro Ile Asp Glu Lys Leu Val Lys
            355                 360                 365
Glu Ala Val Arg Lys Val Gly Asp Gly Tyr Val Phe Glu Glu Asn Gly
            370                 375                 380
Val Pro Arg Tyr Ile Pro Ala Lys Asp Leu Ser Ala Glu Thr Ala Ala
385                 390                 395                 400
Gly Ile Asp Ser Lys Leu Ala Lys Gln Glu Ser Leu Ser His Lys Leu
            405                 410                 415
Gly Ala Lys Lys Thr Asp Leu Pro Ser Ser Asp Arg Glu Phe Tyr Asn
            420                 425                 430
Lys Ala Tyr Asp Leu Leu Ala Arg Ile His Gln Asp Leu Leu Asp Asn
            435                 440                 445
```

```
Lys Gly Arg Gln Val Asp Phe Glu Ala Leu Asp Asn Leu Leu Glu Arg
    450                 455                 460

Leu Lys Asp Val Ser Ser Asp Lys Val Lys Leu Val Asp Asp Ile Leu
465                 470                 475                 480

Ala Phe Leu Ala Pro Ile Arg His Pro Glu Arg Leu Gly Lys Pro Asn
                    485                 490                 495

Ala Gln Ile Thr Tyr Thr Asp Glu Ile Gln Val Ala Lys Leu Ala
                500                 505                 510

Gly Lys Tyr Thr Thr Glu Asp Gly Tyr Ile Phe Asp Pro Arg Asp Ile
                515                 520                 525

Thr Ser Asp Glu Gly Asp Ala Tyr Val Thr Pro His Met Thr His Ser
    530                 535                 540

His Trp Ile Lys Lys Asp Ser Leu Ser Glu Ala Glu Arg Ala Ala Ala
545                 550                 555                 560

Gln Ala Tyr Ala Lys Glu Lys Gly Leu Thr Pro Pro Ser Thr Asp His
                565                 570                 575

Gln Asp Ser Gly Asn Thr Glu Ala Lys Gly Ala Glu Ala Ile Tyr Asn
                580                 585                 590

Arg Val Lys Ala Ala Lys Lys Val Pro Leu Asp Arg Met Pro Tyr Asn
                595                 600                 605

Leu Gln Tyr Thr Val Glu Val Lys Asn Gly Ser Leu Ile Ile Pro His
    610                 615                 620

Tyr Asp His Tyr His Asn Ile Lys Phe Glu Trp Phe Asp Glu Gly Leu
625                 630                 635                 640

Tyr Glu Ala Pro Lys Gly Tyr Ser Leu Glu Asp Leu Leu Ala Thr Val
                645                 650                 655

Lys Tyr Tyr Val Glu His Pro Asn Glu Arg Pro His Ser Asp Asn Gly
                660                 665                 670

Phe Gly Asn Ala Ser Asp His Val Gln Arg Asn Lys Asn Gly Gln Ala
                675                 680                 685

Asp Thr Asn Gln Thr Glu Lys Pro Asn Glu Glu Lys Pro Gln Thr Glu
    690                 695                 700

Lys Pro Glu Glu Glu Thr Pro Arg Glu Glu Lys Pro Gln Ser Glu Lys
705                 710                 715                 720

Pro Glu Ser Pro Lys Pro Thr Glu Glu Pro Glu Glu Ser Pro Glu
                725                 730                 735

Glu Ser Pro Glu Glu Ser Glu Glu Pro Gln Val Glu Thr Glu Lys Val
                740                 745                 750

Lys Glu Lys Leu Arg Glu Ala Glu Asp Leu Leu Gly Lys Ile Gln Asn
                755                 760                 765

Pro Ile Ile Lys Ser Asn Ala Lys Glu Thr Leu Thr Gly Leu Lys Asn
    770                 775                 780

Asn Leu Leu Phe Gly Thr Gln Asp Asn Asn Thr Ile Met Ala Glu Ala
785                 790                 795                 800

Glu Lys Leu Leu Ala Leu Leu Lys Glu Ser Lys
                805                 810

<210> SEQ ID NO 100
<211> LENGTH: 805
<212> TYPE: PRT
<213> ORGANISM: S. pneumoniae

<400> SEQUENCE: 100

Cys Ser Tyr Glu Leu Gly Arg His Gln Ala Gly Gln Asp Lys Lys Glu
```

-continued

```
1               5                   10                  15
Ser Asn Arg Val Ala Tyr Ile Asp Gly Asp Gln Ala Gly Gln Lys Ala
                20                  25                  30

Glu Asn Leu Thr Pro Asp Glu Val Ser Lys Arg Glu Gly Ile Asn Ala
                35                  40                  45

Glu Gln Ile Val Ile Lys Ile Thr Asp Gln Gly Tyr Val Thr Ser His
                50                  55                  60

Gly Asp His Tyr His Tyr Asn Gly Lys Val Pro Tyr Asp Ala Ile
65                      70                  75                  80

Ile Ser Glu Glu Leu Leu Met Lys Asp Pro Asn Tyr Gln Leu Lys Asp
                85                  90                  95

Ser Asp Ile Val Asn Glu Ile Lys Gly Gly Tyr Val Ile Lys Val Asn
                100                 105                 110

Gly Lys Tyr Tyr Val Tyr Leu Lys Asp Ala Ala His Ala Asp Asn Ile
            115                 120                 125

Arg Thr Lys Glu Glu Ile Lys Arg Gln Lys Gln Glu Arg Ser His Asn
            130                 135                 140

His Asn Ser Arg Ala Asp Asn Ala Val Ala Ala Arg Ala Gln Gly
145                 150                 155                 160

Arg Tyr Thr Thr Asp Asp Gly Tyr Ile Phe Asn Ala Ser Asp Ile Ile
                165                 170                 175

Glu Asp Thr Gly Asp Ala Tyr Ile Val Pro His Gly Asp His Tyr His
                180                 185                 190

Tyr Ile Pro Lys Asn Glu Leu Ser Ala Ser Glu Leu Ala Ala Ala Glu
            195                 200                 205

Ala Tyr Trp Asn Gly Lys Gln Gly Ser Arg Pro Ser Ser Ser Ser Ser
        210                 215                 220

Tyr Asn Ala Asn Pro Ala Gln Pro Arg Leu Ser Glu Asn His Asn Leu
225                 230                 235                 240

Thr Val Thr Pro Thr Tyr His Gln Asn Gln Gly Glu Asn Ile Ser Ser
                245                 250                 255

Leu Leu Arg Glu Leu Tyr Ala Lys Pro Leu Ser Glu Arg His Val Glu
                260                 265                 270

Ser Asp Gly Leu Ile Phe Asp Pro Ala Gln Ile Thr Ser Arg Thr Ala
            275                 280                 285

Arg Gly Val Ala Val Pro His Gly Asn His Tyr His Phe Ile Pro Tyr
            290                 295                 300

Glu Gln Met Ser Glu Leu Glu Lys Arg Ile Ala Arg Ile Ile Pro Leu
305                 310                 315                 320

Arg Tyr Arg Ser Asn His Trp Val Pro Asp Ser Arg Pro Glu Glu Pro
                325                 330                 335

Ser Pro Gln Pro Thr Pro Glu Pro Ser Pro Ser Pro Gln Pro Ala Pro
            340                 345                 350

Ser Asn Pro Ile Asp Glu Lys Leu Val Lys Glu Ala Val Arg Lys Val
            355                 360                 365

Gly Asp Gly Tyr Val Phe Glu Glu Asn Gly Val Ser Arg Tyr Ile Pro
        370                 375                 380

Ala Lys Asp Leu Ser Ala Glu Thr Ala Ala Gly Ile Asp Ser Lys Leu
385                 390                 395                 400

Ala Lys Gln Glu Ser Leu Ser His Lys Leu Gly Ala Lys Lys Thr Asp
            405                 410                 415

Leu Pro Ser Ser Asp Arg Glu Phe Tyr Asn Lys Ala Tyr Asp Leu Leu
            420                 425                 430
```

-continued

Ala Arg Ile His Gln Asp Leu Leu Asp Asn Lys Gly Arg Gln Val Asp
        435                 440                 445

Phe Glu Ala Leu Asp Asn Leu Leu Glu Arg Leu Lys Asp Val Ser Ser
450                 455                 460

Asp Lys Val Lys Leu Val Asp Asp Ile Leu Ala Phe Leu Ala Pro Ile
465                 470                 475                 480

Arg His Pro Glu Arg Leu Gly Lys Pro Asn Ala Gln Ile Thr Tyr Thr
                485                 490                 495

Asp Asp Glu Ile Gln Val Ala Lys Leu Ala Gly Lys Tyr Thr Thr Glu
            500                 505                 510

Asp Gly Tyr Ile Phe Asp Pro Arg Asp Ile Thr Ser Asp Glu Gly Asp
            515                 520                 525

Ala Tyr Val Thr Pro His Met Thr His Ser His Trp Ile Lys Lys Asp
    530                 535                 540

Ser Leu Ser Glu Ala Glu Arg Ala Ala Gln Ala Tyr Ala Lys Glu
545                 550                 555                 560

Lys Gly Leu Thr Pro Pro Ser Thr Asp His Gln Asp Ser Gly Asn Thr
                565                 570                 575

Glu Ala Lys Gly Ala Glu Ala Ile Tyr Asn Arg Val Lys Ala Ala Lys
                580                 585                 590

Lys Val Pro Leu Asp Arg Met Pro Tyr Asn Leu Gln Tyr Thr Val Glu
            595                 600                 605

Val Lys Asn Gly Ser Leu Ile Ile Pro His Tyr Asp His Tyr His Asn
610                 615                 620

Ile Lys Phe Glu Trp Phe Asp Glu Gly Leu Tyr Glu Ala Pro Lys Gly
625                 630                 635                 640

Tyr Ser Leu Glu Asp Leu Leu Ala Thr Val Lys Tyr Tyr Val Glu His
                645                 650                 655

Pro Asn Glu Arg Pro His Ser Asp Asn Gly Phe Gly Asn Ala Ser Asp
                660                 665                 670

His Val Gln Arg Asn Lys Asn Gly Gln Ala Asp Thr Asn Gln Thr Glu
            675                 680                 685

Lys Pro Asn Glu Glu Lys Pro Gln Thr Glu Lys Pro Glu Glu Thr
690                 695                 700

Pro Arg Glu Glu Lys Pro Gln Ser Glu Lys Pro Glu Ser Pro Lys Pro
705                 710                 715                 720

Thr Glu Glu Pro Glu Glu Glu Ser Pro Glu Glu Ser Pro Glu Glu Ser
                725                 730                 735

Glu Glu Pro Gln Val Glu Thr Glu Lys Val Lys Glu Lys Leu Arg Glu
            740                 745                 750

Ala Glu Asp Leu Leu Gly Lys Ile Gln Asn Pro Ile Ile Lys Ser Asn
                755                 760                 765

Ala Lys Glu Thr Leu Thr Gly Leu Lys Asn Asn Leu Leu Phe Gly Thr
            770                 775                 780

Gln Asp Asn Asn Thr Ile Met Ala Glu Ala Glu Lys Leu Leu Ala Leu
785                 790                 795                 800

Leu Lys Glu Ser Lys
                805

<210> SEQ ID NO 101
<211> LENGTH: 807
<212> TYPE: PRT
<213> ORGANISM: S. pneumoniae

<400> SEQUENCE: 101

```
Cys Ser Tyr Glu Leu Gly Arg His Gln Ala Gly Gln Val Lys Lys Glu
  1               5                  10                  15

Ser Asn Arg Val Ser Tyr Ile Asp Gly Asp Gln Ala Gly Gln Lys Ala
             20                  25                  30

Glu Asn Leu Thr Pro Asp Glu Val Ser Lys Arg Glu Gly Ile Asn Ala
         35                  40                  45

Glu Gln Ile Val Ile Lys Ile Thr Asp Gln Gly Tyr Val Thr Ser His
 50                  55                  60

Gly Asp His Tyr His Tyr Tyr Asn Gly Lys Val Pro Tyr Asp Ala Ile
 65                  70                  75                  80

Ile Ser Glu Glu Leu Leu Met Lys Asp Pro Asn Tyr Gln Leu Lys Asp
                 85                  90                  95

Ser Asp Ile Val Asn Glu Ile Lys Gly Gly Tyr Val Ile Lys Val Asp
            100                 105                 110

Gly Lys Tyr Tyr Val Tyr Leu Lys Asp Ala Ala His Ala Asp Asn Ile
        115                 120                 125

Arg Thr Lys Glu Glu Ile Lys Arg Gln Lys Gln Glu Arg Ser His Asn
130                 135                 140

His Asn Ser Arg Ala Asp Asn Ala Val Ala Ala Arg Ala Gln Gly Arg
145                 150                 155                 160

Arg Tyr Thr Thr Asp Asp Gly Tyr Ile Phe Asn Ala Ser Asp Ile Ile
                165                 170                 175

Glu Asp Thr Gly Asp Ala Tyr Ile Val Pro His Gly Asn His Phe His
            180                 185                 190

Tyr Ile Pro Lys Ser Asp Leu Ser Ala Ser Glu Leu Ala Ala Ala Gln
        195                 200                 205

Ala Tyr Trp Asn Gly Lys Gln Gly Ser Arg Pro Ser Ser Ser Ser Ser
    210                 215                 220

His Asn Ala Asn Pro Ala Gln Pro Arg Leu Ser Glu Asn His Asn Leu
225                 230                 235                 240

Thr Val Thr Pro Thr Tyr His Gln Asn Gln Gly Glu Asn Ile Ser Ser
                245                 250                 255

Leu Leu Arg Glu Leu Tyr Ala Lys Pro Leu Ser Glu Arg His Val Glu
            260                 265                 270

Ser Asp Gly Leu Ile Phe Asp Pro Ala Gln Ile Thr Ser Arg Thr Ala
        275                 280                 285

Arg Gly Val Ala Val Pro His Gly Asn His Tyr His Phe Ile Pro Tyr
    290                 295                 300

Ser Gln Met Ser Glu Leu Glu Glu Arg Ile Ala Arg Ile Ile Pro Leu
305                 310                 315                 320

Arg Tyr Arg Ser Asn His Trp Val Pro Asp Ser Arg Pro Glu Gln Pro
                325                 330                 335

Ser Pro Gln Ser Thr Pro Glu Pro Ser Pro Ser Pro Gln Ser Ala Pro
            340                 345                 350

Asn Pro Gln Pro Ala Pro Ser Asn Pro Ile Asp Glu Lys Leu Val Lys
        355                 360                 365

Glu Val Val Arg Lys Val Gly Asp Gly Tyr Val Phe Glu Lys Asn Gly
    370                 375                 380

Val Ser Arg Tyr Ile Pro Ala Lys Asn Leu Ser Ala Glu Thr Ala Ala
385                 390                 395                 400

Gly Ile Asp Ser Lys Leu Ala Lys Gln Glu Ser Leu Ser His Lys Leu
                405                 410                 415
```

```
Gly Ala Lys Lys Thr Asp Leu Pro Ser Ser Asp Arg Glu Phe Tyr Asn
            420                 425                 430
Lys Ala Tyr Asp Leu Leu Ala Arg Ile His Gln Asp Leu Leu Asp Asn
            435                 440                 445
Lys Gly Arg Gln Val Asp Phe Glu Ala Leu Asp Asn Leu Leu Glu Arg
            450                 455                 460
Leu Glu Asp Val Pro Ser Asp Lys Val Lys Leu Val Asp Asp Ile Leu
465                 470                 475                 480
Ala Phe Leu Ala Pro Ile Arg His Pro Glu Arg Leu Gly Lys Pro Asn
            485                 490                 495
Ala Gln Ile Thr Tyr Thr Asp Asp Glu Ile Gln Val Ala Lys Leu Ala
            500                 505                 510
Gly Lys Tyr Thr Thr Glu Asp Gly Tyr Ile Phe Asp Pro Arg Asp Ile
            515                 520                 525
Thr Ser Asp Glu Gly Asp Ala Tyr Val Thr Pro His Met Thr His Ser
530                 535                 540
His Trp Ile Lys Lys Asp Ser Leu Ser Glu Ala Glu Arg Ala Ala Ala
545                 550                 555                 560
Gln Ala Tyr Ala Lys Glu Lys Gly Leu Thr Pro Pro Ser Thr Asp His
            565                 570                 575
Gln Asp Ser Gly Asn Thr Glu Ala Lys Gly Ala Glu Ala Ile Tyr Asn
            580                 585                 590
Arg Val Lys Ala Ala Lys Lys Val Pro Leu Asp Arg Met Pro Tyr Asn
            595                 600                 605
Leu Gln Tyr Thr Val Glu Val Lys Asn Gly Ser Leu Ile Ile Pro His
            610                 615                 620
Tyr Asp His Tyr His Asn Ile Lys Phe Glu Trp Phe Asp Glu Gly Leu
625                 630                 635                 640
Tyr Glu Ala Pro Lys Gly Tyr Thr Leu Glu Asp Leu Leu Ala Thr Val
            645                 650                 655
Lys Tyr Tyr Val Glu His Pro Asn Glu Arg Pro His Ser Asp Asn Gly
            660                 665                 670
Phe Gly Asn Ala Ser Asp His Val Gln Arg Asn Lys Asn Gly Gln Ala
            675                 680                 685
Asp Thr Asn Gln Thr Glu Lys Pro Ser Glu Lys Pro Gln Thr Glu
            690                 695                 700
Lys Pro Glu Glu Glu Thr Pro Arg Glu Glu Lys Pro Gln Ser Glu Lys
705                 710                 715                 720
Pro Glu Ser Pro Lys Pro Thr Glu Glu Pro Glu Glu Ser Pro Glu
            725                 730                 735
Glu Ser Glu Glu Pro Gln Val Glu Thr Glu Lys Val Glu Glu Lys Leu
            740                 745                 750
Arg Glu Ala Glu Asp Leu Leu Gly Lys Ile Gln Asp Pro Ile Ile Lys
            755                 760                 765
Ser Asn Ala Lys Glu Thr Leu Thr Gly Leu Lys Asn Asn Leu Leu Phe
            770                 775                 780
Gly Thr Gln Asp Asn Asn Thr Ile Met Ala Glu Ala Glu Lys Leu Leu
785                 790                 795                 800
Ala Leu Leu Lys Glu Ser Lys
            805

<210> SEQ ID NO 102
<211> LENGTH: 821
```

```
<212> TYPE: PRT
<213> ORGANISM: S. pneumoniae

<400> SEQUENCE: 102

Cys Ala Tyr Glu Leu Gly Leu His Gln Ala Gln Thr Val Lys Glu Asn
 1               5                  10                  15

Asn Arg Val Ser Tyr Ile Asp Gly Lys Gln Ala Thr Gln Lys Thr Glu
                20                  25                  30

Asn Leu Thr Pro Asp Glu Val Ser Lys Arg Glu Gly Ile Asn Ala Glu
            35                  40                  45

Gln Ile Val Ile Lys Ile Thr Asp Gln Gly Tyr Val Thr Ser His Gly
 50                  55                  60

Asp His Tyr His Tyr Tyr Asn Gly Lys Val Pro Tyr Asp Ala Ile Ile
65                  70                  75                  80

Ser Glu Glu Leu Leu Met Lys Asp Pro Asn Tyr Gln Leu Lys Asp Ser
                85                  90                  95

Asp Ile Val Asn Glu Ile Lys Gly Tyr Val Ile Lys Val Asn Gly
            100                 105                 110

Lys Tyr Tyr Val Tyr Leu Lys Asp Ala Ala His Ala Asp Asn Val Arg
    115                 120                 125

Thr Lys Glu Glu Ile Asn Arg Gln Lys Gln Glu His Ser Gln His Arg
130                 135                 140

Glu Gly Gly Thr Ser Ala Asn Asp Gly Ala Val Ala Phe Ala Arg Ser
145                 150                 155                 160

Gln Gly Arg Tyr Thr Thr Asp Asp Gly Tyr Ile Phe Asn Ala Ser Asp
                165                 170                 175

Ile Ile Glu Asp Thr Gly Asp Ala Tyr Ile Val Pro His Gly Asp His
            180                 185                 190

Tyr His Tyr Ile Pro Lys Asn Glu Leu Ser Ala Ser Glu Leu Ala Ala
        195                 200                 205

Ala Glu Ala Phe Leu Ser Gly Arg Glu Asn Leu Ser Asn Leu Arg Thr
210                 215                 220

Tyr Arg Arg Gln Asn Ser Asp Asn Thr Pro Arg Thr Asn Trp Val Pro
225                 230                 235                 240

Ser Val Ser Asn Pro Gly Thr Thr Asn Thr Asn Thr Ser Asn Asn Ser
                245                 250                 255

Asn Thr Asn Ser Gln Ala Ser Gln Ser Asn Asp Ile Asp Ser Leu Leu
            260                 265                 270

Lys Gln Leu Tyr Lys Leu Pro Leu Ser Gln Arg His Val Glu Ser Asp
        275                 280                 285

Gly Leu Ile Phe Asp Pro Ala Gln Ile Thr Ser Arg Thr Ala Arg Gly
    290                 295                 300

Val Ala Val Pro His Gly Asn His Tyr His Phe Ile Pro Tyr Glu Gln
305                 310                 315                 320

Met Ser Glu Leu Glu Lys Arg Ile Ala Arg Ile Ile Pro Leu Arg Tyr
                325                 330                 335

Arg Ser Asn His Trp Val Pro Asp Ser Arg Pro Glu Glu Pro Ser Pro
            340                 345                 350

Gln Pro Thr Pro Glu Pro Ser Pro Ser Pro Gln Pro Ala Pro Asn Pro
        355                 360                 365

Gln Pro Ala Pro Ser Asn Pro Ile Asp Glu Lys Leu Val Lys Glu Ala
    370                 375                 380

Val Arg Lys Val Gly Asp Gly Tyr Val Phe Glu Glu Asn Gly Val Ser
385                 390                 395                 400
```

```
Arg Tyr Ile Pro Ala Lys Asn Leu Ser Ala Glu Thr Ala Ala Gly Ile
                405                 410                 415

Asp Ser Lys Leu Ala Lys Gln Glu Ser Leu Ser His Lys Leu Gly Ala
            420                 425                 430

Lys Lys Thr Asp Leu Pro Ser Ser Asp Arg Glu Phe Tyr Asn Lys Ala
        435                 440                 445

Tyr Asp Leu Leu Ala Arg Ile His Gln Asp Leu Leu Asp Asn Lys Gly
    450                 455                 460

Arg Gln Val Asp Phe Glu Ala Leu Asp Asn Leu Leu Glu Arg Leu Lys
465                 470                 475                 480

Asp Val Ser Ser Asp Lys Val Lys Leu Val Asp Asp Ile Leu Ala Phe
                485                 490                 495

Leu Ala Pro Ile Arg His Pro Glu Arg Leu Gly Lys Pro Asn Ala Gln
            500                 505                 510

Ile Thr Tyr Thr Asp Asp Glu Ile Gln Val Ala Lys Leu Ala Gly Lys
        515                 520                 525

Tyr Thr Thr Glu Asp Gly Tyr Ile Phe Asp Pro Arg Asp Ile Thr Ser
    530                 535                 540

Asp Glu Gly Asp Ala Tyr Val Thr Pro His Met Thr His Ser His Trp
545                 550                 555                 560

Ile Lys Lys Asp Ser Leu Ser Glu Ala Glu Arg Ala Ala Ala Gln Ala
                565                 570                 575

Tyr Ala Lys Glu Lys Gly Leu Thr Pro Pro Ser Thr Asp His Gln Asp
            580                 585                 590

Ser Gly Asn Thr Glu Ala Lys Gly Ala Glu Ala Ile Tyr Asn Arg Val
        595                 600                 605

Lys Ala Ala Lys Lys Val Pro Leu Asp Arg Met Pro Tyr Asn Leu Gln
    610                 615                 620

Tyr Thr Val Glu Val Lys Asn Gly Ser Leu Ile Ile Pro His Tyr Asp
625                 630                 635                 640

His Tyr His Asn Ile Lys Phe Glu Trp Phe Asp Glu Gly Leu Tyr Glu
                645                 650                 655

Ala Pro Lys Gly Tyr Thr Leu Glu Asp Leu Leu Ala Thr Val Lys Tyr
            660                 665                 670

Tyr Val Glu His Pro Asn Glu Arg Pro His Ser Asp Asn Gly Phe Gly
        675                 680                 685

Asn Ala Ser Asp His Val Gln Arg Asn Lys Asn Gly Gln Ala Asp Thr
    690                 695                 700

Asn Gln Thr Glu Lys Pro Ser Glu Lys Pro Gln Thr Glu Lys Pro
705                 710                 715                 720

Glu Glu Glu Thr Pro Arg Glu Glu Lys Pro Gln Ser Glu Lys Pro Glu
                725                 730                 735

Ser Pro Lys Pro Thr Glu Glu Pro Glu Glu Ser Pro Glu Glu Ser
            740                 745                 750

Glu Glu Pro Gln Val Glu Thr Glu Lys Val Glu Glu Lys Leu Arg Glu
        755                 760                 765

Ala Glu Asp Leu Leu Gly Lys Ile Gln Asp Pro Ile Ile Lys Ser Asn
    770                 775                 780
```

```
Ala Lys Glu Thr Leu Thr Gly Leu Lys Asn Asn Leu Leu Phe Gly Thr
785                 790                 795                 800

Gln Asp Asn Asn Thr Ile Met Ala Glu Ala Glu Lys Leu Leu Ala Leu
                805                 810                 815

Leu Lys Glu Ser Lys
            820
```

STREPTOCOCCUS ANTIGENS

CROSS-REFERENCE TO RELATED APPLICATIONS

This application is a continuation of U.S. patent application Ser. No. 09/471,255, filed on Dec. 23, 1999, now allowed, which claims the benefit of U.S. Provisional Patent Application No. 60/113,800, filed Dec. 23, 1998, both of which are incorporated by reference in their entireties.

STATEMENT REGARDING SEQUENCE LISTING SUBMITTED ON CD-ROM

The Sequence Listing associated with this application is provided on CD-ROM in lieu of a paper copy, and is hereby incorporated by reference into the specification. Three CD-ROMs are provided, containing identical copies of the sequence listing: CD-ROM No. 1 is labeled COPY 1, contains the file 438c1.app.txt which is 353 KB and created on Aug. 29, 2006; CD-ROM No. 2 is labeled COPY 2, contains the file 438c1.app.txt which is 353 KB and created on Aug. 29, 2006; CD-ROM No. 3 is labeled CRF (Computer Readable Form), contains the file 438c1.app.txt which is 353 KB and created on Aug. 29, 2006.

BACKGROUND OF THE INVENTION

1. Field of the Invention

The present invention is related to antigens, more particularly protein antigens of *Streptococcus pneumoniae* pathogen which are useful as vaccine components for therapy and/or prophylaxis.

2. Description of the Related Art

*S. pneumoniae* is an important agent of disease in man especially among infants, the elderly and immunocompromised persons. It is a bacterium frequently isolated from patients with invasive diseases such as bacteraemia/septicaemia, pneumonia, meningitis with high morbidity and mortality throughout the world. Even with appropriate antibiotic therapy, pneumococcal infections still result in many deaths. Although the advent of antimicrobial drugs has reduced the overall mortality from pneumococcal disease, the presence of resistant pneumococcal organisms has become a major problem in the world today. Effective pneumococcal vaccines could have a major impact on the morbidity and mortality associated with *S. pneumoniae* disease. Such vaccines would also potentially be useful to prevent otitis media in infants and young children.

Efforts to develop a pneumococcal vaccine have generally concentrated on generating immune responses to the pneumococcal capsular polysaccharide. More than 80 pneumococcal capsular serotypes have been identified on the basis of antigenic differences. The currently available pneumococcal vaccine, comprising 23 capsular polysaccharides that most frequently caused disease, has significant shortcomings related primarily to the poor immunogenicity of some capsular polysaccharides, the diversity of the serotypes and the differences in the distribution of serotypes over time, geographic areas and age groups. In particular, the failure of existing vaccines and capsular conjugate vaccines currently in development to protect young children against all serotypes spurres evaluation of other *S. pneumoniae* components. Although immunogenicity of capsular polysaccharides can be improved, serotype specificity will still represent a major limitation of polysaccharide-based vaccines. The use of a antigenically conserved immunogenic pneumococcal protein antigen, either by itself or in combination with additional components, offers the possibility of a protein-based pneumococcal vaccine.

PCT Publication number WO98/18930 published May 7, 1998 entitled "*Streptococcus Pneumoniae* antigens and vaccines" describes certain polypeptides which are claimed to be antigenic. However, no biological activity of these polypeptides is reported.

Therefore their remains an unmet need for *Streptococcus* antigens that may be used as vaccine components for the prophylaxis and/or therapy of *Streptococcus* infection.

BRIEF SUMMARY OF THE INVENTION

According to one aspect, the present invention provides an isolated polynucleotide encoding a polypeptide having at least 70% identity to a second polypeptide comprising a sequence chosen from SEQ ID NOs: 2, 4, 6, 8, 10, 14, 16, 55 to 75, 77 to 79, 81, 83 or fragments, analogs or derivatives thereof.

In other aspects, there are provided vectors comprising polynucleotides of the invention operably linked to an expression control region, as well as host cells transfected with said vectors and methods of producing polypeptides comprising culturing said host cells under conditions suitable for expression.

In yet another aspect, there are provided novel polypeptides encoded by polynucleotides of the invention.

BRIEF DESCRIPTION OF THE SEVERAL VIEWS OF THE DRAWINGS

FIG. 1 is the DNA sequence of BVH-3 gene; SEQ ID NO: 1.

FIG. 2 is the amino acid sequence of BVH-3 protein; SEQ ID NO: 2.

FIG. 3 is the DNA sequence of BVH-11 gene; SEQ ID NO: 3.

FIG. 4 is the amino acid sequence of BVH-11 protein; SEQ ID NO: 4.

FIG. 5 is the DNA sequence of BVH-28 gene; SEQ ID NO: 5.

FIG. 6 is the amino acid sequence of BVH-28 protein; SEQ ID NO: 6.

FIG. 7 is the DNA sequence of BVH-3A gene which corresponds to the 5' terminal end of BVH-3; SEQ ID NO: 7.

FIG. 8 is the amino acid sequence of BVH-3A protein; SEQ ID NO: 8.

FIG. 9 is the DNA sequence of BVH-3B gene which corresponds to the 3' terminal end of BVH-3; SEQ ID NO: 9.

FIG. 10 is the amino acid sequence of BVH-3B protein; SEQ ID NO: 10.

FIGS. 11A and 11B depict the comparison of the predicted amino acid sequences of the BVH-3 open reading frames from WU2 (SEQ ID NO:84), RX1 (SEQ ID NO:85), JNR.7/87 (SEQ ID NO:86), SP64 (SEQ ID NO:87), P4241 (SEQ ID NO:88) and A66 (SEQ ID NO:89) *S. pneumoniae* strains by using the program Clustal W from MacVector sequence analysis software (version 6.5). Underneath the alignment, there is a consensus line where * and . characters indicate identical and similar amino acid residues, respectively.

FIG. 12A-D depicts the comparison of the predicted amino acid sequences of the BVH-11 open reading frames from WU2, Rx1, JNR.7/87, SP64, P4241, A66 and SP63 *S. pneumoniae* strains by using the program Clustal W from MacVector sequence analysis software (version 6.5). Underneath the alignment, there is a consensus line where * and . characters indicate identical and similar amino acid residues, respectively. The aligned amino acid sequences correspond to the following Sequence Identifying Numbers: BVH11-2 SP64, SEQ ID NO:90; BVH11-2 JNR7/87, SEQ ID NO:91; BVH11-2 P4241 SEQ ID NO:92; BVH11-2 A66 SEQ ID NO:93; BVH11-2 WU2, SEQ ID NO:94; BVH11-2 Rx1, SEQ ID NO:95; BVH11 P4241, SEQ ID NO:96; BVH11 WU2, SEQ ID NO:97; BVH11 A66, SEQ ID NO:98; BVH11 Rx1, SEQ ID NO:99; BVH11 JNR7/87, SEQ ID NO:100; BVH11 SP63, SEQ ID NO:101; and BVH11 SP64, SEQ ID NO:102.

FIG. 13 depicts the comparison of the predicted amino acid sequences of the BVH-11 proteins from various *S. pneumoniae* strains. The degrees of identity (I) and similarity (S) were determined by using the program Clustal W from MacVector sequence analysis software (version 6.5).

FIG. 14A-B is a DNA sequence containing the complete BVH-3 gene (open reading frame "ORF" at nucleotides 1777 to 4896); SEQ ID NO: 11.

FIG. 15 is a DNA sequence containing the complete BVH-11 gene (ORF at nucleotides 45 to 2567); SEQ ID NO: 12.

FIG. 16 is a DNA sequence containing the complete BVH-11-2 gene (ORF at nucleotides 114 to 2630); SEQ ID NO: 13.

FIG. 17 is the amino acid sequence of BVH-11-2 protein; SEQ ID NO: 14.

FIG. 18 is the DNA sequence of SP63 BVH-3 gene; SEQ ID NO:15.

FIG. 19 is the amino acid sequence of SP63 BVH-3 protein; SEQ ID NO: 16.

FIG. 20 is the amino acid sequence of BVH-3M protein; SEQ ID NO: 55.

FIG. 21 is the amino acid sequence of BVH-3AD protein; SEQ ID NO: 56.

FIG. 22 is the amino acid sequence of L-BVH-3-AD protein; SEQ ID NO: 57.

FIG. 23 is the amino acid sequence of NEW12 protein; SEQ ID NO: 58.

FIG. 24 is the amino acid sequence of BVH-3C protein; SEQ ID NO: 59.

FIG. 25 is the amino acid sequence of BVH-11M protein; SEQ ID NO: 60.

FIG. 26 is the amino acid sequence of BVH-11A protein; SEQ ID NO: 61.

FIG. 27 is the amino acid sequence of BVH-11B (also called New13) protein; SEQ ID NO: 62.

FIG. 28 is the amino acid sequence of BVH-11C protein; SEQ ID NO: 63.

FIG. 29 is the amino acid sequence of NEW1 protein; SEQ ID NO: 64.

FIG. 30 is the amino acid sequence of NEW2 protein; SEQ ID NO: 65.

FIG. 31 is the amino acid sequence of NEW3 protein; SEQ ID NO: 66.

FIG. 32 is the amino acid sequence of NEW4 protein; SEQ ID NO: 67.

FIG. 33 is the amino acid sequence of NEW5 protein; SEQ ID NO: 68.

FIG. 34 is the amino acid sequence of NEW6 protein; SEQ ID NO: 69.

FIG. 35 is the amino acid sequence of NEW7 protein; SEQ ID NO: 70.

FIG. 36 is the amino acid sequence of NEW8 protein; SEQ ID NO: 71.

FIG. 37 is the amino acid sequence of NEW9 protein; SEQ ID NO: 72.

FIG. 38 is the amino acid sequence of BVH-11-2M protein; SEQ ID NO: 73.

FIG. 39 is the amino acid sequence of NEW10 protein; SEQ ID NO: 74.

FIG. 40 is the amino acid sequence of NEW11 protein; SEQ ID NO: 75.

FIG. 41A-B is the DNA sequence of NEW12 gene; SEQ ID NO: 76.

FIG. 42 is the amino acid sequence of NEW14 protein; SEQ ID NO: 77.

FIG. 43 is the amino acid sequence of NEW15 protein; SEQ ID NO: 78.

FIG. 44 is the amino acid sequence of NEW16 protein; SEQ ID NO: 79.

FIG. 45 is the DNA sequence of GBS BVH-71 gene; SEQ ID NO: 80.

FIG. 46 is the amino acid sequence of GBS BVH-71 protein; SEQ ID NO: 81.

FIG. 47 is the DNA sequence of GAS BVH-71 gene; SEQ ID NO:82.

FIG. 48 is the amino acid sequence of GAS BVH-71 protein; SEQ ID NO:83.

DETAILED DESCRIPTION OF THE INVENTION

According to one aspect, the present invention provides an isolated polynucleotide encoding a polypeptide having at least 70% identity to a second polypeptide comprising a sequence chosen from SEQ ID NOs: 2, 4, 6, 8, 10, 14, 16, 55 to 75, 77 to 79, 81, 83 or fragments, analogs or derivatives thereof.

According to one aspect, the present invention provides an isolated polynucleotide encoding a polypeptide having at least 95% identity to a second polypeptide comprising a sequence chosen from SEQ ID NOs: 2, 4, 6, 8, 10, 14, 16, 55 to 75, 77 to 79, 81, 83 or fragments, analogs or derivatives thereof.

According to one aspect, the present invention provides an isolated polynucleotide encoding a polypeptide having at least 70% identity to a second polypeptide comprising a sequence chosen from SEQ ID NOs: 2, 4, 8, 10, 14, 16, 55 to 75, 77 to 79, 81, 83 or fragments, analogs or derivatives thereof.

According to one aspect, the present invention provides an isolated polynucleotide encoding a polypeptide having at least 70% identity to a second polypeptide comprising a sequence chosen from SEQ ID NOs: 2, 4, 10, 14, 16, 55 to 75, 77 to 79, 81, 83 or fragments, analogs or derivatives thereof.

According to one aspect, the present invention provides an isolated polynucleotide encoding a polypeptide having at least 70% identity to a second polypeptide comprising a sequence chosen from SEQ ID NOs: 2, 4, 8, 10, 14, 16, 55 to 75, 77 to 79 or fragments, analogs or derivatives thereof.

According to one aspect, the present invention provides an isolated polynucleotide encoding a polypeptide having at least 70% identity to a second polypeptide comprising a sequence chosen from SEQ ID NOs: 2, 8, 10, 16, 55, 56, 57, 58, 59, 64, 65, 66, 78 or fragments, analogs or derivatives thereof.

According to one aspect, the present invention provides an isolated polynucleotide encoding a polypeptide having at least 70% identity to a second polypeptide comprising a sequence chosen from SEQ ID NOs: 2, 8, 10, 16, 55, 56, 57, 59, 64, 65, 66, 78 or fragments, analogs or derivatives thereof.

According to one aspect, the present invention provides an isolated polynucleotide encoding a polypeptide having at least 70% identity to a second polypeptide comprising a sequence chosen from SEQ ID NOs: 4, 14, 58, 60, 61, 62, 63, 67, 68, 69, 70, 71, 72, 73, 74, 75, 77, 79 or fragments, analogs or derivatives thereof.

According to one aspect, the present invention provides an isolated polynucleotide encoding a polypeptide having at least 70% identity to a second polypeptide comprising a sequence chosen from SEQ ID NOs: 4, 14, 60, 61, 62, 63, 67, 68, 69, 70, 71, 72, 73, 74, 75, 77, 79 or fragments, analogs or derivatives thereof.

According to one aspect, the present invention provides an isolated polynucleotide encoding a polypeptide having at least 70% identity to a second polypeptide comprising a sequence chosen from SEQ ID NOs: 2, 4, 10, 14, 16, 55 to 75, 77 to 79 or fragments, analogs or derivatives thereof.

According to one aspect, the present invention provides an isolated polynucleotide encoding a polypeptide having at least 70% identity to a second polypeptide comprising sequence chosen from SEQ ID NOs: 10, 55 to 75, 77, 78, 79 or fragments, analogs or derivatives thereof.

According to one aspect, the present invention provides an isolated polynucleotide encoding a polypeptide having at least 70% identity to a second polypeptide comprising sequence chosen from SEQ ID NOs: 55 to 75, 77, 78, 79 or fragments, analogs or derivatives thereof.

According to one aspect, the present invention provides an isolated polynucleotide encoding a polypeptide having at least 70% identity to a second polypeptide comprising a sequence chosen from SEQ ID NOs: 2, 4, 6, 8, 10 or fragments, analogs or derivatives thereof.

According to one aspect, the present invention provides an isolated polynucleotide encoding a polypeptide having at least 70% identity to a second polypeptide comprising a sequence chosen from SEQ ID NOs: 2, 4, 10, 14, 16 or fragments, analogs or derivatives thereof.

According to one aspect, the present invention provides an isolated polynucleotide encoding a polypeptide having at least 70% identity to a second polypeptide comprising a sequence chosen from SEQ ID NOs: 2, 4, 14, 16 or fragments, analogs or derivatives thereof.

According to one aspect, the present invention provides an isolated polynucleotide encoding a polypeptide having at least 70% identity to a second polypeptide comprising sequence SEQ ID NO: 2 or fragments, analogs or derivatives thereof.

According to one aspect, the present invention provides an isolated polynucleotide encoding a polypeptide having at least 70% identity to a second polypeptide comprising sequence SEQ ID NO: 4 or fragments, analogs or derivatives thereof.

According to one aspect, the present invention provides an isolated polynucleotide encoding a polypeptide having at least 70% identity to a second polypeptide comprising sequence SEQ ID NO: 10 or fragments, analogs or derivatives thereof.

According to one aspect, the present invention provides an isolated polynucleotide encoding a polypeptide having at least 70% identity to a second polypeptide comprising sequence SEQ ID NO: 14 or fragments, analogs or derivatives thereof.

According to one aspect, the present invention provides an isolated polynucleotide encoding a polypeptide having at least 70% identity to a second polypeptide comprising sequence SEQ ID NO: 16 or fragments, analogs or derivatives thereof.

According to one aspect, the present invention provides an isolated polynucleotide encoding a polypeptide having at least 70% identity to a second polypeptide comprising sequence SEQ ID NO: 58 or fragments, analogs or derivatives thereof.

According to one aspect, the present invention provides an isolated polynucleotide encoding a polypeptide having at least 70% identity to a second polypeptide comprising sequence SEQ ID NO: 60 or fragments, analogs or derivatives thereof.

According to one aspect, the present invention provides an isolated polynucleotide encoding a polypeptide having at least 70% identity to a second polypeptide comprising sequence SEQ ID NO: 62 or fragments, analogs or derivatives thereof.

According to one aspect, the present invention provides an isolated polynucleotide encoding a polypeptide having at least 70% identity to a second polypeptide comprising sequence SEQ ID NO: 64 or fragments, analogs or derivatives thereof.

According to one aspect, the present invention provides an isolated polynucleotide encoding a polypeptide having at least 70% identity to a second polypeptide comprising sequence SEQ ID NO: 67 or fragments, analogs or derivatives thereof.

According to one aspect, the present invention provides an isolated polynucleotide encoding a polypeptide having at least 70% identity to a second polypeptide comprising sequence SEQ ID NO: 68 or fragments, analogs or derivatives thereof.

According to one aspect, the present invention provides an isolated polynucleotide encoding a polypeptide having at least 70% identity to a second polypeptide comprising sequence SEQ ID NO: 69 or fragments, analogs or derivatives thereof.

According to one aspect, the present invention provides an isolated polynucleotide encoding a polypeptide having at least 70% identity to a second polypeptide comprising sequence SEQ ID NO: 72 or fragments, analogs or derivatives thereof.

According to one aspect, the present invention provides an isolated polynucleotide encoding a polypeptide having at least 70% identity to a second polypeptide comprising sequence SEQ ID NO: 74 or fragments, analogs or derivatives thereof.

According to one aspect, the present invention provides an isolated polynucleotide encoding a polypeptide having at least 70% identity to a second polypeptide comprising sequence SEQ ID NO: 77 or fragments, analogs or derivatives thereof.

According to one aspect, the present invention relates to polypeptides characterized by the amino acid sequence chosen from SEQ ID NOs: 2, 4, 6, 8, 10 or fragments, analogs or derivatives thereof.

According to one aspect, the present invention relates to polypeptides characterized by the amino acid sequence chosen from SEQ ID NOs: 2, 4, 6, 8, 10, 14, 16, 55 to 75, 77 to 79, 81, 83 or fragments, analogs or derivatives thereof.

According to one aspect, the present invention relates to polypeptides characterized by the amino acid sequence chosen from SEQ ID NOs: 2, 4, 8, 10, 14, 16, 55 to 75, 77 to 79, 81, 83 or fragments, analogs or derivatives thereof.

According to one aspect, the present invention relates to polypeptides characterized by the amino acid sequence chosen from SEQ ID NOs: 2, 4, 10, 14, 16, 55 to 75, 77 to 79, 81, 83 or fragments, analogs or derivatives thereof.

According to one aspect, the present invention relates to polypeptides characterized by the amino acid sequence chosen from SEQ ID NOs: 2, 4, 8, 10, 14, 16, 55 to 75, 77 to 79 or fragments, analogs or derivatives thereof.

According to one aspect, the present invention relates to polypeptides characterized by the amino acid sequence chosen from SEQ ID NOs: 2, 4, 10, 14, 16, 55 to 75, 77 to 79 or fragments, analogs or derivatives thereof.

According to one aspect, the present invention relates to polypeptides characterized by the amino acid sequence chosen from SEQ ID NOs: 2, 4, 10, 14, 16 or fragments, analogs or derivatives thereof.

According to one aspect, the present invention relates to polypeptides characterized by the amino acid sequence comprising sequence SEQ ID NO: 2 or fragments, analogs or derivatives thereof.

According to one aspect, the present invention relates to polypeptides characterized by the amino acid sequence comprising sequence SEQ ID NO: 4 or fragments, analogs or derivatives thereof.

According to one aspect, the present invention relates to polypeptides characterized by the amino acid sequence comprising sequence SEQ ID NO: 10 or fragments, analogs or derivatives thereof.

According to one aspect, the present invention relates to polypeptides characterized by the amino acid sequence comprising sequence SEQ ID NO: 14 or fragments, analogs or derivatives thereof.

According to one aspect, the present invention relates to polypeptides characterized by the amino acid sequence comprising sequence SEQ ID NO: 16 or fragments, analogs or derivatives thereof.

According to one aspect, the present invention relates to polypeptides characterized by the amino acid sequence chosen from SEQ ID NOs: 10, 55 to 75, 77, 78, 79 or fragments, analogs or derivatives thereof.

According to one aspect, the present invention relates to polypeptides characterized by the amino acid sequence chosen from SEQ ID NO: 10, 58, 60, 62, 64, 67, 68, 69, 72, 74, 77 or fragments, analogs or derivatives thereof.

According to one aspect, the present invention relates to polypeptides characterized by the amino acid sequence chosen from SEQ ID NO: 10, 58, 60, 62, 64, 67, 68, 69, 72, 74, 77 or fragments, analogs or derivatives thereof.

According to one aspect, the present invention relates to polypeptides characterized by the amino acid sequence chosen from SEQ ID NO: 10, 58, 60, 62, 64, 67, 68, 69, 72, 74, 77 or fragments, analogs or derivatives thereof.

According to one aspect, the present invention relates to polypeptides characterized by the amino acid sequence chosen from SEQ ID NO: 10, 62, 64, 67, 68, 74, 77 or fragments, analogs or derivatives thereof.

According to one aspect, the present invention relates to polypeptides characterized by the amino acid sequence comprising sequence SEQ ID NO: 58 or fragments, analogs or derivatives thereof.

According to one aspect, the present invention relates to polypeptides characterized by the amino acid sequence comprising sequence SEQ ID NO: 62 or fragments, analogs or derivatives thereof.

According to one aspect, the present invention relates to polypeptides characterized by the amino acid sequence comprising sequence SEQ ID NO: 64 or fragments, analogs or derivatives thereof.

According to one aspect, the present invention relates to polypeptides characterized by the amino acid sequence comprising sequence SEQ ID NO: 67 or fragments, analogs or derivatives thereof.

According to one aspect, the present invention relates to polypeptides characterized by the amino acid sequence comprising sequence SEQ ID NO: 68 or fragments, analogs or derivatives thereof.

According to one aspect, the present invention relates to polypeptides characterized by the amino acid sequence comprising sequence SEQ ID NO: 74 or fragments, analogs or derivatives thereof.

According to one aspect, the present invention relates to polypeptides characterized by the amino acid sequence comprising sequence SEQ ID NO: 77 or fragments, analogs or derivatives thereof.

In a further embodiment, the present invention also relates to chimeric polypeptides which comprise one or more polypeptides or fragments, analogs or derivatives thereof as described in the present application.

In a further embodiment, the present invention also relates to chimeric polypeptides which comprise one or more polypeptides or fragments, analogs or derivatives thereof as defined in the figures of the present application.

In a further embodiment, the present application also relates to chimeric polypeptides which comprise two or more polypeptides chosen from SEQ ID NOs: 2, 4, 6, 8, 10, 14, 16, 55 to 75, 77 to 79, 81, 83 or fragments, analogs or derivatives thereof; provided that the polypeptides or fragments, analogs or derivatives thereof are linked as to form a chimeric polypeptide.

In a further embodiment, the chimeric polypeptide will comprise two or more polypeptides chosen from SEQ ID NOs:10, 58, 60, 62, 64, 67, 68, 69, 72, 74, 77 or fragments, analogs or derivatives thereof; provided that the polypeptides or fragments, analogs or derivatives thereof are linked as to form a chimeric polypeptide.

In a further embodiment, the chimeric polypeptide will comprise two or more polypeptides chosen from SEQ ID NOs:10, 58, 60, 62, 64, 67, 68, 74, 77 or fragments, analogs or derivatives thereof; provided that the polypeptides or fragments, analogs or derivatives thereof are linked as to form a chimeric polypeptide.

In a further embodiment, the chimeric polypeptide will comprise two or more polypeptides chosen from SEQ ID NOs:10, 62, 64, 67, 68, 74, 77 or fragments, analogs or derivatives thereof; provided that the polypeptides or fragments, analogs or derivatives thereof are linked as to form a chimeric polypeptide.

In a further embodiment, the chimeric polypeptide will comprise between 2 and 5 polypeptides.

In a further embodiment, the chimeric polypeptide will comprise between 2 and 4 polypeptides.

In a further embodiment, the chimeric polypeptide will comprise between 2 and 3 polypeptides.

In a further embodiment, the chimeric polypeptide will comprise 2 polypeptides.

In a further embodiment, there is provided a chimeric polypeptide of formula (I):

$$A-(B)_m-(C)_n-D \qquad (I)$$

Wherein;
m is 0 or 1,
n is 0 or 1,
A is chosen from SEQ ID NOs: 2, 4, 6, 8, 10, 14, 16, 55 to 75, 77 to 79, 81, 83 or fragments, analogs or derivatives thereof;
B is chosen from SEQ ID NOs: 2, 4, 6, 8, 10, 14, 16, 55 to 75, 77 to 79, 81, 83 or fragments, analogs or derivatives thereof;

C is chosen from SEQ ID NOs: 2, 4, 6, 8, 10, 14, 16, 55 to 75, 77 to 79, 81, 83 or fragments, analogs or derivatives thereof; and D is chosen from SEQ ID NOs: 2, 4, 6, 8, 10, 14, 16, 55 to 75, 77 to 79, 81, 83 or fragments, analogs or derivatives thereof.

In a further embodiment,

A is chosen from SEQ ID NOs:10, 58, 60, 62, 64, 67, 68, 69, 72, 74, 77 or fragments, analogs or derivatives thereof;

B is chosen from SEQ ID NOs:10, 58, 60, 62, 64, 67, 68, 69, 72, 74, 77, or fragments, analogs or derivatives thereof;

C is chosen from SEQ ID NOs:10, 58, 60, 62, 64, 67, 68, 69, 72, 74, 77 or fragments, analogs or derivatives thereof; and D is chosen from SEQ ID NOs:10, 58, 60, 62, 64, 67, 68, 69, 72, 74, 77 or fragments, analogs or derivatives thereof.

In a further embodiment,

A is chosen from SEQ ID NOs:10, 58, 60, 62, 64, 67, 68, 74, 77 or fragments, analogs or derivatives thereof;

B is chosen from SEQ ID NOs:10, 58, 60, 62, 64, 67, 68, 74, 77, or fragments, analogs or derivatives thereof;

C is chosen from SEQ ID NOs:10, 58, 60, 62, 64, 67, 68, 74, 77 or fragments, analogs or derivatives thereof; and D is chosen from SEQ ID NOs:10, 58, 60, 62, 64, 67, 68, 74, 77 or fragments, analogs or derivatives thereof.

In one embodiment, chimeric polypeptides of the present invention comprise those wherein the following embodiments are present, either independently or in combination.

In a further embodiment, A is SEQ ID NOs:10, 58, 62, 64, 67, 68, 74, 77 or fragments, analogs or derivatives thereof.

In a further embodiment, A is SEQ ID NO:10 or fragments, analogs or derivatives thereof.

In a further embodiment, A is SEQ ID NO:58 or fragments, analogs or derivatives thereof.

In a further embodiment, A is SEQ ID NO:62 or fragments, analogs or derivatives thereof.

In a further embodiment, A is SEQ ID NO:64 or fragments, analogs or derivatives thereof.

In a further embodiment, A is SEQ ID NO:67 or fragments, analogs or derivatives thereof.

In a further embodiment, A is SEQ ID NO:68 or fragments, analogs or derivatives thereof.

In a further embodiment, A is SEQ ID NO:74 or fragments, analogs or derivatives thereof.

In a further embodiment, A is SEQ ID NO:77 or fragments, analogs or derivatives thereof.

In a further embodiment, B is SEQ ID NOs:10, 58, 62, 64, 67, 68, 74, 77 or fragments, analogs or derivatives thereof.

In a further embodiment, B is SEQ ID NO:10 or fragments, analogs or derivatives thereof.

In a further embodiment, B is SEQ ID NO:58 or fragments, analogs or derivatives thereof.

In a further embodiment, B is SEQ ID NO:64 or fragments, analogs or derivatives thereof.

In a further embodiment, B is SEQ ID NO:64 or fragments, analogs or derivatives thereof.

In a further embodiment, B is SEQ ID NO:67 or fragments, analogs or derivatives thereof.

In a further embodiment, B is SEQ ID NO:68 or fragments, analogs or derivatives thereof.

In a further embodiment, B is SEQ ID NO:74 or fragments, analogs or derivatives thereof.

In a further embodiment, B is SEQ ID NO: 77 or fragments, analogs or derivatives thereof.

In a further embodiment, C is SEQ ID NOs:10, 58, 62, 64, 67, 68, 74, 77 or fragments, analogs or derivatives thereof.

In a further embodiment, C is SEQ ID NO:10 or fragments, analogs or derivatives thereof.

In a further embodiment, C is SEQ ID NO:58 or fragments, analogs or derivatives thereof.

In a further embodiment, C is SEQ ID NO: 62 or fragments, analogs or derivatives thereof.

In a further embodiment, C is SEQ ID NO:64 or fragments, analogs or derivatives thereof.

In a further embodiment, C is SEQ ID NO: 67 or fragments, analogs or derivatives thereof.

In a further embodiment, C is SEQ ID NO: 68 or fragments, analogs or derivatives thereof.

In a further embodiment, C is SEQ ID NO: 74 or fragments, analogs or derivatives thereof.

In a further embodiment, C is SEQ ID NO: 77 or fragments, analogs or derivatives thereof.

In a further embodiment, D is SEQ ID NO:10, 58, 62, 64, 67, 68, 74, 77 or fragments, analogs or derivatives thereof.

In a further embodiment, D is SEQ ID NO:10 or fragments, analogs or derivatives thereof.

In a further embodiment, D is SEQ ID NO:58 or fragments, analogs or derivatives thereof.

In a further embodiment, D is SEQ ID NO:62 or fragments, analogs or derivatives thereof.

In a further embodiment, D is SEQ ID NO:64 or fragments, analogs or derivatives thereof.

In a further embodiment, D is SEQ ID NO:67 or fragments, analogs or derivatives thereof.

In a further embodiment, D is SEQ ID NO:68 or fragments, analogs or derivatives thereof.

In a further embodiment, D is SEQ ID NO:74 or fragments, analogs or derivatives thereof.

In a further embodiment, D is SEQ ID NO:77 or fragments, analogs or derivatives thereof.

In a further embodiment, m is 0.

In a further embodiment, n is 0.

In a further embodiment, m and n are 0.

In a further embodiment, m and n are 0, A is SEQ ID NO:64 or fragments, analogs or derivatives thereof, B is SEQ ID NO:62 or fragments, analogs or derivatives thereof.

In a further embodiment, m and n are 0, A is SEQ ID NO:62 or fragments, analogs or derivatives thereof, B is SEQ ID NO:64 or fragments, analogs or derivatives thereof.

In accordance with the present invention, all nucleotides encoding polypeptides and chimeric polypeptides are within the scope of the present invention.

In a further embodiment, the polypeptides or chimeric polypeptides in accordance with the present invention are antigenic.

In a further embodiment, the polypeptides or chimeric polypeptides in accordance with the present invention can elicit an immune response in an individual.

In a further embodiment, the present invention also relates to polypeptides which are able to raise antibodies having binding specificity to the polypeptides or chimeric polypeptides of the present invention as defined above.

An antibody that "has binding specificity" is an antibody that recognizes and binds the selected polypeptide but which does not substantially recognize and bind other molecules in a sample, e.g., a biological sample, which naturally includes the selected peptide. Specific binding can be measured using an ELISA assay in which the selected polypeptide is used as an antigen.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

As used herein, "fragments", "derivatives" or "analogs" of the polypeptides of the invention include those polypeptides in which one or more of the amino acid residues are substituted with a conserved or non-conserved amino acid residue (preferably conserved) and which may be natural or unnatural. In one embodiment, derivatives and analogs of polypeptides of the invention will have about 70% identity with those sequences illustrated in the figures or fragments thereof. That is, 70% of the residues are the same. In a further embodiment, polypeptides will have greater than 75% homology. In a further embodiment, polypeptides will have greater than 80% homology. In a further embodiment, polypeptides will have greater than 85% homology. In a further embodiment, polypeptides will have greater than 90% homology. In a further embodiment, polypeptides will have greater than 95% homology. In a further embodiment, polypeptides will have greater than 99% homology. In a further embodiment, derivatives and analogs of polypeptides of the invention will have fewer than about 20 amino acid residue substitutions, modifications or deletions and more preferably less than 10. Preferred substitutions are those known in the art as conserved, i.e., the substituted residues share physical or chemical properties such as hydrophobicity, size, charge or functional groups.

In accordance with the present invention, polypeptides of the invention include both polypeptides and chimeric polypeptides.

Also included are polypeptides which have fused thereto other compounds which alter the polypeptides biological or pharmacological properties, i.e., polyethylene glycol (PEG) to increase half-life; leader or secretory amino acid sequences for ease of purification; prepro- and pro-sequences; and (poly)saccharides.

Furthermore, in those situations where amino acid regions are found to be polymorphic, it may be desirable to vary one or more particular amino acids to more effectively mimic the different epitopes of the different *streptococcus* strains.

Moreover, the polypeptides of the present invention can be modified by terminal —NH$_2$ acylation (e.g., by acetylation, or thioglycolic acid amidation, terminal carbosy amidation, e.g., with ammonia or methylamine) to provide stability, increased hydrophobicity for linking or binding to a support or other molecule.

Also contemplated are hetero and homo polypeptide multimers of the polypeptide fragments, analogues and derivatives. These polymeric forms include, for example, one or more polypeptides that have been cross-linked with cross-linkers such as avidin/biotin, gluteraldehyde or dimethylsuperimidate. Such polymeric forms also include polypeptides containing two or more tandem or inverted contiguous sequences, produced from multicistronic mRNAs generated by recombinant DNA technology.

Preferably, a fragment, analog or derivative of a polypeptide of the invention will comprise at least one antigenic region, i.e., at least one epitope.

In order to achieve the formation of antigenic polymers (i.e., synthetic multimers), polypeptides may be utilized having bishaloacetyl groups, nitroarylhalides, or the like, where the reagents being specific for thio groups. Therefore, the link between two mercapto groups of the different peptides may be a single bond or may be composed of a linking group of at least two, typically at least four, and not more than 16, but usually not more than about 14 carbon atoms.

In a particular embodiment, polypeptide fragments, analogs and derivatives of the invention do not contain a methionine (Met) starting residue. Preferably, polypeptides will not incorporate a leader or secretory sequence (signal sequence). The signal portion of a polypeptide of the invention may be determined according to established molecular biological techniques. In general, the polypeptide of interest may be isolated from a *streptococcus* culture and subsequently sequenced to determine the initial residue of the mature protein and therefore the sequence of the mature polypeptide.

According to another aspect, there are provided vaccine compositions comprising one or more *streptococcus* polypeptides of the invention in admixture with a pharmaceutically acceptable carrier diluent or adjuvant. Suitable adjuvants include oils, i.e., Freund's complete or incomplete adjuvant; salts, i.e., AlK(SO$_4$)$_2$, AlNa(SO$_4$)$_2$, AlNH$_4$(SO$_4$)$_2$, silica, kaolin, carbon polynucleotides, i.e., poly IC and poly AU. Preferred adjuvants include QuilA and Alhydrogel. Vaccines of the invention may be administered parenterally by injection, rapid infusion, nasopharyngeal absorption, dermoabsorption, or bucal or oral. Pharmaceutically acceptable carriers also include tetanus toxoid.

Vaccine compositions of the invention are used for the treatment or prophylaxis of *streptococcus* infection and/or diseases and symptoms mediated by *streptococcus* infection as described in P. R. Murray (Ed, in chief), E. J. Baron, M. A. Pfaller, F. C. Tenover and R. H. Yolken. Manual of Clinical Microbiology, ASM Press, Washington, D.C. sixth edition, 1995, 1482, which are herein incorporated by reference. In one embodiment, vaccine compositions of the present invention are used for the treatment or prophylaxis of meningitis, otitis media, bacteremia or pneumonia. In one embodiment, vaccine compositions of the invention are used for the treatment or prophylaxis of *streptococcus* infection and/or diseases and symptoms mediated by *streptococcus* infection, in particular *S. pneumoniae*, group A *streptococcus* (*pyogenes*), group B *streptococcus* (GBS or *agalactiae*), *dysgalactiae*, *uberis*, *nocardia* as well as *Staphylococcus aureus*. In a further embodiment, the *streptococcus* infection is *S. pneumoniae*.

In a particular embodiment, vaccines are administered to those individuals at risk of *streptococcus* infection such as infants, elderly and immunocompromised individuals.

As used in the present application, the term "individuals" include mammals. In a further embodiment, the mammal is human.

Vaccine compositions are preferably in unit dosage form of about 0.001 to 100 µg/kg (antigen/body weight) and more preferably 0.01 to 10 µg/kg and most preferably 0.1 to 1 µg/kg 1 to 3 times with an interval of about 1 to 6 week intervals between immunizations.

According to another aspect, there are provided polynucleotides encoding polypeptides characterized by the amino acid sequence chosen from SEQ ID NOs: 2, 4, 6, 8, 10, 14, 16, 55 to 75, 77 to 79, 81, 83 or fragments, analogs or derivatives thereof.

In one embodiment, polynucleotides are those illustrated in SEQ ID Nos: 1, 3, 5, 7, 9, 11, 12, 13, 15, 76, 80, 82 which may include the open reading frames (ORF), encoding polypeptides of the invention. It will be appreciated that the polynucleotide sequences illustrated in the figures may be altered with degenerate codons yet still encode the polypeptides of the invention. Accordingly the present invention further provides polynucleotides which hybridize to the polynucleotide sequences herein above described (or the complement sequences thereof) having 50% identity between sequences. In one embodiment, at least 70% identity between sequences. In one embodiment, at least 75% identity between sequences. In one embodiment, at least 80% identity between sequences. In one embodiment, at least 85% identity between sequences. In one embodiment, at least 90% identity between sequences. In a further embodiment, polynucleotides are hybridizable under stringent conditions, i.e., having at least 95% identity. In a further embodiment, more than 97% identity.

In a further embodiment, polynucleotides are those illustrated in SEQ ID NOs: 1, 3, 7, 9, 11, 12, 13, 15, 76, 80, 82 encoding polypeptides of the invention.

In a further embodiment, polynucleotides are those illustrated in SEQ ID NOs: 1, 3, 9, 11, 12, 13, 15, 76, 80, 82 which may include the open reading frames (ORF), encoding polypeptides of the invention.

In a further embodiment, polynucleotides are those illustrated in SEQ ID NOs: 1, 3, 9, 11, 12, 13, 15, 76 which may include the open reading frames (ORF), encoding polypeptides of the invention.

In a further embodiment, polynucleotides are those illustrated in SEQ ID NOs: 1, 3, 7, 9, 11, 12, 13, 15, 76 which may include the open reading frames (ORF), encoding polypeptides of the invention.

In a further embodiment, polynucleotides are those illustrated in SEQ ID NOs: 1, 7, 9, 11, 15, 76 which may include the open reading frames (ORF), encoding polypeptides of the invention.

In a further embodiment, polynucleotides are those illustrated in SEQ ID NOs: 1, 9, 11, 15, 76 which may include the open reading frames (ORF), encoding polypeptides of the invention.

In a further embodiment, polynucleotides are those illustrated in SEQ ID NOs: 1, 7, 9, 11 which may include the open reading frames (ORF), encoding polypeptides of the invention.

In a further embodiment, polynucleotides are those illustrated in SEQ ID NO: 1, encoding polypeptides of the invention.

In a further embodiment, polynucleotides are those illustrated in SEQ ID NO:7, encoding polypeptides of the invention.

In a further embodiment, polynucleotides are those illustrated in SEQ ID NO:9, encoding polypeptides of the invention.

In a further embodiment, polynucleotides are those illustrated in SEQ ID NO:11, encoding polypeptides of the invention.

In a further embodiment, polynucleotides are those illustrated in SEQ ID NO:15, encoding polypeptides of the invention.

In a further embodiment, polynucleotides are those illustrated in SEQ ID NOs: 3, 12, 13, 76, encoding polypeptides of the invention.

In a further embodiment, polynucleotides are those illustrated in SEQ ID NO:3, encoding polypeptides of the invention.

In a further embodiment, polynucleotides are those illustrated in SEQ ID NO:12, encoding polypeptides of the invention.

In a further embodiment, polynucleotides are those illustrated in SEQ ID NO:13, encoding polypeptides of the invention.

In a further embodiment, polynucleotides are those illustrated in SEQ ID NO:76, encoding polypeptides of the invention.

As will be readily appreciated by one skilled in the art, polynucleotides include both DNA and RNA.

The present invention also includes polynucleotides complementary to the polynucleotides described in the present application.

In a further aspect, polynucleotides encoding polypeptides of the invention, or fragments, analogs or derivatives thereof, may be used in a DNA immunization method. That is, they can be incorporated into a vector which is replicable and expressible upon injection thereby producing the antigenic polypeptide in vivo. For example polynucleotides may be incorporated into a plasmid vector under the control of the CMV promoter which is functional in eukaryotic cells. Preferably the vector is injected intramuscularly.

According to another aspect, there is provided a process for producing polypeptides of the invention by recombinant techniques by expressing a polynucleotide encoding said polypeptide in a host cell and recovering the expressed polypeptide product. Alternatively, the polypeptides can be produced according to established synthetic chemical techniques, i.e., solution phase or solid phase synthesis of oligopeptides which are ligated to produce the full polypeptide (block ligation).

General methods for obtention and evaluation of polynucleotides and polypeptides are described in the following references: Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York; PCR Cloning Protocols, from Molecular Cloning to Genetic Engineering, Edited by White B. A., Humana Press, Totowa, N.J., 1997, 490 pages; Protein Purification, Principles and Practices, Scopes R. K., Springer-Verlag, New York, 3rd Edition, 1993, 380 pages; Current Protocols in Immunology, Edited by Coligan J. E. et al., John Wiley & Sons Inc., New York which are herein incorporated by reference.

For recombinant production, host cells are transfected with vectors which encode the polypeptide, and then cultured in a nutrient media modified as appropriate for activating promoters, selecting transformants or amplifying the genes. Suitable vectors are those that are viable and replicable in the chosen host and include chromosomal, non-chromosomal and synthetic DNA sequences, e.g., bacterial plasmids, phage DNA, baculovirus, yeast plasmids, vectors derived from combinations of plasmids and phage DNA. The polypeptide sequence may be incorporated in the vector at the appropriate site using restriction enzymes such that it is operably linked to an expression control region comprising a promoter, ribosome binding site (consensus region or Shine-Dalgarno sequence), and optionally an operator (control element). One can select individual components of the expression control region that are appropriate for a given host and vector according to established molecular biology principles (Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York incorporated herein by reference). Suitable promoters include but are not limited to LTR or SV40 promoter, *E. coli* lac, tac or trp promoters and the phage lambda $P_L$ promoter. Vectors will preferably incorporate an origin of replication as well as selection markers, i.e., ampicilin resistance gene. Suitable bacterial vectors include pET, pQE70, pQE60, pQE-9, pbs, pD10 phagescript, psiX174, pbluescript SK, pbsks, pNH8A, pNH16a, pNH18A, pNH46A, ptrc99a, pKK223-3, pKK233-3, pDR540, pRIT5 and eukaryotic vectors pBlueBacIII, pWLNEO, pSV2CAT, pOG44, pXT1, pSG, pSVK3, pBPV, pMSG and pSVL. Host cells may be bacterial, i.e., *E.* coli, Bacillus subtilis, Streptomyces; fungal, i.e., *Aspergillus niger, Aspergillus nidulins*; yeast, i.e., *Saccharomyces* or eukaryotic, i.e., CHO, COS.

Upon expression of the polypeptide in culture, cells are typically harvested by centrifugation then disrupted by physical or chemical means (if the expressed polypeptide is not secreted into the media) and the resulting crude extract retained to isolate the polypeptide of interest. Purification of the polypeptide from culture media or lysate may be achieved by established techniques depending on the properties of the polypeptide, i.e., using ammonium sulfate or ethanol precipitation, acid extraction, anion or cation exchange chromatography, phosphocellulose chromatography, hydrophobic interaction chromatography, hydroxylapatite chromatography and lectin chromatography. Final purification may be achieved using HPLC.

The polypeptide may be expressed with or without a leader or secretion sequence. In the former case the leader may be removed using post-translational processing (see U.S. Pat. No. 4,431,739; U.S. Pat. No. 4,425,437; and U.S. Pat. No. 4,338,397 incorporated herein by reference) or be chemically removed subsequent to purifying the expressed polypeptide.

According to a further aspect, the *streptococcus* polypeptides of the invention may be used in a diagnostic test for *streptococcus* infection, in particular *S. pneumoniae* infection. Several diagnostic methods are possible, for example detecting *streptococcus* organism in a biological sample, the following procedure may be followed:

a) obtaining a biological sample from a patient;

b) incubating an antibody or fragment thereof reactive with a *streptococcus* polypeptide of the invention with the biological sample to form a mixture; and c) detecting specifically bound antibody or bound fragment in the mixture which indicates the presence of *streptococcus*.

Alternatively, a method for the detection of antibody specific to a *streptococcus* antigen in a biological sample containing or suspected of containing said antibody may be performed as follows:

a) obtaining a biological sample from a patient;

b) incubating one or more *streptococcus* polypeptides of the invention or fragments thereof with the biological sample to form a mixture; and c) detecting specifically bound antigen or bound fragment in the mixture which indicates the presence of antibody specific to *streptococcus*.

One of skill in the art will recognize that this diagnostic test may take several forms, including an immunological test such as an enzyme-linked immunosorbent assay (ELISA), a radio-immunoassay or a latex agglutination assay, essentially to determine whether antibodies specific for the protein are present in an organism.

The DNA sequences encoding polypeptides of the invention may also be used to design DNA probes for use in detecting the presence of *streptococcus* in a biological sample suspected of containing such bacteria. The detection method of this invention comprises:

a) obtaining the biological sample from a patient;

b) incubating one or more DNA probes having a DNA sequence encoding a polypeptide of the invention or fragments thereof with the biological sample to form a mixture; and c) detecting specifically bound DNA probe in the mixture which indicates the presence of *streptococcus* bacteria.

The DNA probes of this invention may also be used for detecting circulating *streptococcus*, i.e., *S. pneumoniae* nucleic acids in a sample, for example using a polymerase chain reaction, as a method of diagnosing *streptococcus* infections. The probe may be synthesized using conventional techniques and may be immobilized on a solid phase, or may be labelled with a detectable label. A preferred DNA probe for this application is an oligomer having a sequence complementary to at least 6 contiguous nucleotides of the *Streptococcus pneumoniae* polypeptides of the invention.

Another diagnostic method for the detection of *streptococcus* in a patient comprises:

a) labelling an antibody reactive with a polypeptide of the invention or fragment thereof with a detectable label;

b) administering the labelled antibody or labelled fragment to the patient; and c) detecting specifically bound labelled antibody or labelled fragment in the patient which indicates the presence of *streptococcus*.

A further aspect of the invention is the use of the *streptococcus* polypeptides of the invention as immunogens for the production of specific antibodies for the diagnosis and in particular the treatment of *streptococcus* infection. Suitable antibodies may be determined using appropriate screening methods, for example by measuring the ability of a particular antibody to passively protect against *streptococcus* infection in a test model. One example of an animal model is the mouse model described in the examples herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal, or preferably monoclonal. It may be specific for a number of epitopes associated with the *Streptococcus pneumoniae* polypeptides but is preferably specific for one.

Without limiting its scope, the present invention also relates to new antigens designated BVH-3, BVH-11, BVH-11-2, BVH-28 and BVH-71. The present invention also relates to truncated polypeptides comprising fragments of the new antigens designated BVH-3, BVH-11, BVH-11-2, BVH-28 and BVH-71. The present invention also relates to chimeric polypeptides comprising fragments of the new antigens designated BVH-3, BVH-11, BVH-11-2, BVH-28 and BVH-71. The following is a reference table summarizing the relation between the antigens of the present invention:

| Family | Nucleotide SEQ ID NO | Polypeptide SEQ ID NO |
|---|---|---|
| BVH-3 | | |
| BVH-3 | 1, 11 | 2 |
| BVH-3A | 7 | 8 |
| BVH-3B | 9 | 10 |
| BVH-3 SP63 | 15 | 16 |
| BVH-3M | | 55 |
| BVH-3AD | | 56 |
| L-BVH-3AD | | 57 |
| New12 | 76 | 58 |
| BVH-3C | | 59 |
| New1 | | 64 |
| New2 | | 65 |
| New3 | | 66 |
| New15 | | 78 |
| BVH-11 | | |
| BVH-11-1 | 3, 12 | 4 |
| BVH-11-2 | 13 | 14 |
| BVH-11M | | 60 |
| BVH-11A | | 61 |
| BVH-11B also referred to as NEW13 | | 62 |
| BVH-11C | | 63 |

-continued

| Family | Nucleotide SEQ ID NO | Polypeptide SEQ ID NO |
|---|---|---|
| New4 | | 67 |
| New5 | | 68 |
| New6 | | 69 |
| New7 | | 70 |
| New8 | | 71 |
| New9 | | 72 |
| BVH-11-2M | | 73 |
| New10 | | 74 |
| New11 | | 75 |
| New12 | 76 | 58 |
| New14 | | 77 |
| New16 | | 79 |
| BVH-28 | | |
| BVH-28 | 5 | 6 |
| BVH-71 | | |
| GBS | 80 | 81 |
| GAS | 82 | 83 |

Example 1

This example illustrates the cloning of S. pneumoniae genes.

The coding region of S. pneumoniae gene BVH-3 (SEQ ID NO: 1) and the coding region of S. pneumoniae gene BVH-28 (SEQ ID NO: 5) were amplified by PCR (DNA Thermal Cycler GeneAmp PCR system 2400 Perkin Elmer, San Jose, Calif.) from genomic DNA of serogroup 6 S. pneumoniae strain SP64 using the oligos that contained base extensions for the addition of restriction sites BglII (AGATCT) and XbaI (TCTAGA). PCR products were purified from agarose gel using a QIAquick gel extraction kit from QIAgen (Chatsworth, Calif.), digested BglII-XbaI (Pharmacia Canada Inc, Baie d'Urfé, Canada), extracted with phenol: chloroform and precipitated with ethanol. The Superlinker vector pSL301 (Invitrogen, San Diego, Calif.) was digested with BglII and XbaI and purified from agarose gel using a QIAquick gel extraction kit from QIAgen (Chatsworth, Calif.). The BglII-XbaI genomic DNA fragments were ligated to the BglII-XbaI pSL301 vector. The ligated products were transformed into E. coli strain DH5a [f80 lacZ DM15 endA1 recA1 hsdR17 ('K$^-$$_m$K$^+$) supE44 thi-1l$^-$ gyrA96 relA1 D(lacZYA-argF)U169] (Gibco BRL, Gaithersburg, Md.) according to the method of Simanis (Hanahan, D. DNA Cloning, 1985, D. M. Glover (ed), pp. 109-135). Recombinant pSL301 plasmids (rpSL301) containing either BVH-3 or BVH-28 gene were purified using a QIAgen kit (Chatsworth, Calif.) and DNA inserts were confirmed by nucleotide sequence analysis (Taq Dye Deoxy Terminator Cycle Sequencing kit, ABI, Foster City, Calif.). Recombinant rpSL301 (rpSL301) were digested with the restriction enzymes BglII (AGATCT) and XhoI (CTCGAG). DNA fragments BglII-XhoI were purified using the QIAquick gel extraction kit from QIAgen (Chatsworth, Calif.). pET-32c(+) expression vector (Novagen, Madison, Wis.) containing the thioredoxin-His•Tag sequence was digested with BamHI (GGATCC) and XhoI and gel extracted using the QIAquick gel extraction kit from QIAgen (Chatsworth, Calif.). The BglII-XhoI DNA fragments were ligated to the BamHI-XhoI pET-32c(+) vector to create the coding sequence for thioredoxin-His•Tag-BVH-3 or thioredoxin-His•Tag-BVH-28 fusion protein. The ligated products were transformed into E. coli strain DH5α [f80 lacZ DM15 endA1 recA1 hsdR17 ('K$^-$$^m$K$^+$) supE44 thi-1l$^-$ gyrA96 relA1 D(lacZYA-argF)U169] (Gibco BRL, Gaithersburg, Md.) according to the method of Simanis (Hanahan, D. DNA Cloning, 1985, D. M. Glover (ed), pp. 109-135). Recombinant pET-32c(+) plasmids were purified using a QIAgen kit (Chatsworth, Calif.) and the nucleotide sequences at the fusion sites of thioredoxin-His•Tag and DNA insert were verified by DNA sequencing (Taq Dye Deoxy Terminator Cycle Sequencing kit, ABI, Foster City, Calif.).

Example 2

This example illustrates the cloning of S. pneumoniae protein genes in CMV plasmid pCMV-GH.

The DNA coding region of a S. pneumoniae protein was inserted in phase downstream of a human growth hormone (hGH) gene which was under the transcriptional control of the cytomegalavirus (CMV) promotor in the plasmid vector pCMV-GH (Tang et al., Nature, 1992, 356:152). The CMV promotor is non functional plasmid in E. coli cells but active upon administration of the plasmid in eukaryotic cells. The vector also incorporated the ampicillin resistance gene.

The coding region of BVH-3 gene (SEQ ID NO: 1) and BVH-28 gene (SEQ ID NO: 5) were obtained from rpSL301 (see Example 1) using restriction enzymes BglII (AGATCT) and XbaI (TCTAGA). The digested products were purified from agarose gel using the QIAquick gel extraction kit from QIAgen (Chatsworth, Calif.). The pCMV-GH vector (Laboratory of Dr. Stephen A. Johnston, Department of Biochemistry, The University of Texas, Dallas, Tex.) containing the human growth hormone to create fusion proteins was digested with BglII and XbaI and purified from agarose gel using the QIAquick gel extraction kit from QIAgen (Chatsworth, Calif.). The BglII-XbaI DNA fragments were ligated to the BglII-XbaI pCMV-GH vector to create the hGH-BVH-3 or hGH-BVH-28 fusion protein under the control of the CMV promoter. The ligated products were transformed into E. coli strain DH5a [f80 lacZ DM15 endA1 recA1 hsdR17 ('K$^-$$^m$K$^+$) supE44 thi-1l$^-$ gyrA96 relA1 D(lacZYA-argF)U 169] (Gibco BRL, Gaithersburg, Md.) according to the method of Simanis (Hanahan, D. DNA Cloning, 1985, D. M. Glover (ed), pp. 109-135). The recombinant pCMV plasmids were purified using a QIAgen kit (QIAgen, Chatsworth, Calif.).

The coding region of BVH-11 gene (SEQ ID NO: 3) was amplified by PCR (DNA Thermal Cycler GeneAmp PCR system 2400 Perkin Elmer, San Jose, Calif.) from genomic DNA of serogroup 6 S. pneumoniae strain SP64 using the oligos that contained base extensions for the addition of restriction sites BglII (AGATCT) and HindIII (AAGCTT). The PCR product was purified from agarose gel using a QIAquick gel extraction kit from QIAgen (Chatsworth, Calif.), digested with restriction enzymes (Pharmacia Canada Inc, Baie d'Urfe, Canada), extracted with phenol: chloroform and precipitated with ethanol. The PCMV-GH vector (Laboratory of Dr. Stephen A. Johnston, Department of Biochemistry, The University of Texas, Dallas, Tex.) was digested with BglII and HindIII and purified from agarose gel using the QIAquick gel extraction kit from QIAgen (Chatsworth, Calif.). The BglII-HindIII DNA fragment was ligated to the BglII-HindIII pCMV-GH vector to create the hGH-BVH-11 fusion protein under the control of the CMV promoter. The ligated products were transformed into E. coli strain DH5α [f80 lacZ DM15 endA1 recA1 hsdR17 ('K$^-$$^m$K$^+$) supE44 thi-1l$^-$ gyrA96 relA1 D(lacZYA-argF)U169] (Gibco BRL, Gaithersburg, Md.) according to the method of Simanis (Hanahan, D. DNA Cloning, 1985, D. M. Glover (ed), pp. 109-135). The recombinant pCMV plasmid was purified using a QIAgen kit (Chatsworth, Calif.) and the nucleotide sequence of the DNA insert was verified by DNA sequencing.

Example 3

This example illustrates the use of DNA to elicit an immune response to S. pneumoniae antigens.

A group of 8 female BALB/c mice (Charles River, St-Constant, Québec, Canada) were immunized by intramuscular injection of 50 µl three times at two- or three-week intervals with 100 µg of recombinant pCMV-GH encoding the BVH-3, BVH-11 or the BVH-28 gene in presence of 50 µg of granulocyte-macrophage colony-stimulating factor (GM-CSF)—expressing plasmid pCMV-GH-GM-CSF (Laboratory of Dr. Stephen A. Johnston, Department of Biochemistry, The University of Texas, Dallas, Tex.). As control, a group of mice were injected with 100 µg of pCMV-GH in presence of 50 µg of pCMV-GH-GM-CSF. Blood samples were collected from the orbital prior to each immunization and seven days following the third injection and serum antibody responses were determined by ELISA using thioredoxin-His•Tag-S. pneumoniae fusion protein as coating antigen. DNA immunization with recombinant plasmid PCMV-GH encoding the BVH-3, BVH-11 or the BVH-28 S. pneumoniae protein induced antibody reactive against the respective recombinant protein. The reciprocal antibody titers, defined as the highest serum dilution at which the absorbance values were 0.1 above the background values, were above $4 \times 10^3$.

Example 4

This example illustrates the production and purification of recombinant S. pneumoniae proteins.

The recombinant pET plasmids containing the BVH-3, BVH-11 or the BVH-28 gene corresponding to the SEQ ID NO: 1, SEQ ID NO: 3 or the SEQ ID NO: 5 respectively were transformed by electroporation (Gene Pulser II apparatus, BIO-RAD Labs, Mississauga, Canada) into E. coli strain AD494 (DE3) (Dara$^-$ leu7697 DlacX74 DphoA PvuII phoR DmalF3 F'[lac$^+$(lacI$^q$) pro] trxB::Kan) (Novagen, Madison, Wis.). In this strain of E. coli, the T7 promotor controlling expression of the fusion protein is specifically recognized by the T7 RNA polymerase (present on the IDE3 prophage) whose gene is under the control of the lac promotor which is inducible by isopropyl-β-d-thio-galactopyranoside (IPTG). The transformant AD494(DE3)/rpET was grown at 37° C. with agitation at 250 rpm in LB broth (peptone 10 g/L, yeast extract 5 g/L, NaCl 10 g/L) containing 100 µg of ampicillin (Sigma-Aldrich Canada Ltd., Oakville, Canada) per ml until the $A_{600}$ reached a value of 0.6. In order to induce the production of the thioredoxin-His•Tag-BVH-3, thioredoxin-His•Tag-BVH-11 or thioredoxin-His•Tag-BVH-28 fusion protein, the cells were incubated for 2 additional hours in the presence of IPTG at a final concentration of 1 mM. Induced cells from a 100 ml culture were pelleted by centrifugation and frozen at −70° C.

The purification of the fusion proteins from the soluble cytoplasmic fraction of IPTG-induced AD494(DE3)/rpET was done by affinity chromatography based on the properties of the His•Tag sequence (6 consecutive histidine residues) to bind to divalent cations (Ni$^{2+}$) immobilized on the His.Bind metal chelation resin. Briefly, the pelleted cells obtained from a 100 mL culture induced with IPTG were resuspended in phosphate-buffered (PBS):500 mM NaCl pH7.1, sonicated and spun at 20,000×g for 20 min to remove debris. The supernatant was filtered (0.22 µm pore size membrane) and deposited on a HiTrap® 1 mL chelating pre-packed ready-to-use column (Pharmacia Biotech, Baie d'Urfé, Canada). The thioredoxin-His•Tag-S. pneumoniae fusion protein was eluted with 1M imidazole-500 mM NaCl-PBS pH7.1. The removal of the salt and imidazole from the sample was done by dialysis against PBS at 4° C. The quantities of fusion protein obtained from the soluble fraction of E. coli was estimated by MicroBCA (Pierce, Rockford, Ill.).

Example 5

This example illustrates the protection of mice against fatal pneumococcal infection by immunization.

Groups of 8 female BALB/c mice (Charles River) were immunized subcutaneously three times at three-week intervals with either 25 µg of affinity purified thioredoxin-His•Tag-BVH-3 fusion protein in presence of 15 µg of QuilA adjuvant (Cedarlane Laboratories Ltd, Hornby, Canada) or, as control, with QuilA adjuvant alone in PBS. Blood samples were collected from the orbital sinus on day 1, 22 and 43 prior to each immunization and seven days (day 50) following the third injection. One week later the mice were challenged with approximately $10^6$ CFU of the type 3 S. pneumoniae strain WU2. Samples of the S. pneumoniae challenge inoculum were plated on chocolate agar plates to determine the CFU and to verify the challenge dose. Deaths were recorded for a period of 14 days and on day 14 post-challenge, the surviving mice were sacrificed and blood samples tested for the presence of S. pneumoniae organisms. The survival data are shown in table 1.

Prechallenge sera were analyzed for the presence of antibodies reactive with S. pneumoniae by standard immunoassays. Elisa and immunoblot analyses indicated that immunization with recombinant S. pneumoniae protein produced in E. coli elicited antibodies reactive with both, recombinant and native pneumococcal protein.

TABLE 1

Protection mediated by recombinant BVH-3 protein

| Immunogen | No. of mice alive:no. of mice dead 14 days post-challenge | Median day of death |
|---|---|---|
| BVH-3 | 8:0 | >14 |
| none | 0:8 | 1 |

All mice immunized with BVH-3 recombinant protein survived to infection while none of the control mice given adjuvant alone survived. There was a significant difference in survival between the two groups of mice (P<0.0001, log rank test for nonparametric analysis of survival curves; P=0.0002, Fisher's exact test). All hemocultures from surviving mice were negative at day 14 post-challenge.

Example 6

This example describes the cloning of BVH-3 and BVH-11 genes from a variety of S. pneumoniae strains and the molecular conservation of these genes.

Molecular analysis of chromosomal DNA from various S. pneumoniae isolates with DNA probes spanning different regions of BVH-3 or BVH-11 revealed the presence of one BVH-3 gene copy and two BVH-11 gene copies. The two BVH-11 gene copies are not identical and the genes were arbitrarily designated BVH-11 (SEQ ID NO:12; ORF at nucleotides 45 to 2567) and BVH-11-2 (SEQ ID NO:13; ORF at nucleotides 114 to 2630).

The first amino acids of the BVH-3 and BVH-11 coding regions have the characteristics of leader sequences also known as signal peptides. The consensus signal peptidase cleavage site L-X-X-C of lipoprotein modification/processing sites was present in the sequences. Mature BVH-3, BVH-11 and BVH-11-2 proteins from *S. pneumoniae* SP64 have 1019, 821 and 819 amino acids, respectively. The regions of *S. pneumoniae* genes coding for mature BVH-3, termed BVH-3M, (nucleotides 1837-4896; SEQ. ID. NO: 11), BVH-11M (nucleotides 102-2567; SEQ. ID. NO: 12) and BVH-11-2M (nucleotides 171-2630; SEQ. ID. NO: 13), were amplified by PCR(DNA Thermal Cycler GeneAmp PCR system 2400 Perkin Elmer, San Jose, Calif.) from genomic DNA of 6 or 7 *S. pneumoniae* strains. Serogroup 6 *S. pneumoniae* SP64 and serogroup 9 SP63 clinical isolates were provided by the laboratoire de la santé publique du Québec, Sainte-Anne-de-Bellevue; serotype 4 strain JNR.7/87 was provided by Andrew Camilli, Tufts University School of Medicine, Boston; Rx1 strain, a nonencapsulated derivative of the type 2 strain D39 and the type 3 strains A66 and WU2 were provided by David E. Briles from University of Alabama, Birmingham and the type 3 clinical isolate P4241 was provided by the centre de recherche en infectiologie du centre hospitalier de l'université Laval, Sainte-Foy. The sets of oligonucleotide primers OCRR479-OCRR480; HAMJ160-OCRR488 and HAMJ160-HAMJ186, that contained base extensions for the addition of restriction sites were used for the amplification of BVH-3, BVH-11 and BVH-11-2 gene, respectively, with the exception of BVH-11 gene from SP64 strain which was amplified using the set of primers consisting of HAMJ487 and OCRR488. Primer sequences are listed below (Table 2). PCR products were purified from agarose gel using a QIAquick gel extraction kit from QIAgen (Chatsworth, Calif.) and digested BglII-XbaI or BglII-HindIII (Pharmacia Canada Inc, Baie d'Urfé, Canada). Digestions were cleaned using a QIAquick PCR purification kit from QIAgen (Chatsworth, Calif.). The PCR products were ligated to the BglII-XbaI or BglII-HindIII pSL301 vector. The ligated products were transformed into *E. coli* strain DH5α[ϕ80 lacZ ΔM15 endA1 recA1 hsdR17 ($r$K$^-$$^m$K$^+$) supE44 thi-1λ$^-$ gyrA96 relA1 Δ(lacZYA-argF)U169] (Gibco BRL, Gaithersburg, Md.) according to the method of Simanis (Hanahan, D. DNA Cloning, 1985, D. M. Glover (ed), pp. 109-135). Recombinant pSL301 plasmids (rpSL301) containing BVH-3, BVH-11 or BVH11-2 were purified using a QIAgen kit (Chatsworth, Calif.) and DNA inserts were sequenced (Taq Dye Deoxy Terminator Cycle Sequencing kit, ABI, Foster City, Calif.). The FIGS. 11 and 12 depict the consensus sequence established from the BVH-3, and BVH-11 deduced amino acid sequences, respectively. Comparison of BVH-3 protein sequences revealed 99 to 100% identity of sequences for all strains with the exception that BVH-3 from serogroup 9 SP63 strain (SEQ. ID. NO: 15 and SEQ. ID. NO: 16) misses a stretch of 177 amino acids corresponding to residues 244 to 420 on BVH-3 protein sequence of *S. pneumoniae* SP64. Analysis of sequences of additional serogroup 9 strains revealed BVH-3 molecule having the same deletion in 3 out of 4 strains thus suggesting that the 3 strains are members of a *S. pneumoniae* serogroup 9 clone.

Comparison of 13 BVH-11 nucleotide sequences obtained from 7 *S. pneumoniae* strains, revealed that the nucleotide sequences are very similar. Computer analysis (MacVector, Clustal W 1.4) using multiple alignment of the predicted BVH-11 protein sequences revealed that these sequences were 75% identical and 82% homologous on a length of 834 amino acids. Pairwise alignment revealed 80 to 100% identity (FIG. 13). The sequences showed great similarity in overall organization. Variability in the primary sequence of these proteins is almost restricted to the last 125 amino acids in the C-terminal portion of the proteins. This region constitutes a domain. Close examination of this domain revealed two groups of sequences. The first 9 sequences from the FIG. 13 belong to one group while the last 4 sequences belong to another group. A 39% identity value is obtained when the domain sequences of the 13 proteins are compared (MacVector, Clustal W 1.4). The identity value increased to more than 92% when sequences belonging to a same group are compared.

Example 7

This example illustrates the homology of portions of BVH-3 and BVH-11 genes.

Molecular analysis with DNA probes derived from BVH-3 and BVH-11 genes indicated that BVH-3 and BVH-11 were related. In dot blot hybridization studies, DNA probe consisting of either, BVH-3 or BVH-11, gene sequence hybridized to both, BVH-3 and BVH-11 genes thus indicating that BVH-3 and BVH-11 genes shared homologous sequences. Comparison of sequences revealed that the ORFs and the proteins were 43 and 33% identical, respectively. Closer examination revealed that the region corresponding to amino acids 1 to 225 in BVH-3 and 1 to 228 in BVH-11 were 73 and 75% identical at the DNA and protein level, respectively. In contrast, the 3' regions corresponding to amino acids 226 to 1039 from BVH-3 and amino acids 229-840 from BVH-11 were only 34 and 22% identical at the DNA and protein level, respectively. Thus the 5' termini of BVH-3 and BVH-11 genes appear to contain highly conserved sequences while the remaining parts of the genes are highly divergent. These results suggest that BVH-3 and BVH-11 might share similar functions mediated by sequences present in the conserved region whereas BVH-3- and BVH-11-specific functions might be mediated by sequences in the divergent region.

Example 8

This example describes the cloning of truncated BVH-3, BVH-11 and BVH-11-2 genes by polymerase chain reaction (PCR) and the expression of truncated BVH-3 and BVH-11 molecules.

Gene fragments were amplified by PCR using pairs of oligonucleotide engineered to amplify fragments spanning the BVH-3 (SEQ ID NO: 1 and SEQ ID NO: 11), BVH-11 (SEQ ID NO: 3 and SEQ ID NO: 12) or BVH-11-2 (SEQ ID NO: 13) gene from *S. pneumoniae* strain SP64. Each of the primers had a restriction endonuclease site at the 5' end, thereby allowing directional in-frame cloning of the amplified product into the digested plasmid vector (Tables 2 and 3). PCR-amplified products were digested with restriction endonucleases and ligated to either linearized plasmid pSL301 (see example 1), pCMV-GH (see example 2) or pET (Novagen, Madison, Wis.) expression vector digested likewise or digested with enzymes that produce compatible cohesive ends. Recombinant pSL301 and recombinant PCMV-GH plasmids were digested with restriction enzymes for the in-frame cloning in pET expression vector. Clones were first stabilized in *E. coli* DH5α before introduction into *E. coli* BL21 (λDE3) or AD494 (λDE3) for expression of truncated BVH-3 or BVH-11 molecules. Each of the resultant plasmid constructs was confirmed by nucleotide sequence analysis. The recombinant proteins were expressed as N-terminal fusions with the thioredoxin and His-tag or as C-terminal fusions with an His-tag. The expressed recombinant proteins were purified from supernatant fractions obtained from centrifugation of sonicated IPTG-induced *E. coli* cultures using a His-Bind metal chelation resin (QIAgen, Chatsworth, Calif.). The gene products generated are listed in the table 3. The gene products corresponding to the N-terminal region including the signal sequence are designated as Lipidated-proteins or lipoproteins (L-proteins). The gene products corresponding to the N-terminal region lacking the signal sequence are identified as protein without signal sequence (w/o ss).

TABLE 2

List of PCR oligonucleotide primers

| Primer | SEQ. ID. | Sequence 5'-3' | Nucleotide position | Restriction sites |
|---|---|---|---|---|
| OCRR 479 | 17 | cagtagatctgtgcctatgcactaaac | SEQ ID 1: 61-78 | BglII |
| OCRR 480 | 18 | gatctctagactactgctattccttacgctatg | SEQ ID 11: 4909-4887 | XbaI |
| OCRR 497 | 19 | atcactcgagcattacctggataatcctgt | SEQ ID 1: 1525-1506 | XhoI |
| OCRR 498 | 20 | ctgctaagcttatgaaagatttagat | SEQ ID 1: 1534-1548 | HindIII |
| OCRR 499 | 21 | gatactcgagctgctattccttac | SEQ ID 11: 4906-4893 | XhoI |
| HAMJ 172 | 22 | gaatctcgagttaagctgctgctaattc | SEQ ID 1: 675-661 | XhoI |
| HAMJ 247 | 23 | gacgctcgagcgctatgaaatcagataaattc | SEQ ID 1: 3117-3096 | XhoI |
| HAMJ 248 | 24 | gacgctcgagggcattacctggataatcctgttcatg | SEQ ID 1: 1527-1501 | XhoI |
| HAMJ 249 | 25 | cagtagatctcttcatcatttattgaaaagagg | SEQ ID 11: 1749-1771 | BglII |
| HAMJ 278 | 26 | ttatttcttccatatggacttgacagaagagcaaattaag | SEQ ID 1: 1414-1437 | NdeI |
| HAMJ 279 | 27 | cgccaagcttcgctatgaaatcagataaattc | SEQ ID 1: 3117-3096 | HindIII |
| HAMJ 280 | 28 | cgccaagcttttccacaatataagtcgattgatt | SEQ ID 1: 2400-2377 | HindIII |
| HAMJ 281 | 29 | ttatttcttccatatggaagtacctatcttggaaaaagaa | SEQ ID 1: 2398-2421 | NdeI |
| HAMJ 300 | 30 | ttatttcttccatatggtgcctatgcactaaaccagc | SEQ ID 1: 62-82 | NdeI |
| HAMJ 313 | 31 | ataagaatgcggccgcttccacaatataagtcgattgatt | SEQ ID 1: 2400-2377 | NotI |
| OCRR 487 | 32 | cagtagatctgtgcttatgaactaggtttgc | SEQ ID 3: 58-79 | BglII |
| OCRR 488 | 33 | gatcaagcttgctgctacctttacttactctc | SEQ ID 12: 2577-2556 | HindIII |
| HAMJ 171 | 34 | ctgagatatccgttatcgttcaaacc | SEQ ID 3: 1060-1075 | EcoRV |
| HAMJ 251 | 35 | ctgcaagcttttaaaggggaataatacg | SEQ ID 3: 1059-1045 | HindIII |
| HAMJ 264 | 36 | cagtagatctgcagaagccttcctatctg | SEQ ID 3: 682-700 | BglII |
| HAMJ 282 | 37 | tcgccaagcttcgttatcgttcaaaccattggg | SEQ ID 3: 1060-1081 | HindIII |
| HAMJ 283 | 38 | ataagaatgcggccgccttactctcctttaataaagccaatagtt | SEQ ID 3: 2520-2492 | NdeI |
| HAMJ 284 | 39 | catgccatggacattgatagtctcttgaaacagc | SEQ ID 3: | NcoI |

TABLE 2-continued

List of PCR oligonucleotide primers

| Primer | SEQ. ID. | Sequence 5'-3' | Nucleotide position | Restriction sites |
|---|---|---|---|---|
| | | | 856-880 | |
| HAMJ 285 | 40 | cgccaagcttcttactctcctttaataaagccaatag | SEQ ID 3: 2520-2494 | HindIII |
| HAMJ 286 | 41 | cgacaagcttaacatggtcgctagcgttacc | SEQ ID 3: 2139-2119 | HindIII |
| HAMJ 287 | 42 | cataccatgggcctttatgaggcacctaag | SEQ ID 3: 2014-2034 | NcoI |
| HAMJ 288 | 43 | cgacaagcttaagtaaatcttcagcctctctcag | SEQ ID 3: 2376-2353 | HindIII |
| HAMJ 289 | 44 | gataccatggctagcgaccatgttcaaagaa | SEQ ID 3: 2125-2146 | NcoI |
| HAMJ 290 | 45 | cgccaagcttatcatccactaacttgactttatcac | SEQ ID 3: 1533-1508 | HindIII |
| HAMJ 291 | 46 | cataccatggatattcttgccttcttagctccg | SEQ ID 3: 1531-1554 | NcoI |
| HAMJ 301 | 47 | catgccatggtgcttatgaactaggtttgc | SEQ ID 3: 59-79 | NcoI |
| HAMJ 302 | 48 | cgccaagctttagcgttaccaaaaccattatc | SEQ ID 3: 2128-2107 | HindIII |
| HAMJ 160 | 49 | gtattagatctgttcctatgaacttggtcgtcacca | SEQ ID 13: 172-196 | BglII |
| HAMJ 186 | 50 | cgcctctagactactgtataggagccgg | SEQ ID 13: 2460-2443 | XbaI |
| HAMJ 292 | 51 | catgccatggaaaacatttcaagccttttacgtg | SEQ ID 11: 754-778 | NcoI |
| HAMJ 293 | 52 | cgacaagcttctgtataggagccggttgactttc | SEQ ID 11: 2457-2434 | HindIII |
| HAMJ 294 | 53 | catgccatggttcgtaaaaataaggcagaccaag | SEQ ID 11: 2038-2062 | NcoI |
| HAMJ 297 | 54 | catgccatggaagccattggaatgggaag | SEQ ID 11: 622-642 | NcoI |

TABLE 3

Lists of truncated BVH-3 and BVH-11 gene products generated from *S. pneumoniae* SP64

| PCR-primer sets | Protein designation | Identification (encoded amino acids) | SEQ. ID. NO. | Cloning vector |
|---|---|---|---|---|
| OCRR479-OCRR480 | BVH-3M | BVH-3 w/o ss (21-1039) | 55 | pSL301 |
| OCRR479-OCRR497 | BVH-3AD | BVH-3 N'end w/o ss (21-509) | 56 | pSL301 |
| HAMJ248-HAMJ249 | L-BVH-3AD | BVH-3 N'end (1-509) | 57 | pET-21(+) |
| OCRR498-OCRR499 | BVH-3B | BVH-3 C'end (512-1039) | 10 | pSL301 |
| OCRR479-HAMJ172 | BVH-3C | BVH-3 N'end w/o ss (21-225) | 59 | pET-32 c(+) |
| OCRR487-OCRR488 | BVH-11M | BVH-11 w/o ss (20-840) | 60 | pCMV-GH |
| HAMJ251-OCRR487 | BVH-11A | BVH-11 N'end w/o ss (20-353) | 61 | pET-32 c(+) |
| HAMJ171-OCRR488 | BVH-11B | BVH-11 C'end (354-840) | 62 | pET-32 a(+) |
| HAMJ264-OCRR488 | BVH-11C | BVH-11 C'end (228-840) | 63 | pET-32 a(+) |
| HAMJ278-HAMJ279 | NEW1 | BVH-3 C'end (472-1039) | 64 | pET-21b(+) |
| HAMJ278-HAMJ280 | NEW2 | BVH-3 C'end (472-800) | 65 | pET-21b(+) |
| HAMJ281-HAMJ279 | NEW3 | BVH-3 C'end (800-1039) | 66 | pET-21b(+) |
| HAMJ284-HAMJ285 | NEW4 | BVH-11 C'end (286-840) | 67 | pET-21d(+) |
| HAMJ284-HAMJ286 | NEW5 | BVH-11 internal (286-713) | 68 | pET-21d(+) |
| HAMJ287-HAMJ288 | NEW6 | BVH-11 internal (672-792) | 69 | pET-21d(+) |
| HAMJ285-HAMJ289 | NEW7 | BVH-11 internal (709-840) | 70 | pET-21d(+) |

TABLE 3-continued

Lists of truncated BVH-3 and BVH-11 gene products generated from
S. pneumoniae SP64

| PCR-primer sets | Protein designation | Identification (encoded amino acids) | SEQ. ID. NO. | Cloning vector |
|---|---|---|---|---|
| HAMJ284-HAMJ290 | NEW8 | BVH-11 internal (286-511) | 71 | pET-21d(+) |
| HAMJ286-HAMJ291 | NEW9 | BVH-11 internal (511-713) | 72 | pET-21d(+) |
| HAMJ160-HAMJ186 | BVH-11-2M | BVH-11-2 w/o ss (20-838) | 73 | pSL301 |
| HAMJ292-HAMJ293 | NEW10 | BVH-11-2 C'end (271-838) | 74 | pET-21d(+) |
| HAMJ293-HAMJ294 | NEW11 | BVH-11-2 C'end (699-838) | 75 | pET-21d(+) |
| HAMJ282-HAMJ283 | BVH-11B | BVH-11 C'end (354-840) | 62 | pET-21b(+) |
| HAMJ286-HAMJ297 | NEW14 | BVH-11-2 internal (227-699) | 77 | pET-21d(+) |
| HAMJ300-HAMJ313 | NEW15 | BVH-3 N'end w/o ss (21-800) | 78 | pET-21b(+) |
| HAMJ301-HAMJ302 | NEW16 | BVH-11 N'end w/o ss (20-709) | 79 | pET-21d(+) |

Example 9

This example describes the isolation of monoclonal antibodies (Mabs) and the use of Mabs to characterize BVH-3, BVH-11 and BVH-11-2 protein epitopes.

Female BALB/c mice (Charles River) were immunized subcutaneously with BVH-3, BVH-11 or BVH-11-2 gene products from S. pneumoniae strain SP64 in presence of 15 µg of QuilA adjuvant (Cedarlane Laboratories Ltd, Hornby, Canada). One set of mice (fusion experiment 1) were immunized on day 1 and 14 with 25 μg of affinity purified thioredoxin-His•Tag-BVH-3M fusion protein. A second group of mice (fusion experiment 2) were immunized three times at three-week intervals with 25 μg of affinity purified thioredoxin-His•Tag-BVH-11M. A third group of mice (fusion experiment 3) were immunized on day 1 and day 15 with 25 μg of affinity purified thioredoxin-His•Tag-BVH-11-2M fusion protein. A fourth group of mice (fusion experiment 4) were immunized on day 1 with 25 μg of affinity purified thioredoxin-His.BVH-11 B fusion protein and boosted by intravenous injection on day 16 and on day 37 with recombinant BVH-11 B in PBS. Three to four days before fusion, mice were injected intravenously with 25 μg of the respective antigen suspended in PBS alone. Hybridomas were produced by fusion of spleen cells with nonsecreting SP2/0 myeloma cells as previously described by J. Hamel et al. [J. Med. Microbiol., 23, pp 163-170 (1987)]. Culture supernatants of hybridomas were initially screened by enzyme-linked-immunoassay according to the procedure described by Hamel et al. (Supra) using plates coated with preparations of purified recombinant proteins or suspensions of heat-killed *S. pneumoniae* cells. Positive hybridomas selected on the basis of ELISA reactivity with a variety of antigens were then cloned by limiting dilutions, expanded and frozen.

Hybridomas were tested by ELISA or Western immunoblotting against BVH-3 and BVH-11 gene products in order to characterize the epitopes recognized by the Mabs. BVH-3 and BVH-11 shared common epitopes with 6 Mabs (H3-1-F9, H3-1-D4, H3-1-H12, H11-1-E7, H11-1-H10 and H11-1.1-G11) showing reactivities with both proteins (Table 4). BVH-11 and BVH-11-2 molecules from *S. pneumoniae* SP64 shared common epitopes not present on BVH-3 with Mabs (3A1, 13C11, 10H10, 1D8, 10G9, 10A2, 3E8, 10D7, 2H7 and 6H7) reactive with both, BVH-11 and BVH-11-2, recombinant proteins (Table 5).

TABLE 4

Reactivity of BVH-3-immunoreactive Mabs with a panel of BVH-3 and BVH-11 gene products

| MAbs | a. Immunoreactivity with | | | | | | |
|---|---|---|---|---|---|---|---|
| | BVH-3M 21-1039 | BVH-3A 21-509 | BVH-3B 512-1039 | BVH-3C 21-225 | NEW2 472-800 | NEW3 800-1039 | BVH-11M 20-840 |
| H3-1-F9 | + | + | − | + | − | − | + |
| H3-1-D4 | + | + | − | + | − | − | + |
| H3-1-H12 | + | + | − | + | − | − | + |
| H3-2-G2 | + | + | − | − | − | − | − |
| H3-3-A1 | + | + | − | − | − | − | − |
| H3-4-D3 | + | − | + | − | − | + | − |
| H11-1-E7 | + | + | − | + | − | − | + |
| H11-1-H10 | + | + | − | + | − | − | + |
| H11-1.1-G11 | + | + | − | + | + | − | + |

TABLE 5

Reactivity of Mabs raised against BVH-11-2 protein from *S. pneumoniae* strain SP64 with a panel of BVH-11 gene products

| | b. Immunoreactivity with | | | | | | | |
|---|---|---|---|---|---|---|---|---|
| | c. BVH-11 products | | | | d. BVH-11-2 products | | | |
| Mabs[a] | BVH-11M 20-840 | NEW8 286-511 | NEW9 511-713 | BVH-11B 354-840 | BVH-11-2 20-838 | NEW10 271-838 | NEW11 699-838 | NEW14 227-699 |
| 3A1 | + | + | − | + | + | + | − | + |
| 13C11 | + | + | + | + | + | + | − | + |
| 10H10 | + | + | + | + | + | + | − | + |
| 1D8 | + | + | − | + | + | + | − | + |
| 10G9 | + | − | − | + | + | + | − | + |
| 10A2 | + | − | − | + | + | + | − | + |
| 3E8 | + | − | − | + | + | + | − | + |
| 10D7 | + | − | − | + | + | + | − | + |
| 2H7 | + | − | − | − | + | − | − | − |
| 6H7 | + | − | − | − | + | − | − | − |
| 3A4 | − | − | − | − | + | + | + | − |
| 14H6 | − | − | − | − | + | + | + | − |
| 7G2 | − | − | − | − | + | + | − | + |
| 13H10 | − | − | − | − | + | − | − | + |
| 7E8 | − | − | − | − | + | − | − | − |
| 7H6 | − | − | − | − | + | − | − | − |

[a]Mabs listed in this table were not reactive with recombinant BVH-3 molecule

The results obtained from the immunoreactivity studies of the Mabs (Table 4 and Table 5) are in agreement with the protein sequences derived from the respective gene sequences. Indeed the Mabs cross-reactive with BVH-3 and BVH-11 molecules recognized BVH-3C protein corresponding to the conserved region, and BVH-11 and BVH-11-2 specific Mabs were reactive with epitopes located on variable parts of these molecules. BVH-3 and BVH-11, and BVH-11 and BVH-11-2 can be distinguished by their reactivity with Mabs.

Example 10

This example illustrates the simultaneous expression of BVH-3 and BVH-11 gene products by *S. pneumoniae*.

A standard Western blot technique was used to investigate whether BVH-3 and BVH-11 genes were expressed in *S. pneumoniae*. *S. pneumoniae* strain SP64 and SP63 were grown overnight at 37° C. in 5% $CO_2$ on chocolate agar plates, bacteria were suspended in PBS and heat-killed at 56° C. for 20 min. For the preparation of antigens, suspensions of *S. pneumoniae* were treated with sample buffer containing SDS and 2-mercaptoethanol for 5 min at 100° C. Pneumococcal protein antigens were resolved by SDS-PAGE electrophoresis according to the method of Laemmli (*Nature*, 227, pp. 680-685 (1970)). After SDS-PAGE, the proteins were transferred electrophoretically from the gel to nitrocellulose paper by the method of Towbin (*Proc. Natl. Acad. Sci. USA*, 76, pp. 4350-4354 (1979)) and probed with mouse antiserum or monoclonal antibodies. The detection of antigens reactive with the antibodies was performed by indirect enzyme-immunoassay using conjugated-anti-mouse immunoglobulins and a colour substrate. When antiserum raised to recombinant BVH-3 was tested against *S. pneumoniae* SP64 antigens, two reactive bands having apparent molecular masses of 127 kDa and 99 kDa were detected. Bands having the same apparent molecular masses were also detected when Mabs H3-1-F9, H3-1-D4, H3-1-H12, H11-1-E7, H11-1-H10 and H11-1.1-G11 were used individually as immunological probes. In contrast, Mabs specific for the BVH-3 molecule detected the 127 kDa band only and Mabs specific for BVH-11 detected the 99 kDa band only thus confirming the identity of the 127 and 99 kDa bands as BVH-3 and BVH-11, respectively. These studies provide evidence that BVH-3 and BVH-11 proteins are simultaneously present on *S. pneumoniae*. Moreover, the results are consistent with our previous observations that BVH-3 and BVH-11 possess epitopes that are common to both proteins and epitopes that are exclusive to either protein.

In *S. pneumoniae* SP64, mature BVH-3, BVH-11 and BVH-11-2 are proteins of 1019, 821 and 819 amino acids with predicted molecular mass of 112.5 kDa, 92.4 kDa, and 91.7 kDa, respectively. Although there is a discrepancy between the molecular mass predicted from the sequence and the molecular mass calculated on SDS-PAGE, BVH-3 can be distinguished from BVH-11 by its higher molecular mass. Moreover, BVH-3 molecules from *S. pneumoniae* strain SP63 have an apparent molecular mass of 112 kDa in SDS-PAGE compared to 127 kDa for BVH-3 of SP64 strain. This data is consistent with the deletion of a stretch of 177 amino acid residues in BVH-3 of *S. pneumoniae* strain SP63.

Example 11

This example describes the protection conferred in experimental infection of mice vaccinated with recombinant BVH-3 or BVH-11 gene products.

Groups of 7 or 8 female BALB/c mice (Charles River) were immunized subcutaneously three times at three-week intervals with either affinity purified thioredoxin-His•Tag-BVH-3M fusion protein, affinity purified thioredoxin-His•Tag-BVH-11M fusion protein or, as control, with QuilA adjuvant alone in PBS. Twelve to 14 days following the third immunization, the mice were challenged intravenously with *S. pneumoniae* WU2 strain or intranasally with P4241 strain. Samples of the *S. pneumoniae* challenge inoculum were plated on chocolate agar plates to determine the CFU and to verify the challenge dose. The challenge dose was approximately $10^6$ CFU. Deaths were recorded for a period of 14 days and on day 14 post-challenge, the surviving mice were sacrificed and blood samples tested for the presence of S. pneumoniae organisms. The survival data are shown in Tables 6 and 7.

TABLE 6

Protection mediated by recombinant BVH-3M and BVH-11M proteins in experimental infection with virulent S. pneumoniae WU2

| Experiment | Immunogen | Alive:dead[a] | Median days alive |
|---|---|---|---|
| 1 | BVH-3M | 8:0 | >14 |
|  | none | 0:8 | 1 |
| 2 | BVH-11M | 8:0 | >14 |
|  | none | 0:8 | 1 |

[a]The number of mice alive:the number of mice dead on day 14 post-challenge.

TABLE 7

Protection mediated by recombinant BVH-3M and BVH-11M proteins in experimental pneumonia with virulent S. pneumoniae P4241

| Experiment | Immunogen | Alive:dead[a] | Median day alive |
|---|---|---|---|
| 1 | BVH-3M | 6:1 | >14 |
|  | none | 1:7 | 4.5 |
| 2 | BVH-3M | 8:0 | >14 |
|  | BVH-11M | 8:0 | >14 |
|  | none | 0:8 | 4 |

[a]The number of mice alive:the number of mice dead on day 14 post-challenge.

All mice immunized with recombinant BVH-3M or BVH-11M protein survived to infection with WU2 while none of the control mice given adjuvant alone survived. All except one mice immunized with recombinant BVH-3M or BVH-11M protein survived to infection with P4241 while only one control mice given adjuvant alone survived. All hemocultures from surviving mice were negative at day 14 post-challenge. These results clearly indicate that both, BVH-3M and BVH-11M, elicit protective anti-pneumococcal immune responses in mice. The fact that these proteins are highly conserved among S. pneumoniae isolates emphasize the potential of BVH-3 and BVH-11 as universal vaccine candidates. Indeed, the BVH-3 and BVH-11 proteins from serogroup 6 S. pneumoniae strain SP64 elicited protection against pneumococcal infections with strains of different capsular serotypes.

Ideally, a vaccine that could protect against pneumococcal disease, could protect against meningitis, otitis media, bacteremia and pneumonia. BVH-3 and BVH-11 were protective against lethal systemic- and pneumonia-infection models thus suggesting that, in humans, BVH-3- and BVH11-protein-based vaccines could reduce the incidence of a wide spectrum of disease caused by virtually all S. pneumoniae independently of the capsular serotype.

Data from Tables 6 and 7 clearly demonstrate that BVH-3 and BVH-11 were, both, protection-eliciting molecules of S. pneumoniae. It was not known, however, whether protection can be mediated by specific sequences that were not shared on BVH-3 and BVH-11 molecules. Groups of female BALB/c mice (Charles River) were immunized subcutaneously three times at three-week intervals with either affinity purified thioredoxin-His•Tag-BVH-3AD, -BVH-3B or -BVH-3C fusion protein in presence of 15 µg of QuilA adjuvant (Cedarlane Laboratories Ltd, Hornby, Canada). Control mice were immunized with QuilA adjuvant alone in PBS or affinity purified thioredoxin-His•Tag or thioredoxin-His•Tag-fusion protein (His-Thio) in presence of QuilA.

To determine the protective ability of a set of truncated proteins, termed NEW4, NEW5, NEW6, NEW7, NEW8, NEW9, NEW10, NEW11, NEW14 and BVH-11 B, groups of female BALB/c mice (Charles River) were immunized subcutaneously two times at three-week intervals with 25 µg of either affinity purified His•Tag-fusion protein in presence of 15 µg of QuilA adjuvant. Ten to 14 days following the last immunization, the mice were challenged with virulent S. pneumoniae. Our results indicate that, BVH-3B, a truncated BVH-3 molecule consisting of amino acids 512-1039, elicited protection against the mouse-virulent strains WU2 and P4241. Similarly, BVH-11 B, NEW4 and NEW5 molecules, three truncated BVH-11 molecules consisting of amino acids 354-840, amino acids 286-840 and amino acids 286-713, respectively, elicited protection against experiment intravenous challenge with WU2 and intranasal challenge with P4241. Moreover, vaccination with NEW10 and NEW14, consisting of amino acids 272-838 and amino acids 227-699 from BVH-11-2 molecule also resulted in protection against death with the pneumococcal strains. These results indicate that the region comprising 428 amino acids extending from amino acids 286-713 and amino acids 272-699 on S. pneumoniae SP64 BVH-11 and BVH-11-2 protein sequences, respectively, contains protective epitopes. This region is highly conserved with a global 91% identity and 94% homology among thirteen BVH-11 protein sequences.

TABLE 8

Evaluation of protection elicited by vaccination of mice with BVH-3 and BVH-11 gene products

| | | Challenge with WU2 | | Challenge with P4241 | |
|---|---|---|---|---|---|
| Experiment | Immunogen | Alive:dead[a] | Median day alive | Alive:dead | Median day alive |
| 1[b] | None | 0:8 | 1.5 | 1:7 | 4.5 |
|  | NEW4 | 8:0 | >14 | 8:0 | >14 |
|  | NEW5 | 8:0 | >14 | 8:0 | >14 |
|  | NEW7 | 0:8 | 2 | 0:8 | 5 |
|  | BVH-11M | 8:0 | >14 | 8:0 | >14 |
| 2[b] | None | 0:8 | 1 | 0:8 | 4 |
|  | NEW5 | 8:0 | >14 | 8:0 | >14 |
|  | NEW8 | 0:8 | 1.5 | 0:8 | 5.5 |
|  | NEW9 | 3:5 | 3.5 | 2:6 | 7 |
|  | BVH-11M | 8:0 | >14 | 8:0 | >14 |
| 3[b] | None | 0:8 | 1 | 0:8 | 4 |
|  | NEW6 | 0:8 | 1 | 4:4 | 10.5[c] |
|  | NEW10 | 8:0 | >14 | 8:0 | >14 |
|  | NEW11 | 0:8 | 1.5 | 1:7 | 6 |
|  | BVH-11M | 8:0 | >14 | 8:0 | >14 |
| 4[b] | None | 0:8 | 2 | 0:8 | 4 |
|  | BVH-11B | 7:1 | >14 | 8:0 | >14 |
|  | NEW14 | 8:0 | >14 | 8:0 | >14 |
| 5 | His-Thio | 0:8 | 2 | | |
|  | BVH-3AD | 1:7 | 2.5 | | |
|  | BVH-3B | 5:3 | >14 | | |
| 6 | His-Thio | 0:8 | 1 | | |
|  | BVH-3C | 0:8 | 1 | | |

[a]The number of mice alive:the number of mice dead on day 14 post-challenge.
[b]The WU2 challenge dose was $10^5$ CFU.
[c]Mice living longer than 14 days were assigned a survival time of 14 days for the determination of median values.

Example 12

This example described the cloning and expression of a chimeric gene encoding for a chimeric polypeptide corresponding to the carboxy-terminal region of BVH-3 in fusion at the C' end to the carboxy-terminal region of BVH-11 and the additive protection observed after vaccination with a chimeric polypeptide.

It is clear from the studies described above that BVH-3 and BVH-11 are serologically distinct molecules simultaneously present on *S. pneumoniae*. The results of immunological studies of mice indicate that both proteins are good vaccine candidates. These proteins have the potential to provide protection against all pneumococci, regardless of serotype. Even though the two proteins share epitopes and sequences, they have different characteristics and may serve different biological functions. Thus, immunization against the two proteins may provide a higher level of protection than that imparted by each individually. To examine this, several avenues where full-length or truncated BVH-3 and BVH-11 are administered in combination or in conjugation can be explored. Here we describe the genetic engineering of a BVH-3-BVH-11 fusion gene and protein, termed NEW12 (SEQ ID NO: 76 and SEQ ID NO: 58, respectively), and the potential use of NEW12 protein as a vaccine.

BVH-3 and BVH-11 gene fragments corresponding to the 3' end of the genes were amplified by PCR using pairs of oligonucleotides engineered to amplify fragments spanning nucleotides 1414 to 3117(SEQ ID NO: 1) and nucleotides 1060 to 2520 (SEQ ID NO: 3) from *S. pneumoniae* strain SP64 BVH-3 and BVH-11 genes, respectively. The primers used, HAMJ278 and HAMJ279; HAMJ282 and HAMJ283 had a restriction endonuclease site at the 5' end, thereby allowing directional in-frame cloning of the amplified product into the digested pET21 b(+) plasmid vector (Table 2). PCR-amplified products were digested with restriction endonucleases and ligated to linearized plasmid pET21b(+) vector digested likewise. The resultant plasmid constructs were confirmed by nucleotide sequence analysis. The recombinant pET21b(+) plasmid containing the NdeI-HindIII BVH-3 PCR product was linearized by digestion with the restriction enzymes HindIII and NotI for the in-frame cloning of the HindIII-NotI DNA fragment obtained from the recombinant pET21(+) vector containing the BVH-11 gene fragment. Clones were first stabilized in *E. coli* DH5 α before introduction into *E. coli* BL21 (λDE3) for expression of a chimeric pneumococcal protein molecule. The recombinant chimeric polypeptide, termed NEW 12, was expressed as C-terminal fusion with an His-tag. The expressed recombinant NEW 12 protein was purified from supernatant fractions obtained from centrifugation of sonicated IPTG-induced *E. coli* cultures using a His-Bind metal chelation resin (QIAgen, Chatsworth, Calif.).

According to the same procedure described above, it is possible to construct other chimeric polypeptides, as a result of a simultaneous expression of New 1 and New 4, New 1 and New 5, New 1 and New 10, or New 1 and New 14. The construction can be with New 1 upstream or downstream of New 4, New 5, New 10, BVH-11 B or New 14. It is also possible to construct other chimeric polypeptides as a result of a simultaneous expression of more than two fragments of either genes of BVH-3, BVH-11 or BVH-11-2.

Groups of 8 female BALB/c mice (Charles River) were immunized subcutaneously two times at three-week intervals with 25 μg of either affinity purified His•Tag-fusion NEW1, BVH-11B or NEW12 protein in presence of 15 μg of QuilA adjuvant. Ten to 14 days following the last immunization, the mice were challenged with virulent *S. pneumoniae*. As demonstrated before, NEW1 and BVH-11 B molecules comprising amino acids 472 to 1039 from BVH-3 protein and amino acids 354-840 from BVH-11 protein, respectively, correspond to portions of the proteins capable of eliciting a protective immune response. To determine if a chimeric polypeptide would significantly improve the protection compared with those seen for the individual counterparts, the challenge dose was adjusted in a manner that protection was not expected with NEW1 and BVH-11B molecules. Interestingly, the chimeric NEW12 protein, elicited protection against the mouse-virulent strains WU2 and P4241. Seven out of 8 mice immunized with NEW12 were still alive 10 days after the challenge while 28 out of 32 mice immunized with NEW1, BVH-11 B, BVH-3M or adjuvant alone were dead by five days post-challenge. Thus, vaccination of mice with NEW12 provided the highest degree of protection against WU2 challenge. These results indicate that immunization with a chimeric polypeptide and possibly a combination of BVH-3 and BVH-11 gene products can provide additional protection to that obtained by administration of BVH-3 or BVH-11 antigens alone.

TABLE 9

Evaluation of protection elicited by vaccination of mice with the chimeric NEW12 molecule

| | Challenge with WU2 | | Challenge with P4241 | |
|---|---|---|---|---|
| Immunogen | Alive:dead$^a$ | Median day alive | Alive:dead | Median day alive |
| None | 0:8 | 1 | 0:8 | 5 |
| NEW1 | 2:6 | 2 | 1:7 | 8 |
| BVH-11B | 1:7 | 3.5 | 8:0 | >14 |
| NEW12 | 6:2 | >14 | 7:1 | >14 |
| BVH-3M | 1:7 | 3 | 8:1 | >14 |

Example 13

This example illustrates the identification of additional BVH-3 and BVH-11 related sequences in *Streptococcus* species other than *S. pneumoniae*.

It was previously shown that BVH-3, BVH-11 and BVH-11-2 are a family of related proteins sharing common sequences. Homology searches were performed with the nucleotide sequence from the conserved region of these genes and compared with GenBank and EMBL sequences using FASTA. The most significant homology was observed with a 2.469-kb gene coding for a calculated 92-kDa protein (SEQ ID NO: 81) of unknown function in *S. agalactiae* also called group B *streptococcus* or GBS. The gene was designated BVH-71. A protein demonstrating 99.2% identity and 99.5% similarity with that of GBS was also identified in *S. pyogenes* also called group A *streptococcus* or GAS (SEQ ID NO: 83). The 5' region of the BVH-71 sequences (SEQ ID NO: 80 and SEQ ID NO: 82), spanning nucleotides 1 to 717, demonstrated 58 and 60% identity with the conserved regions of BVH-3 (nucleotides 1 to 675) and BVH-11 (nucleotides 1 to 684) genes respectively. The first 239 amino acids of the translated sequences of the GBS and GAS BVH-71 open reading frames are 51 and 54% identical to the first 225 and 228 amino acids of BVH-3 and BVH-11, respectively. In addition to structural similarities, streptococcal BVH-3, BVH-11 and BVH-71 proteins also share antigenic epitopes. A 97-kDa band was revealed on Western blots of GAS or GBS whole cells, using Mab H11-1.1-G11 reactive with the BVH-3 and BVH-11 conserved regions. Similarly, GAS and GBS recombinant BVH-71 proteins were detected in Western immunoblot analysis.

These results indicate that BVH-71, BVH-3 and BVH-11 proteins might share similar functions. Our results also suggest that BVH-71 proteins can be used as protein vaccine components of anti-streptococcus. In a further embodiment BVH-71 proteins can be used as protein vaccine components of anti-GAS or anti-GBS vaccines.

What is claimed is:

1. An isolated polypeptide comprising an amino acid sequence at least 95% identical to the full-length amino acid sequence set forth in SEQ ID NO:4 or SEQ ID NO:60, wherein the isolated polypeptide elicits antibodies that specifically bind to a polypeptide consisting of the amino acid sequence set forth in SEQ ID NO:4, and wherein the isolated polypeptide is capable of inducing an immune response to *Streptococcus*.

2. The isolated polypeptide according to claim 1 wherein the *Streptococcus* is *Streptococcus pneumoniae*.

3. An isolated polypeptide comprising the amino acid sequence set forth in SEQ ID NO:4 or SEQ ID NO:60.

4. An immunogenic composition comprising the isolated polypeptide according to either claim 1 or claim 3 and a pharmaceutically acceptable carrier or diluent.

5. A method for inducing an immune response against *Streptococcus*, wherein said *Streptococcus* causes meningitis, otitis media, bacteremia or pneumonia infection in an individual, said method comprising administering to said individual the composition according to claim 4.

6. A method for inducing an immune response against streptococcal infection in an individual susceptible to streptococcal infection, said method comprising administering to said individual the composition according to claim 4.

7. The method according to claim 6, wherein said individual is a mammal.

8. The method according to claim 7, wherein said individual is a human.

9. The method according to claim 6, wherein said streptococcal infection is a *S. pneumoniae*, group A *streptococcus* (*S. pyogenes*), group B *streptococcus* (*S. agalactiae*), *S. dysgalactiae*, or *S. uberis* infection.

10. The method according to claim 6, wherein said streptococcal infection is a *S. pneumoniae* infection.

11. The immunogenic composition according to claim 4 further comprising a pharmaceutically acceptable adjuvant.

12. A method for inducing an immune response against streptococcal infection in an individual susceptible to streptococcal infection, said method comprising administering to said individual the composition according to claim 11.

13. The method according to claim 12, wherein said individual is a mammal.

14. The method according to claim 12, wherein said individual is a human.

15. The method according to claim 12, wherein said streptococcal infection is a *S. pneumoniae*, group A *streptococcus* (*S. pyogenes*), group B *streptococcus* (*S. agalactiae*), *S. dysgalactiae*, or *S. uberis* infection.

16. The method according to claim 12, wherein said streptococcal infection is a *S. pneumoniae* infection.

\* \* \* \* \*